US010975150B2

(12) United States Patent
Penta et al.

(10) Patent No.: US 10,975,150 B2
(45) Date of Patent: Apr. 13, 2021

(54) ANTI-CD74 ANTIBODIES, COMPOSITIONS COMPRISING ANTI-CD74 ANTIBODIES AND METHODS OF USING ANTI-CD74 ANTIBODIES

(71) Applicant: SUTRO BIOPHARMA, INC., South San Francisco, CA (US)

(72) Inventors: Kalyani Penta, Palo Alto, CA (US); Ryan Stafford, Emeryville, CA (US); Avinash Gill, Emeryville, CA (US); Xiaofan Li, Fremont, CA (US); Alice Yam, Tiburon, CA (US); Christopher Thanos, Burlingame, CA (US); Aaron Sato, Burlingame, CA (US)

(73) Assignee: SUTRO BIOPHARMA, INC., South San Francisco, CA (US)

( * ) Notice: Subject to any disclaimer, the term of this patent is extended or adjusted under 35 U.S.C. 154(b) by 176 days.

(21) Appl. No.: 15/327,601

(22) PCT Filed: Jul. 20, 2015

(86) PCT No.: PCT/US2015/041192
§ 371 (c)(1),
(2) Date: Jan. 19, 2017

(87) PCT Pub. No.: WO2016/014434
PCT Pub. Date: Jan. 28, 2016

(65) Prior Publication Data

US 2017/0253656 A1 Sep. 7, 2017

Related U.S. Application Data

(60) Provisional application No. 62/027,637, filed on Jul. 22, 2014.

(51) Int. Cl.

| | |
|---|---|
| ***C07K 16/00*** | (2006.01) |
| ***A61K 39/395*** | (2006.01) |
| ***C07K 16/28*** | (2006.01) |

(52) U.S. Cl.
CPC ...... *C07K 16/2833* (2013.01); *C07K 2317/41* (2013.01); *C07K 2317/51* (2013.01); *C07K 2317/515* (2013.01); *C07K 2317/52* (2013.01); *C07K 2317/55* (2013.01); *C07K 2317/56* (2013.01); *C07K 2317/565* (2013.01); *C07K 2317/622* (2013.01); *C07K 2317/73* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,816,567 | A | 3/1989 | Cabilly et al. |
| 5,204,244 | A | 4/1993 | Fell et al. |
| 5,229,275 | A | 7/1993 | Goroff |
| 5,500,362 | A | 3/1996 | Robinson et al. |
| 5,534,615 | A | 7/1996 | Baker et al. |
| 5,545,807 | A | 8/1996 | Surani et al. |
| 5,565,332 | A | 10/1996 | Hoogenboom et al. |
| 5,567,610 | A | 10/1996 | Borrebaeck et al. |
| 5,573,905 | A | 11/1996 | Lerner et al. |
| 5,585,089 | A | 12/1996 | Queen et al. |
| 5,589,369 | A | 12/1996 | Seidman et al. |
| 5,591,669 | A | 1/1997 | Krimpenfort et al. |
| 5,693,761 | A | 12/1997 | Queen et al. |
| 5,693,762 | A | 12/1997 | Queen et al. |
| 5,821,337 | A | 10/1998 | Carter et al. |
| 5,869,644 | A | 2/1999 | Shortie et al. |
| 6,180,370 | B1 | 1/2001 | Queen et al. |
| 8,258,082 | B2 | 9/2012 | Ladner |
| 8,691,730 | B2 | 4/2014 | Vasquez et al. |
| 2004/0219203 | A1 | 11/2004 | Griffiths et al. |

FOREIGN PATENT DOCUMENTS

| | | |
|---|---|---|
| WO | WO 2005/100402 | 10/2005 |
| WO | WO 2006/029879 | 3/2006 |
| WO | WO 2012/104344 A1 | 8/2012 |

OTHER PUBLICATIONS

Paul, Fundamental Immunology, 3rd Edition, 1993, pp. 292-295.*
Rudikoff et al, Proc. Natl. Acad. Sci. USA, 79(6):1979-1983, Mar. 1982.*
Colman P. M., Research in Immunology, 145:33-36, 1994.*
MacCallunn et al, J. Mol. Biol., 262, 732-745, 1996.*
Pascalis et al, Journal of Immunology, 2002, vol. 169, pp. 3076-3084.*
Casset et al, Biochemical and Biophysical Research Communications, 2003, vol. 307, pp. 198-205.*
Invitation to Pay Additional Fees and, Where Applicable, Protest Fee dated Oct. 28, 2015 for Application No. PCT/US2015/041192, 8 pages.
International Search Report and Written Opinion dated Jan. 21, 2016 for Application No. PCT/US2015/041192, 17 pages.
Berkova et al., "Milatuzumab—apromising new immunotherapeutic agent", *Expert Opinion on Investigational Drugs, Informa Healthcare*, United Kingdom, Jan. 1, 2010, vol. 19, No. 1, pp. 141-149.
Borghese et al., "CD74: An emerging opportunity as a therapeutic target in cancer and autoimmune disease", *Expert Opin. Ther. Targets*, 2011, vol. 15, No. 3, pp. 237-251.
Bruggemann et al., "Comparison of the Effector Functions of Human Immunoglobulins Using a Matched Set of Chimeric Antibodies", *J. Exp. Med.*, Nov. 1987, vol. 166, pp. 1351-1361.

(Continued)

*Primary Examiner* — Mark Halvorson
(74) *Attorney, Agent, or Firm* — Squire Patton Boggs (US) LLP

(57) ABSTRACT

Provided herein are antibodies that selectively bind to CD74 and its isoforms and homologs, and compositions comprising the antibodies. Also provided are methods of using the antibodies, such as therapeutic and diagnostic methods.

29 Claims, 1 Drawing Sheet

Specification includes a Sequence Listing.

(56) References Cited

OTHER PUBLICATIONS

Bruggermann et al., "Designer Mice: The Production of Human Antibody Repertoires in Transgenic Animals", *Year Immunol.* Basel, Karger, 1993, vol. 7, pp. 33-40.
Burton eta al., "CD74 is expressed by multiple myeloma and is a promising target for therapy", *Clinical Cancer Research, The American Association for Cancer Research, US*, Oct. 1, 2004, vol. 10, No. 19, pp. 6606-6611.
Carter et al. "High Level *Escherichia col/* Expression and Production of a Bivalent Humanized Antibody Fragment", *Biotechnology*, Feb. 1992, vol. 10, pp. 163-167.
Claesson et al., "cDNA clone for the human invariant γ chain of class II histocompatibility antigens and its implications for the protein structure", *Proc. Natl. Acad. Sci. U.S.A.*, Dec. 1983, vol. 80, pp. 7395-7399.
Clynes et al. "Fc receptors are required in passive and active immunity to melanoma", *Proc. Natl. Acad. Sci. U.S.A.*, Jan. 1998, vol. 95, pp. 652-656.
Cragg et al., "Antibody specificity controls in vivo effector mechanisms of anti-CD20 reagents", *Blood*, 2004, vol. 103, pp. 2738-2743.
Cragg et al., "Complement-mediated lysis by anti-CD20 mAb correlates with segregation into lipid rafts", *Blood*, 2003, vol. 101, pp. 1045-1052.
Cresswell, "Assembly, Transport, and Function of MHC Class II Molecules", *Ann. Rev. Immunol.*, 1994, vol. 12, pp. 259-293.
Dreir et al., "Ribosome Display: A Technology for Selecting and Evolving Proteins from Large Libraries", *Methods in Molecular Biology*, 2011, vol. 687, pp. 283-306.
Gazzano-Santoro et al., "A non-radioactive complement-dependent cytotoxicity assay for anti-CD20 monoclonal antibody", *Journal of Immunological Methods*, 1996, vol. 202, pp. 163-171.
Gore et al., "Macrophage Migration Inhibitory Factor Induces B Cell Survival by Activation of a CD74-CD44 Receptor Complex", *Journal of Biological Chemistry*, Feb. 1, 2008, vol. 283, No. 5, pp. 2784-2792.
Hanes et al., "In vitro selection and evolution of functional proteins by using ribosome display", *Proc. Natl. Acad. Sci. U.S.A.*, May 1997, vol. 94, pp. 4937-4942.
Heckman et al., "Gene splicing and mutagenesis by PCR-driven overlap extension", *Nature Protocols*, 2007, vol. 2, No. 4, pp. 924-932.
Hellstrom et al., "Strong antitumor activities of IgG3 antibodies to a human melanoma-associated ganglioside", *Proc. Natl. Acad. Sci. U.S.A.*, Mar. 1985, vol. 82, pp. 1499-1502.
Hellstrom et al., "Antitumor effects of L6, an IgG2a antibody that reacts with most human carcinomas", *Proc. Natl. Acad. Sci. U.S.A.*, Sep. 1986, vol. 83, pp. 7059-7063.
Hofman et al., "Gene expression profiling in human gastric mucosa infected with *Helicobacter pylori", Modern Pathology*, 2007, vol. 20, pp. 974-989.
Hoogenboom et al., By-passing Immunisation Human Antibodies from Synthetic Repertoires of Germline $V_H$ Gene Segments Rearranged in Vitro, *J. Mol. Biol.*, 1991, vol. 227, pp. 381-388.
Jakobovits et al., "Germ-line transmission and expression of a human-derived yeast artificial chromosome", *Nature*, Mar. 18, 1993, vol. 362, pp. 255-258.
Jakobovits et al., "Analysis of homozygous mutant chimeric mice: Deletion of the immunoglobulin heavy-chain joining region blocks B-cell development and antibody production", *Proc. Natl. Acad. Sci. U.S.A.*, Mar. 1993, vol. 90, pp. 2551-2555.
Kohler et al., "Continuous cultures of fused cells secreting antibody of predefined specificity", *Nature*, Aug. 7, 1975, vol. 256, pp. 495-497.
Kozbor et al., "A Human Hybrid Myeloma for Production of Human Monoclonal Antibodies", *Journal of Immunology*, Dec. 1984, vol. 133, No. 6, pp. 3001-3005.
Kudo et al., "Structure of the human gene encoding the Invariant 7-chain of class II histocompatibillty Antigens", *Nucleic Acids Research*, 1985, vol. 13, No. 24, pp. 8827-8841.
Marks et al., "By-passing Immunization Human Antibodies from V-gene Libraries Displayed on Phage", *J. Mol. Biol.*, 1991, vol. 222, pp. 581-597.
Pawlak-Byczkowska et al., "Two New Monoclonal Antibodies, Epb-1 and Epb-2, Reactive with Human Lymphoma", *Cancer Research, American Association for Cancer Research, US*, Aug. 15, 1989, vol. 49, No. 16, pp. 4568-4577.
Petkova et al., "Enhanced half-life of genetically engineered human IgG1 antibodies in a humanized FcRn mouse model: Potential application in humorally mediated autoimmune disease", *International Immunology*, 2006, vol. 18, No. 12, pp. 1759-1769.
Queen et al., "A humanized antibody that binds to the interleukin 2 receptor", *Proc. Natl. Acad. Sci. U.S.A.*, Dec. 1989, vol. 86, pp. 10029-10033.
Rader et al., "A phage display approach for rapid antibody humanization: Designed combinatorial V gene libraries", *Proc. Nat. Acad. Sci. U.S.A.*, Jul. 1998, vol. 95, pp. 8910-8915.
Ravetch et al., "Fc receptors", *Annual Review of Immunology*, 1991, vol. 9, pp. 457-492.
Stafford et al., "In vitro Fab display: A cell-free system for IgG discovery", *Protein Engineering, Design & Selection*, 2014, vol. 27, No. 4, pp. 97-109.
Starlets et al., "Cell-surface CD74 initiates a signaling cascade leading to cell proliferation and survival", *Blood*, 2006, vol. 107, pp. 4807-4816.
Stein et al., "Antiproliferative activity of a humanized anti-CD74 monoclonal antibody, hLL1, on B-cell Malignancies", *Blood*, Dec. 1, 2004, vol. 104, No. 12, pp. 3705-3711.
Steinberger et al., "Generation and Characterization of a Recombinant Human CCR5-specific Antibody", *J. Biol. Chem.*, Nov. 17, 2000, vol. 275, No. 46, pp. 36073-36078.
Vera et al., "Upregulation of Macrophage Migration Inhibitory Factor (MIF) and CD74, Receptor for MIF, in Rat Bladder During Persistent Cyclophosphamide-Induced Inflammation", *Experimental Biology and Medicine*, 2008, vol. 233, pp. 620-626.
Wang et al. "Functional Characterization of an scFv-Fc Antibody that Immunotherapeutically Targets the Common Cancer Cell Surface Proteoglycan CSPG4", *Cancer Res.*, Dec. 15, 2011, vol. 71, No. 24, pp. 7410-7422.
Winter et al., "Man-made antibodies", *Nature*, 1991, vol. 349, pp. 293-299.
Yin et al., "Aglycosylated antibodies and antibody fragments produced in a scalable in vitro transcription-translation system", *mAbs*, Mar./Apr. 2012, vol. 4, No. 2, pp. 217-225.
Zawada et al., "Microscale to Manufacturing Scale-up of Cell-Free Cytokine Production A New Approach for Shortening Protein Production Development Timelines", *Biotechnology and Bioengineering*, Jul. 2011, vol. 108, No. 7, pp. 1570-1578.
Zhang et al., "Effect of CD74 on the prognosis of patients with resectable pancreatic cancer", *Hepatobiliary Pancreat. Dis. Int.*, Feb. 15, 2014, vol. 13, No. 1, pp. 81-86.

* cited by examiner

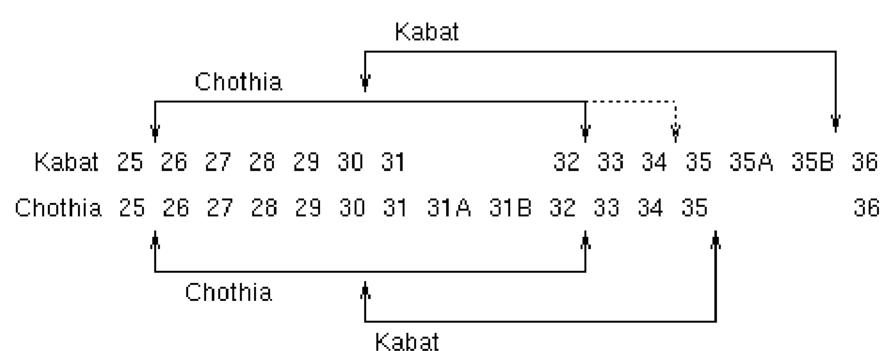
Kabat
Chothia
Kabat 25 26 27 28 29 30 31 32 33 34 35 35A 35B 36
Chothia 25 26 27 28 29 30 31 31A 31B 32 33 34 35 36
Chothia
Kabat

ANTI-CD74 ANTIBODIES, COMPOSITIONS COMPRISING ANTI-CD74 ANTIBODIES AND METHODS OF USING ANTI-CD74 ANTIBODIES

CROSS-REFERENCE TO RELATED APPLICATION

This application is a U.S. national phase entry of International Patent Application No. PCT/US2015/041192, filed Jul. 20, 2015, which in turn claims priority to U.S. Provisional Patent Application No. 62/027,637, filed Jul. 22, 2014. Each of the foregoing applications is incorporated herein by reference in its entirety.

REFERENCE TO SEQUENCE LISTING SUBMITTED VIA EFS-WEB

This application includes an electronically submitted sequence listing in .txt format. The .txt file contains a sequence listing entitled "Sequence Listing.txt," created May 22, 2017, and is 192 kilobytes in size. The sequence listing contained in this .txt file is part of the specification and is incorporated herein by reference in its entirety.

FIELD

Provided herein are antibodies with binding specificity for CD74 and compositions comprising the antibodies, including pharmaceutical compositions, diagnostic compositions and kits. Also provided are methods of using anti-CD74 antibodies for therapeutic and diagnostic purposes.

BACKGROUND

Human leukocyte antigen (HLA) class II histocompatibility antigen gamma chain (also known as HLA-DR antigens-associated invariant chain or CD74 (Cluster of Differentiation 74)) is a protein that is involved in the formation and transport of major histocompatibility complex (MHC) class II protein. See Claesson et al., Proc. Natl. Acad. Sci. U.S.A., 1983, 80:7395-7399; Kudo et al., *Nucleic Acids Res.,* 1985, 13:8827-8841; and Cresswell, *Ann. Rev. Immunol.,* 1994, 12:259-291.

One function of CD74 is to regulate peptide loading onto MHC class II heterodimers in intracellular compartments, to prevent MHC class II from binding cellular peptides. The full range of functionality of cell surface-expressed CD74 is not yet known. However, studies have demonstrated that CD74 is a receptor for the pro-inflammatory cytokine macrophage migration inhibitory factor (MIF). Binding of MIF to CD74 activates downstream signaling through the MAPK and Akt pathways and promotes cell proliferation and survival. See Gore et al., *J. Biol. Chem.,* 2008, 283:2784-2792; and Starlets et al., *Blood,* 2006, 107:4807-4816.

Upregulation of CD74 expression has been observed in cancers and autoimmune disease (Borghese et al., *Exp. Op. Ther. Targets,* 2011, 15:237-251), as well as in infection (Hofman et al., *Modern Pathology,* 2007, 20:974-989) and inflammatory conditions (Vera et al., *Exp. Biol. & Med.,* 2008, 233:620-626). CD74 is known to be expressed at moderate to high levels in multiple myeloma. Burton et al., *Clin. Cancer Res.,* 2004, 10:6606-6611. CD74 expression is also known to be a key factor associated with the progression of pancreatic cancer. Zhang et al., *Hepatobiliary Pancreat. Dis. Int.,* 2014, 13:81-86.

In view of the role of CD74 in multiple disease processes, there is a need for improved methods of modulating the interaction of CD74 with its ligands and the downstream signaling processes activated by CD74. Moreover, given the upregulation of CD74 in several diseases, there is also a need for therapeutics that specifically target cells and tissues overexpressing CD74.

SUMMARY

Provided herein are antibodies that selectively bind CD74. In some embodiments, the antibodies bind to more than one isoform of CD74. In some embodiments, the antibodies bind human CD74. In some embodiments, the antibodies also bind homologs of human CD74. In some aspects, the homolog is a cynomolgus monkey homolog.

In some embodiments, the antibodies have higher melting temperatures than other anti-CD74 antibodies. In some aspects, the Tm2 of the antibodies is higher than other anti-CD74 antibodies. The Tm2 represents the melting temperature of the Fab domain of an IgG. A higher Tm2 therefore promotes stability of the antibody binding site. Such improved stability can lead to better stability of the antibody during storage, as well as improved yield during manufacturing.

In some embodiments, the antibodies comprise at least one CDR sequence defined by a consensus sequence provided in this disclosure. In some embodiments, the antibodies comprise an illustrative CDR, $V_H$, or $V_L$ sequence provided in this disclosure, or a variant thereof. In some aspects, the variant is a variant with a conservative amino acid substitution.

Also provided are compositions and kits comprising the antibodies. In some embodiments, the compositions are pharmaceutical compositions. Any suitable pharmaceutical composition may be used. In some embodiments, the pharmaceutical composition is a composition for parenteral administration.

This disclosure also provides methods of using the anti-CD74 antibodies provided herein. In some embodiments, the method is a method of treatment. In some embodiments, the method is a diagnostic method. In some embodiments, the method is an analytical method. In some embodiments, the method is a method of purifying and/or quantifying CD74.

In some embodiments, the antibodies are used to treat a disease or condition. In some aspects, the disease or condition is selected from a cancer, an autoimmune disease, an infectious disease, and an inflammatory condition. In some aspects, the cancer is pancreatic cancer or multiple myeloma.

BRIEF DESCRIPTION OF THE DRAWINGS

FIG. 1 provides a comparison of the Kabat and Chothia numbering systems for CDR-H1. See Martin A.C.R. (2010). Protein Sequence and Structure Analysis of Antibody Variable Domains. In R. Kontermann & S. Dübel (Eds.), Antibody Engineering vol. 2 (pp. 33-51). Springer-Verlag, Berlin Heidelberg.

DETAILED DESCRIPTION

1. Definitions

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Sambrook et al., *Molecular Cloning: A Laboratory Manual* 2nd ed. (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

As used herein, the singular forms "a," "an," and "the" include the plural referents unless the context clearly indicates otherwise.

The term "about" indicates and encompasses an indicated value and a range above and below that value. In certain embodiments, the term about indicates the designated value ±10%, ±5% or ±1%. In certain embodiments, the term about indicates the designated value ±one standard deviation of that value.

The terms "CD74" and "CD74 antigen" are used interchangeably herein. Unless specified otherwise, the terms include any variants, isoforms and species homologs of human CD74 that are naturally expressed by cells, or that are expressed by cells transfected with a CD74 gene.

At least four human isoforms of CD74 are known to exist, including p43, p41, p35 and p33. Borghese et al., *Expert Opin. Ther. Targets,* 2011, 15:237-251, incorporated by reference in its entirety. These isoforms result from alternative transcript splicing and two translation start sites.

p43 (also known as CD74 isoform 1, isoform a, or "long"; see UniProt entry P04233-1 and NCBI Reference Sequence NP 001020330, each incorporated by reference in its entirety) contains 296 amino acids, with residues 73-296 forming the extracellular portion. Protein constructs of CD74 having the extracellular part of isoform 1 are herein referred to as "variant 1" or "CD74v1."

p35 (also known as CD74 isoform 2, isoform b or "short"; see UniProt entry P04233-2 and NCBI Reference Sequence NP 004346, each incorporated by reference in its entirety) lacks residues 209-272 from the extracellular domain due to alternative splicing. Protein constructs of CD74 having the extracellular part of isoform 2 are herein referred to as "variant 2" or "CD74v2."

p41 and p33 arise from an alternative translation start site (48 nucleotides/16 amino acids downstream) leading to variants lacking the endoplasmic reticulum (ER) retention signal that is present within the eliminated 16 amino acids, but having extracellular domain that is identical to p43 and p35, respectively.

The sequence of another isoform (known as isoform 3 and isoform c), in which residues 148-160 are replaced and residues 161-296 are lacking, is provided in NP 001020329.

The sequences of cynomolgus CD74 homologs are provided in, e.g., NCBI Reference Sequence: XP-001099491.2 and NCBI Reference Sequence: XP-002804624.1.

The term "immunoglobulin" refers to a class of structurally related proteins generally consisting of two pairs of polypeptide chains, one pair of light (L) chains and one pair of heavy (H) chains. In an intact immunoglobulin, all four of these chains are interconnected by disulfide bonds. The structure of immunoglobulins has been well characterized.

See, e.g., Paul, Fundamental Immunology 7th ed., Ch. 5 (2013) Lippincott Williams & Wilkins, Philadelphia, Pa. Briefly, each heavy chain typically comprises a heavy chain variable region ($V_H$) and a heavy chain constant region ($C_H$). The heavy chain constant region typically comprises three domains, $C_{H1}$, $C_{H2}$, and $C_{H3}$. Each light chain typically comprises a light chain variable region ($V_L$) and a light chain constant region. The light chain constant region typically comprises one domain, abbreviated $C_L$.

The term "antibody" describes a type of immunoglobulin molecule and is used herein in its broadest sense. An antibody specifically includes monoclonal antibodies, polyclonal antibodies, intact antibodies, and antibody fragments. Antibodies comprise at least one antigen-binding domain. One example of an antigen-binding domain is an antigen binding domain formed by a $V_H$-$V_L$ dimer. A "CD74 antibody," "anti-CD74 antibody," "CD74 Ab," "CD74-specific antibody" or "anti-CD74 Ab" is an antibody, as described herein, which binds specifically to the antigen CD74.

The $V_H$ and $V_L$ regions may be further subdivided into regions of hypervariability ("hypervariable regions (HVRs);" also called "complementarity determining regions" (CDRs)) interspersed with regions that are more conserved. The more conserved regions are called framework regions (FRs). Each $V_H$ and $V_L$ generally comprises three CDRs and four FRs, arranged in the following order (from N-terminus to C-terminus): FR1-CDR1-FR2-CDR2-FR3-CDR3-FR4. The CDRs are involved in antigen binding, and confer antigen specificity and binding affinity to the antibody. See Kabat et al., *Sequences of Proteins of Immunological Interest* 5th ed. (1991) Public Health Service, National Institutes of Health, Bethesda, Md., incorporated by reference in its entirety.

The light chain from any vertebrate species can be assigned to one of two types, called kappa and lambda, based on the sequence of the constant domain.

The heavy chain from any vertebrate species can be assigned to one of five different classes (or isotypes): IgA, IgD, IgE, IgG, and IgM. These classes are also designated α, δ, ε, γ, and μ, respectively. The IgG and IgA classes are further divided into subclasses on the basis of differences in sequence and function. Humans express the following subclasses: IgG1, IgG2, IgG3, IgG4, IgA1, and IgA2.

The amino acid sequence boundaries of a CDR can be determined by one of skill in the art using any of a number of known numbering schemes, including those described by Kabat et al., supra ("Kabat" numbering scheme); Al-Lazikani et al., 1997, *J. Mol. Biol.,* 273:927-948 ("Chothia" numbering scheme); MacCallum et al., 1996, *J. Mol. Biol.* 262:732-745 ("Contact" numbering scheme); Lefranc et al., *Dev. Comp. Immunol.,* 2003, 27:55-77 ("IMGT" numbering scheme); and Honegge and Plückthun, *J. Mol. Biol.,* 2001, 309:657-70 ("AHo" numbering scheme), each of which is incorporated by reference in its entirety.

Table 1 provides the positions of CDR-L1, CDR-L2, CDR-L3, CDR-H1, CDR-H2, and CDR-H3 as identified by the Kabat and Chothia schemes. For CDR-H1, residue numbering is provided using both the Kabat and Chothia numbering schemes. FIG. 1 provides a comparison of the Kabat and Chothia numbering schemes for CDR-H1. See Martin (2010), supra.

Unless otherwise specified, the numbering scheme used for identification of a particular CDR herein is the Kabat/Chothia numbering scheme. Where these two numbering schemes diverge, the numbering scheme is specified as either Kabat or Chothia.

TABLE 1

| Residues in CDRs according to Kabat and Chothia numbering schemes. | | |
|---|---|---|
| CDR | Kabat | Chothia |
| L1 | L24-L34 | L24-L34 |
| L2 | L50-L56 | L50-L56 |
| L3 | L89-L97 | L89-L97 |
| H1 (Kabat Numbering) | H31-H35B | H26-H32 or H34* |
| H1 (Chothia Numbering) | H31-H35 | H26-H32 |
| H2 | H50-H65 | H52-H56 |
| H3 | H95-H102 | H95-H102 |

*The C-terminus of CDR-H1, when numbered using the Kabat numbering convention, varies between H32 and H34, depending on the length of the CDR, as illustrated in FIG. 1.

The "EU numbering scheme" or "EU index" is generally used when referring to a residue in an antibody heavy chain constant region (e.g., the EU index reported in Kabat et al., supra). Unless stated otherwise, the EU numbering scheme is used to refer to residues in antibody heavy chain constant regions described herein.

An "antibody fragment" comprises a portion of an intact antibody, such as the antigen binding or variable region of an intact antibody. Antibody fragments include, for example, Fv fragments, Fab fragments, F(ab')$_2$ fragments, Fab' fragments, scFv (sFv) fragments, and scFv-Fc fragments.

"Fv" fragments comprise a non-covalently-linked dimer of one heavy chain variable domain and one light chain variable domain.

"Fab" fragments comprise, in addition to the heavy and light chain variable domains, the constant domain of the light chain and the first constant domain ($C_{H1}$) of the heavy chain. Fab fragments may be generated, for example, by papain digestion of a full-length antibody.

"F(ab')$_2$" fragments contain two Fab' fragments joined, near the hinge region, by disulfide bonds. F(ab')$_2$ fragments may be generated, for example, by pepsin digestion of an intact antibody. The F(ab') fragments can be dissociated, for example, by treatment with β-mercaptoethanol.

"Single-chain Fv" or "sFv" or "scFv" antibody fragments comprise a $V_H$ domain and a $V_L$ domain in a single polypeptide chain. The $V_H$ and $V_L$ are generally linked by a peptide linker. See Plückthun A. (1994). Antibodies from *Escherichia coli*. In Rosenberg M. & Moore G. P. (Eds.), *The Pharmacology of Monoclonal Antibodies* vol. 113 (pp. 269-315). Springer-Verlag, New York, incorporated by reference in its entirety. "scFv-Fc" fragments comprise an scFv attached to an Fc domain. For example, an Fc domain may be attached to the C-terminal of the scFv. The Fc domain may follow the $V_H$ or $V_L$, depending on the orientation of the variable domains in the scFv (i.e., $V_H$-$V_L$ or $V_L$-$V_H$). Any suitable Fc domain known in the art or described herein may be used. In some cases, the Fc domain is an IgG1 Fc domain (e.g., SEQ ID NO: 289).

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

The term "chimeric antibody" refers to an antibody in which a portion of the heavy and/or light chain is derived from a particular source or species, while the remainder of the heavy and/or light chain is derived from a different source or species.

"Humanized" forms of non-human antibodies are chimeric antibodies that contain minimal sequence derived from the non-human antibody. A humanized antibody is generally a human immunoglobulin (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. In some instances, selected framework region residues of the recipient antibody are replaced by the corresponding framework region residues from the donor antibody. Humanized antibodies may also comprise residues that are not found in either the recipient antibody or the donor antibody. Such modifications may be made to further refine antibody function. For further details, see Jones et al., *Nature,* 1986, 321:522-525; Riechmann et al., *Nature,* 1988, 332:323-329; and Presta, *Curr. Op. Struct. Biol.,* 1992, 2:593-596, each of which is incorporated by reference in its entirety.

A "human antibody" is one which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies.

An "isolated antibody" is one that has been separated and/or recovered from a component of its natural environment. Components of the natural environment may include enzymes, hormones, and other proteinaceous or nonproteinaceous materials. In some embodiments, an isolated antibody is purified to a degree sufficient to obtain at least 15 residues of N-terminal or internal amino acid sequence, for example by use of a spinning cup sequenator. In some embodiments, an isolated antibody is purified to homogeneity by gel electrophoresis (e.g., SDS-PAGE) under reducing or nonreducing conditions, with detection by Coomassie blue or silver stain. An isolated antibody includes an antibody in situ within recombinant cells, since at least one component of the antibody's natural environment is not present. In some aspects, an isolated antibody is prepared by at least one purification step.

In some embodiments, an isolated antibody is purified to at least 80%, 85%, 90%, 95%, or 99% by weight. In some embodiments, an isolated antibody is provided as a solution comprising at least 85%, 90%, 95%, 98%, 99% to 100% by weight of an antibody, the remainder of the weight comprising the weight of other solutes dissolved in the solvent.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity, which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Affinity can be determined, for example, using surface plasmon resonance (SPR) technology, such as a Biacore® instrument.

With regard to the binding of an antibody to a target molecule, the terms "specific binding," "specifically binds to," "specific for," "selectively binds," and "selective for" a particular antigen (e.g., a polypeptide target) or an epitope on a particular antigen mean binding that is measurably different from a non-specific or non-selective interaction. Specific binding can be measured, for example, by determining binding of a molecule compared to binding of a control molecule. Specific binding can also be determined by competition with a control molecule that is similar to the target, such as an excess of non-labeled target. In that case, specific binding is indicated if the binding of the labeled target to a probe is competitively inhibited by the excess non-labeled target.

The term "$k_d$" ($sec^{-1}$), as used herein, refers to the dissociation rate constant of a particular antibody-antigen interaction. This value is also referred to as the $k_{off}$ value.

The term "$k_a$" ($M^{-1}\times sec^{-1}$), as used herein, refers to the association rate constant of a particular antibody-antigen interaction. This value is also referred to as the $k_{on}$ value.

The term "$K_D$" (M), as used herein, refers to the dissociation equilibrium constant of a particular antibody-antigen interaction. $K_D=k_d/k_a$.

The term "$K_A$" ($M^{-1}$), as used herein, refers to the association equilibrium constant of a particular antibody-antigen interaction. $K_A=k_a/k_d$.

An "affinity matured" antibody is one with one or more alterations in one or more CDRs or FRs that result in an improvement in the affinity of the antibody for its antigen, compared to a parent antibody which does not possess the alteration(s). In one embodiment, an affinity matured antibody has nanomolar or picomolar affinity for the target antigen. Affinity matured antibodies may be produced using a variety of methods known in the art. For example, Marks et al. (*Bio/Technology,* 1992, 10:779-783, incorporated by reference in its entirety) describes affinity maturation by $V_H$ and $V_L$ domain shuffling. Random mutagenesis of CDR and/or framework residues is described by, for example, Barbas et al. (*Proc. Nat. Acad. Sci. U.S.A.,* 1994, 91:3809-3813); Schier et al., *Gene,* 1995, 169:147-155; Yelton et al., *J. Immunol.,* 1995, 155:1994-2004; Jackson et al., *J. Immunol.,* 1995, 154:3310-33199; and Hawkins et al, *J. Mol. Biol.,* 1992, 226:889-896, each of which is incorporated by reference in its entirety.

When used herein in the context of two or more antibodies, the term "competes with" or "cross-competes with" indicates that the two or more antibodies compete for binding to an antigen (e.g., CD74). In one exemplary assay, CD74 is coated on a plate and allowed to bind a first antibody, after which a second, labeled antibody is added. If the presence of the first antibody reduces binding of the second antibody, then the antibodies compete. The term "competes with" also includes combinations of antibodies where one antibody reduces binding of another antibody, but where no competition is observed when the antibodies are added in the reverse order. However, in some embodiments, the first and second antibodies inhibit binding of each other, regardless of the order in which they are added. In some embodiments, one antibody reduces binding of another antibody to its antigen by at least 50%, at least 60%, at least 70%, at least 80%, or at least 90%.

The term "epitope" means a portion of an antigen capable of specific binding to an antibody. Epitopes frequently consist of surface-accessible amino acid residues and/or sugar side chains and may have specific three dimensional structural characteristics, as well as specific charge characteristics. Conformational and non-conformational epitopes are distinguished in that the binding to the former but not the latter is lost in the presence of denaturing solvents. An epitope may comprise amino acid residues that are directly involved in the binding, and other amino acid residues, which are not directly involved in the binding. The epitope to which an antibody binds can be determined using known techniques for epitope determination such as, for example, testing for antibody binding to CD74 variants with different point-mutations.

Percent "identity" between a polypeptide sequence and a reference sequence, is defined as the percentage of amino acid residues in the polypeptide sequence that are identical to the amino acid residues in the reference sequence, after aligning the sequences and introducing gaps, if necessary, to achieve the maximum percent sequence identity. Alignment for purposes of determining percent amino acid sequence identity can be achieved in various ways that are within the skill in the art, for instance, using publicly available computer software such as BLAST, BLAST-2, ALIGN, MEGALIGN (DNASTAR), or CLUSTALW software. Those skilled in the art can determine appropriate parameters for aligning sequences, including any algorithms needed to achieve maximal alignment over the full length of the sequences being compared.

A "conservative substitution" or a "conservative amino acid substitution," refers to the substitution of one or more amino acids with one or more chemically or functionally similar amino acids. Conservative substitution tables providing similar amino acids are well known in the art. Polypeptide sequences having such substitutions are known as "conservatively modified variants." Such conservatively modified variants are in addition to and do not exclude polymorphic variants, interspecies homologs, and alleles. By way of example, the following groups of amino acids are considered conservative substitutions for one another.

| | |
|---|---|
| Acidic Residues | D and E |
| Basic Residues | K, R, and H |
| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y, and W |
| Alcohol Group-Containing Residues | S and T |
| Aliphatic Residues | I, L, V, and M |
| Cycloalkenyl-associated Residues | F, H, W, and Y |
| Hydrophobic Residues | A, C, F, G, H, I, L, M, R, T, V, W, and Y |
| Negatively Charged Residues | D and E |
| Polar Residues | C, D, E, H, K, N, Q, R, S, and T |
| Positively Charged Residues | H, K, and R |
| Small Residues | A, C, D, G, N, P, S, T, and V |
| Very Small Residues | A, G, and S |
| Residues Involved in Turn Formation | A, C, D, E, G, H, K, N, Q, R, S, P, and T |
| Flexible Residues | Q, T, K, S, G, P, D, E, and R |
| Group 1 | A, S, and T |
| Group 2 | D and E |
| Group 3 | N and Q |
| Group 4 | R and K |
| Group 5 | I, L, and M |
| Group 6 | F, Y, and W |
| Group A | A and G |
| Group B | D and E |
| Group C | N and Q |

-continued

| | |
|---|---|
| Group D | R, K, and H |
| Group E | I, L, M, V |
| Group F | F, Y, and W |
| Group G | S and T |
| Group H | C and M |

Additional conservative substitutions may be found, for example, in Creighton, *Proteins: Structures and Molecular Properties* 2nd ed. (1993) W. H. Freeman & Co., New York, N.Y. An antibody generated by making one or more conservative substitutions of amino acid residues in a parent antibody is referred to as a "conservatively modified variant."

The term "amino acid" refers to twenty common naturally occurring amino acids. Naturally occurring amino acids include alanine (Ala; A), arginine (Arg; R), asparagine (Asn; N), aspartic acid (Asp; D), cysteine (Cys; C); glutamic acid (Glu; E), glutamine (Gln; Q), Glycine (Gly; G); histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

"Treating" or "treatment" of any disease or disorder refers, in certain embodiments, to ameliorating a disease or disorder that exists in a subject. In another embodiment, "treating" or "treatment" includes ameliorating at least one physical parameter, which may be indiscernible by the subject. In yet another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying the onset of the disease or disorder.

As used herein, the term "therapeutically effective amount" or "effective amount" refers to an amount of an antibody or composition that when administered to a subject is effective to prevent or ameliorate a disease or the progression of the disease, or result in amelioration of symptoms.

As used herein, the term "inhibits growth" (e.g. referring to cells, such as tumor cells) is intended to include any measurable decrease in cell growth when contacted with a CD74 antibody, as compared to the growth of the same cells not in contact with a CD74 antibody. In some embodiments, growth may be inhibited by at least about 10%, 20%, 30%, 40%, 50%, 60%, 70%, 80%, 90%, 99%, or 100%. The decrease in cell growth can occur by a variety of mechanisms, including but not limited to antibody internalization, apoptosis, necrosis, and/or effector function-mediated activity.

As used herein, the term "subject" means a mammalian subject. Exemplary subjects include, but are not limited to humans, monkeys, dogs, cats, mice, rats, cows, horses, goats and sheep. In certain embodiments, the subject is a human. In some embodiments, the subject has cancer, an inflammatory disease or condition, or an autoimmune disease or condition, that can be treated with an antibody provided herein. In some embodiments, the subject is a human that has or is suspected to have cancer, an inflammatory disease or condition, or an autoimmune disease or condition.

2. Antibodies

Provided herein are antibodies that selectively bind human CD74. In some aspects, the antibody selectively binds to human CD74 isoform 1. In some aspects, the antibody selectively binds to human CD74 isoform 2. In some aspects, the antibody may selectively bind to more than one CD74 isoform, for example, both human CD74 isoforms 1 and 2. In some aspects, the antibody may selectively bind to one or more CD74 isoforms with the same extracellular domain as isoforms 1 and 2, such as p41 and p33, respectively.

In some embodiments, the antibody binds to homologs of human CD74. In some aspects, the antibody binds to a homolog of human CD74 from a species selected from monkeys, dogs, cats, mice, rats, cows, horses, goats and sheep. In some aspects, the homolog is a cynomolgus monkey homolog.

In some embodiments, the antibody has one or more CDRs having particular lengths, in terms of the number of amino acid residues. In some aspects, the Chothia CDR-H1 of the antibody is seven residues in length. In some embodiments, the Kabat CDR-H1 of the antibody is five residues in length. In some aspects, the Chothia CDR-H2 of the antibody is six residues in length. In some embodiments, the Kabat CDR-H2 of the antibody is seventeen residues in length. In some aspects, the Chothia/Kabat CDR-H3 of the antibody is eleven residues in length. In some aspects, the Chothia/Kabat CDR-H3 of the antibody is twelve residues in length. In some aspects, the Chothia/Kabat CDR-H3 of the antibody is thirteen residues in length. In some aspects, the Chothia/Kabat CDR-H3 of the antibody is fourteen residues in length. In some aspects, the Chothia/Kabat CDR-H3 of the antibody is not fifteen residues in length.

In some aspects, the Kabat/Chothia CDR-L1 of the antibody is eleven residues in length. In some aspects, the Kabat/Chothia CDR-L1 of the antibody is twelve residues in length. In some aspects, the Kabat/Chothia CDR-L2 of the antibody is seven residues in length. In some aspects, the Kabat/Chothia CDR-L3 of the antibody is nine residues in length.

In some embodiments, the antibody comprises a light chain. In some aspects, the light chain is selected from a kappa light chain and a lambda light chain.

In some embodiments, the antibody comprises a heavy chain. In some aspects, the heavy chain is selected from IgA, IgD, IgE, IgG, and IgM. In some aspects, the heavy chain is selected from IgG1, IgG2, IgG3, IgG4, IgA1, and IgA2.

In some embodiments, the antibody is an antibody fragment. In some aspects, the antibody fragment is selected from an Fv fragment, a Fab fragment, a $F(ab')_2$ fragment, a Fab' fragment, an scFv (sFv) fragment, and an scFv-Fc fragment.

In some embodiments, the antibody is a monoclonal antibody.

In some embodiments, the antibody is a chimeric, humanized, or human antibody.

In some embodiments, the antibody is an affinity matured antibody. In some aspects, the antibody is an affinity matured antibody derived from an illustrative sequence provided in this disclosure.

In some embodiments, the antibody is internalized by a cell after binding.

In some embodiments, the antibody inhibits the binding of CD74 to its ligands. In some aspects, the antibody inhibits the binding of CD74 to macrophage migration inhibitory factor (MIF).

The antibodies provided herein may be useful for the treatment of a variety of diseases and conditions, including cancers, autoimmune diseases, infection, and inflammation.

2.1. CDR-H3 Sequences

In some embodiments, the antibody comprises a CDR-H3 sequence comprising, consisting of, or consisting essentially of a sequence selected from SEQ ID NOs: 129-156. In some aspects, the antibody comprises a CDR-H3 sequence comprising, consisting of, or consisting essentially of SEQ ID NO: 129. In some aspects, the antibody comprises a CDR-H3 sequence comprising, consisting of, or consisting essentially of SEQ ID NO: 130. In some aspects, the antibody comprises a CDR-H3 sequence comprising, consisting of, or consisting essentially of SEQ ID NO: 131. In some aspects, the antibody comprises a CDR-H3 sequence comprising, consisting of, or consisting essentially of SEQ ID NO: 132. In some aspects, the antibody comprises a CDR-H3 sequence comprising, consisting of, or consisting essentially of SEQ ID NO: 133. In some aspects, the antibody comprises a CDR-H3 sequence comprising, consisting of, or consisting essentially of SEQ ID NO: 134. In some aspects, the antibody comprises a CDR-H3 sequence comprising, consisting of, or consisting essentially of SEQ ID NO: 135. In some aspects, the antibody comprises a CDR-H3 sequence comprising, consisting of, or consisting essentially of SEQ ID NO: 136. In some aspects, the antibody comprises a CDR-H3 sequence comprising, consisting of, or consisting essentially of SEQ ID NO: 137. In some aspects, the antibody comprises a CDR-H3 sequence comprising, consisting of, or consisting essentially of SEQ ID NO: 138. In some aspects, the antibody comprises a CDR-H3 sequence comprising, consisting of, or consisting essentially of SEQ ID NO: 139. In some aspects, the antibody comprises a CDR-H3 sequence comprising, consisting of, or consisting essentially of SEQ ID NO: 140. In some aspects, the antibody comprises a CDR-H3 sequence comprising, consisting of, or consisting essentially of SEQ ID NO: 141. In some aspects, the antibody comprises a CDR-H3 sequence comprising, consisting of, or consisting essentially of SEQ ID NO: 142. In some aspects, the antibody comprises a CDR-H3 sequence comprising, consisting of, or consisting essentially of SEQ ID NO: 143. In some aspects, the antibody comprises a CDR-H3 sequence comprising, consisting of, or consisting essentially of SEQ ID NO: 144. In some aspects, the antibody comprises a CDR-H3 sequence comprising, consisting of, or consisting essentially of SEQ ID NO: 145. In some aspects, the antibody comprises a CDR-H3 sequence comprising, consisting of, or consisting essentially of SEQ ID NO: 146. In some aspects, the antibody comprises a CDR-H3 sequence comprising, consisting of, or consisting essentially of SEQ ID NO: 147. In some aspects, the antibody comprises a CDR-H3 sequence comprising, consisting of, or consisting essentially of SEQ ID NO: 148. In some aspects, the antibody comprises a CDR-H3 sequence comprising, consisting of, or consisting essentially of SEQ ID NO: 149. In some aspects, the antibody comprises a CDR-H3 sequence comprising, consisting of, or consisting essentially of SEQ ID NO: 150. In some aspects, the antibody comprises a CDR-H3 sequence comprising, consisting of, or consisting essentially of SEQ ID NO: 151. In some aspects, the antibody comprises a CDR-H3 sequence comprising, consisting of, or consisting essentially of SEQ ID NO: 152. In some aspects, the antibody comprises a CDR-H3 sequence comprising, consisting of, or consisting essentially of SEQ ID NO: 153. In some aspects, the antibody comprises a CDR-H3 sequence comprising, consisting of, or consisting essentially of SEQ ID NO: 154. In some aspects, the antibody comprises a CDR-H3 sequence comprising, consisting of, or consisting essentially of SEQ ID NO: 155. In some aspects, the antibody comprises a CDR-H3 sequence comprising, consisting of, or consisting essentially of SEQ ID NO: 156.

In some aspects, the CDR-H3 sequence comprises, consists of, or consists essentially of a variant of an illustrative CDR-H3 sequence provided in this disclosure. In some aspects, the CDR-H3 sequence comprises, consists of, or consists essentially of a sequence having at least 70%, 75%, 80%, 85%, 90%, or 95% identity with any of the illustrative CDR-H3 sequences provided in this disclosure. In some aspects, the CDR-H3 sequence comprises, consists of, or consists essentially of any of the illustrative CDR-H3 sequences provided in this disclosure, with 1, 2, or 3 amino acid substitutions. In some aspects, the amino acid substitutions are conservative amino acid substitutions.

In some aspects, the CDR-H3 sequence does not comprise, consist of, or consist essentially of a sequence selected from SEQ ID NOs: 157-160. In some aspects, the CDR-H3 sequence does not comprise, consist of, or consist essentially of SEQ ID NO: 157. In some aspects, the CDR-H3 sequence does not comprise, consist of, or consist essentially of SEQ ID NO: 158. In some aspects, the CDR-H3 sequence does not comprise, consist of, or consist essentially of SEQ ID NO: 159. In some aspects, the CDR-H3 sequence does not comprise, consist of, or consist essentially of SEQ ID NO: 160.

2.2. $V_H$ Sequences Comprising Illustrative CDRs

In some embodiments, the antibody comprises a $V_H$ sequence comprising one or more CDR-H sequences comprising, consisting of, or consisting essentially of one or more illustrative CDR-H sequences provided in this disclosure, and variants thereof.

2.2.1. $V_H$ Sequences Comprising Illustrative Kabat CDRs

In some embodiments, the antibody comprises a $V_H$ sequence comprising one or more Kabat CDR-H sequences comprising, consisting of, or consisting essentially of one or more illustrative Kabat CDR-H sequences provided in this disclosure, and variants thereof.

2.2.1.1. Kabat CDR-H3

In some embodiments, the antibody comprises a $V_H$ sequence comprising a Kabat CDR-H3 sequence comprising, consisting of, or consisting essentially of a sequence selected from SEQ ID NOs: 129-156. In some aspects, the antibody comprises a $V_H$ sequence comprising a Kabat CDR-H3 sequence comprising, consisting of, or consisting essentially of SEQ ID NO: 129. In some aspects, the antibody comprises a $V_H$ sequence comprising a Kabat CDR-H3 sequence comprising, consisting of, or consisting essentially of SEQ ID NO: 130. In some aspects, the antibody comprises a $V_H$ sequence comprising a Kabat CDR-H3 sequence comprising, consisting of, or consisting essentially of SEQ ID NO: 131. In some aspects, the antibody comprises a $V_H$ sequence comprising a Kabat CDR-H3 sequence comprising, consisting of, or consisting essentially of SEQ ID NO: 132. In some aspects, the antibody comprises a $V_H$ sequence comprising a Kabat CDR-H3 sequence comprising, consisting of, or consisting essentially of SEQ ID NO: 133. In some aspects, the antibody comprises a $V_H$ sequence comprising a Kabat CDR-H3 sequence comprising, consisting of, or consisting essentially of SEQ ID NO: 134. In some aspects, the antibody comprises a $V_H$ sequence comprising a Kabat CDR-H3 sequence comprising, consisting of, or consisting essentially of SEQ ID NO: 135. In some aspects, the antibody comprises a $V_H$ sequence comprising a Kabat CDR-H3 sequence comprising, consisting of, or consisting essentially of SEQ ID NO: 136. In some aspects, the antibody comprises a $V_H$ sequence comprising a Kabat CDR-H3 sequence comprising, consisting of, or consisting essentially of SEQ ID NO: 137. In some aspects, the antibody comprises a $V_H$ sequence comprising a Kabat CDR-H3 sequence comprising, consisting of, or consisting essentially of SEQ ID NO: 138. In some aspects, the antibody comprises a $V_H$ sequence comprising a Kabat CDR-H3 sequence comprising, consisting of, or consisting essentially of SEQ ID NO: 139. In some aspects, the antibody comprises a $V_H$ sequence comprising a Kabat CDR-H3 sequence comprising, consisting of, or consisting essentially of SEQ ID NO: 140. In some aspects, the antibody comprises a $V_H$ sequence comprising a Kabat CDR-H3 sequence comprising, consisting of, or consisting essentially of SEQ ID NO: 141. In some aspects, the antibody comprises a $V_H$ sequence comprising a Kabat CDR-H3 sequence comprising, consisting of, or consisting essentially of SEQ ID NO: 142. In some aspects, the antibody comprises a $V_H$ sequence comprising a Kabat CDR-H3 sequence comprising, consisting of, or consisting essentially of SEQ ID NO: 143. In some aspects, the antibody comprises a $V_H$ sequence comprising a Kabat CDR-H3 sequence comprising, consisting of, or consisting essentially of SEQ ID NO: 144. In some aspects, the antibody comprises a $V_H$ sequence comprising a Kabat CDR-H3 sequence comprising, consisting of, or consisting essentially of SEQ ID NO: 145. In some aspects, the antibody comprises a $V_H$ sequence comprising a Kabat CDR-H3 sequence comprising, consisting of, or consisting essentially of SEQ ID NO: 146. In some aspects, the antibody comprises a $V_H$ sequence comprising a Kabat CDR-H3 sequence comprising, consisting of, or consisting essentially of SEQ ID NO: 147. In some aspects, the antibody comprises a $V_H$ sequence comprising a Kabat CDR-H3 sequence comprising, consisting of, or consisting essentially of SEQ ID NO: 148. In some aspects, the antibody comprises a $V_H$ sequence comprising a Kabat CDR-H3 sequence comprising, consisting of, or consisting essentially of SEQ ID NO: 149. In some aspects, the antibody comprises a $V_H$ sequence comprising a Kabat CDR-H3 sequence comprising, consisting of, or consisting essentially of SEQ ID NO: 150. In some aspects, the antibody comprises a $V_H$ sequence comprising a Kabat CDR-H3 sequence comprising, consisting of, or consisting essentially of SEQ ID NO: 151. In some aspects, the antibody comprises a $V_H$ sequence comprising a Kabat CDR-H3 sequence comprising, consisting of, or consisting essentially of SEQ ID NO: 152. In some aspects, the antibody comprises a $V_H$ sequence comprising a Kabat CDR-H3 sequence comprising, consisting of, or consisting essentially of SEQ ID NO: 153. In some aspects, the antibody comprises a $V_H$ sequence comprising a Kabat CDR-H3 sequence comprising, consisting of, or consisting essentially of SEQ ID NO: 154. In some aspects, the antibody comprises a $V_H$ sequence comprising a Kabat CDR-H3 sequence comprising, consisting of, or consisting essentially of SEQ ID NO: 155. In some aspects, the antibody comprises a $V_H$ sequence comprising a Kabat CDR-H3 sequence comprising, consisting of, or consisting essentially of SEQ ID NO: 156.

2.2.1.2. Kabat CDR-H2

In some embodiments, the antibody comprises a $V_H$ sequence comprising a Kabat CDR-H2 sequence comprising, consisting of, or consisting essentially of a sequence selected from SEQ ID NOs: 97-124. In some aspects, the antibody comprises a $V_H$ sequence comprising a Kabat CDR-H2 sequence comprising, consisting of, or consisting essentially of SEQ ID NO: 97. In some aspects, the antibody comprises a $V_H$ sequence comprising a Kabat CDR-H2 sequence comprising, consisting of, or consisting essentially of SEQ ID NO: 98. In some aspects, the antibody comprises a $V_H$ sequence comprising a Kabat CDR-H2 sequence comprising, consisting of, or consisting essentially of SEQ ID NO: 99. In some aspects, the antibody comprises a $V_H$ sequence comprising a Kabat CDR-H2 sequence comprising, consisting of, or consisting essentially of SEQ ID NO: 100. In some aspects, the antibody comprises a $V_H$ sequence comprising a Kabat CDR-H2 sequence comprising, consisting of, or consisting essentially of SEQ ID NO: 101. In some aspects, the antibody comprises a $V_H$ sequence comprising a Kabat CDR-H2 sequence comprising, consisting of, or consisting essentially of SEQ ID NO: 102. In some aspects, the antibody comprises a $V_H$ sequence comprising a Kabat CDR-H2 sequence comprising, consisting of, or consisting essentially of SEQ ID NO: 103. In some aspects, the antibody comprises a $V_H$ sequence comprising a Kabat CDR-H2 sequence comprising, consisting of, or consisting essentially of SEQ ID NO: 104. In some aspects, the antibody comprises a $V_H$ sequence comprising a Kabat CDR-H2 sequence comprising, consisting of, or consisting essentially of SEQ ID NO: 105. In some aspects, the antibody comprises a $V_H$ sequence comprising a Kabat CDR-H2 sequence comprising, consisting of, or consisting essentially of SEQ ID NO: 106. In some aspects, the antibody comprises a $V_H$ sequence comprising a Kabat CDR-H2 sequence comprising, consisting of, or consisting essentially of SEQ ID NO: 107. In some aspects, the antibody comprises a $V_H$ sequence comprising a Kabat CDR-H2 sequence comprising, consisting of, or consisting essentially of SEQ ID NO: 108. In some aspects, the antibody comprises a $V_H$ sequence comprising a Kabat CDR-H2 sequence comprising, consisting of, or consisting essentially of SEQ ID NO: 109. In some aspects, the antibody comprises a $V_H$ sequence comprising a Kabat CDR-H2 sequence comprising, consisting of, or consisting essentially of SEQ ID NO: 110. In some aspects, the antibody comprises a $V_H$ sequence comprising a Kabat CDR-H2 sequence comprising, consisting of, or consisting essentially of SEQ ID NO: 111. In some aspects, the antibody comprises a $V_H$ sequence comprising a Kabat CDR-H2 sequence comprising, consisting of, or consisting essentially of SEQ ID NO: 112. In some aspects, the antibody comprises a $V_H$ sequence comprising a Kabat CDR-H2 sequence comprising, consisting of, or consisting essentially of SEQ ID NO: 113. In some aspects, the antibody comprises a $V_H$ sequence comprising a Kabat CDR-H2 sequence comprising, consisting of, or consisting essentially of SEQ ID NO: 114. In some aspects, the antibody comprises a $V_H$ sequence comprising a Kabat CDR-H2 sequence comprising, consisting of, or consisting essentially of SEQ ID NO: 115. In some aspects, the antibody comprises a $V_H$ sequence comprising a Kabat CDR-H2 sequence comprising, consisting of, or consisting essentially of SEQ ID NO: 116. In some aspects, the antibody comprises a $V_H$ sequence comprising a Kabat CDR-H2 sequence comprising, consisting of, or consisting essentially of SEQ ID NO: 117. In some aspects, the antibody comprises a $V_H$ sequence comprising a Kabat CDR-H2 sequence comprising, consisting of, or consisting essentially of SEQ ID NO: 118. In some aspects, the antibody comprises a $V_H$ sequence comprising a Kabat CDR-H2 sequence comprising, consisting of, or consisting essentially of SEQ ID NO: 119. In some aspects, the antibody comprises a $V_H$ sequence comprising a Kabat CDR-H2 sequence comprising, consisting of, or consisting essentially of SEQ ID NO: 120. In some aspects, the antibody comprises a $V_H$ sequence comprising a Kabat CDR-H2 sequence comprising, consisting of, or consisting essentially of SEQ ID NO: 121. In some aspects, the antibody comprises a $V_H$ sequence comprising a Kabat CDR-H2 sequence comprising, consisting of, or consisting essentially of SEQ ID NO: 122. In some aspects, the antibody comprises a $V_H$ sequence comprising a Kabat CDR-H2 sequence comprising, consisting of, or consisting essentially of SEQ ID NO: 123. In some aspects, the antibody comprises a $V_H$ sequence comprising a Kabat CDR-H2 sequence comprising, consisting of, or consisting essentially of SEQ ID NO: 124.

2.2.1.3. Kabat CDR-H1

In some embodiments, the antibody comprises a $V_H$ sequence comprising a Kabat CDR-H1 sequence comprising, consisting of, or consisting essentially of a sequence selected from SEQ ID NOs: 33-60. In some aspects, the antibody comprises a $V_H$ sequence comprising a Kabat CDR-H1 sequence comprising, consisting of, or consisting essentially of SEQ ID NO: 33. In some aspects, the antibody comprises a $V_H$ sequence comprising a Kabat CDR-H1 sequence comprising, consisting of, or consisting essentially of SEQ ID NO: 34. In some aspects, the antibody comprises a $V_H$ sequence comprising a Kabat CDR-H1 sequence comprising, consisting of, or consisting essentially of SEQ ID NO: 35. In some aspects, the antibody comprises a $V_H$ sequence comprising a Kabat CDR-H1 sequence comprising, consisting of, or consisting essentially of SEQ ID NO: 36 In some aspects, the antibody comprises a $V_H$ sequence comprising a Kabat CDR-H1 sequence comprising, consisting of, or consisting essentially of SEQ ID NO: 37. In some aspects, the antibody comprises a $V_H$ sequence comprising a Kabat CDR-H1 sequence comprising, consisting of, or consisting essentially of SEQ ID NO: 38. In some aspects, the antibody comprises a $V_H$ sequence comprising a Kabat CDR-H1 sequence comprising, consisting of, or consisting essentially of SEQ ID NO: 39. In some aspects, the antibody comprises a $V_H$ sequence comprising a Kabat CDR-H1 sequence comprising, consisting of, or consisting essentially of SEQ ID NO: 40. In some aspects, the antibody comprises a $V_H$ sequence comprising a Kabat CDR-H1 sequence comprising, consisting of, or consisting essentially of SEQ ID NO: 41. In some aspects, the antibody comprises a $V_H$ sequence comprising a Kabat CDR-H1 sequence comprising, consisting of, or consisting essentially of SEQ ID NO: 42. In some aspects, the antibody comprises a $V_H$ sequence comprising a Kabat CDR-H1 sequence comprising, consisting of, or consisting essentially of SEQ ID NO: 43. In some aspects, the antibody comprises a $V_H$ sequence comprising a Kabat CDR-H1 sequence comprising, consisting of, or consisting essentially of SEQ ID NO: 44. In some aspects, the antibody comprises a $V_H$ sequence comprising a Kabat CDR-H1 sequence comprising, consisting of, or consisting essentially of SEQ ID NO: 45. In some aspects, the antibody comprises a $V_H$ sequence comprising a Kabat CDR-H1 sequence comprising, consisting of, or consisting essentially of SEQ ID NO: 46. In some aspects, the antibody comprises a $V_H$ sequence comprising a Kabat CDR-H1 sequence comprising, consisting of, or consisting essentially of SEQ ID NO: 47. In some aspects, the antibody comprises a $V_H$ sequence comprising a Kabat CDR-H1 sequence comprising, consisting of, or consisting essentially of SEQ ID NO: 48. In some aspects, the antibody comprises a $V_H$ sequence comprising a Kabat CDR-H1 sequence comprising, consisting of, or consisting essentially of SEQ ID NO: 49. In some aspects, the antibody comprises a $V_H$ sequence comprising a Kabat CDR-H1 sequence comprising, consisting of, or consisting essentially of SEQ ID NO: 50. In some aspects, the antibody comprises a $V_H$ sequence comprising a Kabat CDR-H1 sequence comprising, consisting of, or consisting essentially of SEQ ID NO: 51. In some aspects, the antibody comprises a $V_H$ sequence comprising a Kabat CDR-H1 sequence comprising, consisting of, or consisting essentially of SEQ ID NO: 52. In some aspects, the antibody comprises a $V_H$ sequence comprising a Kabat CDR-H1 sequence comprising, consisting of, or consisting essentially of SEQ ID NO: 53. In some aspects, the antibody comprises a $V_H$ sequence comprising a Kabat CDR-H1 sequence comprising, consisting of, or consisting essentially of SEQ ID NO: 54. In some aspects, the antibody comprises a $V_H$ sequence comprising a Kabat CDR-H1 sequence comprising, consisting of, or consisting essentially of SEQ ID NO: 55. In some aspects, the antibody comprises a $V_H$ sequence comprising a Kabat CDR-H1 sequence comprising, consisting of, or consisting essentially of SEQ ID NO: 56. In some aspects, the antibody comprises a $V_H$ sequence comprising a Kabat CDR-H1 sequence comprising, consisting of, or consisting essentially of SEQ ID NO: 57. In some aspects, the antibody comprises a $V_H$ sequence comprising a Kabat CDR-H1 sequence comprising, consisting of, or consisting essentially of SEQ ID NO: 58. In some aspects, the antibody comprises a $V_H$ sequence comprising a Kabat CDR-H1 sequence comprising, consisting of, or consisting essentially of SEQ ID NO: 59. In some aspects, the antibody comprises a $V_H$ sequence comprising a Kabat CDR-H1 sequence comprising, consisting of, or consisting essentially of SEQ ID NO: 60.

2.2.1.4. Kabat CDR-H3+Kabat CDR-H2

In some embodiments, the antibody comprises a $V_H$ sequence comprising a Kabat CDR-H3 sequence comprising, consisting of, or consisting essentially of a sequence selected from SEQ ID NOs: 129-156 and a Kabat CDR-H2 sequence comprising, consisting of, or consisting essentially of a sequence selected from SEQ ID NOs: 97-124. In some aspects, the Kabat CDR-H3 sequence and the Kabat CDR-H2 sequence are both from a single illustrative $V_H$ sequence provided in this disclosure. For example, in some aspects, the Kabat CDR-H3 and Kabat CDR-H2 are both from a single illustrative $V_H$ sequence selected from SEQ ID NOs: 230-251 and 273-280.

2.2.1.5. Kabat CDR-H3+Kabat CDR-H1

In some embodiments, the antibody comprises a $V_H$ sequence comprising a Kabat CDR-H3 sequence comprising, consisting of, or consisting essentially of a sequence selected from SEQ ID NOs: 129-156 and a Kabat CDR-H1 sequence comprising, consisting of, or consisting essentially of a sequence selected from SEQ ID NOs: 33-60. In some aspects, the Kabat CDR-H3 sequence and the Kabat CDR-H1 sequence are both from a single illustrative $V_H$ sequence provided in this disclosure. For example, in some aspects, the Kabat CDR-H3 and Kabat CDR-H1 are both from a single illustrative $V_H$ sequence selected from SEQ ID NOs: 230-251 and 273-280.

2.2.1.6. Kabat CDR-H1+Kabat CDR-H2

In some embodiments, the antibody comprises a $V_H$ sequence comprising a Kabat CDR-H1 sequence comprising, consisting of, or consisting essentially of a sequence selected from SEQ ID NOs: 33-60 and a Kabat CDR-H2 sequence comprising, consisting of, or consisting essentially of a sequence selected from SEQ ID NOs: 97-124. In some aspects, the Kabat CDR-H1 sequence and the Kabat CDR-H2 sequence are both from a single illustrative $V_H$ sequence provided in this disclosure. For example, in some aspects, the Kabat CDR-H1 and Kabat CDR-H2 are both from a single illustrative $V_H$ sequence selected from SEQ ID NOs: 230-251 and 273-280.

2.2.1.7. Kabat CDR-H1+Kabat CDR-H2+Kabat CDR-H3

In some embodiments, the antibody comprises a $V_H$ sequence comprising a Kabat CDR-H1 sequence comprising, consisting of, or consisting essentially of a sequence selected from SEQ ID NOs: 33-60, a Kabat CDR-H2 sequence comprising, consisting of, or consisting essentially of a sequence selected from SEQ ID NOs: 97-124, and a Kabat CDR-H3 sequence comprising, consisting of, or consisting essentially of a sequence selected from SEQ ID NOs: 129-156. In some aspects, the Kabat CDR-H1 sequence, Kabat CDR-H2 sequence, and Kabat CDR-H3 sequence are all from a single illustrative $V_H$ sequence provided in this disclosure. For example, in some aspects, the Kabat CDR-H1, Kabat CDR-H2, and Kabat CDR-H3 are all from a single illustrative $V_H$ sequence selected from SEQ ID NOs: 230-251 and 273-280.

2.2.1.8. Variants of $V_H$ Sequences Comprising Illustrative Kabat CDRs

In some embodiments, the $V_H$ sequences provided herein comprise a variant of an illustrative Kabat CDR-H3, CDR-H2, and/or CDR-H1 sequence provided in this disclosure.

In some aspects, the Kabat CDR-H3 sequence comprises, consists of, or consists essentially of a variant of an illustrative Kabat CDR-H3 sequence provided in this disclosure. In some aspects, the Kabat CDR-H3 sequence comprises, consists of, or consists essentially of a sequence having at least 70%, 75%, 80%, 85%, 90%, or 95% identity with any of the illustrative Kabat CDR-H3 sequences provided in this disclosure. In some aspects, the Kabat CDR-H3 sequence comprises, consists of, or consists essentially of any of the illustrative Kabat CDR-H3 sequences provided in this disclosure, with 1, 2, or 3 amino acid substitutions. In some aspects, the amino acid substitutions are conservative amino acid substitutions.

In some aspects, the Kabat CDR-H2 sequence comprises, consists of, or consists essentially of a variant of an illustrative Kabat CDR-H2 sequence provided in this disclosure. In some aspects, the Kabat CDR-H2 sequence comprises, consists of, or consists essentially of a sequence having at least 70%, 75%, 80%, 85%, 90%, or 95% identity with any of the illustrative Kabat CDR-H2 sequences provided in this disclosure. In some aspects, the Kabat CDR-H2 sequence comprises, consists of, or consists essentially of any of the illustrative Kabat CDR-H2 sequences provided in this disclosure, with 1, 2, or 3 amino acid substitutions. In some aspects, the amino acid substitutions are conservative amino acid substitutions.

In some aspects, the Kabat CDR-H1 sequence comprises, consists of, or consists essentially of a variant of an illustrative Kabat CDR-H1 sequence provided in this disclosure. In some aspects, the Kabat CDR-H1 sequence comprises, consists of, or consists essentially of a sequence having at least 70%, 75%, 80%, 85%, 90%, or 95% identity with any of the illustrative Kabat CDR-H1 sequences provided in this disclosure. In some aspects, the Kabat CDR-H1 sequence comprises, consists of, or consists essentially of any of the illustrative Kabat CDR-H1 sequences provided in this disclosure, with 1, 2, or 3 amino acid substitutions. In some aspects, the amino acid substitutions are conservative amino acid substitutions.

2.2.1.9. Excluded $V_H$ Sequences Comprising Kabat CDRs

In some embodiments, the $V_H$ sequences provided herein do not comprise certain Kabat CDR-H3, CDR-H2, and/or CDR-H1 sequences.

In some aspects, the Kabat CDR-H3 sequence does not comprise, consist of, or consist essentially of a sequence selected from SEQ ID NOs: 157-160. In some aspects, the Kabat CDR-H3 sequence does not comprise, consist of, or consist essentially of SEQ ID NO: 157. In some aspects, the Kabat CDR-H3 sequence does not comprise, consist of, or consist essentially of SEQ ID NO: 158. In some aspects, the Kabat CDR-H3 sequence does not comprise, consist of, or consist essentially of SEQ ID NO: 159. In some aspects, the Kabat CDR-H3 sequence does not comprise, consist of, or consist essentially of SEQ ID NO: 160.

In some aspects, the Kabat CDR-H2 sequence does not comprise, consist of, or consist essentially of a sequence selected from SEQ ID NOs: 125-128. In some aspects, the Kabat CDR-H2 sequence does not comprise, consist of, or consist essentially of SEQ ID NO: 125. In some aspects, the Kabat CDR-H2 sequence does not comprise, consist of, or consist essentially of SEQ ID NO: 126. In some aspects, the Kabat CDR-H2 sequence does not comprise, consist of, or consist essentially of SEQ ID NO: 127. In some aspects, the Kabat CDR-H2 sequence does not comprise, consist of, or consist essentially of SEQ ID NO: 128.

In some aspects, the Kabat CDR-H1 sequence does not comprise, consist of, or consist essentially of a sequence selected from SEQ ID NOs: 61-64. In some aspects, the Kabat CDR-H1 sequence does not comprise, consist of, or consist essentially of SEQ ID NO: 61. In some aspects, the Kabat CDR-H1 sequence does not comprise, consist of, or consist essentially of SEQ ID NO: 62. In some aspects, the Kabat CDR-H1 sequence does not comprise, consist of, or consist essentially of SEQ ID NO: 63. In some aspects, the Kabat CDR-H1 sequence does not comprise, consist of, or consist essentially of SEQ ID NO: 64.

2.2.2. $V_H$ Sequences Comprising Illustrative Chothia CDRs

In some embodiments, the antibody comprises a $V_H$ sequence comprising one or more Chothia CDR-H sequences comprising, consisting of, or consisting essentially of one or more illustrative Chothia CDR-H sequences provided in this disclosure, and variants thereof 2.2.2.1. Chothia CDR-H3

In some embodiments, the antibody comprises a $V_H$ sequence comprising a Chothia CDR-H3 sequence comprising, consisting of, or consisting essentially of a sequence selected from SEQ ID NOs: 129-156. In some aspects, the antibody comprises a $V_H$ sequence comprising a Chothia CDR-H3 sequence comprising, consisting of, or consisting essentially of SEQ ID NO: 129. In some aspects, the antibody comprises a $V_H$ sequence comprising a Chothia CDR-H3 sequence comprising, consisting of, or consisting essentially of SEQ ID NO: 130. In some aspects, the antibody comprises a $V_H$ sequence comprising a Chothia CDR-H3 sequence comprising, consisting of, or consisting essentially of SEQ ID NO: 131. In some aspects, the antibody comprises a $V_H$ sequence comprising a Chothia CDR-H3 sequence comprising, consisting of, or consisting essentially of SEQ ID NO: 132. In some aspects, the antibody comprises a $V_H$ sequence comprising a Chothia CDR-H3 sequence comprising, consisting of, or consisting essentially of SEQ ID NO: 133. In some aspects, the antibody comprises a $V_H$ sequence comprising a Chothia CDR-H3 sequence comprising, consisting of, or consisting essentially of SEQ ID NO: 134. In some aspects, the antibody comprises a $V_H$ sequence comprising a Chothia CDR-H3 sequence comprising, consisting of, or consisting essentially of SEQ ID NO: 135. In some aspects, the antibody comprises a $V_H$ sequence comprising a Chothia CDR-H3 sequence comprising, consisting of, or consisting essentially of SEQ ID NO: 136. In some aspects, the antibody comprises a $V_H$ sequence comprising a Chothia CDR-H3 sequence comprising, consisting of, or consisting essentially of SEQ ID NO: 137. In some aspects, the antibody comprises a $V_H$ sequence comprising a Chothia CDR-H3 sequence comprising, consisting of, or consisting essentially of SEQ ID NO: 138. In some aspects, the antibody comprises a $V_H$ sequence comprising a Chothia CDR-H3 sequence comprising, consisting of, or consisting essentially of SEQ ID NO: 139. In some aspects, the antibody comprises a $V_H$ sequence comprising a Chothia CDR-H3 sequence comprising, consisting of, or consisting essentially of SEQ ID NO: 140. In some aspects, the antibody comprises a $V_H$ sequence comprising a Chothia CDR-H3 sequence comprising, consisting of, or consisting essentially of SEQ ID NO: 141. In some aspects, the antibody comprises a $V_H$ sequence comprising a Chothia CDR-H3 sequence comprising, consisting of, or consisting essentially of SEQ ID NO: 142. In some aspects, the antibody comprises a $V_H$ sequence comprising a Chothia CDR-H3 sequence comprising, consisting of, or consisting essentially of SEQ ID NO: 143. In some aspects, the antibody comprises a $V_H$ sequence comprising a Chothia CDR-H3 sequence comprising, consisting of, or consisting essentially of SEQ ID NO: 144. In some aspects, the antibody comprises a $V_H$ sequence comprising a Chothia CDR-H3 sequence comprising, consisting of, or consisting essentially of SEQ ID NO: 145. In some aspects, the antibody comprises a $V_H$ sequence comprising a Chothia CDR-H3 sequence comprising, consisting of, or consisting essentially of SEQ ID NO: 146. In some aspects, the antibody comprises a $V_H$ sequence comprising a Chothia CDR-H3 sequence comprising, consisting of, or consisting essentially of SEQ ID NO: 147. In some aspects, the antibody comprises a $V_H$ sequence comprising a Chothia CDR-H3 sequence comprising, consisting of, or consisting essentially of SEQ ID NO: 148. In some aspects, the antibody comprises a $V_H$ sequence comprising a Chothia CDR-H3 sequence comprising, consisting of, or consisting essentially of SEQ ID NO: 149. In some aspects, the antibody comprises a $V_H$ sequence comprising a Chothia CDR-H3 sequence comprising, consisting of, or consisting essentially of SEQ ID NO: 150. In some aspects, the antibody comprises a $V_H$ sequence comprising a Chothia CDR-H3 sequence comprising, consisting of, or consisting essentially of SEQ ID NO: 151. In some aspects, the antibody comprises a $V_H$ sequence comprising a Chothia CDR-H3 sequence comprising, consisting of, or consisting essentially of SEQ ID NO: 152. In some aspects, the antibody comprises a $V_H$ sequence comprising a Chothia CDR-H3 sequence comprising, consisting of, or consisting essentially of SEQ ID NO: 153. In some aspects, the antibody comprises a $V_H$ sequence comprising a Chothia CDR-H3 sequence comprising, consisting of, or consisting essentially of SEQ ID NO: 154. In some aspects, the antibody comprises a $V_H$ sequence comprising a Chothia CDR-H3 sequence comprising, consisting of, or consisting essentially of SEQ ID NO: 155. In some aspects, the antibody comprises a $V_H$ sequence comprising a Chothia CDR-H3 sequence comprising, consisting of, or consisting essentially of SEQ ID NO: 156.

2.2.2.2. Chothia CDR-H2

In some embodiments, the antibody comprises a $V_H$ sequence comprising a Chothia CDR-H2 sequence comprising, consisting of, or consisting essentially of a sequence selected from SEQ ID NOs: 65-92. In some aspects, the antibody comprises a $V_H$ sequence comprising a Chothia CDR-H2 sequence comprising, consisting of, or consisting essentially of SEQ ID NO: 65. In some aspects, the antibody comprises a $V_H$ sequence comprising a Chothia CDR-H2 sequence comprising, consisting of, or consisting essentially of SEQ ID NO: 66. In some aspects, the antibody comprises a $V_H$ sequence comprising a Chothia CDR-H2 sequence comprising, consisting of, or consisting essentially of SEQ ID NO: 67. In some aspects, the antibody comprises a $V_H$ sequence comprising a Chothia CDR-H2 sequence comprising, consisting of, or consisting essentially of SEQ ID NO: 68. In some aspects, the antibody comprises a $V_H$ sequence comprising a Chothia CDR-H2 sequence comprising, consisting of, or consisting essentially of SEQ ID NO: 69. In some aspects, the antibody comprises a $V_H$ sequence comprising a Chothia CDR-H2 sequence comprising, consisting of, or consisting essentially of SEQ ID NO: 70. In some aspects, the antibody comprises a $V_H$ sequence comprising a Chothia CDR-H2 sequence comprising, consisting of, or consisting essentially of SEQ ID NO: 71. In some aspects, the antibody comprises a $V_H$ sequence comprising a Chothia CDR-H2 sequence comprising, consisting of, or consisting essentially of SEQ ID NO: 72. In some aspects, the antibody comprises a $V_H$ sequence comprising a Chothia CDR-H2 sequence comprising, consisting of, or consisting essentially of SEQ ID NO: 73. In some aspects, the antibody comprises a $V_H$ sequence comprising a Chothia CDR-H2 sequence comprising, consisting of, or consisting essentially of SEQ ID NO: 74. In some aspects, the antibody comprises a $V_H$ sequence comprising a Chothia CDR-H2 sequence comprising, consisting of, or consisting essentially of SEQ ID NO: 75. In some aspects, the antibody comprises a $V_H$ sequence comprising a Chothia CDR-H2 sequence comprising, consisting of, or consisting essentially of SEQ ID NO: 76. In some aspects, the antibody comprises a $V_H$ sequence comprising a Chothia CDR-H2 sequence comprising, consisting of, or consisting essentially of SEQ ID NO: 77. In some aspects, the antibody comprises a $V_H$ sequence comprising a Chothia CDR-H2 sequence comprising, consisting of, or consisting essentially of SEQ ID NO: 78. In some aspects, the antibody comprises a $V_H$ sequence comprising a Chothia CDR-H2 sequence comprising, consisting of, or consisting essentially of SEQ ID NO: 79. In some aspects, the antibody comprises a $V_H$ sequence comprising a Chothia CDR-H2 sequence comprising, consisting of, or consisting essentially of SEQ ID NO: 80. In some aspects, the antibody comprises a $V_H$ sequence comprising a Chothia CDR-H2 sequence comprising, consisting of, or consisting essentially of SEQ ID NO: 81. In some aspects, the antibody comprises a $V_H$ sequence comprising a Chothia CDR-H2 sequence comprising, consisting of, or consisting essentially of SEQ ID NO: 82. In some aspects, the antibody comprises a $V_H$ sequence comprising a Chothia CDR-H2 sequence comprising, consisting of, or consisting essentially of SEQ ID NO: 83. In some aspects, the antibody comprises a $V_H$ sequence comprising a Chothia CDR-H2 sequence comprising, consisting of, or consisting essentially of SEQ ID NO: 84. In some aspects, the antibody comprises a $V_H$ sequence comprising a Chothia CDR-H2 sequence comprising, consisting of, or consisting essentially of SEQ ID NO: 85. In some aspects, the antibody comprises a $V_H$ sequence comprising a Chothia CDR-H2 sequence comprising, consisting of, or consisting essentially of SEQ ID NO: 86. In some aspects, the antibody comprises a $V_H$ sequence comprising a Chothia CDR-H2 sequence comprising, consisting of, or consisting essentially of SEQ ID NO: 87. In some aspects, the antibody comprises a $V_H$ sequence comprising a Chothia CDR-H2 sequence comprising, consisting of, or consisting essentially of SEQ ID NO: 88. In some aspects, the antibody comprises a $V_H$ sequence comprising a Chothia CDR-H2 sequence comprising, consisting of, or consisting essentially of SEQ ID NO: 89. In some aspects, the antibody comprises a $V_H$ sequence comprising a Chothia CDR-H2 sequence comprising, consisting of, or consisting essentially of SEQ ID NO: 90. In some aspects, the antibody comprises a $V_H$ sequence comprising a Chothia CDR-H2 sequence comprising, consisting of, or consisting essentially of SEQ ID NO: 91. In some aspects, the antibody comprises a $V_H$ sequence comprising a Chothia CDR-H2 sequence comprising, consisting of, or consisting essentially of SEQ ID NO: 92.

2.2.2.3. Chothia CDR-H1

In some embodiments, the antibody comprises a $V_H$ sequence comprising a Chothia CDR-H1 sequence comprising, consisting of, or consisting essentially of a sequence selected from SEQ ID NOs: 1-28. In some aspects, the antibody comprises a $V_H$ sequence comprising a Chothia CDR-H1 sequence comprising, consisting of, or consisting essentially of SEQ ID NO: 1. In some aspects, the antibody comprises a $V_H$ sequence comprising a Chothia CDR-H1 sequence comprising, consisting of, or consisting essentially of SEQ ID NO: 2. In some aspects, the antibody comprises a $V_H$ sequence comprising a Chothia CDR-H1 sequence comprising, consisting of, or consisting essentially of SEQ ID NO: 3. In some aspects, the antibody comprises a $V_H$ sequence comprising a Chothia CDR-H1 sequence comprising, consisting of, or consisting essentially of SEQ ID NO: 4 In some aspects, the antibody comprises a $V_H$ sequence comprising a Chothia CDR-H1 sequence comprising, consisting of, or consisting essentially of SEQ ID NO: 5. In some aspects, the antibody comprises a $V_H$ sequence comprising a Chothia CDR-H1 sequence comprising, consisting of, or consisting essentially of SEQ ID NO: 6. In some aspects, the antibody comprises a $V_H$ sequence comprising a Chothia CDR-H1 sequence comprising, consisting of, or consisting essentially of SEQ ID NO: 7. In some aspects, the antibody comprises a $V_H$ sequence comprising a Chothia CDR-H1 sequence comprising, consisting of, or consisting essentially of SEQ ID NO: 8. In some aspects, the antibody comprises a $V_H$ sequence comprising a Chothia CDR-H1 sequence comprising, consisting of, or consisting essentially of SEQ ID NO: 9. In some aspects, the antibody comprises a $V_H$ sequence comprising a Chothia CDR-H1 sequence comprising, consisting of, or consisting essentially of SEQ ID NO: 10. In some aspects, the antibody comprises a $V_H$ sequence comprising a Chothia CDR-H1 sequence comprising, consisting of, or consisting essentially of SEQ ID NO: 11. In some aspects, the antibody comprises a $V_H$ sequence comprising a Chothia CDR-H1 sequence comprising, consisting of, or consisting essentially of SEQ ID NO: 12. In some aspects, the antibody comprises a $V_H$ sequence comprising a Chothia CDR-H1 sequence comprising, consisting of, or consisting essentially of SEQ ID NO: 13. In some aspects, the antibody comprises a $V_H$ sequence comprising a Chothia CDR-H1 sequence comprising, consisting of, or consisting essentially of SEQ ID NO: 14. In some aspects, the antibody comprises a $V_H$ sequence comprising a Chothia CDR-H1 sequence comprising, consisting of, or consisting essentially of SEQ ID NO: 15. In some aspects, the antibody comprises a $V_H$ sequence comprising a Chothia CDR-H1 sequence comprising, consisting of, or consisting essentially of SEQ ID NO: 16. In some aspects, the antibody comprises a $V_H$ sequence comprising a Chothia CDR-H1 sequence comprising, consisting of, or consisting essentially of SEQ ID NO: 17. In some aspects, the antibody comprises a $V_H$ sequence comprising a Chothia CDR-H1 sequence comprising, consisting of, or consisting essentially of SEQ ID NO: 18. In some aspects, the antibody comprises a $V_H$ sequence comprising a Chothia CDR-H1 sequence comprising, consisting of, or consisting essentially of SEQ ID NO: 19. In some aspects, the antibody comprises a $V_H$ sequence comprising a Chothia CDR-H1 sequence comprising, consisting of, or consisting essentially of SEQ ID NO: 20. In some aspects, the antibody comprises a $V_H$ sequence comprising a Chothia CDR-H1 sequence comprising, consisting of, or consisting essentially of SEQ ID NO: 21. In some aspects, the antibody comprises a $V_H$ sequence comprising a Chothia CDR-H1 sequence comprising, consisting of, or consisting essentially of SEQ ID NO: 22. In some aspects, the antibody comprises a $V_H$ sequence comprising a Chothia CDR-H1 sequence comprising, consisting of, or consisting essentially of SEQ ID NO: 23. In some aspects, the antibody comprises a $V_H$ sequence comprising a Chothia CDR-H1 sequence comprising, consisting of, or consisting essentially of SEQ ID NO: 24. In some aspects, the antibody comprises a $V_H$ sequence comprising a Chothia CDR-H1 sequence comprising, consisting of, or consisting essentially of SEQ ID NO: 25. In some aspects, the antibody comprises a $V_H$ sequence comprising a Chothia CDR-H1 sequence comprising, consisting of, or consisting essentially of SEQ ID NO: 26. In some aspects, the antibody comprises a $V_H$ sequence comprising a Chothia CDR-H1 sequence comprising, consisting of, or consisting essentially of SEQ ID NO: 27. In some aspects, the antibody comprises a $V_H$ sequence comprising a Chothia CDR-H1 sequence comprising, consisting of, or consisting essentially of SEQ ID NO: 28.

2.2.2.4. Chothia CDR-H3+Chothia CDR-H2

In some embodiments, the antibody comprises a $V_H$ sequence comprising a Chothia CDR-H3 sequence comprising, consisting of, or consisting essentially of a sequence selected from SEQ ID NOs: 129-156 and a Chothia CDR-H2 sequence comprising, consisting of, or consisting essentially of a sequence selected from SEQ ID NOs: 65-92. In some aspects, the Chothia CDR-H3 sequence and the Chothia CDR-H2 sequence are both from a single illustrative $V_H$ sequence provided in this disclosure. For example, in some aspects, the Chothia CDR-H3 and Chothia CDR-H2 are both from a single illustrative $V_H$ sequence selected from SEQ ID NOs: 230-251 and 273-280.

2.2.2.5. Chothia CDR-H3+Chothia CDR-H1

In some embodiments, the antibody comprises a $V_H$ sequence comprising a Chothia CDR-H3 sequence comprising, consisting of, or consisting essentially of a sequence selected from SEQ ID NOs: 129-156 and a Chothia CDR-H1 sequence comprising, consisting of, or consisting essentially of a sequence selected from SEQ ID NOs: 1-28. In some aspects, the Chothia CDR-H3 sequence and the Chothia CDR-H1 sequence are both from a single illustrative $V_H$ sequence provided in this disclosure. For example, in some aspects, the Chothia CDR-H3 and Chothia CDR-H1 are both from a single illustrative $V_H$ sequence selected from SEQ ID NOs: 230-251 and 273-280.

2.2.2.6. Chothia CDR-H1+Chothia CDR-H2

In some embodiments, the antibody comprises a $V_H$ sequence comprising a Chothia CDR-H1 sequence comprising, consisting of, or consisting essentially of a sequence selected from SEQ ID NOs: 1-28 and a Chothia CDR-H2 sequence comprising, consisting of, or consisting essentially of a sequence selected from SEQ ID NOs: 65-92. In some aspects, the Chothia CDR-H1 sequence and the Chothia CDR-H2 sequence are both from a single illustrative $V_H$ sequence provided in this disclosure. For example, in some aspects, the Chothia CDR-H1 and Chothia CDR-H2 are both from a single illustrative $V_H$ sequence selected from SEQ ID NOs: 230-251 and 273-280.

2.2.2.7. Chothia CDR-H1+Chothia CDR-H2+Chothia CDR-H3

In some embodiments, the antibody comprises a $V_H$ sequence comprising a Chothia CDR-H1 sequence comprising, consisting of, or consisting essentially of a sequence selected from SEQ ID NOs: 1-28, a Chothia CDR-H2 sequence comprising, consisting of, or consisting essentially of a sequence selected from SEQ ID NOs: 65-92, and a Chothia CDR-H3 sequence comprising, consisting of, or consisting essentially of a sequence selected from SEQ ID NOs: 129-156. In some aspects, the Chothia CDR-H1 sequence, Chothia CDR-H2 sequence, and Chothia CDR-H3 sequence are all from a single illustrative $V_H$ sequence provided in this disclosure. For example, in some aspects, the Chothia CDR-H1, Chothia CDR-H2, and Chothia CDR-H3 are all from a single illustrative $V_H$ sequence selected from SEQ ID NOs: 230-251 and 273-280.

2.2.2.8. Variants of $V_H$ Sequences Comprising Illustrative Chothia CDRs

In some embodiments, the $V_H$ sequences provided herein comprise a variant of an illustrative Chothia CDR-H3, CDR-H2, and/or CDR-H1 sequence provided in this disclosure.

In some aspects, the Chothia CDR-H3 sequence comprises, consists of, or consists essentially of a variant of an illustrative Chothia CDR-H3 sequence provided in this disclosure. In some aspects, the Chothia CDR-H3 sequence comprises, consists of, or consists essentially of a sequence having at least 70%, 75%, 80%, 85%, 90%, or 95% identity with any of the illustrative Chothia CDR-H3 sequences provided in this disclosure. In some aspects, the Chothia CDR-H3 sequence comprises, consists of, or consists essentially of any of the illustrative Chothia CDR-H3 sequences provided in this disclosure, with 1, 2, or 3 amino acid substitutions. In some aspects, the amino acid substitutions are conservative amino acid substitutions.

In some aspects, the Chothia CDR-H2 sequence comprises, consists of, or consists essentially of a variant of an illustrative Chothia CDR-H2 sequence provided in this disclosure. In some aspects, the Chothia CDR-H2 sequence comprises, consists of, or consists essentially of a sequence having at least 70%, 75%, 80%, 85%, 90%, or 95% identity with any of the illustrative Chothia CDR-H2 sequences provided in this disclosure. In some aspects, the Chothia CDR-H2 sequence comprises, consists of, or consists essentially of any of the illustrative Chothia CDR-H2 sequences provided in this disclosure, with 1, 2, or 3 amino acid substitutions. In some aspects, the amino acid substitutions are conservative amino acid substitutions.

In some aspects, the Chothia CDR-H1 sequence comprises, consists of, or consists essentially of a variant of an illustrative Chothia CDR-H1 sequence provided in this disclosure. In some aspects, the Chothia CDR-H1 sequence comprises, consists of, or consists essentially of a sequence having at least 70%, 75%, 80%, 85%, 90%, or 95% identity with any of the illustrative Chothia CDR-H1 sequences provided in this disclosure. In some aspects, the Chothia CDR-H1 sequence comprises, consists of, or consists essentially of any of the illustrative Chothia CDR-H1 sequences provided in this disclosure, with 1, 2, or 3 amino acid substitutions. In some aspects, the amino acid substitutions are conservative amino acid substitutions.

2.2.2.9. Excluded $V_H$ Sequences Comprising Chothia CDRs

In some embodiments, the $V_H$ sequences provided herein do not comprise certain Chothia CDR-H3, CDR-H2, and/or CDR-H1 sequences.

In some aspects, the Chothia CDR-H3 sequence does not comprise, consist of, or consist essentially of a sequence selected from SEQ ID NOs: 157-160. In some aspects, the Chothia CDR-H3 sequence does not comprise, consist of, or consist essentially of SEQ ID NO: 157. In some aspects, the Chothia CDR-H3 sequence does not comprise, consist of, or consist essentially of SEQ ID NO: 158. In some aspects, the Chothia CDR-H3 sequence does not comprise, consist of, or consist essentially of SEQ ID NO: 159. In some aspects, the Chothia CDR-H3 sequence does not comprise, consist of, or consist essentially of SEQ ID NO: 160.

In some aspects, the Chothia CDR-H2 sequence does not comprise, consist of, or consist essentially of a sequence selected from SEQ ID NOs: 93-96. In some aspects, the Chothia CDR-H2 sequence does not comprise, consist of, or consist essentially of SEQ ID NO: 93. In some aspects, the Chothia CDR-H2 sequence does not comprise, consist of, or consist essentially of SEQ ID NO: 94. In some aspects, the Chothia CDR-H2 sequence does not comprise, consist of, or consist essentially of SEQ ID NO: 95. In some aspects, the Chothia CDR-H2 sequence does not comprise, consist of, or consist essentially of SEQ ID NO: 96.

In some aspects, the Chothia CDR-H1 sequence does not comprise, consist of, or consist essentially of a sequence selected from SEQ ID NOs: 29-32. In some aspects, the Chothia CDR-H1 sequence does not comprise, consist of, or consist essentially of SEQ ID NO: 29. In some aspects, the Chothia CDR-H1 sequence does not comprise, consist of, or consist essentially of SEQ ID NO: 30. In some aspects, the Chothia CDR-H1 sequence does not comprise, consist of, or consist essentially of SEQ ID NO: 31. In some aspects, the Chothia CDR-H1 sequence does not comprise, consist of, or consist essentially of SEQ ID NO: 32.

2.3. $V_H$ Sequences

In some embodiments, the antibody comprises a $V_H$ sequence comprising, consisting of, or consisting essentially of a sequence selected from SEQ ID NOs: 230-251 and 273-280. In some aspects, the antibody comprises a $V_H$ sequence comprising, consisting of, or consisting essentially of SEQ ID NO: 230. In some aspects, the antibody comprises a $V_H$ sequence comprising, consisting of, or consisting essentially of SEQ ID NO: 231. In some aspects, the antibody comprises a $V_H$ sequence comprising, consisting of, or consisting essentially of SEQ ID NO: 232. In some aspects, the antibody comprises a $V_H$ sequence comprising, consisting of, or consisting essentially of SEQ ID NO: 233. In some aspects, the antibody comprises a $V_H$ sequence comprising, consisting of, or consisting essentially of SEQ ID NO: 234. In some aspects, the antibody comprises a $V_H$ sequence comprising, consisting of, or consisting essentially of SEQ ID NO: 235. In some aspects, the antibody comprises a $V_H$ sequence comprising, consisting of, or consisting essentially of SEQ ID NO: 236. In some aspects, the antibody comprises a $V_H$ sequence comprising, consisting of, or consisting essentially of SEQ ID NO: 237. In some aspects, the antibody comprises a $V_H$ sequence comprising, consisting of, or consisting essentially of SEQ ID NO: 238. In some aspects, the antibody comprises a $V_H$ sequence comprising, consisting of, or consisting essentially of SEQ ID NO: 239. In some aspects, the antibody comprises a $V_H$ sequence comprising, consisting of, or consisting essentially of SEQ ID NO: 240. In some aspects, the antibody comprises a $V_H$ sequence comprising, consisting of, or consisting essentially of SEQ ID NO: 241. In some aspects, the antibody comprises a $V_H$ sequence comprising, consisting of, or consisting essentially of SEQ ID NO: 242. In some aspects, the antibody comprises a $V_H$ sequence comprising, consisting of, or consisting essentially of SEQ ID NO: 243. In some aspects, the antibody comprises a $V_H$ sequence comprising, consisting of, or consisting essentially of SEQ ID NO: 244. In some aspects, the antibody comprises a $V_H$ sequence comprising, consisting of, or consisting essentially of SEQ ID NO: 245. In some aspects, the antibody comprises a $V_H$ sequence comprising, consisting of, or consisting essentially of SEQ ID NO: 246. In some aspects, the antibody comprises a $V_H$ sequence comprising, consisting of, or consisting essentially of SEQ ID NO: 247. In some aspects, the antibody comprises a $V_H$ sequence comprising, consisting of, or consisting essentially of SEQ ID NO: 248. In some aspects, the antibody comprises a $V_H$ sequence comprising, consisting of, or consisting essentially of SEQ ID NO: 249. In some aspects, the antibody comprises a $V_H$ sequence comprising, consisting of, or consisting essentially of SEQ ID NO: 250. In some aspects, the antibody comprises a $V_H$ sequence comprising, consisting of, or consisting essentially of SEQ ID NO: 251. In some aspects, the antibody comprises a $V_H$ sequence comprising, consisting of, or consisting essentially of SEQ ID NO: 273. In some aspects, the antibody comprises a $V_H$ sequence comprising, consisting of, or consisting essentially of SEQ ID NO: 274. In some aspects, the antibody comprises a $V_H$ sequence comprising, consisting of, or consisting essentially of SEQ ID NO: 275. In some aspects, the antibody comprises a $V_H$ sequence comprising, consisting of, or consisting essentially of SEQ ID NO: 276. In some aspects, the antibody comprises a $V_H$ sequence comprising, consisting of, or consisting essentially of SEQ ID NO: 277. In some aspects, the antibody comprises a $V_H$ sequence comprising, consisting of, or consisting essentially of SEQ ID NO: 278. In some aspects, the antibody comprises a $V_H$ sequence comprising, consisting of, or consisting essentially of SEQ ID NO: 279. In some aspects, the antibody comprises a $V_H$ sequence comprising, consisting of, or consisting essentially of SEQ ID NO: 280.

2.3.1. Variants of $V_H$ Sequences

In some embodiments, the $V_H$ sequences provided herein comprise, consist of, or consist essentially of a variant of an illustrative $V_H$ sequence provided in this disclosure.

In some aspects, the $V_H$ sequence comprises, consists of, or consists essentially of a variant of an illustrative $V_H$ sequence provided in this disclosure. In some aspects, the $V_H$ sequence comprises, consists of, or consists essentially of a sequence having at least 85%, 90%, 95%, 96%, 97%, 98%, 99%, or 99.1% identity with any of the illustrative $V_H$ sequences provided in this disclosure. In some aspects, the $V_H$ sequence comprises, consists of, or consists essentially of any of the illustrative $V_H$ sequences provided in this disclosure, with 1-25 amino acid substitutions, 1-20 amino acid substitutions, 1-15 amino acid substitutions, 1-10 amino acid substitutions, 1-5 amino acid substitutions, 1-3 amino acid substitutions, 1-2 amino acid substitutions, or 1 amino acid substitution. In some aspects, the amino acid substitutions are conservative amino acid substitutions.

2.3.2. Excluded $V_H$ Sequences

In some embodiments, the $V_H$ sequences provided herein do not comprise certain $V_H$ sequences.

In some aspects, the $V_H$ sequence does not comprise, consist of, or consist essentially of a sequence selected from SEQ ID NOs: 252-255. In some aspects, the $V_H$ sequence does not comprise, consist of, or consist essentially of SEQ ID NO: 252. In some aspects, the $V_H$ sequence does not comprise, consist of, or consist essentially of SEQ ID NO: 253. In some aspects, the $V_H$ sequence does not comprise, consist of, or consist essentially of SEQ ID NO: 254. In some aspects, the $V_H$ sequence does not comprise, consist of, or consist essentially of SEQ ID NO: 255.

2.4. CDR-L3 Sequences

In some embodiments, the antibody comprises a CDR-L3 sequence comprising, consisting of, or consisting essentially of a sequence selected from SEQ ID NOs: 201-219. In some aspects, the antibody comprises a CDR-L3 sequence comprising, consisting of, or consisting essentially of SEQ ID NO: 201. In some aspects, the antibody comprises a CDR-L3 sequence comprising, consisting of, or consisting essentially of SEQ ID NO: 202. In some aspects, the antibody comprises a CDR-L3 sequence comprising, consisting of, or consisting essentially of SEQ ID NO: 203. In some aspects, the antibody comprises a CDR-L3 sequence comprising, consisting of, or consisting essentially of SEQ ID NO: 204. In some aspects, the antibody comprises a CDR-L3 sequence comprising, consisting of, or consisting essentially of SEQ ID NO: 205. In some aspects, the antibody comprises a CDR-L3 sequence comprising, consisting of, or consisting essentially of SEQ ID NO: 206. In some aspects, the antibody comprises a CDR-L3 sequence comprising, consisting of, or consisting essentially of SEQ ID NO: 207. In some aspects, the antibody comprises a CDR-L3 sequence comprising, consisting of, or consisting essentially of SEQ ID NO: 208. In some aspects, the antibody comprises a CDR-L3 sequence comprising, consisting of, or consisting essentially of SEQ ID NO: 209. In some aspects, the antibody comprises a CDR-L3 sequence comprising, consisting of, or consisting essentially of SEQ ID NO: 210. In some aspects, the antibody comprises a CDR-L3 sequence comprising, consisting of, or consisting essentially of SEQ ID NO: 211. In some aspects, the antibody comprises a CDR-L3 sequence comprising, consisting of, or consisting essentially of SEQ ID NO: 212. In some aspects, the antibody comprises a CDR-L3 sequence comprising, consisting of, or consisting essentially of SEQ ID NO: 213. In some aspects, the antibody comprises a CDR-L3 sequence comprising, consisting of, or consisting essentially of SEQ ID NO: 214. In some aspects, the antibody comprises a CDR-L3 sequence comprising, consisting of, or consisting essentially of SEQ ID NO: 215. In some aspects, the antibody comprises a CDR-L3 sequence comprising, consisting of, or consisting essentially of SEQ ID NO: 216. In some aspects, the antibody comprises a CDR-L3 sequence comprising, consisting of, or consisting essentially of SEQ ID NO: 217. In some aspects, the antibody comprises a CDR-L3 sequence comprising, consisting of, or consisting essentially of SEQ ID NO: 218. In some aspects, the antibody comprises a CDR-L3 sequence comprising, consisting of, or consisting essentially of SEQ ID NO: 219.

In some aspects, the CDR-L3 sequence comprises, consists of, or consists essentially of a variant of an illustrative CDR-L3 sequence provided in this disclosure. In some aspects, the CDR-L3 sequence comprises, consists of, or consists essentially of a sequence having at least 70%, 75%, 80%, 85%, 90%, or 95% identity with any of the illustrative CDR-L3 sequences provided in this disclosure. In some aspects, the CDR-L3 sequence comprises, consists of, or consists essentially of any of the illustrative CDR-L3 sequences provided in this disclosure, with 1, 2, or 3 amino acid substitutions. In some aspects, the amino acid substitutions are conservative amino acid substitutions.

In some aspects, the CDR-L3 sequence does not comprise, consist of, or consist essentially of SEQ ID NO: 220.

2.5. $V_L$ Sequences Comprising Illustrative CDRs

In some embodiments, the antibody comprises a $V_L$ sequence comprising one or more CDR-L sequences comprising, consisting of, or consisting essentially of one or more illustrative CDR-L sequences provided in this disclosure, and variants thereof.

2.5.1. CDR-L3

In some embodiments, the antibody comprises a $V_L$ sequence comprising a CDR-L3 sequence comprising, consisting of, or consisting essentially of a sequence selected from SEQ ID NOs: 201-219. In some aspects, the antibody comprises a $V_L$ sequence comprising a CDR-L3 sequence comprising, consisting of, or consisting essentially of SEQ ID NO: 201. In some aspects, the antibody comprises a $V_L$ sequence comprising a CDR-L3 sequence comprising, consisting of, or consisting essentially of SEQ ID NO: 202. In some aspects, the antibody comprises a $V_L$ sequence comprising a CDR-L3 sequence comprising, consisting of, or consisting essentially of SEQ ID NO: 203. In some aspects, the antibody comprises a $V_L$ sequence comprising a CDR-L3 sequence comprising, consisting of, or consisting essentially of SEQ ID NO: 204. In some aspects, the antibody comprises a $V_L$ sequence comprising a CDR-L3 sequence comprising, consisting of, or consisting essentially of SEQ ID NO: 205. In some aspects, the antibody comprises a $V_L$ sequence comprising a CDR-L3 sequence comprising, consisting of, or consisting essentially of SEQ ID NO: 206. In some aspects, the antibody comprises a $V_L$ sequence comprising a CDR-L3 sequence comprising, consisting of, or consisting essentially of SEQ ID NO: 207. In some aspects, the antibody comprises a $V_L$ sequence comprising a CDR-L3 sequence comprising, consisting of, or consisting essentially of SEQ ID NO: 208. In some aspects, the antibody comprises a $V_L$ sequence comprising a CDR-L3 sequence comprising, consisting of, or consisting essentially of SEQ ID NO: 209. In some aspects, the antibody comprises a $V_L$ sequence comprising a CDR-L3 sequence comprising, consisting of, or consisting essentially of SEQ ID NO: 210. In some aspects, the antibody comprises a $V_L$ sequence comprising a CDR-L3 sequence comprising, consisting of, or consisting essentially of SEQ ID NO: 211. In some aspects, the antibody comprises a $V_L$ sequence comprising a CDR-L3 sequence comprising, consisting of, or consisting essentially of SEQ ID NO: 212. In some aspects, the antibody comprises a $V_L$ sequence comprising a CDR-L3 sequence comprising, consisting of, or consisting essentially of SEQ ID NO: 213. In some aspects, the antibody comprises a $V_L$ sequence comprising a CDR-L3 sequence comprising, consisting of, or consisting essentially of SEQ ID NO: 214. In some aspects, the antibody comprises a $V_L$ sequence comprising a CDR-L3 sequence comprising, consisting of, or consisting essentially of SEQ ID NO: 215. In some aspects, the antibody comprises a $V_L$ sequence comprising a CDR-L3 sequence comprising, consisting of, or consisting essentially of SEQ ID NO: 216. In some aspects, the antibody comprises a $V_L$ sequence comprising a CDR-L3 sequence comprising, consisting of, or consisting essentially of SEQ ID NO: 217. In some aspects, the antibody comprises a $V_L$ sequence comprising a CDR-L3 sequence comprising, consisting of, or consisting essentially of SEQ ID NO: 218. In some aspects, the antibody comprises a $V_L$ sequence comprising a CDR-L3 sequence comprising, consisting of, or consisting essentially of SEQ ID NO: 219.

2.5.2. CDR-L2

In some embodiments, the antibody comprises a $V_L$ sequence comprising a CDR-L2 sequence comprising, consisting of, or consisting essentially of a sequence selected from SEQ ID NOs: 181-199. In some aspects, the antibody comprises a $V_L$ sequence comprising a CDR-L2 sequence comprising, consisting of, or consisting essentially of SEQ ID NO: 181. In some aspects, the antibody comprises a $V_L$ sequence comprising a CDR-L2 sequence comprising, consisting of, or consisting essentially of SEQ ID NO: 182. In some aspects, the antibody comprises a $V_L$ sequence comprising a CDR-L2 sequence comprising, consisting of, or consisting essentially of SEQ ID NO: 183. In some aspects, the antibody comprises a $V_L$ sequence comprising a CDR-L2 sequence comprising, consisting of, or consisting essentially of SEQ ID NO: 184. In some aspects, the antibody comprises a $V_L$ sequence comprising a CDR-L2 sequence comprising, consisting of, or consisting essentially of SEQ ID NO: 185. In some aspects, the antibody comprises a $V_L$ sequence comprising a CDR-L2 sequence comprising, consisting of, or consisting essentially of SEQ ID NO: 186. In some aspects, the antibody comprises a $V_L$ sequence comprising a CDR-L2 sequence comprising, consisting of, or consisting essentially of SEQ ID NO: 187. In some aspects, the antibody comprises a $V_L$ sequence comprising a CDR-L2 sequence comprising, consisting of, or consisting essentially of SEQ ID NO: 188. In some aspects, the antibody comprises a $V_L$ sequence comprising a CDR-L2 sequence comprising, consisting of, or consisting essentially of SEQ ID NO: 189. In some aspects, the antibody comprises a $V_L$ sequence comprising a CDR-L2 sequence comprising, consisting of, or consisting essentially of SEQ ID NO: 190. In some aspects, the antibody comprises a $V_L$ sequence comprising a CDR-L2 sequence comprising, consisting of, or consisting essentially of SEQ ID NO: 191. In some aspects, the antibody comprises a $V_L$ sequence comprising a CDR-L2 sequence comprising, consisting of, or consisting essentially of SEQ ID NO: 192. In some aspects, the antibody comprises a $V_L$ sequence comprising a CDR-L2 sequence comprising, consisting of, or consisting essentially of SEQ ID NO: 193. In some aspects, the antibody comprises a $V_L$ sequence comprising a CDR-L2 sequence comprising, consisting of, or consisting essentially of SEQ ID NO: 194. In some aspects, the antibody comprises a $V_L$ sequence comprising a CDR-L2 sequence comprising, consisting of, or consisting essentially of SEQ ID NO: 195. In some aspects, the antibody comprises a $V_L$ sequence comprising a CDR-L2 sequence comprising, consisting of, or consisting essentially of SEQ ID NO: 196. In some aspects, the antibody comprises a $V_L$ sequence comprising a CDR-L2 sequence comprising, consisting of, or consisting essentially of SEQ ID NO: 197. In some aspects, the antibody comprises a $V_L$ sequence comprising a CDR-L2 sequence comprising, consisting of, or consisting essentially of SEQ ID NO: 198. In some aspects, the antibody comprises a $V_L$ sequence comprising a CDR-L2 sequence comprising, consisting of, or consisting essentially of SEQ ID NO: 199.

2.5.3. CDR-L1

In some embodiments, the antibody comprises a $V_L$ sequence comprising a CDR-L1 sequence comprising, consisting of, or consisting essentially of a sequence selected from SEQ ID NOs: 161-179. In some aspects, the antibody comprises a $V_L$ sequence comprising a CDR-L1 sequence comprising, consisting of, or consisting essentially of SEQ ID NO: 161. In some aspects, the antibody comprises a $V_L$ sequence comprising a CDR-L1 sequence comprising, consisting of, or consisting essentially of SEQ ID NO: 162. In some aspects, the antibody comprises a $V_L$ sequence comprising a CDR-L1 sequence comprising, consisting of, or consisting essentially of SEQ ID NO: 163. In some aspects, the antibody comprises a $V_L$ sequence comprising a CDR-L1 sequence comprising, consisting of, or consisting essentially of SEQ ID NO: 164. In some aspects, the antibody comprises a $V_L$ sequence comprising a CDR-L1 sequence comprising, consisting of, or consisting essentially of SEQ ID NO: 165. In some aspects, the antibody comprises a $V_L$ sequence comprising a CDR-L1 sequence comprising, consisting of, or consisting essentially of SEQ ID NO: 166. In some aspects, the antibody comprises a $V_L$ sequence comprising a CDR-L1 sequence comprising, consisting of, or consisting essentially of SEQ ID NO: 167. In some aspects, the antibody comprises a $V_L$ sequence comprising a CDR-L1 sequence comprising, consisting of, or consisting essentially of SEQ ID NO: 168. In some aspects, the antibody comprises a $V_L$ sequence comprising a CDR-L1 sequence comprising, consisting of, or consisting essentially of SEQ ID NO: 169. In some aspects, the antibody comprises a $V_L$ sequence comprising a CDR-L1 sequence comprising, consisting of, or consisting essentially of SEQ ID NO: 170. In some aspects, the antibody comprises a $V_L$ sequence comprising a CDR-L1 sequence comprising, consisting of, or consisting essentially of SEQ ID NO: 171. In some aspects, the antibody comprises a $V_L$ sequence comprising a CDR-L1 sequence comprising, consisting of, or consisting essentially of SEQ ID NO: 172. In some aspects, the antibody comprises a $V_L$ sequence comprising a CDR-L1 sequence comprising, consisting of, or consisting essentially of SEQ ID NO: 173. In some aspects, the antibody comprises a $V_L$ sequence comprising a CDR-L1 sequence comprising, consisting of, or consisting essentially of SEQ ID NO: 174. In some aspects, the antibody comprises a $V_L$ sequence comprising a CDR-L1 sequence comprising, consisting of, or consisting essentially of SEQ ID NO: 175. In some aspects, the antibody comprises a $V_L$ sequence comprising a CDR-L1 sequence comprising, consisting of, or consisting essentially of SEQ ID NO: 176. In some aspects, the antibody comprises a $V_L$ sequence comprising a CDR-L1 sequence comprising, consisting of, or consisting essentially of SEQ ID NO: 177. In some aspects, the antibody comprises a $V_L$ sequence comprising a CDR-L1 sequence comprising, consisting of, or consisting essentially of SEQ ID NO: 178. In some aspects, the antibody comprises a $V_L$ sequence comprising a CDR-L1 sequence comprising, consisting of, or consisting essentially of SEQ ID NO: 179.

2.5.4. CDR-L3+CDR-L2

In some embodiments, the antibody comprises a $V_L$ sequence comprising a CDR-L3 sequence comprising, consisting of, or consisting essentially of a sequence selected from SEQ ID NOs: 201-219 and a CDR-L2 sequence comprising, consisting of, or consisting essentially of a sequence selected from SEQ ID NOs: 181-199. In some aspects, the CDR-L3 sequence and the CDR-L2 sequence are both from a single illustrative $V_L$ sequence provided in this disclosure. For example, in some aspects, the CDR-L3 and CDR-L2 are both from a single illustrative $V_L$ sequence selected from SEQ ID NOs: 256-270 and 281-288.

2.5.5. CDR-L3+CDR-L1

In some embodiments, the antibody comprises a $V_L$ sequence comprising a CDR-L3 sequence comprising, consisting of, or consisting essentially of a sequence selected from SEQ ID NOs: 201-219 and a CDR-L1 sequence comprising, consisting of, or consisting essentially of a sequence selected from SEQ ID NOs: 161-179. In some aspects, the CDR-L3 sequence and the CDR-L1 sequence are both from a single illustrative $V_L$ sequence provided in this disclosure. For example, in some aspects, the CDR-L3 and CDR-L1 are both from a single illustrative $V_L$ sequence selected from SEQ ID NOs: 256-270 and 281-288.

2.5.6. CDR-L1+CDR-L2

In some embodiments, the antibody comprises a $V_L$ sequence comprising a CDR-L1 sequence comprising, consisting of, or consisting essentially of a sequence selected from SEQ ID NOs: 161-179 and a CDR-L2 sequence comprising, consisting of, or consisting essentially of a sequence selected from SEQ ID NOs: 181-199. In some aspects, the CDR-L1 sequence and the CDR-L2 sequence are both from a single illustrative $V_L$ sequence provided in this disclosure. For example, in some aspects, the CDR-L1 and CDR-L2 are both from a single illustrative $V_L$ sequence selected from SEQ ID NOs: 256-270 and 281-288.

2.5.7. CDR-L1+CDR-L2+CDR-L3

In some embodiments, the antibody comprises a $V_L$ sequence comprising a CDR-L1 sequence comprising, consisting of, or consisting essentially of a sequence selected from SEQ ID NOs: 161-179, a CDR-L2 sequence comprising, consisting of, or consisting essentially of a sequence selected from SEQ ID NOs: 181-199, and a CDR-L3 sequence comprising, consisting of, or consisting essentially of a sequence selected from SEQ ID NOs: 201-219. In some aspects, the CDR-L1 sequence, CDR-L2 sequence, and CDR-L3 sequence are all from a single illustrative $V_L$ sequence provided in this disclosure. For example, in some aspects, the CDR-L1, CDR-L2, and CDR-L3 are all from a single illustrative $V_L$ sequence selected from SEQ ID NOs: 256-270 and 281-288.

2.5.8. Variants of $V_L$ Sequences Comprising Illustrative CDR-Ls

In some embodiments, the $V_L$ sequences provided herein comprise a variant of an illustrative CDR-L3, CDR-L2, and/or CDR-L1 sequence provided in this disclosure.

In some aspects, the CDR-L3 sequence comprises, consists of, or consists essentially of a variant of an illustrative CDR-L3 sequence provided in this disclosure. In some aspects, the CDR-L3 sequence comprises, consists of, or consists essentially of a sequence having at least 70%, 75%, 80%, 85%, 90%, or 95% identity with any of the illustrative CDR-L3 sequences provided in this disclosure. In some aspects, the CDR-L3 sequence comprises, consists of, or consists essentially of any of the illustrative CDR-L3 sequences provided in this disclosure, with 1, 2, or 3 amino acid substitutions. In some aspects, the amino acid substitutions are conservative amino acid substitutions.

In some aspects, the CDR-L2 sequence comprises, consists of, or consists essentially of a variant of an illustrative CDR-L2 sequence provided in this disclosure. In some aspects, the CDR-L2 sequence comprises, consists of, or consists essentially of a sequence having at least 70%, 75%, 80%, 85%, 90%, or 95% identity with any of the illustrative CDR-L2 sequences provided in this disclosure. In some aspects, the CDR-L2 sequence comprises, consists of, or consists essentially of any of the illustrative CDR-L2 sequences provided in this disclosure, with 1, 2, or 3 amino acid substitutions. In some aspects, the amino acid substitutions are conservative amino acid substitutions.

In some aspects, the CDR-L1 sequence comprises, consists of, or consists essentially of a variant of an illustrative CDR-L1 sequence provided in this disclosure. In some aspects, the CDR-L1 sequence comprises, consists of, or consists essentially of a sequence having at least 70%, 75%, 80%, 85%, 90%, or 95% identity with any of the illustrative CDR-L1 sequences provided in this disclosure. In some aspects, the CDR-L1 sequence comprises, consists of, or consists essentially of any of the illustrative CDR-L1 sequences provided in this disclosure, with 1, 2, or 3 amino acid substitutions. In some aspects, the amino acid substitutions are conservative amino acid substitutions.

2.5.9. Excluded $V_L$ Sequences Comprising CDR-Ls

In some embodiments, the $V_L$ sequences provided herein do not comprise certain CDR-L3, CDR-L2, and/or CDR-L1 sequences.

In some aspects, the CDR-L3 sequence does not comprise, consist of, or consist essentially of SEQ ID NO: 220.

In some aspects, the CDR-L2 sequence does not comprise, consist of, or consist essentially of SEQ ID NO: 200.

In some aspects, the CDR-L1 sequence does not comprise, consist of, or consist essentially of SEQ ID NO: 180.

2.6. $V_L$ Sequences

In some embodiments, the antibody comprises a $V_L$ sequence comprising, consisting of, or consisting essentially of a sequence selected from SEQ ID NOs: 256-270 and 281-288. In some aspects, the antibody comprises a $V_L$ sequence comprising, consisting of, or consisting essentially of SEQ ID NO: 256. In some aspects, the antibody comprises a $V_L$ sequence comprising, consisting of, or consisting essentially of SEQ ID NO: 257. In some aspects, the antibody comprises a $V_L$ sequence comprising, consisting of, or consisting essentially of SEQ ID NO: 258. In some aspects, the antibody comprises a $V_L$ sequence comprising, consisting of, or consisting essentially of SEQ ID NO: 259. In some aspects, the antibody comprises a $V_L$ sequence comprising, consisting of, or consisting essentially of SEQ ID NO: 260. In some aspects, the antibody comprises a $V_L$ sequence comprising, consisting of, or consisting essentially of SEQ ID NO: 261. In some aspects, the antibody comprises a $V_L$ sequence comprising, consisting of, or consisting essentially of SEQ ID NO: 262. In some aspects, the antibody comprises a $V_L$ sequence comprising, consisting of, or consisting essentially of SEQ ID NO: 263. In some aspects, the antibody comprises a $V_L$ sequence comprising, consisting of, or consisting essentially of SEQ ID NO: 264. In some aspects, the antibody comprises a $V_L$ sequence comprising, consisting of, or consisting essentially of SEQ ID NO: 265. In some aspects, the antibody comprises a $V_L$ sequence comprising, consisting of, or consisting essentially of SEQ ID NO: 266. In some aspects, the antibody comprises a $V_L$ sequence comprising, consisting of, or consisting essentially of SEQ ID NO: 267. In some aspects, the antibody comprises a $V_L$ sequence comprising, consisting of, or consisting essentially of SEQ ID NO: 268. In some aspects, the antibody comprises a $V_L$ sequence comprising, consisting of, or consisting essentially of SEQ ID NO: 269. In some aspects, the antibody comprises a $V_L$ sequence comprising, consisting of, or consisting essentially of SEQ ID NO: 270. In some aspects, the antibody comprises a $V_L$ sequence comprising, consisting of, or consisting essentially of SEQ ID NO: 281. In some aspects, the antibody comprises a $V_L$ sequence comprising, consisting of, or consisting essentially of SEQ ID NO: 282. In some aspects, the antibody comprises a $V_L$ sequence comprising, consisting of, or consisting essentially of SEQ ID NO: 283. In some aspects, the antibody comprises a $V_L$ sequence comprising, consisting of, or consisting essentially of SEQ ID NO: 284. In some aspects, the antibody comprises a $V_L$ sequence comprising, consisting of, or consisting essentially of SEQ ID NO: 285. In some aspects, the antibody comprises a $V_L$ sequence comprising, consisting of, or consisting essentially of SEQ ID NO: 286. In some aspects, the antibody comprises a $V_L$ sequence comprising, consisting of, or consisting essentially of SEQ ID NO: 287. In some aspects, the antibody comprises a $V_L$ sequence comprising, consisting of, or consisting essentially of SEQ ID NO: 288.

2.6.1. Variants of $V_L$ Sequences

In some embodiments, the $V_L$ sequences provided herein comprise, consist of, or consist essentially of a variant of an illustrative $V_L$ sequence provided in this disclosure.

In some aspects, the $V_L$ sequence comprises, consists of, or consists essentially of a variant of an illustrative $V_L$ sequence provided in this disclosure. In some aspects, the $V_L$ sequence comprises, consists of, or consists essentially of a sequence having at least 85%, 90%, 95%, 96%, 97%, 98%, 99%, or 99.05% identity with any of the illustrative $V_L$ sequences provided in this disclosure. In some aspects, the $V_L$ sequence comprises, consists of, or consists essentially of any of the illustrative $V_L$ sequences provided in this disclosure, with 1-25 amino acid substitutions, 1-20 amino acid substitutions, 1-15 amino acid substitutions, 1-10 amino acid substitutions, 1-5 amino acid substitutions, 1-3 amino acid substitutions, 1-2 amino acid substitutions, or 1 amino acid substitution. In some aspects, the amino acid substitutions are conservative amino acid substitutions.

2.6.2. Excluded $V_L$ Sequences

In some embodiments, the $V_L$ sequences provided herein do not comprise certain $V_L$ sequences.

In some aspects, the $V_L$ sequence does not comprise, consist of, or consist essentially of a sequence selected from SEQ ID NOs: 271-272. In some aspects, the $V_L$ sequence does not comprise, consist of, or consist essentially of SEQ ID NO: 271. In some aspects, the $V_L$ sequence does not comprise, consist of, or consist essentially of SEQ ID NO: 272.

2.7. Pairs 2.7.1. CDR-H3-CDR-L3 Pairs

In some embodiments, the antibody comprises a CDR-H3 sequence and a CDR-L3 sequence. In some aspects, the CDR-H3 sequence is part of a $V_H$ and the CDR-L3 sequence is part of a $V_L$.

In some aspects, the CDR-H3 sequence is a CDR-H3 sequence comprising, consisting of, or consisting essentially of SEQ ID NOs: 129-156 and the CDR-L3 sequence is a CDR-L3 sequence comprising, consisting of, or consisting essentially of SEQ ID NOs: 201-219.

In some aspects, the CDR-H3 sequence is SEQ ID NO: 129, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 130, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 131, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 132, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 133, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 134, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 135, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 136, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 137, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 138, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 139, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 140, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 141, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 142, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 143, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 144, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 145, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 146, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 147, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 148, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 149, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 150, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 151, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 152, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 153, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 154, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

2.7.1.1. Variants of CDR-H3-CDR-L3 Pairs

In some embodiments, the CDR-H3-CDR-L3 pairs provided herein comprise a variant of an illustrative CDR-H3 and/or CDR-L1 sequence provided in this disclosure.

In some aspects, the CDR-H3 sequence comprises, consists of, or consists essentially of a variant of an illustrative CDR-H3 sequence provided in this disclosure. In some aspects, the CDR-H3 sequence comprises, consists of, or consists essentially of a sequence having at least 70%, 75%, 80%, 85%, 90%, or 95% identity with any of the illustrative CDR-H3 sequences provided in this disclosure. In some aspects, the CDR-H3 sequence comprises, consists of, or consists essentially of any of the illustrative CDR-H3 sequences provided in this disclosure, with 1, 2, or 3 amino acid substitutions. In some aspects, the amino acid substitutions are conservative amino acid substitutions.

In some aspects, the CDR-L3 sequence comprises, consists of, or consists essentially of a variant of an illustrative CDR-L3 sequence provided in this disclosure. In some aspects, the CDR-L3 sequence comprises, consists of, or consists essentially of a sequence having at least 70%, 75%, 80%, 85%, 90%, or 95% identity with any of the illustrative CDR-L3 sequences provided in this disclosure. In some aspects, the CDR-L3 sequence comprises, consists of, or consists essentially of any of the illustrative CDR-L3 sequences provided in this disclosure, with 1, 2, or 3 amino acid substitutions. In some aspects, the amino acid substitutions are conservative amino acid substitutions.

2.7.1.2. Excluded CDR-H3-CDR-L3 Pairs

In some embodiments, the CDR-H3-CDR-L3 pairs provided herein do not comprise certain CDR-H3-CDR-L3 pairs.

In some aspects, the CDR-H3 sequence is not SEQ ID NO: 157, and the CDR-L3 sequence not SEQ ID NO: 220. In some aspects, the CDR-H3 sequence is not SEQ ID NO: 158, and the CDR-L3 sequence not SEQ ID NO: 220. In some aspects, the CDR-H3 sequence is not SEQ ID NO: 159, and the CDR-L3 sequence not SEQ ID NO: 220. In some aspects, the CDR-H3 sequence is not SEQ ID NO: 160, and the CDR-L3 sequence not SEQ ID NO: 220.

2.7.2. $V_H$-$V_L$ Pairs

In some embodiments, the antibody comprises a $V_H$ sequence and a $V_L$ sequence.

In some aspects, the $V_H$ sequence is a $V_H$ sequence comprising, consisting of, or consisting essentially of SEQ ID NOs: 230-251 and 273-280, and the $V_L$ sequence is a $V_L$ sequence comprising, consisting of, or consisting essentially of SEQ ID NOs: 256-270 and 281-288.

In some aspects, the $V_H$ sequence is SEQ ID NO: 230, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 231, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 232, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 233, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 234, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 235, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 236, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 237, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 238, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 239, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 240, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 241, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 242, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 243, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 244, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 245, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 246, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 247, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 248, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 249, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 250, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 251, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 273, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 274, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 275, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 276, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 277, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 278, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 279, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 280, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

2.7.2.1. Variants of $V_H$-$V_L$ Pairs

In some embodiments, the $V_H$-$V_L$ pairs provided herein comprise a variant of an illustrative $V_H$ and/or $V_L$ sequence provided in this disclosure.

In some aspects, the $V_H$ sequence comprises, consists of, or consists essentially of a variant of an illustrative $V_H$ sequence provided in this disclosure. In some aspects, the $V_H$ sequence comprises, consists of, or consists essentially of a sequence having at least 85%, 90%, 95%, 96%, 97%, 98%, 99%, or 99.1% identity with any of the illustrative $V_H$ sequences provided in this disclosure. In some aspects, the $V_H$ sequence comprises, consists of, or consists essentially of any of the illustrative $V_H$ sequences provided in this disclosure, with 1-25 amino acid substitutions, 1-20 amino acid substitutions, 1-15 amino acid substitutions, 1-10 amino acid substitutions, 1-5 amino acid substitutions, 1-3 amino acid substitutions, 1-2 amino acid substitutions, or 1 amino acid substitution. In some aspects, the amino acid substitutions are conservative amino acid substitutions.

In some aspects, the $V_L$ sequence comprises, consists of, or consists essentially of a variant of an illustrative $V_L$ sequence provided in this disclosure. In some aspects, the $V_L$ sequence comprises, consists of, or consists essentially of a sequence having at least 85%, 90%, 95%, 96%, 97%, 98%, 99%, or 99.05% identity with any of the illustrative $V_L$ sequences provided in this disclosure. In some aspects, the $V_L$ sequence comprises, consists of, or consists essentially of any of the illustrative $V_L$ sequences provided in this disclosure, with 1-25 amino acid substitutions, 1-20 amino acid substitutions, 1-15 amino acid substitutions, 1-10 amino acid substitutions, 1-5 amino acid substitutions, 1-3 amino acid substitutions, 1-2 amino acid substitutions, or 1 amino acid substitution. In some aspects, the amino acid substitutions are conservative amino acid substitutions.

2.7.2.2. Excluded $V_H$-$V_L$ Pairs

In some embodiments, the $V_H$-$V_L$ pairs provided herein do not comprise certain $V_H$-$V_L$ pairs.

In some aspects, the $V_H$ sequence is not selected from SEQ ID NOs: 252-255, and the $V_L$ sequence is not selected from SEQ ID NOs: 271-272.

In some aspects, the $V_H$ sequence is not SEQ ID NO: 252, and the $V_L$ sequence is not selected from SEQ ID NO: 271-272. In some aspects, the $V_L$ sequence is not SEQ ID NO: 271. In some aspects, the $V_L$ sequence is not SEQ ID NO: 272.

In some aspects, the $V_H$ sequence is not SEQ ID NO: 253, and the $V_L$ sequence is not selected from SEQ ID NO: 271-272. In some aspects, the $V_L$ sequence is not SEQ ID NO: 271. In some aspects, the $V_L$ sequence is not SEQ ID NO: 272.

In some aspects, the $V_H$ sequence is not SEQ ID NO: 254, and the $V_L$ sequence is not selected from SEQ ID NO: 271-272. In some aspects, the $V_L$ sequence is not SEQ ID NO: 271. In some aspects, the $V_L$ sequence is not SEQ ID NO: 272.

In some aspects, the $V_H$ sequence is not SEQ ID NO: 255, and the $V_L$ sequence is not selected from SEQ ID NO: 271-272. In some aspects, the $V_L$ sequence is not SEQ ID NO: 271. In some aspects, the $V_L$ sequence is not SEQ ID NO: 272.

2.8. Consensus Sequences

In particular embodiments, provided herein are anti-CD74 antibodies comprising one or more consensus sequences. Each consensus sequences is based, at least in part, on one or more alignments of two or more useful anti-CD74 CDR sequences provided in this disclosure. Based on such alignments, a person of skill in the art would recognize that different amino acid residues may useful in certain positions of the CDRs. Accordingly, each consensus sequence encompasses two or more useful anti-CD74 CDR sequences.

2.8.1. CDR-H3 Consensus Sequences

In some embodiments, the antibody comprises a CDR-H3 sequence defined by the consensus sequence G-G-$\alpha_3$-$\alpha_4$-$\alpha_5$-$\alpha_6$-$\alpha_7$-$\alpha_8$-$\alpha_9$-$\alpha_{10}$-G-$\alpha_{12}$-D-V, where: $\alpha_3$ is T, S, Q, M, or A; $\alpha_4$ is R, L, or V; $\alpha_5$ is V, E, A, G, I, D, or M; $\alpha_6$ is R, L, H, G, Q, or T; $\alpha_7$ is G or R; $\alpha_8$ is A, L, E, or G; $\alpha_9$ is V, I, M, F, R, or L; $\alpha_{10}$ is Y, H, F, or S; and $\alpha_{12}$ is T, L, H, or N.

In some aspects, if $\alpha_9$ is M, then either $\alpha_3$ is not T, $\alpha_4$ is not L, $\alpha_5$ is not V, $\alpha_6$ is not R, $\alpha_7$ is not G, $\alpha_8$ is not A, $\alpha_{10}$ is not Y, $\alpha_{12}$ is not T, or combinations thereof.

In some aspects, $\alpha_9$ is V, I, F, R, or L.

In some aspects, $\alpha_6$ is L, H, G, Q, or T.

In some aspects, $\alpha_3$ is not T. In some aspects, $\alpha_4$ is not L. In some aspects, $\alpha_5$ is not V. In some aspects, $\alpha_6$ is not R. In some aspects, $\alpha_7$ is not G. In some aspects, $\alpha_8$ is not A. In some aspects, $\alpha_9$ is not M. In some aspects, $\alpha_{10}$ is not Y. In some aspects, $\alpha_{12}$ is not T.

2.8.2. Chothia CDR-H2 Consensus Sequences

In some embodiments, the antibody comprises a Chothia CDR-H2 sequence defined by the consensus sequence $\beta_1$-$\beta_2$-D-$\beta_4$-S-$\beta_6$, where: $\beta_1$ is W or S; $\beta_2$ is Y, D, or H; $\beta_4$ is G or A; and $\beta_6$ is N, I, D, H, K, or R.

In some aspects, β1 is W.

In some aspects, β6 is I.

In some aspects, $\beta_1$ is not S. In some aspects, $\beta_2$ is not Y. In some aspects, $\beta_4$ is not G. In some aspects, $\beta_6$ is not N or I.

2.8.3. Chothia CDR-H1 Consensus Sequences

In some embodiments, the antibody comprises a Chothia CDR-H1 sequence defined by the consensus sequence G-F-$\delta_3$-F-$\delta_5$-$\delta_6$-$\delta_7$, where: $\delta_3$ is T, N, S, A, or D; $\delta_5$ is S, G, D, or A; $\delta_6$ is S or D; and $\delta_7$ is Y, H, or F.

In some aspects, $\delta_3$ is N, S, A, or D.

In some aspects, $\delta_3$ is not T. In some aspects, $\delta_5$ is not S. In some aspects, $\delta_6$ is not S. In some aspects, $\delta_7$ is not Y.

2.8.4. Kabat CDR-H2 Consensus Sequences

In some embodiments, the antibody comprises a Kabat CDR-H2 sequence defined by the consensus sequence V-$\gamma_2$-$\gamma_3$-$\gamma_4$-D-$\gamma_6$-S-$\gamma_8$-$\gamma_9$-$\gamma_{10}$-Y-A-$\gamma_{13}$-S-V-K-G, where: $\gamma_2$ is I, T, or V; $\gamma_3$ is W or S; $\gamma_4$ is Y, D, or H; $\gamma_6$ is G or A; $\gamma_8$ is N, I, D, H, K, or R; $\gamma_9$ is K, E, R, S, T, or D; $\gamma_{10}$ is Y, I, V, K, or N; and $\gamma_{13}$ is D or G.

In some aspects, γ9 is E, R, S, T, or D.

In some aspects, $\gamma_2$ is not I. In some aspects, $\gamma_3$ is not S or W. In some aspects, $\gamma_4$ is not Y. In some aspects, $\gamma_6$ is not G. In some aspects, $\gamma_8$ is not N or I. In some aspects, $\gamma_9$ is not K. In some aspects, $\gamma_{10}$ is not Y. In some aspects, $\gamma_{13}$ is not D.

In some embodiments, the antibody comprises a Kabat CDR-H2 sequence defined by the consensus sequence V-$\sigma_2$-W-$\sigma_4$-D-$\sigma_6$-S-$\sigma_8$-$\sigma_9$-$\sigma_{10}$-Y-A-$\sigma_{13}$-S-V-K-G, where: $\sigma_2$ is I, T, or V; $\sigma_4$ is Y, D, or H; $\sigma_6$ is G or A; $\sigma_8$ is N, I, D, H, K, or R; $\sigma_9$ is K, E, R, S, T, or D; $\sigma_{10}$ is Y, I, V, K, or N; and $\sigma_{13}$ is D or G.

In some aspects, if $\sigma_2$ is I, then either $\sigma_4$ is not Y, $\sigma_6$ is not G, a is not N, $\sigma_9$ is not K, $\sigma_{10}$ is not Y, $\sigma_{13}$ is not D, or combinations thereof.

In some aspects, $\sigma_2$ is not I. In some aspects, $\sigma_3$ is not S or W. In some aspects, $\sigma_4$ is not Y. In some aspects, $\sigma_6$ is not G. In some aspects, $\sigma_8$ is not N or I. In some aspects, $\sigma_9$ is not K. In some aspects, $\sigma_m$ is not Y. In some aspects, $\sigma_{13}$ is not D.

2.8.5. Kabat CDR-H1 Consensus Sequences

In some embodiments, the antibody comprises a Kabat CDR-H1 sequence defined by the consensus sequence $\varepsilon_1$-$\varepsilon_2$-$\varepsilon_3$-M-H, where: $\varepsilon_1$ is S or D; $\varepsilon_2$ is Y, H, or F; and $\varepsilon_3$ is G or A.

In some aspects, $\varepsilon_1$ is D.

In some aspects, $\varepsilon_1$ is not S. In some aspects, $\varepsilon_2$ is not Y. In some aspects, $\varepsilon_3$ is not A or G.

2.8.6. CDR-L3 Consensus Sequences

In some embodiments, the antibody comprises a CDR-L3 sequence defined by the consensus sequence Q-$\Theta_2$-$\Theta_3$-$\Theta_4$-$\Theta_5$-$\Theta_6$-P-$\Theta_8$-T, where: $\Theta_2$ is Q or H; $\Theta_3$ is Y, H, Q, or N; $\Theta_4$ is N, Y, Q, H, or C; $\Theta_5$ is T, S, I, Y, P, L, or A; $\Theta_6$ is Y, T, W, or A; and $\Theta_8$ is L or P.

In some aspects, $\Theta_5$ is T, I, Y, P, L, or A.

In some aspects, $\Theta_2$ is not Q. In some aspects, $\Theta_3$ is not Y. In some aspects, $\Theta_4$ is not N. In some aspects, $\Theta_5$ is not S. In some aspects, $\Theta_6$ is not Y. In some aspects, $\Theta_8$ is not L.

2.8.7. CDR-L2 Consensus Sequences

In some embodiments, the antibody comprises a CDR-L2 sequence defined by the consensus sequence $\pi_1$-$\pi_2$-$\pi_3$-$\pi_4$-$\pi_5$-$\pi_6$-$\pi_7$, where: $\pi_1$ is G, A, L, S, or N; $\pi_2$ is A, S, G, or R; $\pi_3$ is S, D, T, N, or R; $\pi_4$ is S, R, Y, Q, or L; $\pi_5$ is L or R; $\pi_6$ is Q or A; and $\pi_7$ is S, T, or I.

In some aspects, $\pi_7$ is S.

In some aspects, $\pi_1$ is not A. In some aspects, $\pi_2$ is not A. In some aspects, $\pi_3$ is not S. In some aspects, $\pi_4$ is not S. In some aspects, $\pi_5$ is not L. In some aspects, $\pi_6$ is not Q. In some aspects, $\pi_7$ is not S.

2.8.8. CDR-L1 Consensus Sequences

In some embodiments, the antibody comprises a CDR-L1 sequence defined by the consensus sequence R-A-$\mu_3$-Q-$\mu_5$-$\mu_6$-$\mu_7$-$\mu_8$-$\mu_9$-$\mu_{10}$-$\mu_{11}$-$\mu_{12}$, where: $\mu_3$ is S or G; $\mu_5$ is G, S, D, or R; $\mu_6$ is V, I, or L; $\mu_7$ is S, G, F, A, or Y; $\mu_8$ is S, R, or G; $\mu_9$ is S, I, N, R, or nothing (i.e., not present); $\mu_{10}$ is W, Y, F, E, or D; $\mu_{11}$ is L or V; and $\mu_{12}$ is A, S, or G.

In some aspects, $\mu_7$ is G, F, A, or Y.

In some aspects, $\mu_3$ is not S. In some aspects, $\mu_5$ is not G. In some aspects, $\mu_6$ is not I. In some aspects, $\mu_7$ is not S. In some aspects, $\mu_8$ is not S. In some aspects, $\mu_9$ is present. In some aspects, $\mu_{10}$ is not W. In some aspects, $\mu_{11}$ is not L. In some aspects, $\mu_{12}$ is not A.

3. Thermostability

In some embodiments, the antibody is characterized by particular thermostability parameters. As described in Example 16, the thermostability of an antibody may be characterized by measuring its melting temperatures. The melting temperatures include Tm1 and Tm2. Tm1 represents the melting of the Fc domain of an IgG, while Tm2 represents the melting of the Fab domain of an IgG.

In some embodiments, the Tm2 of the antibody is at least 75° C., 75.5° C., 76° C., 76.5° C., 77° C., 77.5° C., 78° C., 78.5° C., or 79° C. In some embodiments, the Tm2 of the antibody is between about 75° C. and about 80° C. In some embodiments, the Tm2 of the antibody is between about 76° C. and about 79° C. In some embodiments, the Tm2 of the antibody is between about 77° C. and about 78° C. In some aspects, the Tm2s described above are for aglycosylated versions of the antibody.

In some embodiments, the Tm1 of the antibody is between about 59° C. and about 62.2° C. In some embodiments, the Tm1 of the antibody is less than 62.2° C. In some embodiments, the Tm1 of the antibody is less than 61° C. In some embodiments, the Tm1 of the antibody is less than 60° C. In some aspects, the Tm1s described above are for aglycosylated versions of the antibody.

4. Affinity

In some embodiments, the affinity of the antibody for CD74, as indicated by $K_D$, is less than about $10^{-5}$ M, less than about $10^{-6}$ M, less than about $10^{-7}$ M, less than about $10^{-8}$ M, less than about $10^{-9}$ M, less than about $10^{-10}$ M, less than about $10^{-11}$ M, or less than about $10^{-12}$ M. In some embodiments, the affinity of the antibody is between about $10^{-7}$ M and $10^{-11}$ M. In some embodiments, the affinity of the antibody is between about $10^{-7}$ M and $10^{-10}$ M. In some embodiments, the affinity of the antibody is between about $10^{-7}$ M and $10^{-9}$ M. In some embodiments, the affinity of the antibody is between about $10^{-7}$ M and $10^{-8}$ M. In some embodiments, the affinity of the antibody is between about $10^{-8}$ M and $10^{-11}$ M. In some embodiments, the affinity of the antibody is between about $10^{-9}$ M and $10^{-11}$ M. In some embodiments, the affinity of the antibody is between about $10^{-10}$ M and $10^{-11}$ M. In some embodiments, the affinity of the antibody is between about $1.08\times10^{-7}$ M and $9.57\times10^{-10}$ M. In some embodiments, the affinity of the antibody is $2.52\times10^{-10}$ M, or less. In some embodiments, the affinity of the antibody is about $2.52\times10^{-10}$ M. In some embodiments, the affinity of the antibody is about $3.54\times10^{-10}$ M. In some embodiments, the affinity of the antibody is between about $2.52\times10^{-10}$ M and about $3.54\times10^{-10}$ M. In some aspects, the $K_D$ is determined at 25° C.

In some embodiments the antibody has a $k_a$ of at least about $10^5$ $M^{-1}\times sec^{-1}$. In some embodiments the antibody has a $k_a$ of at least about $10^6$ $M^{-1}\times sec^{-1}$. In some embodiments the antibody has a $k_a$ of between about $10^5$ $M^{-1}\times sec^{-1}$ and about $10^6$ $M^{-1}\times sec^{-1}$. In some embodiments the antibody has a $k_a$ of between about $1.66\times10^5$ $M^{-1}\times sec^{-1}$ and about $1.07\times10^6$ $M^{-1}\times sec^{-1}$. In some embodiments the antibody has a $k_a$ of about $3.09\times10^5$ $M^{-1}\times sec^{-1}$, or more. In some embodiments the antibody has a $k_a$ of about $3.09\times10^5$ $M^{-1}\times sec^{-1}$. In some embodiments the antibody has a $k_a$ of about $3.38\times10^5$ $M^{-1}\times sec^{-1}$. In some embodiments the antibody has a $k_a$ between about $3.09\times10^5$ $M^{-1}\times sec^{-1}$ and about $3.38\times10^5$ $M^{-1}\times sec^{-1}$. In some aspects, the $k_a$ is determined at 25° C.

In some embodiments the antibody has a $k_d$ of about $10^{-4}$ $sec^{-1}$ or less. In some embodiments the antibody has a $k_d$ of about $10^{-5}$ $sec^{-1}$ or less. In some embodiments the antibody has a $k_d$ of between about $10^{-4}$ $sec^{-1}$ and about $10^{-5}$ $sec^{-1}$. In some embodiments the antibody has a $k_d$ of between about $2.35\times10^{-4}$ $sec^{-1}$ and about $7.10\times10^{-5}$ $sec^{-1}$. In some embodiments the antibody has a $k_d$ of about $7.77\times10^{-5}$ $sec^{-1}$, or less. In some embodiments the antibody has a $k_d$ of about $7.77\times10^{-5}$ $sec^{-1}$. In some embodiments the antibody has a $k_d$ of about $1.20\times10^{-4}$ $sec^{-1}$. In some embodiments the antibody has a $k_d$ between about $1.20\times10^{-4}$ $sec^{-1}$ and about $7.77\times10^{-5}$ $sec^{-1}$. In some aspects, the $k_d$ is determined at 25° C.

5. $IC_{50}$ in Secondary Antibody-Drug Conjugate (ADC) Assay

In some embodiments, the antibody has an $IC_{50}$ in a secondary antibody-drug conjugate (ADC) cell killing assay, as described in Example 5. In some embodiments, the $IC_{50}$ is from about 0.001 to about 1 nM. In some aspects, the $IC_{50}$ is from about 0.001 to about 0.5 nM. In some aspects, the $IC_{50}$ is from about 0.001 to about 0.25 nM. In some aspects, the $IC_{50}$ is from about 0.001 to about 0.1 nM. In some aspects, the $IC_{50}$ is from about 0.001 to about 0.05 nM. In some aspects, the $IC_{50}$ is from about 0.001 to about 0.025 nM. In some aspects, the $IC_{50}$ is from about 0.001 to about 0.009 nM. In some aspects, the $IC_{50}$ is from about 0.001 to about 0.005 nM.

6. Glycosylation Variants

In certain embodiments, an antibody may be altered to increase, decrease or eliminate the extent to which it is glycosylated. Glycosylation of polypeptides is typically either "N-linked" or "O-linked."

"N-linked" glycosylation refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site.

"O-linked" glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition or deletion of N-linked glycosylation sites to the antibody may be accomplished by altering the amino acid sequence such that one or more of the above-described tripeptide sequences is created or removed. Addition or deletion of O-linked glycosylation sites may be accomplished by addition, deletion, or substitution of one or more serine or threonine residues in or to (as the case may be) the sequence of an antibody.

7. Fc Variants

In certain embodiments, amino acid modifications may be introduced into the Fc region of an antibody provided herein to generate an Fc region variant. In certain embodiments, the Fc region variant possesses some, but not all, effector functions. Such antibodies may be useful, for example, in applications in which the half-life of the antibody in vivo is important, yet certain effector functions are unnecessary or deleterious. Examples of effector functions include complement-dependent cytotoxicity (CDC) and antibody-directed complement-mediated cytotoxicity (ADCC). Numerous substitutions or substitutions or deletions with altered effector function are known in the art.

An alteration in CDC and/or ADCC activity can be confirmed using in vitro and/or in vivo assays. For example, Fc receptor (FcR) binding assays can be conducted to measure FcγR binding. The primary cells for mediating ADCC, NK cells, express FcγRIII only, whereas monocytes express FcγRI, FcγRII and FcγRIII. FcR expression on hematopoietic cells is summarized in Ravetch and Kinet, *Ann. Rev. Immunol.,* 1991, 9:457-492.

Non-limiting examples of in vitro assays to assess ADCC activity of a molecule of interest are provided in U.S. Pat. Nos. 5,500,362 and 5,821,337; Hellstrom et al., *Proc. Natl. Acad. Sci. U.S.A.,* 1986, 83:7059-7063; Hellstrom et al., *Proc. Natl. Acad. Sci. U.S.A.,* 1985, 82:1499-1502; and Bruggemann et al., *J. Exp. Med.,* 1987, 166:1351-1361. Useful effector cells for such assays include peripheral blood mononuclear cells (PBMC) and Natural Killer (NK) cells. Alternatively, or additionally, ADCC activity of the molecule of interest may be assessed in vivo, using an animal model such as that disclosed in Clynes et al. *Proc. Natl. Acad. Sci. U.S.A.,* 1998, 95:652-656.

C1q binding assays may also be carried out to confirm that the antibody is unable to bind C1q and hence lacks CDC activity. Examples of C1q binding assays include those described in WO 2006/029879 and WO 2005/100402.

Complement activation assays include those described, for example, in Gazzano-Santoro et al., *J. Immunol. Methods,* 1996, 202:163-171; Cragg et al., *Blood,* 2003, 101: 1045-1052; and Cragg and Glennie, *Blood,* 2004, 103:2738-2743.

FcRn binding and in vivo clearance (half-life determination) can also be measured, for example, using the methods described in Petkova et al., *Intl. Immunol.,* 2006, 18:1759-1769.

8. Preparation of Antibodies 8.1. Antigen Preparation

The CD74 antigen to be used for production of antibodies may be intact CD74 or a fragment of CD74. Other forms of CD74 useful for generating antibodies will be apparent to those skilled in the art.

8.2. Monoclonal Antibodies

Monoclonal antibodies may be obtained, for example, using the hybridoma method first described by Kohler et al., *Nature,* 1975, 256:495-497, and/or by recombinant DNA methods (see e.g., U.S. Pat. No. 4,816,567). Monoclonal antibodies may also be obtained, for example, using phage or yeast-based libraries. See e.g., U.S. Pat. Nos. 8,258,082 and 8,691,730.

In the hybridoma method, a mouse or other appropriate host animal is immunized to elicit lymphocytes that produce or are capable of producing antibodies that will specifically bind to the protein used for immunization. Alternatively, lymphocytes may be immunized in vitro. Lymphocytes are then fused with myeloma cells using a suitable fusing agent, such as polyethylene glycol, to form a hybridoma cell. See Goding J. W., *Monoclonal Antibodies: Principles and Practice* 3rd ed. (1986) Academic Press, San Diego, Calif.

The hybridoma cells are seeded and grown in a suitable culture medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Useful myeloma cells are those that fuse efficiently, support stable high-level production of antibody by the selected antibody-producing cells, and are sensitive media conditions, such as the presence or absence of HAT medium. Among these, preferred myeloma cell lines are murine myeloma lines, such as those derived from MOP-21 and MC-11 mouse tumors (available from the Salk Institute Cell Distribution Center, San Diego, Calif.), and SP-2 or X63-Ag8-653 cells (available from the American Type Culture Collection, Rockville, Md.). Human myeloma and mouse-human heteromyeloma cell lines also have been described for the production of human monoclonal antibodies. See e.g., Kozbor, *J. Immunol.,* 1984, 133:3001.

After the identification of hybridoma cells that produce antibodies of the desired specificity, affinity, and/or biological activity, selected clones may be subcloned by limiting dilution procedures and grown by standard methods. See Goding, supra. Suitable culture media for this purpose include, for example, D-MEM or RPMI-1640 medium. In addition, the hybridoma cells may be grown in vivo as ascites tumors in an animal.

DNA encoding the monoclonal antibodies may be readily isolated and sequenced using conventional procedures (e.g., by using oligonucleotide probes that are capable of binding specifically to genes encoding the heavy and light chains of the monoclonal antibodies). Thus, the hybridoma cells can serve as a useful source of DNA encoding antibodies with the desired properties. Once isolated, the DNA may be placed into expression vectors, which are then transfected into host cells such as bacteria (e.g., *E. coli*), yeast (e.g., *Saccharomyces* or *Pichia* sp.), COS cells, Chinese hamster ovary (CHO) cells, or myeloma cells that do not otherwise produce antibody, to produce the monoclonal antibodies.

8.3. Humanized Antibodies

Humanized antibodies may be generated by replacing most, or all, of the structural portions of a monoclonal antibody with corresponding human antibody sequences. Consequently, a hybrid molecule is generated in which only the antigen-specific variable, or CDR, is composed of non-human sequence. Methods to obtain humanized antibodies include those described in, for example, Winter and Milstein, *Nature,* 1991, 349:293-299; Rader et al., *Proc. Nat. Acad. Sci. U.S.A.,* 1998, 95:8910-8915; Steinberger et al., *J. Biol. Chem.,* 2000, 275:36073-36078; Queen et al., *Proc. Natl. Acad. Sci. U.S.A.,* 1989, 86:10029-10033; and U.S. Pat. Nos. 5,585,089, 5,693,761, 5,693,762, and 6,180,370.

8.4. Human Antibodies

Human antibodies can be generated by a variety of techniques known in the art, for example by using transgenic animals (e.g., humanized mice). See, e.g., Jakobovits et al., *Proc. Natl. Acad. Sci. U.S.A.,* 1993, 90:2551; Jakobovits et al., *Nature,* 1993, 362:255-258; Bruggermann et al., *Year in Immuno.,* 1993, 7:33; and U.S. Pat. Nos. 5,591,669, 5,589,369 and 5,545,807. Human antibodies can also be derived from phage-display libraries (see e.g., Hoogenboom et al., *J. Mol. Biol.,* 1991, 227:381-388; Marks et al., *J. Mol. Biol.,* 1991, 222:581-597; and U.S. Pat. Nos. 5,565,332 and 5,573,905). Human antibodies may also be generated by in vitro activated B cells (see e.g., U.S. Pat. Nos. 5,567,610 and 5,229,275). Human antibodies may also be derived from yeast-based libraries (see e.g., U.S. Pat. No. 8,691,730).

9. Vectors, Host Cells, and Recombinant Methods

The invention also provides isolated nucleic acids encoding anti-CD74 antibodies, vectors and host cells comprising the nucleic acids, and recombinant techniques for the production of the antibodies.

For recombinant production of the antibody, the nucleic acid encoding it may be isolated and inserted into a replicable vector for further cloning (i.e., amplification of the DNA) or expression. In some aspects, the nucleic acid may be produced by homologous recombination, for example as described in U.S. Pat. No. 5,204,244.

Many different vectors are known in the art. The vector components generally include, but are not limited to, one or more of the following: a signal sequence, an origin of replication, one or more marker genes, an enhancer element, a promoter, and a transcription termination sequence, for example as described in U.S. Pat. No. 5,534,615.

Illustrative examples of suitable host cells are provided below. these host cells are not meant to be limiting.

Suitable host cells include any prokaryotic (e.g., bacterial), lower eukaryotic (e.g., yeast), or higher eukaryotic (e.g., mammalian) cells. Suitable prokaryotes include eubacteria, such as Gram-negative or Gram-positive organisms, for example, Enterobacteriaceae such as *Escherichia* (*E. coli*), *Enterobacter, Erwinia, Klebsiella, Proteus, Salmonella* (*S. typhimurium*), *Serratia* (*S. marcescans*), *Shigella*, Bacilli (*B. subtilis* and *B. licheniformis*), *Pseudomonas* (*P. aeruginosa*), and *Streptomyces*. One useful *E. coli* cloning host is *E. coli* 294, although other strains such as *E. coli* B, *E. coli* X1776, and *E. coli* W3110 are suitable.

In addition to prokaryotes, eukaryotic microbes such as filamentous fungi or yeast are also suitable cloning or expression hosts for anti-CD74 antibody-encoding vectors. *Saccharomyces cerevisiae*, or common baker's yeast, is a commonly used lower eukaryotic host microorganism. However, a number of other genera, species, and strains are available and useful, such as *Schizosaccharomyces pombe, Kluyveromyces* (*K. lactis, K. fragilis, K. bulgaricus K. wickeramii, K. waltii, K. drosophilarum, K. thermotolerans*, and *K. marxianus*), *Yarrowia, Pichia pastoris, Candida* (*C. albicans*), *Trichoderma reesia, Neurospora crassa, Schwanniomyces* (*S. occidentalis*), and filamentous fungi such as, for example *Penicillium, Tolypocladium*, and *Aspergillus* (*A. nidulans* and *A. niger*).

Useful mammalian host cells include COS-7 cells, HEK293 cells; baby hamster kidney (BHK) cells; Chinese hamster ovary (CHO); mouse sertoli cells; African green monkey kidney cells (VERO-76), and the like.

The host cells used to produce the anti-CD74 antibody of this invention may be cultured in a variety of media. Commercially available media such as, for example, Ham's F10, Minimal Essential Medium (MEM), RPMI-1640, and Dulbecco's Modified Eagle's Medium (DMEM) are suitable for culturing the host cells. In addition, any of the media described in Ham et al., *Meth. Enz.,* 1979, 58:44; Barnes et al., *Anal. Biochem.,* 1980, 102:255; and U.S. Pat. Nos. 4,767,704, 4,657,866, 4,927,762, 4,560,655, and 5,122,469, or WO 90/03430 and WO 87/00195 may be used.

Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics, trace elements (defined as inorganic compounds usually present at final concentrations in the micromolar range), and glucose or an equivalent energy source. Any other necessary supplements may also be included at appropriate concentrations that would be known to those skilled in the art.

The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. For example, Carter et al. (*Bio/Technology,* 1992, 10:163-167) describes a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation.

In some embodiments, the antibody is produced in a cell-free system. In some aspects, the cell-free system is an in vitro transcription and translation system as described in Yin et al., *mAbs,* 2012, 4:217-225, incorporated by reference in its entirety. In some aspects, the cell-free system utilizes a cell-free extract from a eukaryotic cell or from a prokaryotic cell. In some aspects, the prokaryotic cell is *E. coli*. Cell-free expression of the antibody may be useful, for example, where the antibody accumulates in a cell as an insoluble aggregate, or where yields from periplasmic expression are low.

Where the antibody is secreted into the medium, supernatants from such expression systems are generally first concentrated using a commercially available protein concentration filter, for example, an Amicon® or Millipore® Pellcon® ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being a particularly useful purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.,* 1983, 62:1-13). Protein G is useful for all mouse isotypes and for human γ3 (Guss et al., *EMBO J.,* 1986, 5:1567-1575).

The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the BakerBond ABX® resin is useful for purification.

Other techniques for protein purification, such as fractionation on an ion-exchange column, ethanol precipitation, Reverse Phase HPLC, chromatography on silica, chromatography on heparin Sepharose®, chromatofocusing, SDS-PAGE, and ammonium sulfate precipitation are also available, and can be applied by one of skill in the art.

Following any preliminary purification step(s), the mixture comprising the antibody of interest and contaminants may be subjected to low pH hydrophobic interaction chromatography using an elution buffer at a pH between about 2.5-4.5, generally performed at low salt concentrations (e.g., from about 0-0.25 M salt).

10. Pharmaceutical Compositions and Methods of Administration

The antibodies provided herein can be formulated into pharmaceutical compositions using methods available in the art and those disclosed herein. Any of the antibodies provided herein can be provided in the appropriate pharmaceutical composition and be administered by a suitable route of administration.

The methods provided herein encompass administering pharmaceutical compositions comprising at least one antibody provided herein and one or more compatible and pharmaceutically acceptable carriers. In this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" includes a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water can be used as a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in Martin, E. W., *Remington's Pharmaceutical Sciences.*

In clinical practice the pharmaceutical compositions or antibodies provided herein may be administered by any route known in the art. In certain embodiments, a pharmaceutical composition or antibody provided herein is administered parenterally.

The compositions for parenteral administration can be emulsions or sterile solutions. Parenteral compositions may include, for example, propylene glycol, polyethylene glycol, vegetable oils, and injectable organic esters (e.g., ethyl oleate). These compositions can also contain wetting, isotonizing, emulsifying, dispersing and stabilizing agents. Sterilization can be carried out in several ways, for example using a bacteriological filter, by radiation or by heating. Parenteral compositions can also be prepared in the form of sterile solid compositions which can be dissolved at the time of use in sterile water or any other injectable sterile medium.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic antibodies.

Typical pharmaceutical compositions and dosage forms comprise one or more excipients. Suitable excipients are well-known to those skilled in the art of pharmacy, and non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific antibody in the dosage form. The composition or single unit dosage form, if desired, can also contain minor amounts of wetting or emulsifying agents, or pH buffering agents.

Lactose free compositions provided herein can comprise excipients that are well known in the art and are listed, for example, in the U.S. Pharmocopia (USP) SP (XXI)/NF (XVI). In general, lactose free compositions comprise an active ingredient, a binder/filler, and a lubricant in pharmaceutically compatible and pharmaceutically acceptable amounts. Exemplary lactose free dosage forms comprise an active ingredient, microcrystalline cellulose, pre gelatinized starch, and magnesium stearate.

Further encompassed herein are anhydrous pharmaceutical compositions and dosage forms comprising an antibody, since water can facilitate the degradation of some antibodies.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Further provided are pharmaceutical compositions and dosage forms that comprise one or more excipients that reduce the rate by which an antibody will decompose. Such antibodies, which are referred to herein as "stabilizers," include, but are not limited to, antioxidants such as ascorbic acid, pH buffers, or salt buffers.

10.1. Parenteral Dosage Forms

In certain embodiments, provided are parenteral dosage forms. Parenteral dosage forms can be administered to subjects by various routes including, but not limited to, subcutaneous, intravenous (including bolus injection), intramuscular, and intraarterial. Because their administration typically bypasses subjects' natural defenses against contaminants, parenteral dosage forms are typically, sterile or capable of being sterilized prior to administration to a subject. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Excipients that increase the solubility of one or more of the antibodies disclosed herein can also be incorporated into the parenteral dosage forms.

10.2. Dosage and Unit Dosage Forms

In human therapeutics, the doctor will determine the posology which he considers most appropriate according to a preventive or curative treatment and according to the age, weight, stage of the infection and other factors specific to the subject to be treated.

The amount of the antibody or composition which will be effective in the prevention or treatment of a disorder or one or more symptoms thereof will vary with the nature and severity of the disease or condition, and the route by which the antibody is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of the antibody per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). In certain embodiment, the dosage of the antibody provided herein, based on weight of the antibody, administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the composition or a composition provided herein administered to prevent, treat, manage, or ameliorate a disorder, or one or more symptoms thereof in a subject is 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.25 mg to 2.5 mg, 0.5 mg to 20 mg, 0.5 to 15 mg, 0.5 to 12 mg, 0.5 to 10 mg, 0.5 mg to 7.5 mg, 0.5 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

The dose can be administered according to a suitable schedule, for example, once, two times, three times, or for times weekly. It may be necessary to use dosages of the antibody outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the antibodies provided herein are also encompassed by the herein described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiments, treatment or prevention can be initiated with one or more loading doses of an antibody or composition provided herein followed by one or more maintenance doses.

In certain embodiments, a dose of an antibody or composition provided herein can be administered to achieve a steady-state concentration of the antibody in blood or serum of the subject. The steady-state concentration can be determined by measurement according to techniques available to those of skill or can be based on the physical characteristics of the subject such as height, weight and age.

In certain embodiments, administration of the same composition may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least 1 day, 2 days, 3 days, 5 days, 10 days, 15 days, 30 days, 45 days, 2 months, 75 days, 3 months, or 6 months.

11. Therapeutic Applications

For therapeutic applications, the antibodies of the invention are administered to a mammal, generally a human, in a pharmaceutically acceptable dosage form such as those known in the art and those discussed above. For example, the antibodies of the invention may be administered to a human intravenously as a bolus or by continuous infusion over a period of time, by intramuscular, intraperitoneal, intra-cerebrospinal, subcutaneous, intra-articular, intrasynovial, intrathecal, or intratumoral routes. The antibodies also are suitably administered by peritumoral, intralesional, or perilesional routes, to exert local as well as systemic therapeutic effects. The intraperitoneal route may be particularly useful, for example, in the treatment of ovarian tumors.

The antibodies provided herein may be useful for the treatment of any disease or condition involving upregulation of CD74. Upregulation of CD74 expression has been observed in cancers and autoimmune disease (Borghese et al., *Exp. Op. Ther. Targets,* 2011, 15:237-251, incorporated by reference in its entirety), as well as in infection (Hofman et al., *Modern Pathology,* 2007, 20:974-989, incorporated by reference in its entirety) and inflammatory conditions (Vera et al., *Exp. Biol. & Med.,* 2008, 233:620-626, incorporated by reference in its entirety). CD74 is known to be expressed at moderate to high levels in multiple myeloma. Burton et al., *Clin. Cancer Res.,* 2004, 10:6606-6611, incorporated by reference in its entirety. CD74 expression is also known to be a key factor associated with the progression of pancreatic cancer. Zhang et al., *Hepatobiliary Pancreat. Dis. Int.,* 2014, 13:81-86, incorporated by reference in its entirety.

12. Diagnostic Applications

In some embodiments, the antibodies provided herein are used in diagnostic applications. For example, an ant-CD74 antibody may be useful in assays for CD74 protein. In some aspects the antibody can be used to detect the expression of CD74 in various cells and tissues. These assays may be useful, for example, diagnosing cancer, infection and autoimmune disease.

In some diagnostic applications, the antibody may be labeled with a detectable moiety. Suitable detectable moieties include, but are not limited to radioisotopes, fluorescent labels, and enzyme-substrate labels. In another embodiment of the invention, the anti-CD74 antibody need not be labeled, and the presence thereof can be detected using a labeled antibody which specifically binds to the anti-CD74 antibody.

13. Affinity Purification Reagents

The antibodies of the invention may be used as affinity purification agents. In this process, the antibodies may be immobilized on a solid phase such a resin or filter paper, using methods well known in the art. The immobilized antibody is contacted with a sample containing the CD74 protein (or fragment thereof) to be purified, and thereafter the support is washed with a suitable solvent that will remove substantially all the material in the sample except the CD74 protein, which is bound to the immobilized antibody. Finally, the support is washed with another suitable solvent, such as glycine buffer, pH 5.0, that will release the CD74 protein from the antibody.

14. Kits

In some embodiments, an antibody of the present invention can be provided in a kit, i.e., a packaged combination of reagents in predetermined amounts with instructions for performing a procedure. In some embodiments, the procedure is a diagnostic assay. In other embodiments, the procedure is a therapeutic procedure.

EXAMPLES

Example 1: Generation and Primary Screening of Anti-CD74 Antibodies

Antibody Fab or scFv libraries were constructed using a standard overlap extension PCR protocol with mutagenic primers targeting CDRs. See Heckman and Pease, *Nat. Protoc.,* 2007, 2:924-932. Selections for novel antibodies were performed using standard ribosome display protocols. See Dreir and Plückthun, *Methods Mol. Biol.,* 2011, Clifton, N.J., 687:283-306. Specifically, scFv- or Fab-based selection formats were performed according to published protocols. See Hanes and Plückthun, *Proc. Natl. Acad. Sci. U.S.A.,* 1997, 94:4937-4942, and Stafford et al., *Protein Eng. Des. Sel. PEDS,* 2014, 27:97-109. After multiple rounds of selection, the DNA from RT-PCR output was cloned into an optimized vector for cell-free expression using standard molecular biology techniques. See Yin et al., *mAbs,* 2012, 4:217-225.

Libraries of antibody variants isolated by the selections were transformed into *E. coli* and grown on agar plates with antibiotic (kanamycin). Individual colonies were picked and grown in liquid broth (TB+kanamycin). Overnight cultures were used to prepare glycerol stocks, and for rolling circle amplification (RCA) to amplify the DNA encoding the variant of interest. The variants were then expressed in a cell-free protein synthesis reaction as described in Zawada et al. (*Biotechnol. Bioeng.,* 2011, 108:1570-1578) with the modifications described below.

Cell-free extracts were treated with 50 μM iodoacetamide for 30 minutes at room temperature (RT; 20° C.) and added to a premix containing all other components except for the DNA template from the variant of interest. Cell free reactions, at a final volume of 604, were initiated by addition of 10% (v/v) amplified variant DNA template and incubated at 30° C. for 12 h on a shaker at 650 rpm in 96-well plates. A total of 88 variants (and 12 control wells, including on-plate and externally added controls) were synthesized on each plate, and about 12-14 plates were screened for each selection campaign. The reaction was incubated further at 4° C. for 6 h. The final concentration in the protein synthesis reaction was 40% cell extract which was engineered to also express disulfide bond isomerase (DsbC), 2 mM glutathione disulfide (GSSG), 8 mM magnesium glutamate, 10 mM ammonium glutamate, 130 mM potassium glutamate, 35 mM sodium pyruvate, 1.2 mM AMP, 0.86 mM each of GMP, UMP, and CMP, 2 mM amino acids (except 1 mM for tyrosine and phenylalanine), 4 mM sodium oxalate, 1 mM putrescine, 1.5 mM spermidine, 15 mM potassium phosphate, 100 nM T7 RNAP, Following synthesis, each reaction was diluted 1:50 into PBST (PBS at pH 7.4 with Tween-20+0.2% BSA).

Variants were analyzed using an ELISA-based assay, using 384-well plates prepared by pre-coating with 2 μg/mL hu-CD74 antigen (R&D SYSTEMS catalog #3590-CD-050; GenBank Accession No. NP_004346; GI No. GI:10835071) diluted in sodium bicarbonate buffer, and then blocked with BSA. Automated high-throughput liquid handling systems (Biomek FX® workstations) were programmed to carry out the ELISA steps, namely, addition of 30 μL of diluted cell-free reactions to assay plates, plate washing, addition of secondary antibody (anti-human Fc, HRP conjugated), addition of detection substrate (SuperSignal®, Thermo-Fisher/Pierce) and reading plate signals on a SepctraMax® M5 (Molecular Devices) plate reader. Signals obtained for all variants were graphed, and the top hits were picked on the basis of the signal:noise ratio, or by raw signal intensity, depending on the intensity of background signal. Cells containing about 300-400 of the top hits were selected from the glycerol stocks, and the sequences of the scFvs in the cells were determined using RCA sequencing. The sequences were analyzed to select variants with unique CDRs and minimal mutations in the framework regions. The selected sequences were then subjected to secondary screening, as described in Example 2.

Example 2: Production and Purification of Selected Antibody Variants

Cells containing the top 88 hits from the primary screening were isolated from glycerol stocks and cultured overnight in liquid broth (TB+kanamycin), in 96-well plates. Plasmid DNA was isolated from the overnight cultures with a QiaPrep 96 Turbo® plasmid preparation kit (Qiagen) according to the manufacturer's instructions. Cell-free reactions were prepared to express the variants as described above, except that plasmid DNA template was added at a final concentration of 7.5 μg/mL of 6×His tagged heavy chain, and 2.5 μg/mL of light chain DNA template. Controls were also expressed in the same plate. After overnight incubation (30° C., 12 hours, followed by 6 hours at 40° C.), the mixture was centrifuged at 5000×g, 4° C. for 10 min. IMAC purification protocols were employed to capture antibody variants from the cell-free supernatant using a semi-automated high throughput batch purification method. Each milliliter of clarified supernatant was mixed in a 96-well deep well plate with 50 μL of IMAC resin (Ni Sepharose® High Performance, GE Healthcare) previously equilibrated in IMAC binding buffer (50 mM Tris pH 8.0, 300 mM NaCl, 10 mM imidazole) by pipetting up and down for 15 minutes at slow mixing speed. The resin slurry was then transferred to a filter plate, and washed twice with IMAC binding buffer, and finally His-tagged antibody variants were eluted using 200 μL IMAC elution buffer (50 mM Tris pH 8.0, 300 mM NaCl, 500 mM imidazole). Purified variants were buffer exchanged into PBS using a 96-well ZEBA plate (7 kD MWCO, Thermo-Fisher). Because the His tag is C-terminal, this procedure allows isolation of full length protein. To quantitate the variants following purification, purified samples were analyzed using a HT Protein Express® assay on a LabChip GXII® (Perkin Elmer). Samples were prepared for analysis according to the protocol provided by manufacturer, and protein concentrations were calculated by comparison to a trastuzumab standard curve (1000–10 μg/mL) run under same conditions.

Example 3: Analysis of Off-Rates of Selected Antibody Variants

All variants that were produced as described in Example 2, and that had measurable protein concentrations, were subject to off-rate ranking using a Biacore® T200 instrument. Anti-human Fc antibody (GE Healthcare) was directly coupled to a CM5 chip using amine coupling. Antibody variants were captured on the anti-human Fc surface, and off-rate was measured by flowing 50 nM huCD74 antigen over the antibodies.

Example 4: Kinetic Analysis of Selected Antibody Variants

Affinity measurements ($K_D$) were obtained, using the Biacore® T200 instrument, for variants with "slow" off-rates and good cell killing properties (as described in Example 5).

Anti-human Fc IgG (Human Antibody Capture Kit, GE Life Sciences) was immobilized onto a CM5 chip (GE Life Sciences) using amine coupling chemistry (Amine Coupling Kit, GE Life Sciences). The immobilization steps were carried out at a flow rate of 25 μl/min in 1×HBS-EP+buffer (GE Life Sciences; 10× stock diluted before use). The sensor surfaces were activated for 7 min with a mixture of NHS (0.05 M) and EDC (0.2 M). The Anti-human Fc IgG was injected over all 4 flow cells at a concentration of 25 μg/ml in 10 mM sodium acetate, pH 5.0, for 7 min. Ethanolamine (1 M, pH 8.5) was injected for 7 min to block any remaining activated groups. An average of 12,500 response units (RU) of capture antibody was immobilized on each flow cell.

Kinetic binding experiments were performed at 25° C. using 1×HBS-EP+buffer. Kinetic data was collected by injecting test and control antibodies at concentrations of 10, 5 and 2.5 μg/mL for 12 s at a flow rate of 10 μl/min on flow cells 2, 3 and 4 respectively, followed by a buffer wash for 30 s at the same flow rate. Kinetic characterization of antibody samples was carried out with 8 concentrations of a 1:2 dilution series of rhCD74 antigen (R&D Systems) and 2 injections of 0 nM antigen (buffer only). After capturing ligand (antibody) on the anti-human Fc surface, the analyte (antigen) was bound at 50, 25, 12.5, 6.3, 3.1, 1.6, 0.8, 0.4 and 0 nM for 180 seconds, followed by a 900 second dissociation phase at a flow rate of 50 μl/min. Between each ligand capture and analyte binding cycle, regeneration was carried out using 2 injections of 3M $MgCl_2$ for 30 seconds at 30 μL/min, followed by a 30 second buffer wash step.

The data was fit with the Biacore T200 Evaluation software, using a 1:1 Langmuir binding model. $K_D$ (affinity, nM) was determined as a ratio of the kinetic rate constants calculated from the fits of the association and dissociation phases.

Example 5: Secondary ADC Cell Killing Activity

The internalization ability of selected antibodies was evaluated by a secondary antibody-drug conjugate (ADC) cell killing assay on CD74 positive SU-DHL-6 cells. SU-DHL-6 cells were obtained from ATCC (CRL-2959) and maintained in RPMI, high glucose (Cellgro®, Mediatech, Manassas, Va.) supplemented with 20% heat-inactivated fetal bovine serum (HyClone™; Thermo-Scientific, Waltham, Mass.), 2 mM GlutaMAX™ (Invitrogen, Carlsbad, Calif.) and 1× penicillin/streptomycin (Cellgro®, Mediatech, Manassas, Va.). Cells were collected and counted by the Vi-CELL™ cell viability analyzers (Beckman Coulter, Brea, Calif.). A total of $2\times10^4$ cells in a volume of 40 μl were seeded in each well of a 96-well half area flat bottom white polystyrene plate. Antibodies were formulated at 4× starting concentration in the cell culture medium and filtered through MultiScreen® HTS 96-well filter plates (Millipore; Billerica, Mass.). 20 μl of the serially diluted antibody (1:3 serial dilution starting from 200 nM) was added into treatment wells and 20 μl of anti-hFc-MMAF (MORADEC) was then added into each well at a fixed final concentration of 5 μg/mL. Assay plates were cultured at 37° C. in a $CO_2$ incubator for 72 hrs before the cell viability assay. For cell viability measurement, 80 μl of CellTiter-Glo® reagent (Promega, Madison, Wis.) was added into each well, and plates were processed as per product instructions. Relative luminescence was measured on an EnVision® plate reader (Perkin Elmer, Waltham, Mass.). Relative luminescence readings were converted to percent viability using untreated cells as controls. Data was fitted with non-linear regression analysis, using log(inhibitor) vs. response-variable slope, four parameter fit equation using GraphPad Prism (GraphPad v 5.0 software, San Diego, Calif.). Data was expressed as relative cell viability (ATP content) percent vs. dose of antibody in nM.

Example 6: FACS-Based Cell Binding to Determine Cross-Reactivity with Cynomolgus Monkey CD74

CHO cells were transfected to stably express CD74 from cynomolgus monkey (cyno-CD74; GI #s 544440372, gene; 544440373, protein) on the cell surface. CHO parental and CHO-cyno-CD74 stable cells were washed twice with calcium and magnesium-free Hanks Balanced Salt Solution (HBSS), harvested with HyQTase® (Hyclone, Thermo Scientific, Waltham, Mass.) and suspended in FACS buffer (DPBS buffer supplemented with 1% bovine serum albumin). A total of 200,000 cells per sample were incubated on ice for 60 mins with 100 nM of anti-CD74 antibodies. Cells were washed twice with ice-cold FACS buffer and incubated with 5 μg/ml Alexa Fluor®-647 labeled goat anti-human Fcγ antibody (Jackson Immunoresearch Laboratories, West Grove, Pa.) on ice for 60 mins. Unstained cells, human IgG1 (isotype control) and secondary antibody were used as controls. Samples were washed twice using FACS buffer and analyzed using a BD FACSCalibur™ system (BD BioSciences, San Jose, Calif.). Mean fluorescence intensities were plotted using GraphPad Prism (GraphPad v 5.00 software, San Diego, Calif.).

The following eight antibodies exhibited cross-reactivity to cynomolgus monkey CD74:

1. HC 1251_A06/LC 1275_C10
2. HC 1251_B08/LC 1275_C10
3. HC 1251_B09/LC 1275_C10

Example 7: Anti-CD74 scFv Antibodies Produced by Randomization of $V_H$ CDRs Table 2 provides the $k_a$, $k_d$, $K_D$, Rmax, $Chi^2$, and secondary ADC data for four scFv clones selected from a library of scFvs with randomized $V_H$ CDRs. The scFvs are based on the VH3-23 heavy chain germline and the Vk3-A27 light chain germline.

TABLE 2

Characteristics of 1193 scFv clones.

| Clone ID | Sample Description | $k_a$ (1/Ms) | $k_d$ (1/s) | $K_D$ (M) | Rmax (RU) | $Chi^2$ ($RU^2$) | 2nd ADC Cell Killing IC50, nM |
|---|---|---|---|---|---|---|---|
| 1193-B06 (SEQ ID NO: 221) | scFv Selection VH3-23 Vk3-A27 | 9.46E+05 | 2.74E−02 | 2.90E−08 | 59.29 | 0.95 | 10.32 |
| 1193-C08 (SEQ ID NO: 222) | HC only randomization | 1.16E+05 | 9.08E−03 | 7.82E−08 | 18.8 | 0.13 | ~8.664 |
| 1193-E06b (SEQ ID NO: 223) | | 9.75E+05 | 6.51E−04 | 6.68E−10 | 116.49 | 13.42 | 8.667 |
| 1193-H04b (SEQ ID NO: 224) | | 1.29E+05 | 8.24E−03 | 6.38E−08 | 44.61 | 5.15 | ~14.77 |

Example 8: Anti-CD74 Fab Antibodies Produced by Randomization of Heavy Chain CDRs Table 3 provides the $k_a$, $k_d$, $K_D$, Rmax, $Chi^2$, and secondary ADC data for four Fab clones selected from a library of Fabs with randomized heavy chain CDRs. All heavy chains were paired with the light chain from trastuzumab (SEQ ID NO: 290).

TABLE 3

Characteristics of 1198 heavy chain clones.

| $V_H$ Clone ID | Sample Description | $k_a$ (1/Ms) | $k_d$ (1/s) | $K_D$ (M) | Rmax (RU) | $Chi^2$ ($RU^2$) | 2nd ADC Cell Killing IC50, nM |
|---|---|---|---|---|---|---|---|
| 1198-A01 (SEQ ID NO: 230) | Fab Selection with HC library paired with | 1.79E+05 | 1.19E−03 | 6.60E−09 | 21.54 | 0.91 | ~279.5 |
| 1198-B10 (SEQ ID NO: 231) | trastuzumab LC. | 2.41E+05 | 2.86E−03 | 1.19E−08 | 6.8 | 0.53 | ~7.607E+07 |

TABLE 3-continued

| Characteristics of 1198 heavy chain clones. | | | | | | | |
|---|---|---|---|---|---|---|---|
| $V_H$ Clone ID | Sample Description | $k_a$ (1/Ms) | $k_d$ (1/s) | $K_D$ (M) | Rmax (RU) | $Chi^2$ ($RU^2$) | 2nd ADC Cell Killing IC50, nM |
| 1198-D03 (SEQ ID NO: 232) | | 1.95E+06 | 6.36E−03 | 3.25E−09 | 51.66 | 8.84 | ~2.695E+09 |
| 1198-D04 (SEQ ID NO: 233) | | 2.68E+05 | 1.77E−03 | 6.58E−09 | 19.9 | 1.2 | ~186.7 |

Example 9: Anti-CD74 Heavy Chains Produced by Randomization of Heavy Chain CDRs Table 4 provides the $k_a$, $k_d$, $K_D$, Rmax, $Chi^2$, and secondary ADC data for sequences of thirteen heavy chains selected from a library of Fabs with soft randomized CDRs, paired with a light chain having a $V_L$ sequence provided in SEQ ID NO: 272. Soft randomization was performed by utilizing a mixture of 70% wild type (i.e., parent) nucleotide and 10% each of the remaining three nucleotides for each position within a codon. The antibodies are based on the VH3-33 heavy chain germline and the Vk1-12 light chain germline.

TABLE 4

| Characteristics of 1251 heavy chain clones. | | | | | | | |
|---|---|---|---|---|---|---|---|
| $V_H$ Clone ID | Sample Descr. | $k_a$ (1/Ms) | $k_d$ (1/s) | $K_D$ (M) | Rmax (RU) | $Chi^2$ (RU2) | 2nd ADC Cell Killing IC50, nM |
| 1251-A02 (SEQ ID NO: 234) | VH3-33 VK1-12 (HC soft randomized) | 1.51E+06 | 3.02E−04 | 2.00E−10 | 124.1 | 7.21 | 0.009 |
| 1251-A03 (SEQ ID NO: 235) | | 1.65E+06 | 3.05E−04 | 1.84E−10 | 118.8 | 8.58 | 0.010 |
| 1251-A06 (SEQ ID NO: 236) | | 8.73E+05 | 9.99E−05 | 1.14E−10 | 105.4 | 3.93 | 0.0002 |
| 1251-B08 (SEQ ID NO: 238) | | 4.75E+05 | 1.06E−04 | 2.24E−10 | 157.2 | 2.65 | 0.007 |
| 1251-B09 (SEQ ID NO: 240) | | 9.68E+05 | 2.18E−04 | 2.25E−10 | 142.4 | 3.79 | 0.007 |
| 1251-C03 (SEQ ID NO: 242) | | 7.22E+05 | 1.18E−03 | 1.63E−09 | 76 | 1.57 | 0.050 |
| 1251-D02 (SEQ ID NO: 243) | | 8.85E+05 | 1.67E−04 | 1.89E−10 | 74.1 | 2.14 | 0.014 |
| 1251-D06 (SEQ ID NO: 244) | | 2.30E+06 | 1.73E−04 | 7.52E−11 | 161.2 | 18 | 0.004 |
| 1251-D09 (SEQ ID NO: 245) | | 9.89E+05 | 1.37E−04 | 1.39E−10 | 107.1 | 5.7 | 0.007 |
| 1251-E06 (SEQ ID NO: 246) | | 1.13E+06 | 4.26E−04 | 3.76E−10 | 143.9 | 8.25 | 0.015 |
| 1251-F06 (SEQ ID NO: 247) | | 2.15E+06 | 7.79E−04 | 3.63E−10 | 82.8 | 4.93 | 0.017 |
| 1251-F07 (SEQ ID NO: 248) | | 6.78E+05 | 1.25E−04 | 1.85E−10 | 123.8 | 6.16 | 0.009 |
| 1251-G02 (SEQ ID NO: 249) | | 1.29E+06 | 8.40E−04 | 6.51E−10 | 130.4 | 7.78 | 0.013 |

Example 10: Anti-CD74 Light Chains Produced by Randomization of Light Chain CDRs Table 5 provides the $k_a$, $k_d$, $K_D$, Rmax, $Chi^2$, and secondary ADC data for four light chains selected from a library of Fabs with soft randomized CDRs, paired with one of two heavy chains (HC 1251-A06 (SEQ ID NO: 310); or HC 1251-F07 (SEQ ID NO: 311)) in Fab format. The antibodies are based on the VH3-33 heavy chain germline and the Vk1-12 light chain germline.

TABLE 5

Characteristics of 1275 light chain clones.

| $V_L$ Clone ID | Sample Description | $k_a$ (1/Ms) | $k_d$ (1/s) | $K_D$ (M) | Rmax (RU) | $Chi^2$ ($RU^2$) | 2nd ADC Cell Killing IC50, nM |
|---|---|---|---|---|---|---|---|
| 1275-C10 (SEQ ID NO: 256) | HC 1251-A06/ VK1-12 (LC soft randomization) | 9.01E+05 | 2.34E−04 | 2.60E−10 | 61.7 | 0.438 | 0.0034 |
| 1275-D01 (SEQ ID NO: 258) | HC 1251-A06/ VK1-12 (LC soft randomization) | 6.59E+05 | 4.75E−04 | 7.21E−10 | 18.6 | 0.118 | 0.0003 |
| 1275-D10 (SEQ ID NO: 259) | HC 1251-A06/ VK1-12 (LC soft randomization) | 4.20E+05 | 2.35E−04 | 5.59E−10 | 175.6 | 1.93 | 0.0070 |
| 1275-G02 (SEQ ID NO: 260) | HC 1251-F07/ VK1-12 (LC soft randomization) | 5.63E+05 | 2.97E−04 | 5.28E−10 | 107.4 | 1.47 | 0.0200 |

Example 11: Further Anti-CD74 Fab Light Chains Produced by Randomization of Light Chain CDRs Table 6 provides the $k_a$, $k_d$, $K_D$, Rmax, $Chi^2$, and secondary ADC data for seven light chains selected from a library of Fabs with randomized light chain CDRs, paired with $V_H$ 1251-A06 (SEQ ID NO: 236) in Fab format. The antibodies are based on the VH3-33 heavy chain germline and the Vk1-12 light chain germline.

TABLE 6

Characteristics of 1337 light chain clones.

| $V_L$ Clone ID | Sample Descr. | $k_a$ (1/Ms) | $k_d$ (1/s) | $K_D$ (M) | Rmax (RU) | $Chi^2$ ($RU^2$) | 2nd ADC Cell Killing IC50, nM |
|---|---|---|---|---|---|---|---|
| 1337-A04 (SEQ ID NO: 261) | HC 1251-A06/ VK1-12 (LC library) | 7.75E+05 | 1.23E−04 | 1.58E−10 | 355.9 | 0.961 | 0.004 |
| 1337-A05 (SEQ ID NO: 262) | | 8.69E+05 | 1.56E−04 | 1.79E−10 | 326.9 | 2.9 | 0.004 |
| 1337-A06 (SEQ ID NO: 263) | | 7.85E+05 | 1.44E−04 | 1.84E−10 | 258 | 0.311 | 0.004 |
| 1337-A07 (SEQ ID NO: 265) | | 7.85E+05 | 1.41E−04 | 1.80E−10 | 138.3 | 0.895 | 0.004 |
| 1337-A08 (SEQ ID NO: 266) | | 7.49E+05 | 1.34E−04 | 1.78E−10 | 107.5 | 0.321 | 0.007 |
| 1337-A09 (SEQ ID NO: 267) | | 9.94E+05 | 1.34E−04 | 1.35E−10 | 146.5 | 2.38 | 0.004 |
| 1337-A10 (SEQ ID NO: 269) | | 9.35E+05 | 1.61E−04 | 1.72E−10 | 117.6 | 1.04 | 0.006 |

Example 12: Anti-CD74 Fab Antibodies Produced by Trinucleotide-Directed Mutagenesis (TRIM)

Table 7 provides secondary ADC data for two heavy chains selected from a library of Fabs generated by trinucleotide-directed mutagenesis (TRIM). See U.S. Pat. No. 5,869,644. The heavy chains were paired with the trastuzumab light chain (SEQ ID NO: 290).

TABLE 7

Secondary ADC data for 1445 Fab TRIM clones.

| $V_H$ Clone ID | Sample Description | 2nd ADC Cell Killing IC50, nM |
|---|---|---|
| 1445-A03 (SEQ ID NO: 250) | CD74 Fab TRIM selection | ~0.7 |
| 1445-B09 (SEQ ID NO: 251) | | ~0.45 |

Example 13: Anti-CD74 scFv-Fc Antibodies Produced by Soft Randomization

Table 8 provides secondary ADC data for four scFv-Fc clones generated from the soft randomization of 1193-E06b scFvs. See Wang et al. (*Cancer Res.*, 2011, 71:7410-7422) for an example of scFv-Fc constructs.

TABLE 8

| Secondary ADS data for 1447 scFv-Fc clones. | | |
|---|---|---|
| Clone ID | Sample Description | 2nd ADC Cell Killing IC50, nM |
| 1447-F11 (SEQ ID NO: 227) | TRIM Loop Length scFv-Fc, CD74 | ~0.9 |
| 1447-E08 (SEQ ID NO: 226) | 1193-E06b AffMat | ~2.56 |
| 1447-D11 (SEQ ID NO: 225) | | ~1.35 |
| 1447-G01 (SEQ ID NO: 228) | | ~0.65 |

Example 14: Biophysical Properties and Biological Activity of Selected Heavy Chain and Light Chain Pairs in IgG Format Table 9 provides a matrix of heavy chain and light chain pairs that were evaluated. In Table 9, "(wt)" indicates that the heavy chain or light chain was used as isolated from the respective library (i.e., without reverting mutated residues to the residues found in the canonical germline gene). In contrast, "(g)" indicates that the heavy chain or light chain sequence has been altered to restore mutated framework residues to the residues most commonly found at the respective position for a particular germline. Mutated framework residues may arise, for example, from errors introduced during amplification of the variable regions during cloning.

The sequence identification numbers in Table 9 refer to the molecules as actually tested—i.e., with an N-terminal methionine (M) residue and, in some cases, a C-terminal tag with the sequence GGSHHHHHH (SEQ ID NO: 303). These sequences are optional. The sequences of the heavy chain constant regions and light chain constant regions used to produce the heavy and light chains are provided in SEQ ID NOs: 304 (HC constant) and 305 (LC constant).

TABLE 9

| Matrix of evaluated HC/LC pairs. | | | | | | | | |
|---|---|---|---|---|---|---|---|---|
| | 1275_C10 (wt) SEQ ID NO: 295 | LC 1275_C10 (g) SEQ ID NO: 296 | 1337_A07 (wt) SEQ ID NO: 297 | LC 1337_A07 (g) SEQ ID NO: 298 | 1337_A09 (wt) SEQ ID NO: 299 | LC 1337_A09 (g) SEQ ID NO: 300 | 1337_A10 (wt) SEQ ID NO: 301 | LC 1337_A10 (g) SEQ ID NO: 302 |
| HC 1251_A06 (wt) SEQ ID NO: 291 | 1251_A06 (wt)/ 1275_C10 (wt) | 1251_A06 (wt)/ 1275_C10 (g) | 1251_A06 (wt)/ 1337_A07 (wt) | 1251_A06 (wt)/ 1337_A07 (g) | 1251_A06 (wt)/ 1337_A09 (wt) | 1251_A06 (wt)/ 1337_A09 (g) | 1251_A06 (wt)/ 1337_A10 (wt) | 1251_A06 (wt)/ 1337_A10 (g) |
| HC 1251_A06 (g) SEQ ID NO: 292 | 1251_A06 (g)/ 1275_C10 (wt) | 1251_A06 (g)/ 1275_C10 (g) | 1251_A06 (g)/ 1337_A07 (wt) | 1251_A06 (g)/ 1337_A07 (g) | 1251_A06 (g)/ 1337_A09 (wt) | 1251_A06 (g)/ 1337_A09 (g) | 1251_A06 (g)/ 1337_A10 (wt) | 1251_A06 (g)/ 1337_A10 (g) |
| HC 1251_B08 (wt) SEQ ID NO: 293 | 1251_B08 (wt)/ 1275_C10 (wt) | 1251_B08 (wt)/ 1275_C10 (g) | 1251_B08 (wt)/ 1337_A07 (wt) | 1251_B08 (wt)/ 1337_A07 (g) | 1251_B08 (wt)/ 1337_A09 (wt) | 1251_B08 (wt)/ 1337_A09 (g) | 1251_B08 (wt)/ 1337_A10 (wt) | 1251_B08 (wt)/ 1337_A10 (g) |
| HC 1251_B08 (g) SEQ ID NO: 294 | 1251_B08 (g)/ 1275_C10 (wt) | 1251_B08 (g)/ 1275_C10 (g) | 1251_B08 (g)/ 1337_A07 (wt) | 1251_B08 (g)/ 1337_A07 (g) | 1251_B08 (g)/ 1337_A09 (wt) | 1251_B08 (g)/ 1337_A09 (g) | 1251_B08 (g)/ 1337_A10 (wt) | 1251_B08 (g)/ 1337_A10 (g) |

Other heavy chains produced and tested in combination with 1275-C10, 1337-A04, 1337-A-7, 1337-A09, and 1337-A10 light chains include 1251-A03 (SEQ ID NO: 306), 1251-B09 (SEQ ID NO: 307), and 1251-B10 (SEQ ID NO: 308).

Table 10 provides the $k_a$, $k_d$, $K_D$, Rmax, $Chi^2$, and secondary ADC data for the 32 heavy chain-light chain pairs provided in Table 9.

TABLE 10

| Characteristics of HC/LC pairs. | | | | | | |
|---|---|---|---|---|---|---|
| CLONE ID | $k_a$ (1/Ms) | $k_d$ (1/s) | $K_D$ (M) | Rmax (RU) | $Chi^2$ ($RU^2$) | 2ND ADC CELL KILL ACTIVITY IC50, nM |
| HC 1251_A06 (wt)/ LC 1275_C10 (wt) | 6.54E+05 | 1.60E−04 | 2.45E−10 | 264.7 | 1.6 | 0.008 |
| HC 1251_A06 (wt)/ LC 1275_C10 (g) | 4.78E+05 | 1.66E−04 | 3.48E−10 | 360.2 | 0.7 | 0.01 |

TABLE 10-continued

Characteristics of HC/LC pairs.

| CLONE ID | $k_a$ (1/Ms) | $k_d$ (1/s) | $K_D$ (M) | Rmax (RU) | $Chi^2$ ($RU^2$) | 2ND ADC CELL KILL ACTIVITY IC50, nM |
|---|---|---|---|---|---|---|
| HC 1251_A06 (wt)/ LC 1337_A09 (wt) | 5.88E+05 | 9.19E−05 | 1.56E−10 | 289.1 | 1.1 | 0.01 |
| HC 1251_A06 (wt)/ LC 1337_A09 (g) | 6.10E+05 | 1.10E−04 | 1.80E−10 | 229.9 | 1.2 | 0.011 |
| HC 1251_A06 (wt)/ LC 1337_A07 (wt) | 5.98E+05 | 1.00E−04 | 1.68E−10 | 320.8 | 2.1 | 0.007 |
| HC 1251_A06 (wt)/ LC 1337_A07 (g) | 6.60E+05 | 1.36E−04 | 2.05E−10 | 269.4 | 1.3 | 0.01 |
| HC 1251_A06 (wt)/ LC 1337_A10 (wt) | 8.47E+05 | 1.74E−04 | 2.05E−10 | 203.0 | 1.1 | 0.006 |
| HC 1251_A06 (wt)/ LC 1337_A10 (g) | 5.71E+05 | 2.35E−04 | 4.11E−10 | 333.9 | 1.0 | 0.011 |
| HC 1251_A06 (g)/ LC 1275_C10 (wt) | 5.20E+05 | 1.77E−04 | 3.41E−10 | 246.5 | 0.8 | 0.01 |
| HC 1251_A06 (g)/ LC 1275_C10 (g) | 7.05E+05 | 1.48E−04 | 2.09E−10 | 311.5 | 4.2 | 0.007 |
| HC 1251_A06 (g)/ LC 1337_A09 (wt) | 4.57E+05 | 8.63E−05 | 1.89E−10 | 388.4 | 2.3 | 0.004 |
| HC 1251_A06 (g)/ LC 1337_A09 (g) | 5.52E+05 | 7.26E−05 | 1.31E−10 | 342.9 | 2.7 | 0.002 |
| HC 1251_A06 (g)/ LC 1337_A07 (wt) | 5.68E+05 | 9.40E−05 | 1.66E−10 | 333.8 | 1.0 | 0.001 |
| HC 1251_A06 (g)/ LC 1337_A07 (g) | 4.24E+05 | 7.10E−05 | 1.68E−10 | 396.8 | 0.8 | 0.005 |
| HC 1251_A06 (g)/ LC 1337_A10 (wt) | 4.79E+05 | 9.03E−05 | 1.88E−10 | 407.6 | 1.5 | 0.002 |
| HC 1251_A06 (g)/ LC 1337_A10 (g) | 3.80E+05 | 1.48E−04 | 3.89E−10 | 326.1 | 2.8 | 0.005 |
| HC 1251_B08 (wt)/ LC 1275_C10 (wt) | 6.23E+05 | 1.19E−04 | 1.91E−10 | 318.8 | 6.9 | 0.01 |
| HC 1251_B08 (wt)/ LC 1275_C10 (g) | 2.84E+05 | 1.24E−04 | 4.37E−10 | 335.0 | 4.4 | 0.013 |
| HC 1251_B08 (wt)/ LC 1337_A09 (wt) | 1.07E+06 | 1.16E−04 | 1.08E−10 | 213.3 | 2.3 | 0.006 |
| HC 1251_B08 (wt)/ LC 1337_A09 (g) | 3.32E+05 | 1.15E−04 | 3.47E−10 | 268.2 | 1.5 | 0.016 |
| HC 1251_B08 (wt)/ LC 1337_A07 (wt) | 3.79E+05 | 8.01E−05 | 2.11E−10 | 265.4 | 2.4 | 0.016 |
| HC 1251_B08 (wt)/ LC 1337_A07 (g) | 2.32E+05 | 1.42E−04 | 6.11E−10 | 228.1 | 0.8 | 0.037 |
| HC 1251_B08 (wt)/ LC 1337_A10 (wt) | 4.91E+05 | 1.15E−04 | 2.35E−10 | 292.8 | 0.4 | 0.017 |
| HC 1251_B08 (wt)/ LC 1337_A10 (g) | 1.91E+05 | 1.83E−04 | 9.57E−10 | 208.5 | 0.1 | 0.046 |
| HC 1251_B08 (g)/ LC 1275_C10 (wt) | 1.80E+05 | 1.55E−04 | 8.62E−10 | 304.1 | 0.4 | 0.018 |
| HC 1251_B08 (g)/ LC 1275_C10 (g) | 3.06E+05 | 1.02E−04 | 3.32E−10 | 400.0 | 0.5 | 0.011 |
| HC 1251_B08 (g)/ LC 1337_A09 (wt) | 1.66E+05 | 1.06E−04 | 6.40E−10 | 331.0 | 0.3 | 0.025 |
| HC 1251_B08 (g)/ LC 1337_A09 (g) | 3.09E+05 | 7.77E−05 | 2.52E−10 | 351.5 | 2.4 | 0.01 |
| HC 1251_B08 (g)/ LC 1337_A07 (wt) | 2.65E+05 | 9.23E−05 | 3.49E−10 | 394.2 | 2.8 | 0.013 |
| HC 1251_B08 (g)/ LC 1337_A07 (g) | 3.25E+05 | 7.76E−05 | 2.39E−10 | 388.6 | 1.9 | 0.006 |
| HC 1251_B08 (g)/ LC 1337_A10 (wt) | 3.12E+05 | 1.20E−04 | 3.85E−10 | 425.5 | 2.2 | 0.003 |
| HC 1251_B08 (g)/ LC 1337_A10 (g) | 3.92E+05 | 9.97E−05 | 2.54E−10 | 496.7 | 3.6 | 0.007 |

Example 15: Affinity of Anti-CD74 scFv-Fc (1251-B08-gm_1337-A09-gm) for CD74

The heavy chain 1251-B08-(g) and light chain 1337-A09-(g) sequences are formatted into an scFv-Fc format. The amino acid sequence of the scFv-Fc is provided in SEQ ID NO: 229. The amino acid sequence of the Fc constant region is provided in SEQ ID NO: 309.

Purified ScFv-Fc is captured on an anti-human Fc surface at a concentration of 10 μg/mL, and different concentrations of antigen (20 nM, 10 nM, 5 nM and 0 nM of human CD74, R&D Systems) are passed over the chip surface to which the ScFv-Fc is bound. Data is fit to a 1:1 binding model using BIACORE evaluation software. Table 11 shows the $k_a$, $k_d$, $K_D$, Rmax, and $Chi^2$ for this scFv-Fc.

TABLE 11

| Characteristics of scFv-Fc clone. | | | | | | |
|---|---|---|---|---|---|---|
| CLONE ID | Description | $k_a$ (1/Ms) | $k_d$ (1/s) | $K_D$ (M) | Rmax (RU) | $Chi^2$ ($RU^2$) |
| SP-007377 (SEQ ID NO: 229) | 1251-B08-gm_1337_A09-gm ScFvFc | 3.38E+05 | 1.20E−04 | 3.54E−10 | 146.7 | 0.111 |

Example 16: Thermal Stability of Aglycosylated Anti-CD74 IgG Antibodies

This example describes experiments designed to measure the thermal stability (Tm) of aglycosylated anti-CD74 parent antibody and variants. The thermal shift assay was carried out by mixing the protein to be assayed (anti-CD74 parent antibody and variants) with an environmentally sensitive dye (SYPRO Orange, Life Technologies Cat #S-6650) in a phosphate buffered solution (PBS), and monitoring the fluorescence of the mixture in real time as it underwent controlled thermal denaturation. The final concentration of the protein in the assay mixture was between 100-250 μg/mL, and the dye was diluted 1:1000 from the original stock (stock dye is 5000× in DMSO). After dispensing 5 μL aliquots of the protein-dye mixture in a 384-well microplate (Bio-Rad Cat #MSP-3852), the plate was sealed with an optically clear sealing film (Bio-Rad Cat #MSB-1001), and placed in a 384-well plate real-time thermocycler (Bio-Rad CFX384 Real Time System). The protein-dye mixture was heated from 25° C. to 95° C., at increments of 0.1° C. per cycle (~1.5° C. per minute), allowing 3 seconds of equilibration at each temperature before taking a fluorescence measurement. At the end of the experiment, the melting temperatures (Tm1 and Tm2) were determined using the Bio-Rad CFX manager software. Tm1 represents the melting of the Fc domain. Tm2 represents the melting of the Fab domain. The Tm2 for certain illustrative antibodies provided in this disclosure is higher than the Tm2 for the parent antibody.

For protein samples with complex thermal transition profiles, the melting temperatures are calculated from the negative first-order derivative plot of fluorescence intensity (Y-axis) against temperature (X-axis), or by fitting the data to the Boltzmann sigmoidal model. The difference in melting temperatures of anti-CD74 variants compared to the wild-type protein is a measure of the thermal shift for the protein being assayed. The results for these studies are provided in Table 12.

TABLE 12

| Thermostability data for anti-CD-74 IgG antibodies. | | | |
|---|---|---|---|
| Protein ID | Description | Tm1 (° C.) | Tm2 (° C.) |
| Study 50-31-A03 | HC 1251_A06 (wt)/ LC 1337_A09 (wt) (SEQ ID NOs: 291/299) | 62.2 | 75.4 |
| Study 50-31-A05 | HC 1251_A06 (wt)/ LC 1337_A07 (wt) (SEQ ID NOs: 291/299) | 62.2 | 75.0 |
| Study 50-31-C03 | HC 1251_B08 (wt)/ LC 1337_A09 (wt) (SEQ ID NOs: 293/299) | 62.3 | 78.6 |
| Study 50-31-C05 | HC 1251_B08 (wt)/ LC 1337_A07 (wt) (SEQ ID NOs: 293/297) | 62.2 | 77.6 |
| Study 50-31-B04 | HC 1251_A06 (g)/ LC 1337_A09 (g) (SEQ ID NOs: 292/300) | 59.9 | 76.3 |
| Study 50-31-B06 | HC 1251_A06 (g)/ LC 1337_A07 (g) (SEQ ID NOs: 292/298) | 59.6 | 76.8 |
| Study 50-31-D04 | HC 1251_B08 (g)/ LC 1337_A09 (g) (SEQ ID NOs: 294/300) | 59.7 | 77.6 |
| Study 50-31-D06 | HC 1251_B08 (g)/ LC 1337_A07 (g) (SEQ ID NOs: 294/298) | 59.7 | 79.6 |
| Study 50-31-E01 | HC VH19 (wt)/LC VL26 (wt) (VH/VL SEQ ID NOs: 252/272) | 62.2 | 73.4 |

* Where not included in the sequence, heavy chain and light chain constant regions were SEQ ID NOs 304 and 305, respectively.

Example 17: Sequences

Table 13 provides sequences referred to herein.

TABLE 13

| Sequences. | | | | |
|---|---|---|---|---|
| SEQ ID NO | Molecule | Region | Scheme | Sequence |
| 1 | 1193-B06 | CDR-H1 | Chothia | GFTFTGN |
| 2 | 1193-C08 | CDR-H1 | Chothia | GFTFNNN |
| 3 | 1193-E06b | CDR-H1 | Chothia | GFTFNNT |
| 4 | 1193-H04b | CDR-H1 | Chothia | GFTFTSS |
| 5 | 1198-A01 | CDR-H1 | Chothia | GFTFSDY |
| 6 | 1198-B10 | CDR-H1 | Chothia | GFNISGS |

TABLE 13-continued

| Sequences. | | | | |
|---|---|---|---|---|
| SEQ ID NO | Molecule | Region | Scheme | Sequence |
| 7 | 1198-D03 | CDR-H1 | Chothia | GFNINNY |
| 8 | 1198-D04 | CDR-H1 | Chothia | GFNINNY |
| 9 | 1251-A02 | CDR-H1 | Chothia | GFAFSDH |
| 10 | 1251-A03 | CDR-H1 | Chothia | GFAFSDH |
| 11 | 1251-A06 | CDR-H1 | Chothia | GFDFSSY |
| 12 | 1251-B08 | CDR-H1 | Chothia | GFNFSDY |
| 13 | 1251-B09 | CDR-H1 | Chothia | GFNFSDY |
| 14 | 1251-B10 | CDR-H1 | Chothia | GFNFSSH |
| 15 | 1251-C03 | CDR-H1 | Chothia | GFNFSSY |
| 16 | 1251-D02 | CDR-H1 | Chothia | GFSFASH |
| 17 | 1251-D06 | CDR-H1 | Chothia | GFSFGSY |
| 18 | 1251-D09 | CDR-H1 | Chothia | GFSFSSY |
| 19 | 1251-E06 | CDR-H1 | Chothia | GFTFDSY |
| 20 | 1251-F06 | CDR-H1 | Chothia | GFTFSSF |
| 21 | 1251-F07 | CDR-H1 | Chothia | GFTFSSH |
| 22 | 1251-G02 | CDR-H1 | Chothia | GFTFSSY |
| 23 | 1445-A03 | CDR-H1 | Chothia | GFNISGY |
| 24 | 1445-B09 | CDR-H1 | Chothia | GFNITGT |
| 25 | 1447-D11 | CDR-H1 | Chothia | GFTFNNT |
| 26 | 1447-E08 | CDR-H1 | Chothia | GFTFNDT |
| 27 | 1447-F11 | CDR-H1 | Chothia | GFTFDNT |
| 28 | 1447-G01 | CDR-H1 | Chothia | GFTFNTS |
| 29 | VH11-[19] | CDR-H1 | Chothia | GFTFSSY |
| 30 | VHS-[7] | CDR-H1 | Chothia | GFTFSSY |
| 31 | VH6-[11] | CDR-H1 | Chothia | GFTFSSY |
| 32 | VH8-[15] | CDR-H1 | Chothia | GFTFSSY |
| 33 | 1193-B06 | CDR-H1 | Kabat | GNWMS |
| 34 | 1193-C08 | CDR-H1 | Kabat | NNWMS |
| 35 | 1193-E06b | CDR-H1 | Kabat | NTDMS |
| 36 | 1193-H04b | CDR-H1 | Kabat | SSWMS |
| 37 | 1198-A01 | CDR-H1 | Kabat | DYDMS |
| 38 | 1198-B10 | CDR-H1 | Kabat | GSWIH |
| 39 | 1198-D03 | CDR-H1 | Kabat | NYDIH |
| 40 | 1198-D04 | CDR-H1 | Kabat | NYDIH |
| 41 | 1251-A02 | CDR-H1 | Kabat | DHGMH |
| 42 | 1251-A03 | CDR-H1 | Kabat | DHGMH |
| 43 | 1251-A06 | CDR-H1 | Kabat | SYGMH |

TABLE 13-continued

Sequences.

| SEQ ID NO | Molecule | Region | Scheme | Sequence |
|---|---|---|---|---|
| 44 | 1251-B08 | CDR-H1 | Kabat | DYGMH |
| 45 | 1251-B09 | CDR-H1 | Kabat | DYGMH |
| 46 | 1251-B10 | CDR-H1 | Kabat | SHGMH |
| 47 | 1251-C03 | CDR-H1 | Kabat | SYGMH |
| 48 | 1251-D02 | CDR-H1 | Kabat | SHGMH |
| 49 | 1251-D06 | CDR-H1 | Kabat | SYGMH |
| 50 | 1251-D09 | CDR-H1 | Kabat | SYGMH |
| 51 | 1251-E06 | CDR-H1 | Kabat | SYGMH |
| 52 | 1251-F06 | CDR-H1 | Kabat | SFGMH |
| 53 | 1251-F07 | CDR-H1 | Kabat | SHGMH |
| 54 | 1251-G02 | CDR-H1 | Kabat | SYGMH |
| 55 | 1445-A03 | CDR-H1 | Kabat | GYYIH |
| 56 | 1445-B09 | CDR-H1 | Kabat | GTGIH |
| 57 | 1447-D11 | CDR-H1 | Kabat | NTDMS |
| 58 | 1447-E08 | CDR-H1 | Kabat | DTDMS |
| 59 | 1447-F11 | CDR-H1 | Kabat | NTDMS |
| 60 | 1447-G01 | CDR-H1 | Kabat | TSDMS |
| 61 | VH11-[19] | CDR-H1 | Kabat | SYGMH |
| 62 | VHS-[7] | CDR-H1 | Kabat | SYAMH |
| 63 | VH6-[11] | CDR-H1 | Kabat | SYAMH |
| 64 | VH8-[15] | CDR-H1 | Kabat | SYAMH |
| 65 | 1193-B06 | CDR-H2 | Chothia | YGTSGA |
| 66 | 1193-C08 | CDR-H2 | Chothia | NGDDGY |
| 67 | 1193-E06b | CDR-H2 | Chothia | NGSGGA |
| 68 | 1193-H04b | CDR-H2 | Chothia | NGYNGI |
| 69 | 1198-A01 | CDR-H2 | Chothia | AQDGSY |
| 70 | 1198-B10 | CDR-H2 | Chothia | YPDDGD |
| 71 | 1198-D03 | CDR-H2 | Chothia | DPYNGA |
| 72 | 1198-D04 | CDR-H2 | Chothia | DPYNGT |
| 73 | 1251-A02 | CDR-H2 | Chothia | WYDGSH |
| 74 | 1251-A03 | CDR-H2 | Chothia | WYDGSH |
| 75 | 1251-A06 | CDR-H2 | Chothia | WDDGSD |
| 76 | 1251-B08 | CDR-H2 | Chothia | WYDGSI |
| 77 | 1251-B09 | CDR-H2 | Chothia | WYDGSR |
| 78 | 1251-B10 | CDR-H2 | Chothia | WHDGSD |
| 79 | 1251-C03 | CDR-H2 | Chothia | WYDGSI |
| 80 | 1251-D02 | CDR-H2 | Chothia | WDDGSD |

TABLE 13-continued

Sequences.

| SEQ ID NO | Molecule | Region | Scheme | Sequence |
|---|---|---|---|---|
| 81 | 1251-D06 | CDR-H2 | Chothia | WYDGSK |
| 82 | 1251-D09 | CDR-H2 | Chothia | WYDASI |
| 83 | 1251-E06 | CDR-H2 | Chothia | WYDGSN |
| 84 | 1251-F06 | CDR-H2 | Chothia | WYDGSN |
| 85 | 1251-F07 | CDR-H2 | Chothia | WDDGSN |
| 86 | 1251-G02 | CDR-H2 | Chothia | WHDGSK |
| 87 | 1445-A03 | CDR-H2 | Chothia | SPTGGY |
| 88 | 1445-B09 | CDR-H2 | Chothia | TPYNGT |
| 89 | 1447-D11 | CDR-H2 | Chothia | NGSGGS |
| 90 | 1447-E08 | CDR-H2 | Chothia | NGAGGA |
| 91 | 1447-F11 | CDR-H2 | Chothia | NGSGGV |
| 92 | 1447-G01 | CDR-H2 | Chothia | NGSGGA |
| 93 | VH11-[19] | CDR-H2 | Chothia | WYDGSN |
| 94 | VH5-[7] | CDR-H2 | Chothia | SYDGSN |
| 95 | VH6-[11] | CDR-H2 | Chothia | SYDGSI |
| 96 | VH8-[15] | CDR-H2 | Chothia | SYDGSN |
| 97 | 1193-B06 | CDR-H2 | Kabat | IIYGTSGATYYADSVKG |
| 98 | 1193-C08 | CDR-H2 | Kabat | IINGDDGYTYYADRVKG |
| 99 | 1193-E06b | CDR-H2 | Kabat | IINGSGGATNYADSVKG |
| 100 | 1193-H04b | CDR-H2 | Kabat | IINGYNGITYYADSVKG |
| 101 | 1198-A01 | CDR-H2 | Kabat | FIAQDGSYKYYVDSVKG |
| 102 | 1198-B10 | CDR-H2 | Kabat | YIYPDDGDTYYADSVKG |
| 103 | 1198-D03 | CDR-H2 | Kabat | NIDPYNGATYYADSVKG |
| 104 | 1198-D04 | CDR-H2 | Kabat | NIDPYNGTTYYADSVKG |
| 105 | 1251-A02 | CDR-H2 | Kabat | VIWYDGSHKIYADSVKG |
| 106 | 1251-A03 | CDR-H2 | Kabat | VIWYDGSHKIYADSVKG |
| 107 | 1251-A06 | CDR-H2 | Kabat | VIWDDGSDRYYADSVKG |
| 108 | 1251-B08 | CDR-H2 | Kabat | VIWYDGSISYYADSVKG |
| 109 | 1251-B09 | CDR-H2 | Kabat | VTWYDGSREYYADSVKG |
| 110 | 1251-B10 | CDR-H2 | Kabat | VIWHDGSDKYYADSVKG |
| 111 | 1251-C03 | CDR-H2 | Kabat | VIWYDGSIKNYADSVKG |
| 112 | 1251-D02 | CDR-H2 | Kabat | VIWDDGSDRYYADSVKG |
| 113 | 1251-D06 | CDR-H2 | Kabat | VVWYDGSKTIYADSVKG |
| 114 | 1251-D09 | CDR-H2 | Kabat | VIWYDASIRKYAGSVKG |
| 115 | 1251-E06 | CDR-H2 | Kabat | VIWYDGSNKVYADSVKG |
| 116 | 1251-F06 | CDR-H2 | Kabat | VIWYDGSNEYYADSVKG |
| 117 | 1251-F07 | CDR-H2 | Kabat | VIWDDGSNEVYADSVKG |

TABLE 13-continued

| Sequences. | | | | |
|---|---|---|---|---|
| SEQ ID NO | Molecule | Region | Scheme | Sequence |
| 118 | 1251-G02 | CDR-H2 | Kabat | VIWHDGSKDYYADSVKG |
| 119 | 1445-A03 | CDR-H2 | Kabat | EISPTGGYTYYADSVKG |
| 120 | 1445-B09 | CDR-H2 | Kabat | IITPYNGTTNYADSVKG |
| 121 | 1447-D11 | CDR-H2 | Kabat | VINGSGGSSNYADSVKG |
| 122 | 1447-E08 | CDR-H2 | Kabat | MINGAGGASFYADSVRG |
| 123 | 1447-F11 | CDR-H2 | Kabat | IINGSGGVTNYADSVRG |
| 124 | 1447-G01 | CDR-H2 | Kabat | IINGSGGATNYADSVKG |
| 125 | VH11-[19] | CDR-H2 | Kabat | VIWYDGSNKYYADSVKG |
| 126 | VHS-[7] | CDR-H2 | Kabat | VISYDGSNKYYADSVKG |
| 127 | VH6-[11] | CDR-H2 | Kabat | VISYDGSIKYYADSVKG |
| 128 | VH8-[15] | CDR-H2 | Kabat | VISYDGSNKYYADSVKG |
| 129 | 1193-B06 | CDR-H3 | K/C | PSMSGSRGFDY |
| 130 | 1193-C08 | CDR-H3 | K/C | VALGRPRRFDY |
| 131 | 1193-E06b | CDR-H3 | K/C | FENEWEVSMDY |
| 132 | 1193-H04b | CDR-H3 | K/C | PSAPGARRFDY |
| 133 | 1198-A01 | CDR-H3 | K/C | SKLFRAGQFDY |
| 134 | 1198-B10 | CDR-H3 | K/C | EGSHNLDKMDY |
| 135 | 1198-D03 | CDR-H3 | K/C | VLWGFWAPFDY |
| 136 | 1198-D04 | CDR-H3 | K/C | VPWGFWAPFDY |
| 137 | 1251-A02 | CDR-H3 | K/C | GGSLAGGAVYGTDV |
| 138 | 1251-A03 | CDR-H3 | K/C | GGSLAGGAVYGTDV |
| 139 | 1251-A06 | CDR-H3 | K/C | GGTRVLGAIHGTDV |
| 140 | 1251-B08 | CDR-H3 | K/C | GGTVEHGAVYGTDV |
| 141 | 1251-B09 | CDR-H3 | K/C | GGTLVHGALYGNDV |
| 142 | 1251-B10 | CDR-H3 | K/C | GGTRVLGAVYGLDV |
| 143 | 1251-C03 | CDR-H3 | K/C | GGALMRGEFSGHDV |
| 144 | 1251-D02 | CDR-H3 | K/C | GGTRVLGAIHGTDV |
| 145 | 1251-D06 | CDR-H3 | K/C | GGTLVRGAVYGLDV |
| 146 | 1251-D09 | CDR-H3 | K/C | GGTVERGAIYGTDV |
| 147 | 1251-E06 | CDR-H3 | K/C | GGMVGQGAMFGLDV |
| 148 | 1251-F06 | CDR-H3 | K/C | GGSLVTRGVYGLDV |
| 149 | 1251-F07 | CDR-H3 | K/C | GGTRIRGLRYGTDV |
| 150 | 1251-G02 | CDR-H3 | K/C | GGQLDHGAIYGLDV |
| 151 | 1445-A03 | CDR-H3 | K/C | EHGLVYGQPMDY |
| 152 | 1445-B09 | CDR-H3 | K/C | GGYGYYYPPFDY |
| 153 | 1447-D11 | CDR-H3 | K/C | YETEWEVSLDY |
| 154 | 1447-E08 | CDR-H3 | K/C | FENQWEVTFDY |

TABLE 13-continued

Sequences.

| SEQ ID NO | Molecule | Region | Scheme | Sequence |
|---|---|---|---|---|
| 155 | 1447-F11 | CDR-H3 | K/C | YESEWEVSLDY |
| 156 | 1447-G01 | CDR-H3 | K/C | YENEMEVSMDY |
| 157 | VH11-[19] | CDR-H3 | K/C | GGTLVRGAMYGTDV |
| 158 | VHS-[7] | CDR-H3 | K/C | GRYYGSGSYSSYFDY |
| 159 | VH6-[11] | CDR-H3 | K/C | GREITSQNIVILLDY |
| 160 | VH8-[15] | CDR-H3 | K/C | GREITSQNIVILLDY |
| 161 | 1193-B06 | CDR-L1 | K/C | RAGQSVSSSYLA |
| 162 | 1193-C08 | CDR-L1 | K/C | RASQSVSSNYLA |
| 163 | 1193-E06b | CDR-L1 | K/C | RASQSVSSSYLA |
| 164 | 1193-H04b | CDR-L1 | K/C | RASQSVSSSYLA |
| 165 | 1275-C10 | CDR-L1 | K/C | RASQGVSSWLA |
| 166 | 1275-D01 | CDR-L1 | K/C | RASQGIGRWLA |
| 167 | 1275-D10 | CDR-L1 | K/C | RASQGVFSWLA |
| 168 | 1275-G02 | CDR-L1 | K/C | RASQGLGSFLA |
| 169 | 1337-A04 | CDR-L1 | K/C | RASQDIGRWVA |
| 170 | 1337-A05 | CDR-L1 | K/C | RASQGIGRWVA |
| 171 | 1337-A06 | CDR-L1 | K/C | RASQDIGSWVA |
| 172 | 1337-A07 | CDR-L1 | K/C | RASQGISSWVA |
| 173 | 1337-A08 | CDR-L1 | K/C | RASQDIGSWVA |
| 174 | 1337-A09 | CDR-L1 | K/C | RASQGIGSWLA |
| 175 | 1337-A10 | CDR-L1 | K/C | RASQGISSWVA |
| 176 | 1447-D11 | CDR-L1 | K/C | RASQSVSSSYLA |
| 177 | 1447-E08 | CDR-L1 | K/C | RASQRVAGIDLS |
| 178 | 1447-F11 | CDR-L1 | K/C | RASQSVYRSYLA |
| 179 | 1447-G01 | CDR-L1 | K/C | RASQSVSSRELG |
| 180 | VL-5[23] & VL6-[26] | CDR-L1 | K/C | RASQGISSWLA |
| 181 | 1193-B06 | CDR-L2 | K/C | GASSRAT |
| 182 | 1193-C08 | CDR-L2 | K/C | GASSRAT |
| 183 | 1193-E06b | CDR-L2 | K/C | GASSRAT |
| 184 | 1193-H04b | CDR-L2 | K/C | GASSRAT |
| 185 | 1275-C10 | CDR-L2 | K/C | SARYLQS |
| 186 | 1275-D01 | CDR-L2 | K/C | GRSSLQS |
| 187 | 1275-D10 | CDR-L2 | K/C | NATQLQS |
| 188 | 1275-G02 | CDR-L2 | K/C | LGNLLQI |
| 189 | 1337-A04 | CDR-L2 | K/C | GASSLQS |
| 190 | 1337-A05 | CDR-L2 | K/C | GADRLQS |
| 191 | 1337-A06 | CDR-L2 | K/C | GADRLQS |

TABLE 13-continued

| SEQ ID NO | Molecule | Region | Scheme | Sequence |
|---|---|---|---|---|
| | Sequences. | | | |
| 192 | 1337-A07 | CDR-L2 | K/C | GASRLQS |
| 193 | 1337-A08 | CDR-L2 | K/C | ASDSLQS |
| 194 | 1337-A09 | CDR-L2 | K/C | AADRLQS |
| 195 | 1337-A10 | CDR-L2 | K/C | GSSRLQS |
| 196 | 1447-D11 | CDR-L2 | K/C | GASSRAT |
| 197 | 1447-E08 | CDR-L2 | K/C | GASSRAT |
| 198 | 1447-F11 | CDR-L2 | K/C | GASSRAT |
| 199 | 1447-G01 | CDR-L2 | K/C | GASSRAT |
| 200 | VL-5[23] & VL6-[26] | CDR-L2 | K/C | AASSLQS |
| 201 | 1193-B06 | CDR-L3 | K/C | QQHYTTPPT |
| 202 | 1193-C08 | CDR-L3 | K/C | QQHYTTPPT |
| 203 | 1193-E06b | CDR-L3 | K/C | QQHYTTPPT |
| 204 | 1193-H04b | CDR-L3 | K/C | QQHYTTPPT |
| 205 | 1275-C10 | CDR-L3 | K/C | QQYNLYPLT |
| 206 | 1275-D01 | CDR-L3 | K/C | QQYNIYPLT |
| 207 | 1275-D10 | CDR-L3 | K/C | QQYYYYPLT |
| 208 | 1275-G02 | CDR-L3 | K/C | QQYNAYPLT |
| 209 | 1337-A04 | CDR-L3 | K/C | QQYNTYPLT |
| 210 | 1337-A05 | CDR-L3 | K/C | QQYNSYPLT |
| 211 | 1337-A06 | CDR-L3 | K/C | QQYNSYPLT |
| 212 | 1337-A07 | CDR-L3 | K/C | QQYHTYPLT |
| 213 | 1337-A08 | CDR-L3 | K/C | QQYNSYPLT |
| 214 | 1337-A09 | CDR-L3 | K/C | QQYHTYPLT |
| 215 | 1337-A10 | CDR-L3 | K/C | QQYNTYPLT |
| 216 | 1447-D11 | CDR-L3 | K/C | QHNQPTPPT |
| 217 | 1447-E08 | CDR-L3 | K/C | QQHNTTPPT |
| 218 | 1447-F11 | CDR-L3 | K/C | QQHQTAPPT |
| 219 | 1447-G01 | CDR-L3 | K/C | QQQCSWPPT |
| 220 | VL-5[23] & VL6-[26] | CDR-L3 | K/C | QQYNSYPLT |
| 221 | 1193-B06 | scFv | | EVQLLESGGGLVQPGGSLRLSCAASGFTF TGNWMSWVRQAPGKGLEWVGIIYGTSGAT YYADSVKGRFTISRDNSKNTLYLQMNSLR AEDTAVYYCAKPSMSGSRGFDYWGQGTLV TVSSGGGGSGGGGSGGGGSEIVLTQSPGT LSLSPGERATLSCRAGQSVSSSYLAWYQQ KPGQAPRLLIYGASSRATGIPDRFSGSGS GTDFTLTISRLEPEDFAVYYCQQHYTTPP TFGQGTKVEIK |
| 222 | 1193-C08 | scFv | | EVQLLESGGGLVQPGGSLRLSCAASGFTF NNNWMSWVRQAPGKGLEWVGIINGDDGYT YYADRVKGRFTIIRDNSKNTLYLQMNSLR AEDTAVYYCAKVALGRPRRFDYWGQGTLV TVSSGGGGSGGGGSGGGGSEIVLTQSPGT LSLTPGERATLSCRASQSVSSNYLAWYQQ |

TABLE 13-continued

Sequences.

| SEQ ID NO | Molecule | Region | Scheme | Sequence |
|---|---|---|---|---|
| | | | | KPGQAPRLLIYGASSRATGIPDRFSGSGS GTDFTLTISRLEPEDFAMYYCQQHYTTPP TFGQGTKVEIK |
| 223 | 1193-E06b | scFv | | EVQLLESGGGLVQPGGSLRLSCAASGFTF NNTDMSWVRQAPGKGLEWVGIINGSGGAT NYADSVKGRFTISRDNSKNTLYLQMNSLR AEDTAVYYCAKFENEWEVSMDYWGQGTLV TVSSGGGGSGGGGSGGGGSEIVLTQSPGT LSLSPGERATLSCRASQSVSSSYLAWYQQ KPGQAPRLLIYGASSRATGIPDRFSGSGS GTDFTLTISRLEPEDFAVYYCQQHYTTPP TFGQGTKVEIK |
| 224 | 1193-H04b | scFv | | EVQLLESGGGLVQPGGSLRLSCAASGFTF TSSWMSWVRQAPGKGLEWVGIINGYNGIT YYADSVKGRFTISRDNSKNTLYLQMNSLR AEDTAVYYCAKPSAPGARRFDYWGQGTLV TVSSGGGGSGGGGSGGGGSEIVLTQSPGT LSLSPGEATLSCRASQSVSSSYLAWYQQR PGQAPRLLIYGASSRATGIPDRFSGSGSG TDFTLTISRLEPEDFAVYYCQQHYTTPPT FGQGTKVEIK |
| 225 | 1447-D11 | scFv | | EVQLLESGGGLVQPGGSLRLSCAASGFTF NNTDMSWVRQAPGKGLEWVGVINGSGGSS NYADSVKGRFTISRDNSKNTLYLQMNSLR AEDTAVYYCAKYETEWEVSLDYWGQGTLV TVSSGGGGSGGGGSGGGGSEIVLTQSPGT LSLSPGERATLSCRASQSVSSSYLAWYQQ KPGQAPRLLIYGASSRATGIPDRFSGSGS GTDFTLTISRLEPEDFAVYYCQHNQPTPP TFGQGTKVEIK |
| 226 | 1447-E08 | scFv | | EVQLLESGGGLVQPGGSLRLSCAASGFTF NDTDMSWVRQAPGKGLEWVGMINGAGGAS FYADSVRGRFTISRDNSKNTLYLQMNSLR AEDTAVYYCAKFENQWEVTFDYWGQGTLV TVSSGGGGSGGGGSGGGGSEIVLTQSPGT LSLSPGERATLSCRASQRVAGIDLSWYQQ KPGQAPRLLIYGASSRATGIPDRFSGSGS GTDFTLTISRLEPEDFAVYYCQQHNTTPP TFGQGTKVEIK |
| 227 | 1447-F11 | scFv | | EVQLLESGGGLVQTGGSLRLSCAASGFTF DNTDMSWVRQAPGKGLEWVGIINGSGGVT NYADSVRGRFTISRDNSKNTLYLQMNSLR AEDTAVYYCAKYESEWEVSLDYWGQGTLV TVSSGGGGSGGGGSGGGGSEIVLTQSPGT LSLSPGERATLSCRASQSVYRSYLAWYQQ KPGQAPRLLIYGASSRATGIPDRFSGSGS GTDFTLTISRLEPEDFAVYYCQQHQTAPP TFGQGTKVEIK |
| 228 | 1447-G01 | scFv | | EVQLLESGGGLVQPGGSLRLSCAASGFTF NTSDMSWVRQAPGKGLEWVGIINGSGGAT NYADSVKGRFTISRDNSKNTLYLQMNSLR AEDTAVYYCAKYENEMEVSMDYWGQGTLV TVSSGGGGSGGGGSGGGGSEIVLTQSPGT LSLSPGERATLSCRASQSVSSRELGWYQQ KPGQAPRLLIYGASSRATGIPDRFSGSGS GTDFTLTISRLEPEDFAVYYCQQQCSWPP TFGQGTKVEIK |
| 229 | 1251-B08-g_1337-A09-g scFv-Fc | scFv-Fc | | QVQLVESGGGVVQPGRSLRLSCAASGFNF SDYGMHWVRQAPGKGLEWVAVIWYDISGS YYADSVKGRFTISRDNSKNTLYLQMNSLR AEDTAVYYCARGGTVEHGAVYGTDVWGQG TTVTVSSGGGGSGGGGSGGGGSDIQMTQS PSSVSASVGDRVTITCRASQGIGSWLAWY QQKPGKAPKLLIYAADRLQSGVPSRFSGS GSGTDFTLTISSLQPEDFATYYCQQYHTY PLTFGGGTKVEIKAAGSDQEPKSSDKTHT CPPCSAPELLGGSSVFLFPPKPKDTLMIS |

TABLE 13-continued

| Sequences. | | | | |
|---|---|---|---|---|
| SEQ ID NO | Molecule | Region | Scheme | Sequence |
| | | | | RTPEVTCVVVDVSHEDPEVKFNWYVDGVE VHNAKTKPREEQYNSTYRVVSVLTVLHQD WLNGKEYKCKVSNKALPAPIEKTISKAKG QPREPQVYTLPPSRDELTKNQVSLTCLVK GFYPSDIAVEWESNGQPENNYKTTPPVLD SDGSFFLYSKLTVDKSRWQQGNVFSCSVM HEALHNHYTQKSLSLSPGKGSGDYKDDDD KGSGHHHHHH |
| 230 | 1198-A01 | VH | | EVQLVESGGGLVQPGGSLRLSCAASGFTF SDYDMSWVRQAPGKGLEWVGFIAQDGSYK YYVDSVKGRFTISRDNAKNSLYLQMNSLR AEDTAVYYCARSKLFRAGQFDYWGQGTLV TVSS |
| 231 | 1198-B10 | VH | | EVQLVESGGGLVQPGGSLRLSCAASGFNI SGSWIHWVRQAPGKGLEWVGYIYPDDGDT YYADSVKGRFTISADTSKNTAYLQMNSLR AEDTAVYYCAREGSHNLDKMDYWGQGTLV TVSS |
| 232 | 1198-D03 | VH | | EVQLVESGGGLVQPGGSLRLSCAASGFNI NNYDIHWVRQAPGKGLEWVANIDPYNGAT YYADSVKGRFTISADTSKNTAYLQMNSLR AEDTAVYYCARVLWGFWAPFDYWGQGTLV TVSS |
| 233 | 1198-D04 | VH | | EVQLVESGGGLVQPGGSLRLSCAASGFNI NNYDIHWVRQAPGKGLEWVANIDPYNGTT YYADSVKGRFTISADTSKNTAYLQMNSLR AEDTAVYYCARVPWGFWAPFDYWGQGTLV TVSS |
| 234 | 1251-A02 | VH | | QVQLVESGGGVVQPGRSLRLSCAASGFAF SDHGMHWVRQAPDKGLEWVAVIWYDGSHK IYADSVKGRFTISRDNSKNTLYLQMNSLR AEDTAVYYCARGGSLAGGAVYGTDVWGQG TTVTVSS |
| 235 | 1251-A03 | VH | | QVQLVESGGGVVQPGRSLRLSCAASGFAF SDHGMHWVRQAPDKGLEWVAVIWYDGSHK IYADSVKGRFTISRDNSKNTLYLQMNSLR AEDTAVYYCARGGSLAGGAVYGTDVWGQG TTVTVSS |
| 236 | 1251-A06 | VH | | QVQLVESGGGVVQPGRSLRLSCAASGFDF SSYGMHWVRQAPDKGLEWVAVIWDDGSDR Y YADSVKGRFTISRDNSKNTLYLQMNSLRA EDTAVYYCARGGTRVLGAIHGTDVWGQGT TVTVSS |
| 237 | 1251-A06-g | VH | | QVQLVESGGGVVQPGRSLRLSCAASGFDF SSYGMHWVRQAPGKGLEWVAVIWDDGSDR Y YADSVKGRFTISRDNSKNTLYLQMNSLRA EDTAVYYCARGGTRVLGAIHGTDVWGQGT TVTVSS |
| 238 | 1251-B08 | VH | | QVQLVESGGGVVQPGRSLRLSCAASGFNF SDYGMHWVRQAPDKGLEWVAVIWYDGSIS Y YADSVKGRFTISRDNSKNTLYLQMNSLRA EDTAVYYCARGGTVEHGAVYGTDVWGQGA TV TVSS |
| 239 | 1251-B08-g | VH | | QVQLVESGGGVVQPGRSLRLSCAASGFNF SDYGMHWVRQAPGKGLEWVAVIWYDGSIS Y YADSVKGRFTISRDNSKNTLYLQMNSLRA EDTAVYYCARGGTVEHGAVYGTDVWGQGT TV TVSS |

TABLE 13-continued

| SEQ ID NO | Molecule | Region | Scheme | Sequence |
|---|---|---|---|---|
| | | Sequences. | | |
| 240 | 1251-B09 | VH | | QVQLVESGGGVVQPGRSLRLSCAASGFNF SDYGMHWVRQAPDKGLEWVAVTWYDGSRE Y YADSVKGRFTISRDNSKNTLYLQMNSLRA EDTAVYYCARGGTLVHGALYGNDVWGQGT TV TVSS |
| 241 | 1251-B10 | VH | | QVQLVESGGGVVQPGRSLRLSCAASGFNF SSHGMHWVRQAPDKGLEWVAVIWHDGSDK Y YADSVKGRFTISRDNSKNTLYLQMNSLRA EDTAVYYCARGGTRVLGAVYGLDVWGQGT TV TVSS |
| 242 | 1251-C03 | VH | | QVQLVESGGGVVQPGRSLRLSCAASGFNF SSYGMHWVRQAPDKGLEWVAVIWYDGS1K NYADSVKGRFTISRDNSKNTLYLQMNSLR AEDTAVYYCARGGALMRGEFSGHDVWGQG TTVTVSS |
| 243 | 1251-D02 | VH | | QVQLVESGGGVVQPGRSLRLSCAASGFSF ASHGMHWVRQAPDKGLEWVAVIWDDGSDR YYADSVKGRFTISRDNSKNTLYLQMNSLR AEDTAVYYCARGGTRVLGAIHGTDVWGQG TTVTVSS |
| 244 | 1251-D06 | VH | | QVQLVESGGGVVQPGRSLRLSCAASGFSF GSYGMHWVRQAPDKGLEWVAVVWYDGSKT IYADSVKGRFTISRDNSKNTLYLQMNSLR AEDTAVYYCARGGTLVRGAVYGLDVWGQG TTVTVSS |
| 245 | 1251-D09 | VH | | QVQLVESGGGVVQPGRSLRLSCAASGFSF SSYGMHWVRQAPDKGLEWVAVIWYDASIR KYAGSVKGRFTISRDNSKNTLYLQMNSLR AEDTAVYYCARGGTVERGAIYGTDVWGQG TTVTVSS |
| 246 | 1251-E06 | VH | | QVQLVESGGGVVQPGRSLRLSCAASGFTF DSYGMHWVRQAPDKGLEWVAVIWYDGSNK VYADSVKGRFTISRDNSKNTLYLQMNSLR AEDTAVYYCARGGMVGQGAMFGLDVWGQG TTVTVSS |
| 247 | 1251-F06 | VH | | QVQLVESGGGVVQPGRSLRLSCAASGFTF SSFGMHWVRQAPDKGLEWVAVIWYDGSNE YYADSVKGRFTISRDNSKNTLYLQMNSLR AEDTAVYYCARGGSLVTRGVYGLDVWGQG TTVTVSS |
| 248 | 1251-F07 | VH | | QVQLVESGGGVVQPGRSLRLSCAASGFTF SSHGMHWVRQAPDKGLEWVAVIWDDGSNE VYADSVKGRFTISRDNSKNTLYLQMNSLR AEDTAVYYCARGGTRIRGLRYGTDVWGQG TTVTVSS |
| 249 | 1251-G02 | VH | | QVQLVESGGGVVQPGRSLRLSCAASGFTF SSYGMHWVRQAPDKGLEWVAVIWHDGSKD YYADSVKGRFTISRDNSKNTLYLQMNSLR AEDTAVYYCARGGQLDHGAIYGLDVWGQG TTVTVSS |
| 250 | 1445-A03 | VH | | EVQLVESGGGLVQPGGSLRLSCAASGFNI SGYYIHWVRQAPGKGLEWVAEISPTGGYT YYADSVKGRFTISADTSKNTAYLQMNSLR AEDTAVYYCAREHGLVYGQPMDYWGQGTL VTVSS |
| 251 | 1445-B09 | VH | | EVQLVESGGGLVQPGGSLRLSCAASGFNI TGTGHWVRQAPGKGLEWVG IITPYNGTT NYADSVKGRFTISADTSKNTAYLQMNSLR AEDTAVYYCARGGYGYYYPPFDYWGQGTL VTVSS |

TABLE 13-continued

| Sequences. | | | | |
|---|---|---|---|---|
| SEQ ID NO | Molecule | Region | Scheme | Sequence |
| 252 | VH11-[19] | VH | | QVQLVESGGGVVQPGRSLRLSCAASGFTF SSYGMHWVRQAPDKGLEWVAVIWYDGSNK YYADSVKGRFTISRDNSKNTLYLQMNSLR AEDTAVYYCARGGTLVRGAMYGTDVWGQG TTVTVSS |
| 253 | VH5-[7] | VH | | QVQLVESGGGVVQPGRSLRLSCAASGFTF SSYAMHWVRQAPGKGLEWVAVISYDGSNK YYADSVKGRFTISRDNSKNTLYLQMNSLR AEDTAVYYCASGRYYGSGSYSSYFDYWGQ GTLVTVSS |
| 254 | VH6-[11] | VH | | QVQLVESGGGVVQPGRSLRLSCAASGFTF SSYAMHWVRQAPGKGLEWVAVISYDGSIK YYADSVKGRFTISRDNSKNTLYLQMNSLR VEDTAVFYCARGREITSQNIVILLDYWGQ GTLVTVTS |
| 255 | VH8-[15] | VH | | QVQLVESGGGVVQPGRSLRLSCAASGFTF SSYAMHWVRQAPGKGLEWVAVISYDGSNK YYADSVKGRFTISRDNSKNTLYLQMNSLR AEDTAVYYCARGREITSQNIVILLDYWGQ GTLVTVSS |
| 256 | 1275-C10 | VL | | DIQMTQSPSSLSASVGDRVTITCRASQGV SSWLAWYQQKPEKAPKSLIYSARYLQSGV P SRFSGSGSGTDFTLTISSLQPEDFATYYC QQYNLYPLTFGGGTKVEIK |
| 257 | 1275-C10-g | VL | | DIQMTQSPSSVSASVGDRVTITCRASQGV SSWLAWYQQKPGKAPKLLIYSARYLQSGV P SRFSGSGSGTDFTLTISSLQPEDFATYYC QQYNLYPLTFGGGTKVEIK |
| 258 | 1275-D01 | VL | | DIQMTQSPSSLSASVGDRVTITCRASQGI GRWLAWYQQKPEKAPKSLIYGRSSLQSGV PSRFSGSGSGTDFTLTISSLQPEDFATYY CQQYNIYPLTFGGGTKVEIK |
| 259 | 1275-D10 | VL | | DIQMTQSPSSLSASVGDRVTITCRASQGV FSWLAWYQQKPEKAPKSLIYNATQLQSGV PSRFSGSGSGTDFTLTISSLQPEDFATYY CQQYYYYPLTFGGGTKVEIK |
| 260 | 1275-G02 | VL | | DIQMTQSPSSLSASVGDRVTITCRASQGL GSFLAWYQQKPEKAPKSLIYLGNLLQIGV PSRFSGSGSGTDFTLTISSLQPEDFATYY CQQYNAYPLTFGGGTKVEIK |
| 261 | 1337-A04 | VL | | DIQMTQSPSSLSASVGDRVTITCRASQDI GRWVAWYQQKPEKAPKSLIYGASSLQSGV P SRFSGSGSGTDFTLTISSLQPEDFATYYC QQYNTYPLTFGGGTKVEIK |
| 262 | 1337-A05 | VL | | DIQMTQSPSSLSASVGDRVTITCRASQGI GRWVAWYQQKPEKAPKSLIYGADRLQSGV PSRFSGSGSGTDFTLTISSLQPEDFATYY CQQYNSYPLTFGGGTKVEIK |
| 263 | 1337-A06 | VL | | DIQMTQSPSSLSASVGDRVTITCRASQDI GSWVAWYQQKPEKAPKSLIYGADRLQSGV PSRFSGSGSGTDFTLTISSLQPEDFATYY CQQYNSYPLTFGGGTKVEIK |
| 264 | 1337-A07-g | VL | | DIQMTQSPSSVSASVGDRVTITCRASQGI SSWVAWYQQKPGKAPKLLIYGASRLQSGV P SRFSGSGSGTDFTLTISSLQPEDFATYYC QQYHTYPLTFGGGTKVEIK |

TABLE 13-continued

Sequences.

| SEQ ID NO | Molecule | Region | Scheme | Sequence |
|---|---|---|---|---|
| 265 | 1337-A07 | VL | | DIQMTQSPSSLSASVGDRVTITCRASQGI SSWVAWYQQKPEKAPKSLIYGASRLQSGV P SRFSGSGSGTDFTLTISSLQPEDFATYYC QQYHTYPLTFGGGTKVEIK |
| 266 | 1337-A08 | VL | | DIQMTQSPSSLSASVGDRVTITCRASQDI GSWVAWYQQKPEKAPKSLIYASDSLQSGV PSRFSGSGSGTDFTLTISSLQPEDFATYY CQQYNSYPLTFGGGTKVEIK |
| 267 | 1337-A09 | VL | | DIQMTQSPSSLSASVGDRVTITCRASQGI GSWLAWYQQKPEKAPKSLIYAADRLQSGV P SRFSGSGSGTDFTLTISSLQPEDFATYYC QQYHTYPLTFGGGTKVEIK |
| 268 | 1337-A09-g | VL | | DIQMTQSPSSVSASVGDRVTITCRASQGI GSWLAWYQQKPGKAPKLLIYAADRLQSGV P SRFSGSGSGTDFTLTISSLQPEDFATYYC QQYHTYPLTFGGGTKVEIK |
| 269 | 1337-A10 | VL | | DIQMTQSPSSLSASVGDRVTITCRASQGI SSWVAWYQQKPEKAPKSLIYGSSRLQSGV P SRFSGSGSGTDFTLTISSLQPEDFATYYC QQYNTYPLTFGGGTKVEIK |
| 270 | 1337-A10-g | VL | | DIQMTQSPSSVSASVGDRVTITCRASQGI SSWVAWYQQKPGKAPKLLIYGSSRLQSGV PSRFSGSGSGTDFTLTISSLQPEDFATYY CQQYNTYPLTFGGGTKVEIK |
| 271 | VL5-[23] | VL | | DIQMTQSPSSLSASVGDRVTITCRASQGI SSWLAWFQQKPEKAPKSLIYAASSLQSGV PSRFSGSGSGTDFTLTISSLQPEDFATYY CQQYNSYPLTFGGGTKVEIK |
| 272 | VL6-[26] | VL | | DIQMTQSPSSLSASVGDRVTITCRASQGI SSWLAWYQQKPEKAPKSLIYAASSLQSGV PSRFSGSGSGTDFTLTISSLQPEDFATYY CQQYNSYPLTFGGGTKVEIK |
| 273 | 1193-B06 | VH | | EVQLLESGGGLVQPGGSLRLSCAASGFTF TGNWMSWVRQAPGKGLEWVGIIYGTSGAT YYADSVKGRFTISRDNSKNTLYLQMNSLR AEDTAVYYCAKPSMSGSRGFDYWGQGTLV TVSS |
| 274 | 1193-C08 | VH | | EVQLLESGGGLVQPGGSLRLSCAASGFTF NNNWMSWVRQAPGKGLEWVGIINGDDGYT YYADRVKGRFTIIRDNSKNTLYLQMNSLR AEDTAVYYCAKVALGRPRRFDYWGQGTLV TVSS |
| 275 | 1193-E06b | VH | | EVQLLESGGGLVQPGGSLRLSCAASGFTF NNTDMSWVRQAPGKGLEWVGIINGSGGAT NYADSVKGRFTISRDNSKNTLYLQMNSLR AEDTAVYYCAKFENEWEVSMDYWGQGTLV TVSS |
| 276 | 1193-H04b | VH | | EVQLLESGGGLVQPGGSLRLSCAASGFTF TSSWMSWVRQAPGKGLEWVGIINGYNGIT YYADSVKGRFTISRDNSKNTLYLQMNSLR AEDTAVYYCAKPSAPGARRFDYWGQGTLV TVSS |
| 277 | 1447-D11 | VH | | EVQLLESGGGLVQPGGSLRLSCAASGFTF NNTDMSWVRQAPGKGLEWVGVINGSGGSS NYADSVKGRFTISRDNSKNTLYLQMNSLR AEDTAVYYCAKYETEWEVSLDYWGQGTLV TVSS |

TABLE 13-continued

Sequences.

| SEQ ID NO | Molecule | Region | Scheme | Sequence |
|---|---|---|---|---|
| 278 | 1447-E08 | VH | | EVQLLESGGGLVQPGGSLRLSCAASGFTF NDTDMSWVRQAPGKGLEWVGMINGAGGAS FYADSVRGRFTISRDNSKNTLYLQMNSLR AEDTAVYYCAKFENQWEVTFDYWGQGTLV TVSS |
| 279 | 1447-F11 | VH | | EVQLLESGGGLVQTGGSLRLSCAASGFTF DNTDMSWVRQAPGKGLEWVGIINGSGGVT NYADSVRGRFTISRDNSKNTLYLQMNSLR AEDTAVYYCAKYESEWEVSLDYWGQGTLV TVSS |
| 280 | 1447-G01 | VH | | EVQLLESGGGLVQPGGSLRLSCAASGFTF NTSDMSWVRQAPGKGLEWVGIINGSGGAT NYADSVKGRFTISRDNSKNTLYLQMNSLR AEDTAVYYCAKYENEMEVSMDYWGQGTLV TVSS |
| 281 | 1193-B06 | VL | | EIVLTQSPGTLSLSPGERATLSCRAGQSV SSSYLAWYQQKPGQAPRLLIYGASSRATG IPDRFSGSGSGTDFTLTISRLEPEDFAVY YCQQHYTTPPTFGQGTKVEIK |
| 282 | 1193-C08 | VL | | EIVLTQSPGTLSLTPGERATLSCRASQSV SSNYLAWYQQKPGQAPRLLIYGASSRATG IPDRFSGSGSGTDFTLTISRLEPEDFAMY YCQQHYTTPPTFGQGTKVEIK |
| 283 | 1193-E06b | VL | | EIVLTQSPGTLSLSPGERATLSCRASQSV SSSYLAWYQQKPGQAPRLLIYGASSRATG IPDRFSGSGSGTDFTLTISRLEPEDFAVY YCQQHYTTPPTFGQGTKVEIK |
| 284 | 1193-H04b | VL | | EIVLTQSPGTLSLSPGEATLSCRASQSVS SSYLAWYQQRPGQAPRLLIYGASSRATGI PDRFSGSGSGTDFTLTISRLEPEDFAVYY CQQHYTTPPTFGQGTKVEIK |
| 285 | 1447-D11 | VL | | EIVLTQSPGTLSLSPGERATLSCRASQSV SSSYLAWYQQKPGQAPRLLIYGASSRATG IPDRFSGSGSGTDFTLTISRLEPEDFAVY YCQHNQPTPPTFGQGTKVEIK |
| 286 | 1447-E08 | VL | | EIVLTQSPGTLSLSPGERATLSCRASQRV AGIDLSWYQQKPGQAPRLLIYGASSRATG IPDRFSGSGSGTDFTLTISRLEPEDFAVY YCQQHNTTPPTFGQGTKVEIK |
| 287 | 1447-F11 | VL | | EIVLTQSPGTLSLSPGERATLSCRASQSV YRSYLAWYQQKPGQAPRLLIYGASSRATG IPDRFSGSGSGTDFTLTISRLEPEDFAVY YCQQHQTAPPTFGQGTKVEIK |
| 288 | 1447-G01 | VL | | EIVLTQSPGTLSLSPGERATLSCRASQSV SSRELGWYQQKPGQAPRLLIYGASSRATG IPDRFSGSGSGTDFTLTISRLEPEDFAVY YCQQQCSWPPTFGQGTKVEIK |
| 289 | IgG1 Fc from scFv-Fc | | | AAGSDQEPKSSDKTHTCPPCSAPELLGGSS VFLFPPKPKDTLMISRTPEVTCVVVDVSHE DPEVKFNWYVDGVEVHNAKTKPREEQYNST YRVVSVLTVLHQDWLNGKEYKCKVSNKALP APIEKTISKAKGQPREPQVYTLPPSRDELT KNQVSLTCLVKGFYPSDIAVEWESNGQPEN NYKTTPPVLDSDGSFFLYSKLTVDKSRWQQ GNVFSCSVMHEALHNHYTQKSLSLSPGKGS GDYKDDDDKGSG |
| 290 | Trastuzumab LC | LC | | DIQMTQSPSSLSASVGDRVTITCRASQDV NTAVAWYQQKPGKAPKLLIYSASFLYSGV PSRFSGSRSGTDFTLTISSLQPEDFATYY CQQHYTTPPTFGQGTKVEIK |

TABLE 13-continued

| Sequences. | | | | |
|---|---|---|---|---|
| SEQ ID NO | Molecule | Region | Scheme | Sequence |
| 291 | 1251-A06-(wt) | HC | | MQVQLVESGGGVVQPGRSLRLSCAASGFD FSSYGMHWVRQAPDKGLEWVAVIWDDGSD RY YADSVKGRFTISRDNSKNTLYLQMNSLRA EDTAVYYCARGGTRVLGAIHGTDVWGQGT TV TVSSASTKGPSVFPLAPSSKSTSGGTAAL GCLVEDYFPEPATVSWNSGALTSGVHTFP AV LQSSGLYSLSSVVTVPSSSLGTQTYICNV NHKPSNTKVDKKVEPKSCDKTHTCPPCPA PE LLGGPSVFLFPPKPKDTLMISRTPEVTCV VVDVSHEDPEVKFNWYVDGVEVHNAKTKP RE EQYNSTYRVVSVLTVLHQDWLNGKEYKCK VSNKALPAPIEKTISKAKGQPREPQVYTL PP SREEMTKNQVSLTCLVKGFYPSDIAVEWE SNGQPENNYKTTPPVLDSDGSFFLYSKLT VD KSRWQQGNVFSCSVMHEALHNHYTQKSLS LSPGKGGSHHHHHH |
| 292 | 1251-A06-(g) | HC | | MQVQLVESGGGVVQPGRSLRLSCAASGFD FSSYGMHWVRQAPGKGLEWVAVIWDDGSD RY YADSVKGRFTISRDNSKNTLYLQMNSLRA EDTAVYYCARGGTRVLGAIHGTDVWGQGT TV TVSSASTKGPSVFPLAPSSKSTSGGTAAL GCLVKDYFPEPVTVSWNSGALTSGVHTFP AV LQSSGLYSLSSVVTVPSSSLGTQTYICNV NHKPSNTKVDKKVEPKSCDKTHTCPPCPA PE LLGGPSVFLFPPKPKDTLMISRTPEVTCV VVDVSHEDPEVKFNWYVDGVEVHNAKTKP RE EQYNSTYRVVSVLTVLHQDWLNGKEYKCK VSNKALPAPIEKTISKAKGQPREPQVYTL PP SREEMTKNQVSLTCLVKGFYPSDIAVEWE SNGQPENNYKTTPPVLDSDGSFFLYSKLT VD KSRWQQGNVFSCSVMHEALHNHYTQKSLS LSPGK |
| 293 | 1251-B08-(wt) | HC | | MQVQLVESGGGVVQPGRSLRLSCAASGFN FSDYGMHWVRQAPDKGLEWVAVIWYDGSI SY YADSVKGRFTISRDNSKNTLYLQMNSLRA EDTAVYYCARGGTVEHGAVYGTDVWGQGA TV TVSSASTKGPSVFPLAPSSKSTSGGTAAL GCLVKDYFPEPVTVSWNSGALTSGVHTFP AV LQSSGLYSLSSVVTVPSSSLGTQTYICNV NHKPSNTKVDKKVEPKSCDKTHTCPPCPA PE LLGGPSVFLFPPKPKDTLMISRTPEVTCV VVDVSHEDPEVKFNWYVDGVEVHNAKTKP RE EQYNSTYRVVSVLTVLHQDWLNGKEYKCK VSNKALPAPIEKTISKAKGQPREPQVYTL PP SREEMTKNQVSLTCLVKGFYPSDIAVEWE SNGQPENNYKTTPPVLDSDGSFFLYSKLT VD KSRWQQGNVFSCSVMHEALHNHYTQKSLS LSPGKGGSHHHHHH |

TABLE 13-continued

| Sequences. | | | | |
|---|---|---|---|---|
| SEQ ID NO | Molecule | Region | Scheme | Sequence |
| 294 | 1251-608-(g) | HC | | MQVQLVESGGGVVQPGRSLRLSCAASGFN FSDYGMHWVRQAPGKGLEWVAVIWYDGSI SY YADSVKGRFTISRDNSKNTLYLQMNSLRA EDTAVYYCARGGTVEHGAVYGTDVWGQGT TV TVSSASTKGPSVFPLAPSSKSTSGGTAAL GCLVKDYFPEPVTVSWNSGALTSGVHTFP AV LQSSGLYSLSSVVTVPSSSLGTQTYICNV NHKPSNTKVDKKVEPKSCDKTHTCPPCPA PE LLGGPSVFLFPPKPKDTLMISRTPEVTCV VVDVSHEDPEVKFNWYVDGVEVHNAKTKP RE EQYNSTYRVVSVLTVLHQDWLNGKEYKCK VSNKALPAPIEKTISKAKGQPREPQVYTL PP SREEMTKNQVSLTCLVKGFYPSDIAVEWE SNGQPENNYKTTPPVLDSDGSFFLYSKLT VD KSRWQQGNVFSCSVMHEALHNHYTQKSLS LSPGK |
| 295 | 1275-C10-(wt) | LC | | MDIQMTQSPSSLSASVGDRVTITCRASQG VSSWLAWYQQKPEKAPKSLIYSARYLQSG VP SRFSGSGSGTDFTLTISSLQPEDFATYYC QQYNLYPLTFGGGTKVEIKRTVAAPSVFI FP PSDEQLKSGTASVVCLLNNFYPREAKVQW KVDNALQSGNSQESVTEQDSKDSTYSLSS TL TLSKADYEKHKVYACEVTHQGLSSPVTKS FNRGEC |
| 296 | 1275-C10-(g) | LC | | MDIQMTQSPSSVSASVGDRVTITCRASQG VSSWLAWYQQKPGKAPKLLIYSARYLQSG VP SRFSGSGSGTDFTLTISSLQPEDFATYYC QQYNLYPLTFGGGTKVEIKRTVAAPSVFI FP PSDEQLKSGTASVVCLLNNFYPREAKVQW KVDNALQSGNSQESVTEQDSKDSTYSLSS TL TLSKADYEKHKVYACEVTHQGLSSPVTKS FNRGEC |
| 297 | 1337-A07-(wt) | LC | | MDIQMTQSPSSLSASVGDRVTITCRASQG ISSWVAWYQQKPEKAPKSLIYGASRLQSG VP SRFSGSGSGTDFTLTISSLQPEDFATYYC QQYHTYPLTFGGGTKVEIKRTVAAPSVFI FP PSDEQLKSGTASVVCLLNNFYPREAKVQW KVDNALQSGNSQESVTEQDSKDSTYSLSS TL TLSKADYEKHKVYACEVTHQGLSSPVTKS FNRGEC |
| 298 | 1337-A07-(g) | LC | | MDIQMTQSPSSVSASVGDRVTITCRASQG ISSWVAWYQQKPGKAPKLLIYGASRLQSG VP SRFSGSGSGTDFTLTISSLQPEDFATYYC QQYHTYPLTFGGGTKVEIKRTVAAPSVFI FP PSDEQLKSGTASVVCLLNNFYPREAKVQW KVDNALQSGNSQESVTEQDSKDSTYSLSS TL TLSKADYEKHKVYACEVTHQGLSSPVTKS FNRGEC |

TABLE 13-continued

| Sequences. | | | | |
|---|---|---|---|---|
| SEQ ID NO | Molecule | Region | Scheme | Sequence |
| 299 | 1337-A09-(wt) | LC | | MDIQMTQSPSSLSASVGDRVTITCRASQGIGSWLAWYQQKPEKAPKSLIYAADRLQSGVPSRFSGSGSGTDFTLTISSLQPEDFATYYCQQYHTYPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 300 | 1337-A09-(g) | LC | | MDIQMTQSPSSVSASVGDRVTITCRASQGIGSWLAWYQQKPGKAPKLLIYAADRLQSGVPSRFSGSGSGTDFTLTISSLQPEDFATYYCQQYHTYPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 301 | 1337-A10-(wt) | LC | | MDIQMTQSPSSLSASVGDRVTITCRASQGISSWVAWYQQKPEKAPKSLIYGSSRLQSGVPSRFSGSGSGTDFTLTISSLQPEDFATYYCQQYNTYPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 302 | 1337-A10-(g) | LC | | MDIQMTQSPSSVSASVGDRVTITCRASQGISSWVAWYQQKPGKAPKLLIYGSSRLQSGVPSRFSGSGSGTDFTLTISSLQPEDFATYYCQQYNTYPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 303 | C-term His Tag | Tag | | GGSHHHHHH |
| 304 | HC Constant | HC Constant | | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 305 | LC Constant | LC Constant | | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

TABLE 13-continued

| Sequences. | | | | |
|---|---|---|---|---|
| SEQ ID NO | Molecule | Region | Scheme | Sequence |
| 306 | 1251-A03 | HC | | MQVQLVESGGGVVQPGRSLRLSCAASGFA FSDHGMHWVRQAPDKGLEWVAVIWYDGSH KI YADSVKGRFTISRDNSKNTLYLQMNSLRA EDTAVYYCARGGSLAGGAVYGTDVWGQGT TV TVSSASTKGPSVFPLAPSSKSTSGGTAAL GCLVKDYFPEPVTVSWNSGALTSGVHTFP AV LQSSGLYSLSSVVTVPSSSLGTRTYICNV NHKPSNTKVDKKVEPKSCDKTHTCPPCPA PE LLGGPSVFLFPPKPKDTLMISRTPEVTCV VVDVSHEDPEVKFNWYVDGVEVHNAKTKP RE EQYNSTYRVVSVLTVLHQDWLNGKEYKCK VSNKALPAPIEKTISKAKGQPREPQVYTL PP SREEMTKNQVSLTCLVKGFYPSDIAVEWE SNGQPENNYKTTPPVLDSDGSFFLYSKLT VD KSRWQQGNVFSCSVMHEALHNHYTQKSLS LSPGKGGSHHHHHH |
| 307 | 1251-B09 | HC | | MQVQLVESGGGVVQPGRSLRLSCAASGFN FSDYGMHWVRQAPDKGLEWVAVTWYDGSR EY YADSVKGRFTISRDNSKNTLYLQMNSLRA EDTAVYYCARGGTLVHGALYGNDVWGQGT TV TVSSASTKGPSVFPLAPSSKSTSGGTAAL GCLVKDYFPEPVTVSWNSGALTSGVHTFP AV LQSSGLYSLSSVVTVPSSSLGTQTYICNV NHKPSNTKVDKKVEPKSCDKTHTCPPCPA PE LLGGPSVFLFPPKPKDTLMISRTPEVTCV VVDVSHEDPEVKFNWYVDGVEVHNAKTKP RE EQYNSTYRVVSVLTVLHQDWLNGKEYKCK VSNKALPAPIEKTISKAKGQPREPQVYTL PP SREEMTKNQVSLTCLVKGFYPSDIAVEWE SNGQPENNYKTTPPVLDSDGSFFLYSKLT VD KSRWQQGNVFSCSVMHEALHNHYTQKSLS LSPGKGGSHHHHHH |
| 308 | 1251-B10 | HC | | MQVQLVESGGGVVQPGRSLRLSCAASGFN FSSHGMHWVRQAPDKGLEWVAVIWHDGSD KY YADSVKGRFTISRDNSKNTLYLQMNSLRA EDTAVYYCARGGTRVLGAVYGLDVWGQGT TV TVSSASTKGPSVFPLAPSSKSTSGGTAAL GCLVKDYFPEPVTVSWNSGALTSGVHTFP AV LQSSGLYSLSSVVTVPSSSLGTQTYICNV NHKPSSTKVDKKVEPKSCDKTHTCPPCPA PE LLGGPSVFLFPPKPKDTLMISRTPEVTCV VVDVSHEDPEVKFNWYVDGVEVHNAKTKP RE EQYNSTYRVVSVLTVLHQDWLNGKEYKCK VSNKALPAPIEKTISKAKGQPREPQVYTL PP SREEMTKNQVSLTCLVKGFYPSDIAVEWE SNGQPENNYKTTPPVLDSDGSFFLYSKLT VD KSRWQQGNVFSCSVMHEALHNHYTQKSLS LSPGKGGSHHHHHH |

TABLE 13-continued

| SEQ ID NO | Molecule | Region | Scheme | Sequence |
|---|---|---|---|---|
| | | Sequences. | | |
| 309 | Fc Constant | Fc Constant | | AAGSDQEPKSSDKTHTCPPCSAPELLGGSSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 310 | 1251-A06 HC | HC | | MQVQLVESGGGVVQPGRSLRLSCAASGFDFSSYGMHWVRQAPDKGLEWVAVIWDDGSDRYYADSVKGRFTISRDNSKNTLYLQMNSLRAEDTAVYYCARGGTRVLGAIHGTDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGKGGSHHHHHH |
| 311 | 1251-F07 HC | HC | | MQVQLVESGGGVVQPGRSLRLSCAASGFTFSSHGMHWVRQAPDKGLEWVAVIWDDGSNEVYADSVKGRFTISRDNSKNTLYLQMNSLRAEDTAVYYCARGGTRIRGLRYGTDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGKGGSHHHHHH |
| 312 | Trastuzumab | CDR-L1 | K/C | RASQDVNTAVA |
| 313 | Trastuzumab | CDR-L2 | K/C | SASFLYS |
| 314 | Trastuzumab | CDR-L3 | K/C | QQHYTTPPT |

EQUIVALENTS

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in this application, in applications claiming priority from this application, or in related applications. Such claims, whether directed to a different invention or to the same invention, and whether broader, narrower, equal, or different in scope in comparison to the original claims, also are regarded as included within the subject matter of the inventions of the present disclosure.

What is claimed is:

1. An isolated antibody that specifically binds to CD74, wherein the antibody comprises:

a. $V_H$ comprising: a CDR-H1 comprising at least one of SEQ ID NOs: 12 and 44;

a CDR-H2 comprising at least one of SEQ ID NOs: 76 and 108; and a CDR-H3 comprising SEQ ID NO: 140; and b. a $V_L$ region comprising a CDR-L1 comprising SEQ ID NO:174; a CDR-L2 comprising SEQ ID NO:194, and a CDR-L3 comprising SEQ ID NO:214.

2. An isolated antibody that specifically binds to CD74, wherein the antibody comprises:

a. three heavy chain CDRs and three light chain CDRs of the $V_H$ region SEQ ID NO: 236, and the $V_L$ region SEQ ID NO: 267;

b. three heavy chain CDRs and three light chain CDRs of the $V_H$ region SEQ ID NO: 238, and the $V_L$ region SEQ ID NO: 256;

c. three heavy chain CDRs and three light chain CDRs of the $V_H$ region SEQ ID NO: 238, and the $V_L$ region SEQ ID NO: 265;

d. three heavy chain CDRs and three light chain CDRs of the $V_H$ region SEQ ID NO: 238, and the $V_L$ region SEQ ID NO: 267;

e. three heavy chain CDRs and three light chain CDRs of the $V_H$ region SEQ ID NO: 238, and the $V_L$ region SEQ ID NO: 269;

f. three heavy chain CDRs and three light chain CDRs of the $V_H$ region SEQ ID NO: 238, and the $V_L$ region SEQ ID NO: 271;

g. three heavy chain CDRs and three light chain CDRs of the $V_H$ region SEQ ID NO: 240, and the $V_L$ region SEQ ID NO: 267.

3. The isolated antibody of claim 2 that specifically binds to CD74, wherein the antibody comprises:

k. a $V_H$ comprising: a CDR-H1 comprising at least one of SEQ ID NOs: 11 and 43; a CDR-H2 comprising at least one of SEQ ID NOs: 75 and 107; and a CDR-H3 comprising SEQ ID NO: 139, and a $V_L$ region comprising a CDR-L1 comprising SEQ ID NO:174; a CDR-L2 comprising SEQ ID NO:194, and a CDR-L3 comprising SEQ ID NO:214;

m. a $V_H$ comprising: a CDR-H1 comprising at least one of SEQ ID NOs: 12 and 44; a CDR-H2 comprising at least one of SEQ ID NOs: 76 and 108; and a CDR-H3 comprising SEQ ID NO: 140, and a $V_L$ region comprising a CDR-L1 comprising SEQ ID NO:165; a CDR-L2 comprising SEQ ID NO:185, and a CDR-L3 comprising SEQ ID NO:205;

n. a $V_H$ comprising: a CDR-H1 comprising at least one of SEQ ID NOs: 12 and 44; a CDR-H2 comprising at least one of SEQ ID NOs: 76 and 108; and a CDR-H3 comprising SEQ ID NO: 140, and a $V_L$ region comprising a CDR-L1 comprising SEQ ID NO:172; a CDR-L2 comprising SEQ ID NO:192, and a CDR-L3 comprising SEQ ID NO:212;

o. a $V_H$ comprising: a CDR-H1 comprising at least one of SEQ ID NOs: 12 and 44; a CDR-H2 comprising at least one of SEQ ID NOs: 76 and 108; and a CDR-H3 comprising SEQ ID NO: 140, and a $V_L$ region comprising a CDR-L1 comprising SEQ ID NO:174; a CDR-L2 comprising SEQ ID NO:194, and a CDR-L3 comprising SEQ ID NO:214;

p. a $V_H$ comprising: a CDR-H1 comprising at least one of SEQ ID NOs: 12 and 44; a CDR-H2 comprising at least one of SEQ ID NOs: 76 and 108; and a CDR-H3 comprising SEQ ID NO: 140, and a $V_L$ region comprising a CDR-L1 comprising SEQ ID NO:175; a CDR-L2 comprising SEQ ID NO:195, and a CDR-L3 comprising SEQ ID NO:215;

y. a $V_H$ comprising: a CDR-H1 comprising at least one of SEQ ID NOs: 13 and 45; a CDR-H2 comprising at least one of SEQ ID NOs: 77 and 109; and a CDR-H3 comprising SEQ ID NO: 141, and a $V_L$ region comprising a CDR-L1 comprising SEQ ID NO:174; a CDR-L2 comprising SEQ ID NO:194, and a CDR-L3 comprising SEQ ID NO:214;

tt. a $V_H$ comprising: a CDR-H1 comprising at least one of SEQ ID NOs: 12 and 44; a CDR-H2 comprising at least one of SEQ ID NOs: 76 and 108; and a CDR-H3 comprising SEQ ID NO: 140, and a $V_L$ region comprising a CDR-L1 comprising SEQ ID NO: 180; a CDR-L2 comprising SEQ ID NO: 200, and a CDR-L3 comprising SEQ ID NO: 220.

4. The antibody of claim 3, wherein:

e. the $V_H$ region is SEQ ID NO: 236, and the $V_L$ region is SEQ ID NO: 267;

q. the $V_H$ region is SEQ ID NO: 238, and the $V_L$ region is SEQ ID NO: 256;

s. the $V_H$ region is SEQ ID NO: 238, and the $V_L$ region is SEQ ID NO: 265;

u. the $V_H$ region is SEQ ID NO: 238, and the $V_L$ region is SEQ ID NO: 267;

w. the $V_H$ region is SEQ ID NO: 238, and the $V_L$ region is SEQ ID NO: 269;

x. the $V_H$ region is SEQ ID NO: 238, and the $V_L$ region is SEQ ID NO: 271;

hh. the $V_H$ region is SEQ ID NO: 240, and the $V_L$ region is SEQ ID NO: 267.

5. The antibody of claim 4, further comprising at least one constant region domain comprising a sequence selected from SEQ ID NO: 304 and SEQ ID NO: 305.

6. The antibody of claim 4, wherein the antibody is a monoclonal antibody.

7. The antibody of claim 4, wherein the antibody is an IgA, an IgD, an IgE, an IgG, or an IgM.

8. The antibody of claim 4, wherein the antibody is humanized or human.

9. The antibody of claim 4, wherein the antibody is aglycosylated.

10. The antibody of claim 4, wherein the antibody is an antibody fragment.

11. The antibody of claim 10, wherein the antibody fragment is selected from an Fv fragment, a Fab fragment, a $F(ab')_2$ fragment, a Fab' fragment, an scFv (sFv) fragment, and an scFv-Fc fragment.

12. The antibody of claim 11, wherein the antibody is an scFv fragment.

13. The antibody of claim 11, wherein the antibody is an scFv-Fc fragment.

14. The antibody of claim 13, wherein the scFv-Fc fragment comprises SEQ ID NO: 229.

15. The antibody of claim 4, wherein the antibody has a $k_a$ of at least about $10^5$ $M^{-1}\times sec^{-1}$ at a temperature of 25° C.

16. The antibody of claim 4, wherein the antibody has a $k_d$ of $10^{-3}$ $sec^{-1}$ or less at a temperature of 25° C.

17. The antibody of claim 4, wherein the antibody has a $K_D$ of $10^{-9}$ M or less at a temperature of 25° C.

18. The antibody of claim 4, wherein the antibody is internalized after binding to CD74 on the surface of a cell.

19. The antibody of claim 4, wherein the Tm2 of the antibody is at least 75° C., 75.5° C., 76° C., 76.5° C., 77° C., 77.5° C., 78° C., 78.5° C., or 79° C.

20. The antibody of claim 4, wherein the Tm1 of the antibody is less than 61° C. or less than 60° C.

21. A kit comprising an antibody of claim 4, and instructions for use of the antibody.

22. A pharmaceutical composition comprising the antibody of claim 4 and a pharmaceutically acceptable carrier.

23. A polynucleotide encoding an antibody of claim 4.

24. A vector comprising the polynucleotide of claim 23.

25. A host cell comprising the vector of claim 24.

26. The host cell of claim 25, wherein the host cell is selected from a bacterial cell, a fungal cell, and a mammalian cell.

27. The host cell of claim 25, wherein the host cell is selected from an *E. coli* cell, a *Saccharomyces cerevisiae* cell, and a CHO cell.

28. A method of treating a disease or condition in a subject in need thereof, comprising administering to the subject an effective amount of an antibody of claim 4, or a pharmaceutical composition of claim 22, wherein the disease or condition is selected from a cancer, an autoimmune disease, an inflammatory disease, and an infection.

29. The method of claim 28, wherein the cancer is selected from multiple myeloma and pancreatic cancer.

* * * * *

SEQUENCE LISTING

```
<160> NUMBER OF SEQ ID NOS: 311

<210> SEQ ID NO 1
<211> LENGTH: 7
<212> TYPE: PRT
<213> ORGANISM: Artificial Sequence
<220> FEATURE:
<223> OTHER INFORMATION: Synthetic:  1193-B06 / CDR-H1 / Chothia

<400> SEQUENCE: 1

Gly Phe Thr Phe Thr Gly Asn
1               5


<210> SEQ ID NO 2
<211> LENGTH: 7
<212> TYPE: PRT
<213> ORGANISM: Artificial Sequence
<220> FEATURE:
<223> OTHER INFORMATION: Synthetic:  1193-C08 / CDR-H1 / Chothia

<400> SEQUENCE: 2

Gly Phe Thr Phe Asn Asn Asn
1               5


<210> SEQ ID NO 3
<211> LENGTH: 7
<212> TYPE: PRT
<213> ORGANISM: Artificial Sequence
<220> FEATURE:
<223> OTHER INFORMATION: Synthetic:  1193-E06b / CDR-H1 / Chothia

<400> SEQUENCE: 3

Gly Phe Thr Phe Asn Asn Thr
1               5


<210> SEQ ID NO 4
<211> LENGTH: 7
<212> TYPE: PRT
<213> ORGANISM: Artificial Sequence
<220> FEATURE:
<223> OTHER INFORMATION: Synthetic:  1193-H04b / CDR-H1 / Chothia

<400> SEQUENCE: 4

Gly Phe Thr Phe Thr Ser Ser
1               5


<210> SEQ ID NO 5
<211> LENGTH: 7
<212> TYPE: PRT
<213> ORGANISM: Artificial Sequence
<220> FEATURE:
<223> OTHER INFORMATION: Synthetic:  1198-A01 / CDR-H1 / Chothia

<400> SEQUENCE: 5

Gly Phe Thr Phe Ser Asp Tyr
1               5


<210> SEQ ID NO 6
<211> LENGTH: 7
<212> TYPE: PRT
<213> ORGANISM: Artificial Sequence
```

<220> FEATURE:
<223> OTHER INFORMATION: Synthetic: 1198-B10 / CDR-H1 / Chothia

<400> SEQUENCE: 6

Gly Phe Asn Ile Ser Gly Ser
1 5

<210> SEQ ID NO 7
<211> LENGTH: 7
<212> TYPE: PRT
<213> ORGANISM: Artificial Sequence
<220> FEATURE:
<223> OTHER INFORMATION: Synthetic: 1198-D03 / CDR-H1 / Chothia

<400> SEQUENCE: 7

Gly Phe Asn Ile Asn Asn Tyr
1 5

<210> SEQ ID NO 8
<211> LENGTH: 7
<212> TYPE: PRT
<213> ORGANISM: Artificial Sequence
<220> FEATURE:
<223> OTHER INFORMATION: Synthetic: 1198-D04 / CDR-H1 / Chothia

<400> SEQUENCE: 8

Gly Phe Asn Ile Asn Asn Tyr
1 5

<210> SEQ ID NO 9
<211> LENGTH: 7
<212> TYPE: PRT
<213> ORGANISM: Artificial Sequence
<220> FEATURE:
<223> OTHER INFORMATION: Synthetic: 1251-A02 / CDR-H1 / Chothia

<400> SEQUENCE: 9

Gly Phe Ala Phe Ser Asp His
1 5

<210> SEQ ID NO 10
<211> LENGTH: 7
<212> TYPE: PRT
<213> ORGANISM: Artificial Sequence
<220> FEATURE:
<223> OTHER INFORMATION: Synthetic: 1251-A03 / CDR-H1 / Chothia

<400> SEQUENCE: 10

Gly Phe Ala Phe Ser Asp His
1 5

<210> SEQ ID NO 11
<211> LENGTH: 7
<212> TYPE: PRT
<213> ORGANISM: Artificial Sequence
<220> FEATURE:
<223> OTHER INFORMATION: Synthetic: 1251-A06 / CDR-H1 / Chothia

<400> SEQUENCE: 11

Gly Phe Asp Phe Ser Ser Tyr
1 5

<210> SEQ ID NO 12
<211> LENGTH: 7
<212> TYPE: PRT
<213> ORGANISM: Artificial Sequence
<220> FEATURE:

<223> OTHER INFORMATION: Synthetic: 1251-B08 / CDR-H1 / Chothia

<400> SEQUENCE: 12

Gly Phe Asn Phe Ser Asp Tyr
1 5

<210> SEQ ID NO 13
<211> LENGTH: 7
<212> TYPE: PRT
<213> ORGANISM: Artificial Sequence
<220> FEATURE:
<223> OTHER INFORMATION: Synthetic: 1251-B09 / CDR-H1 / Chothia

<400> SEQUENCE: 13

Gly Phe Asn Phe Ser Asp Tyr
1 5

<210> SEQ ID NO 14
<211> LENGTH: 7
<212> TYPE: PRT
<213> ORGANISM: Artificial Sequence
<220> FEATURE:
<223> OTHER INFORMATION: Synthetic: 1251-B10 / CDR-H1 / Chothia

<400> SEQUENCE: 14

Gly Phe Asn Phe Ser Ser His
1 5

<210> SEQ ID NO 15
<211> LENGTH: 7
<212> TYPE: PRT
<213> ORGANISM: Artificial Sequence
<220> FEATURE:
<223> OTHER INFORMATION: Synthetic: 1251-C03 / CDR-H1 / Chothia

<400> SEQUENCE: 15

Gly Phe Asn Phe Ser Ser Tyr
1 5

<210> SEQ ID NO 16
<211> LENGTH: 7
<212> TYPE: PRT
<213> ORGANISM: Artificial Sequence
<220> FEATURE:
<223> OTHER INFORMATION: Synthetic: 1251-D02 / CDR-H1 / Chothia

<400> SEQUENCE: 16

Gly Phe Ser Phe Ala Ser His
1 5

<210> SEQ ID NO 17
<211> LENGTH: 7
<212> TYPE: PRT
<213> ORGANISM: Artificial Sequence
<220> FEATURE:
<223> OTHER INFORMATION: Synthetic: 1251-D06 / CDR-H1 / Chothia

<400> SEQUENCE: 17

Gly Phe Ser Phe Gly Ser Tyr
1 5

<210> SEQ ID NO 18
<211> LENGTH: 7
<212> TYPE: PRT
<213> ORGANISM: Artificial Sequence
<220> FEATURE:
<223> OTHER INFORMATION: Synthetic: 1251-D09 / CDR-H1 / Chothia

<400> SEQUENCE: 18

Gly Phe Ser Phe Ser Ser Tyr
1 5

<210> SEQ ID NO 19
<211> LENGTH: 7
<212> TYPE: PRT
<213> ORGANISM: Artificial Sequence
<220> FEATURE:
<223> OTHER INFORMATION: Synthetic: 1251-E06 / CDR-H1 / Chothia

<400> SEQUENCE: 19

Gly Phe Thr Phe Asp Ser Tyr
1 5

<210> SEQ ID NO 20
<211> LENGTH: 7
<212> TYPE: PRT
<213> ORGANISM: Artificial Sequence
<220> FEATURE:
<223> OTHER INFORMATION: Synthetic: 1251-F06 / CDR-H1 / Chothia

<400> SEQUENCE: 20

Gly Phe Thr Phe Ser Ser Phe
1 5

<210> SEQ ID NO 21
<211> LENGTH: 7
<212> TYPE: PRT
<213> ORGANISM: Artificial Sequence
<220> FEATURE:
<223> OTHER INFORMATION: Synthetic: 1251-F07 / CDR-H1 / Chothia

<400> SEQUENCE: 21

Gly Phe Thr Phe Ser Ser His
1 5

<210> SEQ ID NO 22
<211> LENGTH: 7
<212> TYPE: PRT
<213> ORGANISM: Artificial Sequence
<220> FEATURE:
<223> OTHER INFORMATION: Synthetic: 1251-G02 / CDR-H1 / Chothia

<400> SEQUENCE: 22

Gly Phe Thr Phe Ser Ser Tyr
1 5

<210> SEQ ID NO 23
<211> LENGTH: 7
<212> TYPE: PRT
<213> ORGANISM: Artificial Sequence
<220> FEATURE:
<223> OTHER INFORMATION: Synthetic: 1445-A03 / CDR-H1 / Chothia

<400> SEQUENCE: 23

Gly Phe Asn Ile Ser Gly Tyr
1 5

<210> SEQ ID NO 24
<211> LENGTH: 7
<212> TYPE: PRT
<213> ORGANISM: Artificial Sequence
<220> FEATURE:
<223> OTHER INFORMATION: Synthetic: 1445-B09 / CDR-H1 / Chothia

<400> SEQUENCE: 24

Gly Phe Asn Ile Thr Gly Thr
1 5

<210> SEQ ID NO 25
<211> LENGTH: 7
<212> TYPE: PRT
<213> ORGANISM: Artificial Sequence
<220> FEATURE:
<223> OTHER INFORMATION: Synthetic: 1447-D11 / CDR-H1 / Chothia

<400> SEQUENCE: 25

Gly Phe Thr Phe Asn Asn Thr
1 5

<210> SEQ ID NO 26
<211> LENGTH: 7
<212> TYPE: PRT
<213> ORGANISM: Artificial Sequence
<220> FEATURE:
<223> OTHER INFORMATION: Synthetic: 1447-E08 / CDR-H1 / Chothia

<400> SEQUENCE: 26

Gly Phe Thr Phe Asn Asp Thr
1 5

<210> SEQ ID NO 27
<211> LENGTH: 7
<212> TYPE: PRT
<213> ORGANISM: Artificial Sequence
<220> FEATURE:
<223> OTHER INFORMATION: Synthetic: 1447-F11 / CDR-H1 / Chothia

<400> SEQUENCE: 27

Gly Phe Thr Phe Asp Asn Thr
1 5

<210> SEQ ID NO 28
<211> LENGTH: 7
<212> TYPE: PRT
<213> ORGANISM: Artificial Sequence
<220> FEATURE:
<223> OTHER INFORMATION: Synthetic: 1447-G01 / CDR-H1 / Chothia

<400> SEQUENCE: 28

Gly Phe Thr Phe Asn Thr Ser
1 5

<210> SEQ ID NO 29
<211> LENGTH: 7
<212> TYPE: PRT
<213> ORGANISM: Artificial Sequence
<220> FEATURE:
<223> OTHER INFORMATION: Synthetic: VH11-[19] / CDR-H1 / Chothia

<400> SEQUENCE: 29

Gly Phe Thr Phe Ser Ser Tyr
1 5

<210> SEQ ID NO 30
<211> LENGTH: 7
<212> TYPE: PRT
<213> ORGANISM: Artificial Sequence
<220> FEATURE:
<223> OTHER INFORMATION: Synthetic: VH5-[7] / CDR-H1 / Chothia

<400> SEQUENCE: 30

Gly Phe Thr Phe Ser Ser Tyr
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic:  VH6-[11] / CDR-H1 / Chothia

<400> SEQUENCE: 31

Gly Phe Thr Phe Ser Ser Tyr
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic:  VH8-[15] / CDR-H1 / Chothia

<400> SEQUENCE: 32

Gly Phe Thr Phe Ser Ser Tyr
1               5

<210> SEQ ID NO 33
<211> LENGTH: 5
<212> TYPE: PRT
<213> ORGANISM: Artificial Sequence
<220> FEATURE:
<223> OTHER INFORMATION: Synthetic:  1193-B06 / CDR-H1 / Kabat

<400> SEQUENCE: 33

Gly Asn Trp Met Ser
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic:  1193-C08 / CDR-H1 / Kabat

<400> SEQUENCE: 34

Asn Asn Trp Met Ser
1               5

<210> SEQ ID NO 35
<211> LENGTH: 5
<212> TYPE: PRT
<213> ORGANISM: Artificial Sequence
<220> FEATURE:
<223> OTHER INFORMATION: Synthetic:  1193-E06b / CDR-H1 / Kabat

<400> SEQUENCE: 35

Asn Thr Asp Met Ser
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic:  1193-H04b / CDR-H1 / Kabat

<400> SEQUENCE: 36

Ser Ser Trp Met Ser
1 5

<210> SEQ ID NO 37
<211> LENGTH: 5
<212> TYPE: PRT
<213> ORGANISM: Artificial Sequence
<220> FEATURE:
<223> OTHER INFORMATION: Synthetic: 1198-A01 / CDR-H1 / Kabat

<400> SEQUENCE: 37

Asp Tyr Asp Met Ser
1 5

<210> SEQ ID NO 38
<211> LENGTH: 5
<212> TYPE: PRT
<213> ORGANISM: Artificial Sequence
<220> FEATURE:
<223> OTHER INFORMATION: Synthetic: 1198-B10 / CDR-H1 / Kabat

<400> SEQUENCE: 38

Gly Ser Trp Ile His
1 5

<210> SEQ ID NO 39
<211> LENGTH: 5
<212> TYPE: PRT
<213> ORGANISM: Artificial Sequence
<220> FEATURE:
<223> OTHER INFORMATION: Synthetic: 1198-D03 / CDR-H1 / Kabat

<400> SEQUENCE: 39

Asn Tyr Asp Ile His
1 5

<210> SEQ ID NO 40
<211> LENGTH: 5
<212> TYPE: PRT
<213> ORGANISM: Artificial Sequence
<220> FEATURE:
<223> OTHER INFORMATION: Synthetic: 1198-D04 / CDR-H1 / Kabat

<400> SEQUENCE: 40

Asn Tyr Asp Ile His
1 5

<210> SEQ ID NO 41
<211> LENGTH: 5
<212> TYPE: PRT
<213> ORGANISM: Artificial Sequence
<220> FEATURE:
<223> OTHER INFORMATION: Synthetic: 1251-A02 / CDR-H1 / Kabat

<400> SEQUENCE: 41

Asp His Gly Met His
1 5

<210> SEQ ID NO 42
<211> LENGTH: 5
<212> TYPE: PRT
<213> ORGANISM: Artificial Sequence
<220> FEATURE:
<223> OTHER INFORMATION: Synthetic: 1251-A03 / CDR-H1 / Kabat

<400> SEQUENCE: 42

Asp His Gly Met His

```
1               5


<210> SEQ ID NO 43
<211> LENGTH: 5
<212> TYPE: PRT
<213> ORGANISM: Artificial Sequence
<220> FEATURE:
<223> OTHER INFORMATION: Synthetic:  1251-A06 / CDR-H1 / Kabat

<400> SEQUENCE: 43

Ser Tyr Gly Met His
1               5


<210> SEQ ID NO 44
<211> LENGTH: 5
<212> TYPE: PRT
<213> ORGANISM: Artificial Sequence
<220> FEATURE:
<223> OTHER INFORMATION: Synthetic:  1251-B08 / CDR-H1 / Kabat

<400> SEQUENCE: 44

Asp Tyr Gly Met His
1               5


<210> SEQ ID NO 45
<211> LENGTH: 5
<212> TYPE: PRT
<213> ORGANISM: Artificial Sequence
<220> FEATURE:
<223> OTHER INFORMATION: Synthetic:  1251-B09 / CDR-H1 / Kabat

<400> SEQUENCE: 45

Asp Tyr Gly Met His
1               5


<210> SEQ ID NO 46
<211> LENGTH: 5
<212> TYPE: PRT
<213> ORGANISM: Artificial Sequence
<220> FEATURE:
<223> OTHER INFORMATION: Synthetic:  1251-B10 / CDR-H1 / Kabat

<400> SEQUENCE: 46

Ser His Gly Met His
1               5


<210> SEQ ID NO 47
<211> LENGTH: 5
<212> TYPE: PRT
<213> ORGANISM: Artificial Sequence
<220> FEATURE:
<223> OTHER INFORMATION: Synthetic:  1251-C03 / CDR-H1 / Kabat

<400> SEQUENCE: 47

Ser Tyr Gly Met His
1               5


<210> SEQ ID NO 48
<211> LENGTH: 5
<212> TYPE: PRT
<213> ORGANISM: Artificial Sequence
<220> FEATURE:
<223> OTHER INFORMATION: Synthetic:  1251-D02 / CDR-H1 / Kabat

<400> SEQUENCE: 48

Ser His Gly Met His
1               5
```

<210> SEQ ID NO 49
<211> LENGTH: 5
<212> TYPE: PRT
<213> ORGANISM: Artificial Sequence
<220> FEATURE:
<223> OTHER INFORMATION: Synthetic: 1251-D06 / CDR-H1 / Kabat

<400> SEQUENCE: 49

Ser Tyr Gly Met His
1 5

<210> SEQ ID NO 50
<211> LENGTH: 5
<212> TYPE: PRT
<213> ORGANISM: Artificial Sequence
<220> FEATURE:
<223> OTHER INFORMATION: Synthetic: 1251-D09 / CDR-H1 / Kabat

<400> SEQUENCE: 50

Ser Tyr Gly Met His
1 5

<210> SEQ ID NO 51
<211> LENGTH: 5
<212> TYPE: PRT
<213> ORGANISM: Artificial Sequence
<220> FEATURE:
<223> OTHER INFORMATION: Synthetic: 1251-E06 / CDR-H1 / Kabat

<400> SEQUENCE: 51

Ser Tyr Gly Met His
1 5

<210> SEQ ID NO 52
<211> LENGTH: 5
<212> TYPE: PRT
<213> ORGANISM: Artificial Sequence
<220> FEATURE:
<223> OTHER INFORMATION: Synthetic: 1251-F06 / CDR-H1 / Kabat

<400> SEQUENCE: 52

Ser Phe Gly Met His
1 5

<210> SEQ ID NO 53
<211> LENGTH: 5
<212> TYPE: PRT
<213> ORGANISM: Artificial Sequence
<220> FEATURE:
<223> OTHER INFORMATION: Synthetic: 1251-F07 / CDR-H1 / Kabat

<400> SEQUENCE: 53

Ser His Gly Met His
1 5

<210> SEQ ID NO 54
<211> LENGTH: 5
<212> TYPE: PRT
<213> ORGANISM: Artificial Sequence
<220> FEATURE:
<223> OTHER INFORMATION: Synthetic: 1251-G02 / CDR-H1 / Kabat

<400> SEQUENCE: 54

Ser Tyr Gly Met His
1 5

<210> SEQ ID NO 55
<211> LENGTH: 5
<212> TYPE: PRT
<213> ORGANISM: Artificial Sequence
<220> FEATURE:
<223> OTHER INFORMATION: Synthetic: 1445-A03 / CDR-H1 / Kabat

<400> SEQUENCE: 55

Gly Tyr Tyr Ile His
1 5

<210> SEQ ID NO 56
<211> LENGTH: 5
<212> TYPE: PRT
<213> ORGANISM: Artificial Sequence
<220> FEATURE:
<223> OTHER INFORMATION: Synthetic: 1445-B09 / CDR-H1 / Kabat

<400> SEQUENCE: 56

Gly Thr Gly Ile His
1 5

<210> SEQ ID NO 57
<211> LENGTH: 5
<212> TYPE: PRT
<213> ORGANISM: Artificial Sequence
<220> FEATURE:
<223> OTHER INFORMATION: Synthetic: 1447-D11 / CDR-H1 / Kabat

<400> SEQUENCE: 57

Asn Thr Asp Met Ser
1 5

<210> SEQ ID NO 58
<211> LENGTH: 5
<212> TYPE: PRT
<213> ORGANISM: Artificial Sequence
<220> FEATURE:
<223> OTHER INFORMATION: Synthetic: 1447-E08 / CDR-H1 / Kabat

<400> SEQUENCE: 58

Asp Thr Asp Met Ser
1 5

<210> SEQ ID NO 59
<211> LENGTH: 5
<212> TYPE: PRT
<213> ORGANISM: Artificial Sequence
<220> FEATURE:
<223> OTHER INFORMATION: Synthetic: 1447-F11 / CDR-H1 / Kabat

<400> SEQUENCE: 59

Asn Thr Asp Met Ser
1 5

<210> SEQ ID NO 60
<211> LENGTH: 5
<212> TYPE: PRT
<213> ORGANISM: Artificial Sequence
<220> FEATURE:
<223> OTHER INFORMATION: Synthetic: 1447-G01 / CDR-H1 / Kabat

<400> SEQUENCE: 60

Thr Ser Asp Met Ser
1 5

<210> SEQ ID NO 61
<211> LENGTH: 5
<212> TYPE: PRT
<213> ORGANISM: Artificial Sequence
<220> FEATURE:
<223> OTHER INFORMATION: Synthetic: VH11-[19] / CDR-H1 / Kabat

<400> SEQUENCE: 61

Ser Tyr Gly Met His
1 5

<210> SEQ ID NO 62
<211> LENGTH: 5
<212> TYPE: PRT
<213> ORGANISM: Artificial Sequence
<220> FEATURE:
<223> OTHER INFORMATION: Synthetic: VH5-[7] / CDR-H1 / Kabat

<400> SEQUENCE: 62

Ser Tyr Ala Met His
1 5

<210> SEQ ID NO 63
<211> LENGTH: 5
<212> TYPE: PRT
<213> ORGANISM: Artificial Sequence
<220> FEATURE:
<223> OTHER INFORMATION: Synthetic: VH6-[11] / CDR-H1 / Kabat

<400> SEQUENCE: 63

Ser Tyr Ala Met His
1 5

<210> SEQ ID NO 64
<211> LENGTH: 5
<212> TYPE: PRT
<213> ORGANISM: Artificial Sequence
<220> FEATURE:
<223> OTHER INFORMATION: Synthetic: VH8-[15] / CDR-H1 / Kabat

<400> SEQUENCE: 64

Ser Tyr Ala Met His
1 5

<210> SEQ ID NO 65
<211> LENGTH: 6
<212> TYPE: PRT
<213> ORGANISM: Artificial Sequence
<220> FEATURE:
<223> OTHER INFORMATION: Synthetic: 1193-B06 / CDR-H2 / Chothia

<400> SEQUENCE: 65

Tyr Gly Thr Ser Gly Ala
1 5

<210> SEQ ID NO 66
<211> LENGTH: 6
<212> TYPE: PRT
<213> ORGANISM: Artificial Sequence
<220> FEATURE:
<223> OTHER INFORMATION: Synthetic: 1193-C08 / CDR-H2 / Chothia

<400> SEQUENCE: 66

Asn Gly Asp Asp Gly Tyr
1 5

<210> SEQ ID NO 67

```
<211> LENGTH: 6
<212> TYPE: PRT
<213> ORGANISM: Artificial Sequence
<220> FEATURE:
<223> OTHER INFORMATION: Synthetic:  1193-E06b / CDR-H2 / Chothia

<400> SEQUENCE: 67

Asn Gly Ser Gly Gly Ala
1               5


<210> SEQ ID NO 68
<211> LENGTH: 6
<212> TYPE: PRT
<213> ORGANISM: Artificial Sequence
<220> FEATURE:
<223> OTHER INFORMATION: Synthetic:  1193-H04b / CDR-H2 / Chothia

<400> SEQUENCE: 68

Asn Gly Tyr Asn Gly Ile
1               5


<210> SEQ ID NO 69
<211> LENGTH: 6
<212> TYPE: PRT
<213> ORGANISM: Artificial Sequence
<220> FEATURE:
<223> OTHER INFORMATION: Synthetic:  1198-A01 / CDR-H2 / Chothia

<400> SEQUENCE: 69

Ala Gln Asp Gly Ser Tyr
1               5


<210> SEQ ID NO 70
<211> LENGTH: 6
<212> TYPE: PRT
<213> ORGANISM: Artificial Sequence
<220> FEATURE:
<223> OTHER INFORMATION: Synthetic:  1198-B10 / CDR-H2 / Chothia

<400> SEQUENCE: 70

Tyr Pro Asp Asp Gly Asp
1               5


<210> SEQ ID NO 71
<211> LENGTH: 6
<212> TYPE: PRT
<213> ORGANISM: Artificial Sequence
<220> FEATURE:
<223> OTHER INFORMATION: Synthetic:  1198-D03 / CDR-H2 / Chothia

<400> SEQUENCE: 71

Asp Pro Tyr Asn Gly Ala
1               5


<210> SEQ ID NO 72
<211> LENGTH: 6
<212> TYPE: PRT
<213> ORGANISM: Artificial Sequence
<220> FEATURE:
<223> OTHER INFORMATION: Synthetic:  1198-D04 / CDR-H2 / Chothia

<400> SEQUENCE: 72

Asp Pro Tyr Asn Gly Thr
1               5


<210> SEQ ID NO 73
<211> LENGTH: 6
```

<212> TYPE: PRT
<213> ORGANISM: Artificial Sequence
<220> FEATURE:
<223> OTHER INFORMATION: Synthetic: 1251-A02 / CDR-H2 / Chothia

<400> SEQUENCE: 73

Trp Tyr Asp Gly Ser His
1 5

<210> SEQ ID NO 74
<211> LENGTH: 6
<212> TYPE: PRT
<213> ORGANISM: Artificial Sequence
<220> FEATURE:
<223> OTHER INFORMATION: Synthetic: 1251-A03 / CDR-H2 / Chothia

<400> SEQUENCE: 74

Trp Tyr Asp Gly Ser His
1 5

<210> SEQ ID NO 75
<211> LENGTH: 6
<212> TYPE: PRT
<213> ORGANISM: Artificial Sequence
<220> FEATURE:
<223> OTHER INFORMATION: Synthetic: 1251-A06 / CDR-H2 / Chothia

<400> SEQUENCE: 75

Trp Asp Asp Gly Ser Asp
1 5

<210> SEQ ID NO 76
<211> LENGTH: 6
<212> TYPE: PRT
<213> ORGANISM: Artificial Sequence
<220> FEATURE:
<223> OTHER INFORMATION: Synthetic: 1251-B08 / CDR-H2 / Chothia

<400> SEQUENCE: 76

Trp Tyr Asp Gly Ser Ile
1 5

<210> SEQ ID NO 77
<211> LENGTH: 6
<212> TYPE: PRT
<213> ORGANISM: Artificial Sequence
<220> FEATURE:
<223> OTHER INFORMATION: Synthetic: 1251-B09 / CDR-H2 / Chothia

<400> SEQUENCE: 77

Trp Tyr Asp Gly Ser Arg
1 5

<210> SEQ ID NO 78
<211> LENGTH: 6
<212> TYPE: PRT
<213> ORGANISM: Artificial Sequence
<220> FEATURE:
<223> OTHER INFORMATION: Synthetic: 1251-B10 / CDR-H2 / Chothia

<400> SEQUENCE: 78

Trp His Asp Gly Ser Asp
1 5

<210> SEQ ID NO 79
<211> LENGTH: 6
<212> TYPE: PRT

<213> ORGANISM: Artificial Sequence
<220> FEATURE:
<223> OTHER INFORMATION: Synthetic: 1251-C03 / CDR-H2 / Chothia

<400> SEQUENCE: 79

Trp Tyr Asp Gly Ser Ile
1 5

<210> SEQ ID NO 80
<211> LENGTH: 6
<212> TYPE: PRT
<213> ORGANISM: Artificial Sequence
<220> FEATURE:
<223> OTHER INFORMATION: Synthetic: 1251-D02 / CDR-H2 / Chothia

<400> SEQUENCE: 80

Trp Asp Asp Gly Ser Asp
1 5

<210> SEQ ID NO 81
<211> LENGTH: 6
<212> TYPE: PRT
<213> ORGANISM: Artificial Sequence
<220> FEATURE:
<223> OTHER INFORMATION: Synthetic: 1251-D06 / CDR-H2 / Chothia

<400> SEQUENCE: 81

Trp Tyr Asp Gly Ser Lys
1 5

<210> SEQ ID NO 82
<211> LENGTH: 6
<212> TYPE: PRT
<213> ORGANISM: Artificial Sequence
<220> FEATURE:
<223> OTHER INFORMATION: Synthetic: 1251-D09 / CDR-H2 / Chothia

<400> SEQUENCE: 82

Trp Tyr Asp Ala Ser Ile
1 5

<210> SEQ ID NO 83
<211> LENGTH: 6
<212> TYPE: PRT
<213> ORGANISM: Artificial Sequence
<220> FEATURE:
<223> OTHER INFORMATION: Synthetic: 1251-E06 / CDR-H2 / Chothia

<400> SEQUENCE: 83

Trp Tyr Asp Gly Ser Asn
1 5

<210> SEQ ID NO 84
<211> LENGTH: 6
<212> TYPE: PRT
<213> ORGANISM: Artificial Sequence
<220> FEATURE:
<223> OTHER INFORMATION: Synthetic: 1251-F06 / CDR-H2 / Chothia

<400> SEQUENCE: 84

Trp Tyr Asp Gly Ser Asn
1 5

<210> SEQ ID NO 85
<211> LENGTH: 6
<212> TYPE: PRT
<213> ORGANISM: Artificial Sequence
<220> FEATURE:
<223> OTHER INFORMATION: Synthetic: 1251-F07 / CDR-H2 / Chothia

<400> SEQUENCE: 85

Trp Asp Asp Gly Ser Asn
1 5

<210> SEQ ID NO 86
<211> LENGTH: 6
<212> TYPE: PRT
<213> ORGANISM: Artificial Sequence
<220> FEATURE:
<223> OTHER INFORMATION: Synthetic: 1251-G02 / CDR-H2 / Chothia

<400> SEQUENCE: 86

Trp His Asp Gly Ser Lys
1 5

<210> SEQ ID NO 87
<211> LENGTH: 6
<212> TYPE: PRT
<213> ORGANISM: Artificial Sequence
<220> FEATURE:
<223> OTHER INFORMATION: Synthetic: 1445-A03 / CDR-H2 / Chothia

<400> SEQUENCE: 87

Ser Pro Thr Gly Gly Tyr
1 5

<210> SEQ ID NO 88
<211> LENGTH: 6
<212> TYPE: PRT
<213> ORGANISM: Artificial Sequence
<220> FEATURE:
<223> OTHER INFORMATION: Synthetic: 1445-B09 / CDR-H2 / Chothia

<400> SEQUENCE: 88

Thr Pro Tyr Asn Gly Thr
1 5

<210> SEQ ID NO 89
<211> LENGTH: 6
<212> TYPE: PRT
<213> ORGANISM: Artificial Sequence
<220> FEATURE:
<223> OTHER INFORMATION: Synthetic: 1447-D11 / CDR-H2 / Chothia

<400> SEQUENCE: 89

Asn Gly Ser Gly Gly Ser
1 5

<210> SEQ ID NO 90
<211> LENGTH: 6
<212> TYPE: PRT
<213> ORGANISM: Artificial Sequence
<220> FEATURE:
<223> OTHER INFORMATION: Synthetic: 1447-E08 / CDR-H2 / Chothia

<400> SEQUENCE: 90

Asn Gly Ala Gly Gly Ala
1 5

<210> SEQ ID NO 91
<211> LENGTH: 6
<212> TYPE: PRT
<213> ORGANISM: Artificial Sequence
<220> FEATURE:

<223> OTHER INFORMATION: Synthetic: 1447-F11 / CDR-H2 / Chothia

<400> SEQUENCE: 91

Asn Gly Ser Gly Gly Val
1 5

<210> SEQ ID NO 92
<211> LENGTH: 6
<212> TYPE: PRT
<213> ORGANISM: Artificial Sequence
<220> FEATURE:
<223> OTHER INFORMATION: Synthetic: 1447-G01 / CDR-H2 / Chothia

<400> SEQUENCE: 92

Asn Gly Ser Gly Gly Ala
1 5

<210> SEQ ID NO 93
<211> LENGTH: 6
<212> TYPE: PRT
<213> ORGANISM: Artificial Sequence
<220> FEATURE:
<223> OTHER INFORMATION: Synthetic: VH11-[19] / CDR-H2 / Chothia

<400> SEQUENCE: 93

Trp Tyr Asp Gly Ser Asn
1 5

<210> SEQ ID NO 94
<211> LENGTH: 6
<212> TYPE: PRT
<213> ORGANISM: Artificial Sequence
<220> FEATURE:
<223> OTHER INFORMATION: Synthetic: VH5-[7] / CDR-H2 / Chothia

<400> SEQUENCE: 94

Ser Tyr Asp Gly Ser Asn
1 5

<210> SEQ ID NO 95
<211> LENGTH: 6
<212> TYPE: PRT
<213> ORGANISM: Artificial Sequence
<220> FEATURE:
<223> OTHER INFORMATION: Synthetic: VH6-[11] / CDR-H2 / Chothia

<400> SEQUENCE: 95

Ser Tyr Asp Gly Ser Ile
1 5

<210> SEQ ID NO 96
<211> LENGTH: 6
<212> TYPE: PRT
<213> ORGANISM: Artificial Sequence
<220> FEATURE:
<223> OTHER INFORMATION: Synthetic: VH8-[15] / CDR-H2 / Chothia

<400> SEQUENCE: 96

Ser Tyr Asp Gly Ser Asn
1 5

<210> SEQ ID NO 97
<211> LENGTH: 17
<212> TYPE: PRT
<213> ORGANISM: Artificial Sequence
<220> FEATURE:
<223> OTHER INFORMATION: Synthetic: 1193-B06 / CDR-H2 / Kabat

<400> SEQUENCE: 97

Ile Ile Tyr Gly Thr Ser Gly Ala Thr Tyr Tyr Ala Asp Ser Val Lys
1 5 10 15

Gly

<210> SEQ ID NO 98
<211> LENGTH: 17
<212> TYPE: PRT
<213> ORGANISM: Artificial Sequence
<220> FEATURE:
<223> OTHER INFORMATION: Synthetic: 1193-C08 / CDR-H2 / Kabat

<400> SEQUENCE: 98

Ile Ile Asn Gly Asp Asp Gly Tyr Thr Tyr Tyr Ala Asp Arg Val Lys
1 5 10 15

Gly

<210> SEQ ID NO 99
<211> LENGTH: 17
<212> TYPE: PRT
<213> ORGANISM: Artificial Sequence
<220> FEATURE:
<223> OTHER INFORMATION: Synthetic: 1193-E06b / CDR-H2 / Kabat

<400> SEQUENCE: 99

Ile Ile Asn Gly Ser Gly Gly Ala Thr Asn Tyr Ala Asp Ser Val Lys
1 5 10 15

Gly

<210> SEQ ID NO 100
<211> LENGTH: 17
<212> TYPE: PRT
<213> ORGANISM: Artificial Sequence
<220> FEATURE:
<223> OTHER INFORMATION: Synthetic: 1193-H04b / CDR-H2 / Kabat

<400> SEQUENCE: 100

Ile Ile Asn Gly Tyr Asn Gly Ile Thr Tyr Tyr Ala Asp Ser Val Lys
1 5 10 15

Gly

<210> SEQ ID NO 101
<211> LENGTH: 17
<212> TYPE: PRT
<213> ORGANISM: Artificial Sequence
<220> FEATURE:
<223> OTHER INFORMATION: Synthetic: 1198-A01 / CDR-H2 / Kabat

<400> SEQUENCE: 101

Phe Ile Ala Gln Asp Gly Ser Tyr Lys Tyr Tyr Val Asp Ser Val Lys
1 5 10 15

Gly

<210> SEQ ID NO 102
<211> LENGTH: 17
<212> TYPE: PRT
<213> ORGANISM: Artificial Sequence
<220> FEATURE:
<223> OTHER INFORMATION: Synthetic: 1198-B10 / CDR-H2 / Kabat

<400> SEQUENCE: 102

Tyr Ile Tyr Pro Asp Asp Gly Asp Thr Tyr Tyr Ala Asp Ser Val Lys 1 5 10 15

Gly

<210> SEQ ID NO 103
<211> LENGTH: 17
<212> TYPE: PRT
<213> ORGANISM: Artificial Sequence
<220> FEATURE:
<223> OTHER INFORMATION: Synthetic: 1198-D03 / CDR-H2 / Kabat

<400> SEQUENCE: 103

Asn Ile Asp Pro Tyr Asn Gly Ala Thr Tyr Tyr Ala Asp Ser Val Lys
1 5 10 15

Gly

<210> SEQ ID NO 104
<211> LENGTH: 17
<212> TYPE: PRT
<213> ORGANISM: Artificial Sequence
<220> FEATURE:
<223> OTHER INFORMATION: Synthetic: 1198-D04 / CDR-H2 / Kabat

<400> SEQUENCE: 104

Asn Ile Asp Pro Tyr Asn Gly Thr Thr Tyr Tyr Ala Asp Ser Val Lys
1 5 10 15

Gly

<210> SEQ ID NO 105
<211> LENGTH: 17
<212> TYPE: PRT
<213> ORGANISM: Artificial Sequence
<220> FEATURE:
<223> OTHER INFORMATION: Synthetic: 1251-A02 / CDR-H2 / Kabat

<400> SEQUENCE: 105

Val Ile Trp Tyr Asp Gly Ser His Lys Ile Tyr Ala Asp Ser Val Lys
1 5 10 15

Gly

<210> SEQ ID NO 106
<211> LENGTH: 17
<212> TYPE: PRT
<213> ORGANISM: Artificial Sequence
<220> FEATURE:
<223> OTHER INFORMATION: Synthetic: 1251-A03 / CDR-H2 / Kabat

<400> SEQUENCE: 106

Val Ile Trp Tyr Asp Gly Ser His Lys Ile Tyr Ala Asp Ser Val Lys
1 5 10 15

Gly

<210> SEQ ID NO 107
<211> LENGTH: 17
<212> TYPE: PRT
<213> ORGANISM: Artificial Sequence
<220> FEATURE:
<223> OTHER INFORMATION: Synthetic: 1251-A06 / CDR-H2 / Kabat

<400> SEQUENCE: 107

Val Ile Trp Asp Asp Gly Ser Asp Arg Tyr Tyr Ala Asp Ser Val Lys
1 5 10 15

Gly

```
<210> SEQ ID NO 108
<211> LENGTH: 17
<212> TYPE: PRT
<213> ORGANISM: Artificial Sequence
<220> FEATURE:
<223> OTHER INFORMATION: Synthetic:  1251-B08 / CDR-H2 / Kabat

<400> SEQUENCE: 108

Val Ile Trp Tyr Asp Gly Ser Ile Ser Tyr Tyr Ala Asp Ser Val Lys
1               5                   10                  15

Gly


<210> SEQ ID NO 109
<211> LENGTH: 17
<212> TYPE: PRT
<213> ORGANISM: Artificial Sequence
<220> FEATURE:
<223> OTHER INFORMATION: Synthetic:  1251-B09 / CDR-H2 / Kabat

<400> SEQUENCE: 109

Val Thr Trp Tyr Asp Gly Ser Arg Glu Tyr Tyr Ala Asp Ser Val Lys
1               5                   10                  15

Gly


<210> SEQ ID NO 110
<211> LENGTH: 17
<212> TYPE: PRT
<213> ORGANISM: Artificial Sequence
<220> FEATURE:
<223> OTHER INFORMATION: Synthetic:  1251-B10 / CDR-H2 / Kabat

<400> SEQUENCE: 110

Val Ile Trp His Asp Gly Ser Asp Lys Tyr Tyr Ala Asp Ser Val Lys
1               5                   10                  15

Gly


<210> SEQ ID NO 111
<211> LENGTH: 17
<212> TYPE: PRT
<213> ORGANISM: Artificial Sequence
<220> FEATURE:
<223> OTHER INFORMATION: Synthetic:  1251-C03 / CDR-H2 / Kabat

<400> SEQUENCE: 111

Val Ile Trp Tyr Asp Gly Ser Ile Lys Asn Tyr Ala Asp Ser Val Lys
1               5                   10                  15

Gly


<210> SEQ ID NO 112
<211> LENGTH: 17
<212> TYPE: PRT
<213> ORGANISM: Artificial Sequence
<220> FEATURE:
<223> OTHER INFORMATION: Synthetic:  1251-D02 / CDR-H2 / Kabat

<400> SEQUENCE: 112

Val Ile Trp Asp Asp Gly Ser Asp Arg Tyr Tyr Ala Asp Ser Val Lys
1               5                   10                  15

Gly


<210> SEQ ID NO 113
<211> LENGTH: 17
<212> TYPE: PRT
```

<213> ORGANISM: Artificial Sequence
<220> FEATURE:
<223> OTHER INFORMATION: Synthetic: 1251-D06 / CDR-H2 / Kabat

<400> SEQUENCE: 113

Val Val Trp Tyr Asp Gly Ser Lys Thr Ile Tyr Ala Asp Ser Val Lys
1 5 10 15

Gly

<210> SEQ ID NO 114
<211> LENGTH: 17
<212> TYPE: PRT
<213> ORGANISM: Artificial Sequence
<220> FEATURE:
<223> OTHER INFORMATION: Synthetic: 1251-D09 / CDR-H2 / Kabat

<400> SEQUENCE: 114

Val Ile Trp Tyr Asp Ala Ser Ile Arg Lys Tyr Ala Gly Ser Val Lys
1 5 10 15

Gly

<210> SEQ ID NO 115
<211> LENGTH: 17
<212> TYPE: PRT
<213> ORGANISM: Artificial Sequence
<220> FEATURE:
<223> OTHER INFORMATION: Synthetic: 1251-E06 / CDR-H2 / Kabat

<400> SEQUENCE: 115

Val Ile Trp Tyr Asp Gly Ser Asn Lys Val Tyr Ala Asp Ser Val Lys
1 5 10 15

Gly

<210> SEQ ID NO 116
<211> LENGTH: 17
<212> TYPE: PRT
<213> ORGANISM: Artificial Sequence
<220> FEATURE:
<223> OTHER INFORMATION: Synthetic: 1251-F06 / CDR-H2 / Kabat

<400> SEQUENCE: 116

Val Ile Trp Tyr Asp Gly Ser Asn Glu Tyr Tyr Ala Asp Ser Val Lys
1 5 10 15

Gly

<210> SEQ ID NO 117
<211> LENGTH: 17
<212> TYPE: PRT
<213> ORGANISM: Artificial Sequence
<220> FEATURE:
<223> OTHER INFORMATION: Synthetic: 1251-F07 / CDR-H2 / Kabat

<400> SEQUENCE: 117

Val Ile Trp Asp Asp Gly Ser Asn Glu Val Tyr Ala Asp Ser Val Lys
1 5 10 15

Gly

<210> SEQ ID NO 118
<211> LENGTH: 17
<212> TYPE: PRT
<213> ORGANISM: Artificial Sequence
<220> FEATURE:
<223> OTHER INFORMATION: Synthetic: 1251-G02 / CDR-H2 / Kabat

<400> SEQUENCE: 118

Val Ile Trp His Asp Gly Ser Lys Asp Tyr Tyr Ala Asp Ser Val Lys
1 5 10 15

Gly

<210> SEQ ID NO 119
<211> LENGTH: 17
<212> TYPE: PRT
<213> ORGANISM: Artificial Sequence
<220> FEATURE:
<223> OTHER INFORMATION: Synthetic: 1445-A03 / CDR-H2 / Kabat

<400> SEQUENCE: 119

Glu Ile Ser Pro Thr Gly Gly Tyr Thr Tyr Tyr Ala Asp Ser Val Lys
1 5 10 15

Gly

<210> SEQ ID NO 120
<211> LENGTH: 17
<212> TYPE: PRT
<213> ORGANISM: Artificial Sequence
<220> FEATURE:
<223> OTHER INFORMATION: Synthetic: 1445-B09 / CDR-H2 / Kabat

<400> SEQUENCE: 120

Ile Ile Thr Pro Tyr Asn Gly Thr Thr Asn Tyr Ala Asp Ser Val Lys
1 5 10 15

Gly

<210> SEQ ID NO 121
<211> LENGTH: 17
<212> TYPE: PRT
<213> ORGANISM: Artificial Sequence
<220> FEATURE:
<223> OTHER INFORMATION: Synthetic: 1447-D11 / CDR-H2 / Kabat

<400> SEQUENCE: 121

Val Ile Asn Gly Ser Gly Gly Ser Ser Asn Tyr Ala Asp Ser Val Lys
1 5 10 15

Gly

<210> SEQ ID NO 122
<211> LENGTH: 17
<212> TYPE: PRT
<213> ORGANISM: Artificial Sequence
<220> FEATURE:
<223> OTHER INFORMATION: Synthetic: 1447-E08 / CDR-H2 / Kabat

<400> SEQUENCE: 122

Met Ile Asn Gly Ala Gly Gly Ala Ser Phe Tyr Ala Asp Ser Val Arg
1 5 10 15

Gly

<210> SEQ ID NO 123
<211> LENGTH: 17
<212> TYPE: PRT
<213> ORGANISM: Artificial Sequence
<220> FEATURE:
<223> OTHER INFORMATION: Synthetic: 1447-F11 / CDR-H2 / Kabat

<400> SEQUENCE: 123

Ile Ile Asn Gly Ser Gly Gly Val Thr Asn Tyr Ala Asp Ser Val Arg
1 5 10 15

Gly

<210> SEQ ID NO 124
<211> LENGTH: 17
<212> TYPE: PRT
<213> ORGANISM: Artificial Sequence
<220> FEATURE:
<223> OTHER INFORMATION: Synthetic: 1447-G01 / CDR-H2 / Kabat

<400> SEQUENCE: 124

Ile Ile Asn Gly Ser Gly Gly Ala Thr Asn Tyr Ala Asp Ser Val Lys
1 5 10 15

Gly

<210> SEQ ID NO 125
<211> LENGTH: 17
<212> TYPE: PRT
<213> ORGANISM: Artificial Sequence
<220> FEATURE:
<223> OTHER INFORMATION: Synthetic: VH11-[19] / CDR-H2 / Kabat

<400> SEQUENCE: 125

Val Ile Trp Tyr Asp Gly Ser Asn Lys Tyr Tyr Ala Asp Ser Val Lys
1 5 10 15

Gly

<210> SEQ ID NO 126
<211> LENGTH: 17
<212> TYPE: PRT
<213> ORGANISM: Artificial Sequence
<220> FEATURE:
<223> OTHER INFORMATION: Synthetic: VH5-[7] / CDR-H2 / Kabat

<400> SEQUENCE: 126

Val Ile Ser Tyr Asp Gly Ser Asn Lys Tyr Tyr Ala Asp Ser Val Lys
1 5 10 15

Gly

<210> SEQ ID NO 127
<211> LENGTH: 17
<212> TYPE: PRT
<213> ORGANISM: Artificial Sequence
<220> FEATURE:
<223> OTHER INFORMATION: Synthetic: VH6-[11] / CDR-H2 / Kabat

<400> SEQUENCE: 127

Val Ile Ser Tyr Asp Gly Ser Ile Lys Tyr Tyr Ala Asp Ser Val Lys
1 5 10 15

Gly

<210> SEQ ID NO 128
<211> LENGTH: 17
<212> TYPE: PRT
<213> ORGANISM: Artificial Sequence
<220> FEATURE:
<223> OTHER INFORMATION: Synthetic: VH8-[15] / CDR-H2 / Kabat

<400> SEQUENCE: 128

Val Ile Ser Tyr Asp Gly Ser Asn Lys Tyr Tyr Ala Asp Ser Val Lys
1 5 10 15

Gly

<210> SEQ ID NO 129
<211> LENGTH: 11
<212> TYPE: PRT
<213> ORGANISM: Artificial Sequence
<220> FEATURE:
<223> OTHER INFORMATION: Synthetic: 1193-B06 / CDR-H3 / K/C

<400> SEQUENCE: 129

Pro Ser Met Ser Gly Ser Arg Gly Phe Asp Tyr
1 5 10

<210> SEQ ID NO 130
<211> LENGTH: 11
<212> TYPE: PRT
<213> ORGANISM: Artificial Sequence
<220> FEATURE:
<223> OTHER INFORMATION: Synthetic: 1193-C08 / CDR-H3 / K/C

<400> SEQUENCE: 130

Val Ala Leu Gly Arg Pro Arg Arg Phe Asp Tyr
1 5 10

<210> SEQ ID NO 131
<211> LENGTH: 11
<212> TYPE: PRT
<213> ORGANISM: Artificial Sequence
<220> FEATURE:
<223> OTHER INFORMATION: Synthetic: 1193-E06b / CDR-H3 / K/C

<400> SEQUENCE: 131

Phe Glu Asn Glu Trp Glu Val Ser Met Asp Tyr
1 5 10

<210> SEQ ID NO 132
<211> LENGTH: 11
<212> TYPE: PRT
<213> ORGANISM: Artificial Sequence
<220> FEATURE:
<223> OTHER INFORMATION: Synthetic: 1193-H04b / CDR-H3 / K/C

<400> SEQUENCE: 132

Pro Ser Ala Pro Gly Ala Arg Arg Phe Asp Tyr
1 5 10

<210> SEQ ID NO 133
<211> LENGTH: 11
<212> TYPE: PRT
<213> ORGANISM: Artificial Sequence
<220> FEATURE:
<223> OTHER INFORMATION: Synthetic: 1198-A01 / CDR-H3 / K/C

<400> SEQUENCE: 133

Ser Lys Leu Phe Arg Ala Gly Gln Phe Asp Tyr
1 5 10

<210> SEQ ID NO 134
<211> LENGTH: 11
<212> TYPE: PRT
<213> ORGANISM: Artificial Sequence
<220> FEATURE:
<223> OTHER INFORMATION: Synthetic: 1198-B10 / CDR-H3 / K/C

<400> SEQUENCE: 134

Glu Gly Ser His Asn Leu Asp Lys Met Asp Tyr
1 5 10

<210> SEQ ID NO 135

<211> LENGTH: 11
<212> TYPE: PRT
<213> ORGANISM: Artificial Sequence
<220> FEATURE:
<223> OTHER INFORMATION: Synthetic: 1198-D03 / CDR-H3 / K/C

<400> SEQUENCE: 135

Val Leu Trp Gly Phe Trp Ala Pro Phe Asp Tyr
1 5 10

<210> SEQ ID NO 136
<211> LENGTH: 11
<212> TYPE: PRT
<213> ORGANISM: Artificial Sequence
<220> FEATURE:
<223> OTHER INFORMATION: Synthetic: 1198-D04 / CDR-H3 / K/C

<400> SEQUENCE: 136

Val Pro Trp Gly Phe Trp Ala Pro Phe Asp Tyr
1 5 10

<210> SEQ ID NO 137
<211> LENGTH: 14
<212> TYPE: PRT
<213> ORGANISM: Artificial Sequence
<220> FEATURE:
<223> OTHER INFORMATION: Synthetic: 1251-A02 / CDR-H3 / K/C

<400> SEQUENCE: 137

Gly Gly Ser Leu Ala Gly Gly Ala Val Tyr Gly Thr Asp Val
1 5 10

<210> SEQ ID NO 138
<211> LENGTH: 14
<212> TYPE: PRT
<213> ORGANISM: Artificial Sequence
<220> FEATURE:
<223> OTHER INFORMATION: Synthetic: 1251-A03 / CDR-H3 / K/C

<400> SEQUENCE: 138

Gly Gly Ser Leu Ala Gly Gly Ala Val Tyr Gly Thr Asp Val
1 5 10

<210> SEQ ID NO 139
<211> LENGTH: 14
<212> TYPE: PRT
<213> ORGANISM: Artificial Sequence
<220> FEATURE:
<223> OTHER INFORMATION: Synthetic: 1251-A06 / CDR-H3 / K/C

<400> SEQUENCE: 139

Gly Gly Thr Arg Val Leu Gly Ala Ile His Gly Thr Asp Val
1 5 10

<210> SEQ ID NO 140
<211> LENGTH: 14
<212> TYPE: PRT
<213> ORGANISM: Artificial Sequence
<220> FEATURE:
<223> OTHER INFORMATION: Synthetic: 1251-B08 / CDR-H3 / K/C

<400> SEQUENCE: 140

Gly Gly Thr Val Glu His Gly Ala Val Tyr Gly Thr Asp Val
1 5 10

<210> SEQ ID NO 141
<211> LENGTH: 14

<212> TYPE: PRT
<213> ORGANISM: Artificial Sequence
<220> FEATURE:
<223> OTHER INFORMATION: Synthetic: 1251-B09 / CDR-H3 / K/C

<400> SEQUENCE: 141

Gly Gly Thr Leu Val His Gly Ala Leu Tyr Gly Asn Asp Val
1 5 10

<210> SEQ ID NO 142
<211> LENGTH: 14
<212> TYPE: PRT
<213> ORGANISM: Artificial Sequence
<220> FEATURE:
<223> OTHER INFORMATION: Synthetic: 1251-B10 / CDR-H3 / K/C

<400> SEQUENCE: 142

Gly Gly Thr Arg Val Leu Gly Ala Val Tyr Gly Leu Asp Val
1 5 10

<210> SEQ ID NO 143
<211> LENGTH: 14
<212> TYPE: PRT
<213> ORGANISM: Artificial Sequence
<220> FEATURE:
<223> OTHER INFORMATION: Synthetic: 1251-C03 / CDR-H3 / K/C

<400> SEQUENCE: 143

Gly Gly Ala Leu Met Arg Gly Glu Phe Ser Gly His Asp Val
1 5 10

<210> SEQ ID NO 144
<211> LENGTH: 14
<212> TYPE: PRT
<213> ORGANISM: Artificial Sequence
<220> FEATURE:
<223> OTHER INFORMATION: Synthetic: 1251-D02 / CDR-H3 / K/C

<400> SEQUENCE: 144

Gly Gly Thr Arg Val Leu Gly Ala Ile His Gly Thr Asp Val
1 5 10

<210> SEQ ID NO 145
<211> LENGTH: 14
<212> TYPE: PRT
<213> ORGANISM: Artificial Sequence
<220> FEATURE:
<223> OTHER INFORMATION: Synthetic: 1251-D06 / CDR-H3 / K/C

<400> SEQUENCE: 145

Gly Gly Thr Leu Val Arg Gly Ala Val Tyr Gly Leu Asp Val
1 5 10

<210> SEQ ID NO 146
<211> LENGTH: 14
<212> TYPE: PRT
<213> ORGANISM: Artificial Sequence
<220> FEATURE:
<223> OTHER INFORMATION: Synthetic: 1251-D09 / CDR-H3 / K/C

<400> SEQUENCE: 146

Gly Gly Thr Val Glu Arg Gly Ala Ile Tyr Gly Thr Asp Val
1 5 10

<210> SEQ ID NO 147
<211> LENGTH: 14
<212> TYPE: PRT

<213> ORGANISM: Artificial Sequence
<220> FEATURE:
<223> OTHER INFORMATION: Synthetic: 1251-E06 / CDR-H3 / K/C

<400> SEQUENCE: 147

Gly Gly Met Val Gly Gln Gly Ala Met Phe Gly Leu Asp Val
1 5 10

<210> SEQ ID NO 148
<211> LENGTH: 14
<212> TYPE: PRT
<213> ORGANISM: Artificial Sequence
<220> FEATURE:
<223> OTHER INFORMATION: Synthetic: 1251-F06 / CDR-H3 / K/C

<400> SEQUENCE: 148

Gly Gly Ser Leu Val Thr Arg Gly Val Tyr Gly Leu Asp Val
1 5 10

<210> SEQ ID NO 149
<211> LENGTH: 14
<212> TYPE: PRT
<213> ORGANISM: Artificial Sequence
<220> FEATURE:
<223> OTHER INFORMATION: Synthetic: 1251-F07 / CDR-H3 / K/C

<400> SEQUENCE: 149

Gly Gly Thr Arg Ile Arg Gly Leu Arg Tyr Gly Thr Asp Val
1 5 10

<210> SEQ ID NO 150
<211> LENGTH: 14
<212> TYPE: PRT
<213> ORGANISM: Artificial Sequence
<220> FEATURE:
<223> OTHER INFORMATION: Synthetic: 1251-G02 / CDR-H3 / K/C

<400> SEQUENCE: 150

Gly Gly Gln Leu Asp His Gly Ala Ile Tyr Gly Leu Asp Val
1 5 10

<210> SEQ ID NO 151
<211> LENGTH: 12
<212> TYPE: PRT
<213> ORGANISM: Artificial Sequence
<220> FEATURE:
<223> OTHER INFORMATION: Synthetic: 1445-A03 / CDR-H3 / K/C

<400> SEQUENCE: 151

Glu His Gly Leu Val Tyr Gly Gln Pro Met Asp Tyr
1 5 10

<210> SEQ ID NO 152
<211> LENGTH: 12
<212> TYPE: PRT
<213> ORGANISM: Artificial Sequence
<220> FEATURE:
<223> OTHER INFORMATION: Synthetic: 1445-B09 / CDR-H3 / K/C

<400> SEQUENCE: 152

Gly Gly Tyr Gly Tyr Tyr Tyr Pro Pro Phe Asp Tyr
1 5 10

<210> SEQ ID NO 153
<211> LENGTH: 11
<212> TYPE: PRT
<213> ORGANISM: Artificial Sequence

```
<220> FEATURE:
<223> OTHER INFORMATION: Synthetic:  1447-D11 / CDR-H3 / K/C

<400> SEQUENCE: 153

Tyr Glu Thr Glu Trp Glu Val Ser Leu Asp Tyr
1               5                   10


<210> SEQ ID NO 154
<211> LENGTH: 11
<212> TYPE: PRT
<213> ORGANISM: Artificial Sequence
<220> FEATURE:
<223> OTHER INFORMATION: Synthetic:  1447-E08 / CDR-H3 / K/C

<400> SEQUENCE: 154

Phe Glu Asn Gln Trp Glu Val Thr Phe Asp Tyr
1               5                   10


<210> SEQ ID NO 155
<211> LENGTH: 11
<212> TYPE: PRT
<213> ORGANISM: Artificial Sequence
<220> FEATURE:
<223> OTHER INFORMATION: Synthetic:  1447-F11 / CDR-H3 / K/C

<400> SEQUENCE: 155

Tyr Glu Ser Glu Trp Glu Val Ser Leu Asp Tyr
1               5                   10


<210> SEQ ID NO 156
<211> LENGTH: 11
<212> TYPE: PRT
<213> ORGANISM: Artificial Sequence
<220> FEATURE:
<223> OTHER INFORMATION: Synthetic:  1447-G01 / CDR-H3 / K/C

<400> SEQUENCE: 156

Tyr Glu Asn Glu Met Glu Val Ser Met Asp Tyr
1               5                   10


<210> SEQ ID NO 157
<211> LENGTH: 14
<212> TYPE: PRT
<213> ORGANISM: Artificial Sequence
<220> FEATURE:
<223> OTHER INFORMATION: Synthetic:  VH11-[19] / CDR-H3 / K/C

<400> SEQUENCE: 157

Gly Gly Thr Leu Val Arg Gly Ala Met Tyr Gly Thr Asp Val
1               5                   10


<210> SEQ ID NO 158
<211> LENGTH: 15
<212> TYPE: PRT
<213> ORGANISM: Artificial Sequence
<220> FEATURE:
<223> OTHER INFORMATION: Synthetic:  VH5-[7] / CDR-H3 / K/C

<400> SEQUENCE: 158

Gly Arg Tyr Tyr Gly Ser Gly Ser Tyr Ser Ser Tyr Phe Asp Tyr
1               5                   10                  15


<210> SEQ ID NO 159
<211> LENGTH: 15
<212> TYPE: PRT
<213> ORGANISM: Artificial Sequence
<220> FEATURE:
```

<223> OTHER INFORMATION: Synthetic: VH6-[11] / CDR-H3 / K/C

<400> SEQUENCE: 159

Gly Arg Glu Ile Thr Ser Gln Asn Ile Val Ile Leu Leu Asp Tyr
1 5 10 15

<210> SEQ ID NO 160
<211> LENGTH: 15
<212> TYPE: PRT
<213> ORGANISM: Artificial Sequence
<220> FEATURE:
<223> OTHER INFORMATION: Synthetic: VH8-[15] / CDR-H3 / K/C

<400> SEQUENCE: 160

Gly Arg Glu Ile Thr Ser Gln Asn Ile Val Ile Leu Leu Asp Tyr
1 5 10 15

<210> SEQ ID NO 161
<211> LENGTH: 12
<212> TYPE: PRT
<213> ORGANISM: Artificial Sequence
<220> FEATURE:
<223> OTHER INFORMATION: Synthetic: 1193-B06 / CDR-L1 / K/C

<400> SEQUENCE: 161

Arg Ala Gly Gln Ser Val Ser Ser Ser Tyr Leu Ala
1 5 10

<210> SEQ ID NO 162
<211> LENGTH: 12
<212> TYPE: PRT
<213> ORGANISM: Artificial Sequence
<220> FEATURE:
<223> OTHER INFORMATION: Synthetic: 1193-C08 / CDR-L1 / K/C

<400> SEQUENCE: 162

Arg Ala Ser Gln Ser Val Ser Ser Asn Tyr Leu Ala
1 5 10

<210> SEQ ID NO 163
<211> LENGTH: 12
<212> TYPE: PRT
<213> ORGANISM: Artificial Sequence
<220> FEATURE:
<223> OTHER INFORMATION: Synthetic: 1193-E06b / CDR-L1 / K/C

<400> SEQUENCE: 163

Arg Ala Ser Gln Ser Val Ser Ser Ser Tyr Leu Ala
1 5 10

<210> SEQ ID NO 164
<211> LENGTH: 12
<212> TYPE: PRT
<213> ORGANISM: Artificial Sequence
<220> FEATURE:
<223> OTHER INFORMATION: Synthetic: 1193-H04b / CDR-L1 / K/C

<400> SEQUENCE: 164

Arg Ala Ser Gln Ser Val Ser Ser Ser Tyr Leu Ala
1 5 10

<210> SEQ ID NO 165
<211> LENGTH: 11
<212> TYPE: PRT
<213> ORGANISM: Artificial Sequence
<220> FEATURE:
<223> OTHER INFORMATION: Synthetic: 1275-C10 / CDR-L1 / K/C

<400> SEQUENCE: 165

Arg Ala Ser Gln Gly Val Ser Ser Trp Leu Ala
1 5 10

<210> SEQ ID NO 166
<211> LENGTH: 11
<212> TYPE: PRT
<213> ORGANISM: Artificial Sequence
<220> FEATURE:
<223> OTHER INFORMATION: Synthetic: 1275-D01 / CDR-L1 / K/C

<400> SEQUENCE: 166

Arg Ala Ser Gln Gly Ile Gly Arg Trp Leu Ala
1 5 10

<210> SEQ ID NO 167
<211> LENGTH: 11
<212> TYPE: PRT
<213> ORGANISM: Artificial Sequence
<220> FEATURE:
<223> OTHER INFORMATION: Synthetic: 1275-D10 / CDR-L1 / K/C

<400> SEQUENCE: 167

Arg Ala Ser Gln Gly Val Phe Ser Trp Leu Ala
1 5 10

<210> SEQ ID NO 168
<211> LENGTH: 11
<212> TYPE: PRT
<213> ORGANISM: Artificial Sequence
<220> FEATURE:
<223> OTHER INFORMATION: Synthetic: 1275-G02 / CDR-L1 / K/C

<400> SEQUENCE: 168

Arg Ala Ser Gln Gly Leu Gly Ser Phe Leu Ala
1 5 10

<210> SEQ ID NO 169
<211> LENGTH: 11
<212> TYPE: PRT
<213> ORGANISM: Artificial Sequence
<220> FEATURE:
<223> OTHER INFORMATION: Synthetic: 1337-A04 / CDR-L1 / K/C

<400> SEQUENCE: 169

Arg Ala Ser Gln Asp Ile Gly Arg Trp Val Ala
1 5 10

<210> SEQ ID NO 170
<211> LENGTH: 11
<212> TYPE: PRT
<213> ORGANISM: Artificial Sequence
<220> FEATURE:
<223> OTHER INFORMATION: Synthetic: 1337-A05 / CDR-L1 / K/C

<400> SEQUENCE: 170

Arg Ala Ser Gln Gly Ile Gly Arg Trp Val Ala
1 5 10

<210> SEQ ID NO 171
<211> LENGTH: 11
<212> TYPE: PRT
<213> ORGANISM: Artificial Sequence
<220> FEATURE:
<223> OTHER INFORMATION: Synthetic: 1337-A06 / CDR-L1 / K/C

<400> SEQUENCE: 171

Arg Ala Ser Gln Asp Ile Gly Ser Trp Val Ala
1 5 10

<210> SEQ ID NO 172
<211> LENGTH: 11
<212> TYPE: PRT
<213> ORGANISM: Artificial Sequence
<220> FEATURE:
<223> OTHER INFORMATION: Synthetic: 1337-A07 / CDR-L1 / K/C

<400> SEQUENCE: 172

Arg Ala Ser Gln Gly Ile Ser Ser Trp Val Ala
1 5 10

<210> SEQ ID NO 173
<211> LENGTH: 11
<212> TYPE: PRT
<213> ORGANISM: Artificial Sequence
<220> FEATURE:
<223> OTHER INFORMATION: Synthetic: 1337-A08 / CDR-L1 / K/C

<400> SEQUENCE: 173

Arg Ala Ser Gln Asp Ile Gly Ser Trp Val Ala
1 5 10

<210> SEQ ID NO 174
<211> LENGTH: 11
<212> TYPE: PRT
<213> ORGANISM: Artificial Sequence
<220> FEATURE:
<223> OTHER INFORMATION: Synthetic: 1337-A09 / CDR-L1 / K/C

<400> SEQUENCE: 174

Arg Ala Ser Gln Gly Ile Gly Ser Trp Leu Ala
1 5 10

<210> SEQ ID NO 175
<211> LENGTH: 11
<212> TYPE: PRT
<213> ORGANISM: Artificial Sequence
<220> FEATURE:
<223> OTHER INFORMATION: Synthetic: 1337-A10 / CDR-L1 / K/C

<400> SEQUENCE: 175

Arg Ala Ser Gln Gly Ile Ser Ser Trp Val Ala
1 5 10

<210> SEQ ID NO 176
<211> LENGTH: 12
<212> TYPE: PRT
<213> ORGANISM: Artificial Sequence
<220> FEATURE:
<223> OTHER INFORMATION: Synthetic: 1447-D11 / CDR-L1 / K/C

<400> SEQUENCE: 176

Arg Ala Ser Gln Ser Val Ser Ser Ser Tyr Leu Ala
1 5 10

<210> SEQ ID NO 177
<211> LENGTH: 12
<212> TYPE: PRT
<213> ORGANISM: Artificial Sequence
<220> FEATURE:
<223> OTHER INFORMATION: Synthetic: 1447-E08 / CDR-L1 / K/C

<400> SEQUENCE: 177

Arg Ala Ser Gln Arg Val Ala Gly Ile Asp Leu Ser
1 5 10

<210> SEQ ID NO 178
<211> LENGTH: 12
<212> TYPE: PRT
<213> ORGANISM: Artificial Sequence
<220> FEATURE:
<223> OTHER INFORMATION: Synthetic: 1447-F11 / CDR-L1 / K/C

<400> SEQUENCE: 178

Arg Ala Ser Gln Ser Val Tyr Arg Ser Tyr Leu Ala
1 5 10

<210> SEQ ID NO 179
<211> LENGTH: 12
<212> TYPE: PRT
<213> ORGANISM: Artificial Sequence
<220> FEATURE:
<223> OTHER INFORMATION: Synthetic: 1447-G01 / CDR-L1 / K/C

<400> SEQUENCE: 179

Arg Ala Ser Gln Ser Val Ser Ser Arg Glu Leu Gly
1 5 10

<210> SEQ ID NO 180
<211> LENGTH: 11
<212> TYPE: PRT
<213> ORGANISM: Artificial Sequence
<220> FEATURE:
<223> OTHER INFORMATION: Synthetic: VL-5[23] & VL6-[26] / CDR-L1 / K/C

<400> SEQUENCE: 180

Arg Ala Ser Gln Gly Ile Ser Ser Trp Leu Ala
1 5 10

<210> SEQ ID NO 181
<211> LENGTH: 7
<212> TYPE: PRT
<213> ORGANISM: Artificial Sequence
<220> FEATURE:
<223> OTHER INFORMATION: Synthetic: 1193-B06 / CDR-L2 / K/C

<400> SEQUENCE: 181

Gly Ala Ser Ser Arg Ala Thr
1 5

<210> SEQ ID NO 182
<211> LENGTH: 7
<212> TYPE: PRT
<213> ORGANISM: Artificial Sequence
<220> FEATURE:
<223> OTHER INFORMATION: Synthetic: 1193-C08 / CDR-L2 / K/C

<400> SEQUENCE: 182

Gly Ala Ser Ser Arg Ala Thr
1 5

<210> SEQ ID NO 183
<211> LENGTH: 7
<212> TYPE: PRT
<213> ORGANISM: Artificial Sequence
<220> FEATURE:
<223> OTHER INFORMATION: Synthetic: 1193-E06b / CDR-L2 / K/C

<400> SEQUENCE: 183

Gly Ala Ser Ser Arg Ala Thr
1 5

<210> SEQ ID NO 184
<211> LENGTH: 7
<212> TYPE: PRT
<213> ORGANISM: Artificial Sequence
<220> FEATURE:
<223> OTHER INFORMATION: Synthetic: 1193-H04b / CDR-L2 / K/C

<400> SEQUENCE: 184

Gly Ala Ser Ser Arg Ala Thr
1 5

<210> SEQ ID NO 185
<211> LENGTH: 7
<212> TYPE: PRT
<213> ORGANISM: Artificial Sequence
<220> FEATURE:
<223> OTHER INFORMATION: Synthetic: 1275-C10 / CDR-L2 / K/C

<400> SEQUENCE: 185

Ser Ala Arg Tyr Leu Gln Ser
1 5

<210> SEQ ID NO 186
<211> LENGTH: 7
<212> TYPE: PRT
<213> ORGANISM: Artificial Sequence
<220> FEATURE:
<223> OTHER INFORMATION: Synthetic: 1275-D01 / CDR-L2 / K/C

<400> SEQUENCE: 186

Gly Arg Ser Ser Leu Gln Ser
1 5

<210> SEQ ID NO 187
<211> LENGTH: 7
<212> TYPE: PRT
<213> ORGANISM: Artificial Sequence
<220> FEATURE:
<223> OTHER INFORMATION: Synthetic: 1275-D10 / CDR-L2 / K/C

<400> SEQUENCE: 187

Asn Ala Thr Gln Leu Gln Ser
1 5

<210> SEQ ID NO 188
<211> LENGTH: 7
<212> TYPE: PRT
<213> ORGANISM: Artificial Sequence
<220> FEATURE:
<223> OTHER INFORMATION: Synthetic: 1275-G02 / CDR-L2 / K/C

<400> SEQUENCE: 188

Leu Gly Asn Leu Leu Gln Ile
1 5

<210> SEQ ID NO 189
<211> LENGTH: 7
<212> TYPE: PRT
<213> ORGANISM: Artificial Sequence
<220> FEATURE:
<223> OTHER INFORMATION: Synthetic: 1337-A04 / CDR-L2 / K/C

<400> SEQUENCE: 189

Gly Ala Ser Ser Leu Gln Ser 1 5

<210> SEQ ID NO 190
<211> LENGTH: 7
<212> TYPE: PRT
<213> ORGANISM: Artificial Sequence
<220> FEATURE:
<223> OTHER INFORMATION: Synthetic: 1337-A05 / CDR-L2 / K/C

<400> SEQUENCE: 190

Gly Ala Asp Arg Leu Gln Ser
1 5

<210> SEQ ID NO 191
<211> LENGTH: 7
<212> TYPE: PRT
<213> ORGANISM: Artificial Sequence
<220> FEATURE:
<223> OTHER INFORMATION: Synthetic: 1337-A06 / CDR-L2 / K/C

<400> SEQUENCE: 191

Gly Ala Asp Arg Leu Gln Ser
1 5

<210> SEQ ID NO 192
<211> LENGTH: 7
<212> TYPE: PRT
<213> ORGANISM: Artificial Sequence
<220> FEATURE:
<223> OTHER INFORMATION: Synthetic: 1337-A07 / CDR-L2 / K/C

<400> SEQUENCE: 192

Gly Ala Ser Arg Leu Gln Ser
1 5

<210> SEQ ID NO 193
<211> LENGTH: 7
<212> TYPE: PRT
<213> ORGANISM: Artificial Sequence
<220> FEATURE:
<223> OTHER INFORMATION: Synthetic: 1337-A08 / CDR-L2 / K/C

<400> SEQUENCE: 193

Ala Ser Asp Ser Leu Gln Ser
1 5

<210> SEQ ID NO 194
<211> LENGTH: 7
<212> TYPE: PRT
<213> ORGANISM: Artificial Sequence
<220> FEATURE:
<223> OTHER INFORMATION: Synthetic: 1337-A09 / CDR-L2 / K/C

<400> SEQUENCE: 194

Ala Ala Asp Arg Leu Gln Ser
1 5

<210> SEQ ID NO 195
<211> LENGTH: 7
<212> TYPE: PRT
<213> ORGANISM: Artificial Sequence
<220> FEATURE:
<223> OTHER INFORMATION: Synthetic: 1337-A10 / CDR-L2 / K/C

<400> SEQUENCE: 195

Gly Ser Ser Arg Leu Gln Ser
1 5

<210> SEQ ID NO 196
<211> LENGTH: 7
<212> TYPE: PRT
<213> ORGANISM: Artificial Sequence
<220> FEATURE:
<223> OTHER INFORMATION: Synthetic: 1447-D11 / CDR-L2 / K/C

<400> SEQUENCE: 196

Gly Ala Ser Ser Arg Ala Thr
1 5

<210> SEQ ID NO 197
<211> LENGTH: 7
<212> TYPE: PRT
<213> ORGANISM: Artificial Sequence
<220> FEATURE:
<223> OTHER INFORMATION: Synthetic: 1447-E08 / CDR-L2 / K/C

<400> SEQUENCE: 197

Gly Ala Ser Ser Arg Ala Thr
1 5

<210> SEQ ID NO 198
<211> LENGTH: 7
<212> TYPE: PRT
<213> ORGANISM: Artificial Sequence
<220> FEATURE:
<223> OTHER INFORMATION: Synthetic: 1447-F11 / CDR-L2 / K/C

<400> SEQUENCE: 198

Gly Ala Ser Ser Arg Ala Thr
1 5

<210> SEQ ID NO 199
<211> LENGTH: 7
<212> TYPE: PRT
<213> ORGANISM: Artificial Sequence
<220> FEATURE:
<223> OTHER INFORMATION: Synthetic: 1447-G01 / CDR-L2 / K/C

<400> SEQUENCE: 199

Gly Ala Ser Ser Arg Ala Thr
1 5

<210> SEQ ID NO 200
<211> LENGTH: 7
<212> TYPE: PRT
<213> ORGANISM: Artificial Sequence
<220> FEATURE:
<223> OTHER INFORMATION: Synthetic: VL-5[23] & VL6-[26] / CDR-L2 / K/C

<400> SEQUENCE: 200

Ala Ala Ser Ser Leu Gln Ser
1 5

<210> SEQ ID NO 201
<211> LENGTH: 9
<212> TYPE: PRT
<213> ORGANISM: Artificial Sequence
<220> FEATURE:
<223> OTHER INFORMATION: Synthetic: 1193-B06 / CDR-L3 / K/C

<400> SEQUENCE: 201

Gln Gln His Tyr Thr Thr Pro Pro Thr
1 5

<210> SEQ ID NO 202
<211> LENGTH: 9
<212> TYPE: PRT
<213> ORGANISM: Artificial Sequence
<220> FEATURE:
<223> OTHER INFORMATION: Synthetic: 1193-C08 / CDR-L3 / K/C

<400> SEQUENCE: 202

Gln Gln His Tyr Thr Thr Pro Pro Thr
1 5

<210> SEQ ID NO 203
<211> LENGTH: 9
<212> TYPE: PRT
<213> ORGANISM: Artificial Sequence
<220> FEATURE:
<223> OTHER INFORMATION: Synthetic: 1193-E06b / CDR-L3 / K/C

<400> SEQUENCE: 203

Gln Gln His Tyr Thr Thr Pro Pro Thr
1 5

<210> SEQ ID NO 204
<211> LENGTH: 9
<212> TYPE: PRT
<213> ORGANISM: Artificial Sequence
<220> FEATURE:
<223> OTHER INFORMATION: Synthetic: 1193-H04b / CDR-L3 / K/C

<400> SEQUENCE: 204

Gln Gln His Tyr Thr Thr Pro Pro Thr
1 5

<210> SEQ ID NO 205
<211> LENGTH: 9
<212> TYPE: PRT
<213> ORGANISM: Artificial Sequence
<220> FEATURE:
<223> OTHER INFORMATION: Synthetic: 1275-C10 / CDR-L3 / K/C

<400> SEQUENCE: 205

Gln Gln Tyr Asn Leu Tyr Pro Leu Thr
1 5

<210> SEQ ID NO 206
<211> LENGTH: 9
<212> TYPE: PRT
<213> ORGANISM: Artificial Sequence
<220> FEATURE:
<223> OTHER INFORMATION: Synthetic: 1275-D01 / CDR-L3 / K/C

<400> SEQUENCE: 206

Gln Gln Tyr Asn Ile Tyr Pro Leu Thr
1 5

<210> SEQ ID NO 207
<211> LENGTH: 9
<212> TYPE: PRT
<213> ORGANISM: Artificial Sequence
<220> FEATURE:
<223> OTHER INFORMATION: Synthetic: 1275-D10 / CDR-L3 / K/C

<400> SEQUENCE: 207

Gln Gln Tyr Tyr Tyr Tyr Pro Leu Thr
1 5

<210> SEQ ID NO 208
<211> LENGTH: 9
<212> TYPE: PRT
<213> ORGANISM: Artificial Sequence
<220> FEATURE:
<223> OTHER INFORMATION: Synthetic: 1275-G02 / CDR-L3 / K/C

<400> SEQUENCE: 208

Gln Gln Tyr Asn Ala Tyr Pro Leu Thr
1 5

<210> SEQ ID NO 209
<211> LENGTH: 9
<212> TYPE: PRT
<213> ORGANISM: Artificial Sequence
<220> FEATURE:
<223> OTHER INFORMATION: Synthetic: 1337-A04 / CDR-L3 / K/C

<400> SEQUENCE: 209

Gln Gln Tyr Asn Thr Tyr Pro Leu Thr
1 5

<210> SEQ ID NO 210
<211> LENGTH: 9
<212> TYPE: PRT
<213> ORGANISM: Artificial Sequence
<220> FEATURE:
<223> OTHER INFORMATION: Synthetic: 1337-A05 / CDR-L3 / K/C

<400> SEQUENCE: 210

Gln Gln Tyr Asn Ser Tyr Pro Leu Thr
1 5

<210> SEQ ID NO 211
<211> LENGTH: 9
<212> TYPE: PRT
<213> ORGANISM: Artificial Sequence
<220> FEATURE:
<223> OTHER INFORMATION: Synthetic: 1337-A06 / CDR-L3 / K/C

<400> SEQUENCE: 211

Gln Gln Tyr Asn Ser Tyr Pro Leu Thr
1 5

<210> SEQ ID NO 212
<211> LENGTH: 9
<212> TYPE: PRT
<213> ORGANISM: Artificial Sequence
<220> FEATURE:
<223> OTHER INFORMATION: Synthetic: 1337-A07 / CDR-L3 / K/C

<400> SEQUENCE: 212

Gln Gln Tyr His Thr Tyr Pro Leu Thr
1 5

<210> SEQ ID NO 213
<211> LENGTH: 9
<212> TYPE: PRT
<213> ORGANISM: Artificial Sequence
<220> FEATURE:
<223> OTHER INFORMATION: Synthetic: 1337-A08 / CDR-L3 / K/C

<400> SEQUENCE: 213

Gln Gln Tyr Asn Ser Tyr Pro Leu Thr
1 5

<210> SEQ ID NO 214

<211> LENGTH: 9
<212> TYPE: PRT
<213> ORGANISM: Artificial Sequence
<220> FEATURE:
<223> OTHER INFORMATION: Synthetic: 1337-A09 / CDR-L3 / K/C

<400> SEQUENCE: 214

Gln Gln Tyr His Thr Tyr Pro Leu Thr
1 5

<210> SEQ ID NO 215
<211> LENGTH: 9
<212> TYPE: PRT
<213> ORGANISM: Artificial Sequence
<220> FEATURE:
<223> OTHER INFORMATION: Synthetic: 1337-A10 / CDR-L3 / K/C

<400> SEQUENCE: 215

Gln Gln Tyr Asn Thr Tyr Pro Leu Thr
1 5

<210> SEQ ID NO 216
<211> LENGTH: 9
<212> TYPE: PRT
<213> ORGANISM: Artificial Sequence
<220> FEATURE:
<223> OTHER INFORMATION: Synthetic: 1447-D11 / CDR-L3 / K/C

<400> SEQUENCE: 216

Gln His Asn Gln Pro Thr Pro Pro Thr
1 5

<210> SEQ ID NO 217
<211> LENGTH: 9
<212> TYPE: PRT
<213> ORGANISM: Artificial Sequence
<220> FEATURE:
<223> OTHER INFORMATION: Synthetic: 1447-E08 / CDR-L3 / K/C

<400> SEQUENCE: 217

Gln Gln His Asn Thr Thr Pro Pro Thr
1 5

<210> SEQ ID NO 218
<211> LENGTH: 9
<212> TYPE: PRT
<213> ORGANISM: Artificial Sequence
<220> FEATURE:
<223> OTHER INFORMATION: Synthetic: 1447-F11 / CDR-L3 / K/C

<400> SEQUENCE: 218

Gln Gln His Gln Thr Ala Pro Pro Thr
1 5

<210> SEQ ID NO 219
<211> LENGTH: 9
<212> TYPE: PRT
<213> ORGANISM: Artificial Sequence
<220> FEATURE:
<223> OTHER INFORMATION: Synthetic: 1447-G01 / CDR-L3 / K/C

<400> SEQUENCE: 219

Gln Gln Gln Cys Ser Trp Pro Pro Thr
1 5

<210> SEQ ID NO 220
<211> LENGTH: 9

```
<212> TYPE: PRT
<213> ORGANISM: Artificial Sequence
<220> FEATURE:
<223> OTHER INFORMATION: Synthetic:  VL-5[23] & VL6-[26] / CDR-L3 / K/C

<400> SEQUENCE: 220

Gln Gln Tyr Asn Ser Tyr Pro Leu Thr
1               5


<210> SEQ ID NO 221
<211> LENGTH: 243
<212> TYPE: PRT
<213> ORGANISM: Artificial Sequence
<220> FEATURE:
<223> OTHER INFORMATION: Synthetic:  1193-B06 / scFv

<400> SEQUENCE: 221

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Gly Asn
            20                  25                  30

Trp Met Ser Trp Val Arg Gln Ala Pro Gly Lys Gly Leu Glu Trp Val
        35                  40                  45

Gly Ile Ile Tyr Gly Thr Ser Gly Ala Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Ser Met Ser Gly Ser Arg Gly Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Ile Val Leu Thr Gln Ser Pro Gly
    130                 135                 140

Thr Leu Ser Leu Ser Pro Gly Glu Arg Ala Thr Leu Ser Cys Arg Ala
145                 150                 155                 160

Gly Gln Ser Val Ser Ser Ser Tyr Leu Ala Trp Tyr Gln Gln Lys Pro
                165                 170                 175

Gly Gln Ala Pro Arg Leu Leu Ile Tyr Gly Ala Ser Ser Arg Ala Thr
            180                 185                 190

Gly Ile Pro Asp Arg Phe Ser Gly Ser Gly Ser Gly Thr Asp Phe Thr
        195                 200                 205

Leu Thr Ile Ser Arg Leu Glu Pro Glu Asp Phe Ala Val Tyr Tyr Cys
    210                 215                 220

Gln Gln His Tyr Thr Thr Pro Pro Thr Phe Gly Gln Gly Thr Lys Val
225                 230                 235                 240

Glu Ile Lys


<210> SEQ ID NO 222
<211> LENGTH: 243
<212> TYPE: PRT
<213> ORGANISM: Artificial Sequence
<220> FEATURE:
<223> OTHER INFORMATION: Synthetic:  1193-C08 / scFv

<400> SEQUENCE: 222

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Asn Asn Asn
            20                  25                  30

Trp Met Ser Trp Val Arg Gln Ala Pro Gly Lys Gly Leu Glu Trp Val
        35                  40                  45

Gly Ile Ile Asn Gly Asp Asp Gly Tyr Thr Tyr Tyr Ala Asp Arg Val
    50                  55                  60

Lys Gly Arg Phe Thr Ile Ile Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Ala Leu Gly Arg Pro Arg Arg Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Ile Val Leu Thr Gln Ser Pro Gly
    130                 135                 140

Thr Leu Ser Leu Thr Pro Gly Glu Arg Ala Thr Leu Ser Cys Arg Ala
145                 150                 155                 160

Ser Gln Ser Val Ser Ser Asn Tyr Leu Ala Trp Tyr Gln Gln Lys Pro
                165                 170                 175

Gly Gln Ala Pro Arg Leu Leu Ile Tyr Gly Ala Ser Ser Arg Ala Thr
            180                 185                 190

Gly Ile Pro Asp Arg Phe Ser Gly Ser Gly Ser Gly Thr Asp Phe Thr
        195                 200                 205

Leu Thr Ile Ser Arg Leu Glu Pro Glu Asp Phe Ala Met Tyr Tyr Cys
    210                 215                 220

Gln Gln His Tyr Thr Thr Pro Pro Thr Phe Gly Gln Gly Thr Lys Val
225                 230                 235                 240

Glu Ile Lys


<210> SEQ ID NO 223
<211> LENGTH: 243
<212> TYPE: PRT
<213> ORGANISM: Artificial Sequence
<220> FEATURE:
<223> OTHER INFORMATION: Synthetic:  1193-E06b / scFv

<400> SEQUENCE: 223

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asn Thr
            20                  25                  30

Asp Met Ser Trp Val Arg Gln Ala Pro Gly Lys Gly Leu Glu Trp Val
        35                  40                  45

Gly Ile Ile Asn Gly Ser Gly Gly Ala Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Glu Asn Glu Trp Glu Val Ser Met Asp Tyr Trp Gly Gln
            100                 105                 110

Gly Thr Leu Val Thr Val Ser Ser Gly Gly Gly Gly Ser Gly Gly Gly
        115                 120                 125
```

```
Gly Ser Gly Gly Gly Gly Ser Glu Ile Val Leu Thr Gln Ser Pro Gly
    130                 135                 140

Thr Leu Ser Leu Ser Pro Gly Glu Arg Ala Thr Leu Ser Cys Arg Ala
145                 150                 155                 160

Ser Gln Ser Val Ser Ser Ser Tyr Leu Ala Trp Tyr Gln Gln Lys Pro
                165                 170                 175

Gly Gln Ala Pro Arg Leu Leu Ile Tyr Gly Ala Ser Ser Arg Ala Thr
            180                 185                 190

Gly Ile Pro Asp Arg Phe Ser Gly Ser Gly Ser Gly Thr Asp Phe Thr
        195                 200                 205

Leu Thr Ile Ser Arg Leu Glu Pro Glu Asp Phe Ala Val Tyr Tyr Cys
    210                 215                 220

Gln Gln His Tyr Thr Thr Pro Pro Thr Phe Gly Gln Gly Thr Lys Val
225                 230                 235                 240

Glu Ile Lys


<210> SEQ ID NO 224
<211> LENGTH: 242
<212> TYPE: PRT
<213> ORGANISM: Artificial Sequence
<220> FEATURE:
<223> OTHER INFORMATION: Synthetic:  1193-H04b / scFv

<400> SEQUENCE: 224

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Ser Ser
            20                  25                  30

Trp Met Ser Trp Val Arg Gln Ala Pro Gly Lys Gly Leu Glu Trp Val
        35                  40                  45

Gly Ile Ile Asn Gly Tyr Asn Gly Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Ser Ala Pro Gly Ala Arg Arg Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Ile Val Leu Thr Gln Ser Pro Gly
    130                 135                 140

Thr Leu Ser Leu Ser Pro Gly Glu Ala Thr Leu Ser Cys Arg Ala Ser
145                 150                 155                 160

Gln Ser Val Ser Ser Ser Tyr Leu Ala Trp Tyr Gln Gln Arg Pro Gly
                165                 170                 175

Gln Ala Pro Arg Leu Leu Ile Tyr Gly Ala Ser Ser Arg Ala Thr Gly
            180                 185                 190

Ile Pro Asp Arg Phe Ser Gly Ser Gly Ser Gly Thr Asp Phe Thr Leu
        195                 200                 205

Thr Ile Ser Arg Leu Glu Pro Glu Asp Phe Ala Val Tyr Tyr Cys Gln
    210                 215                 220

Gln His Tyr Thr Thr Pro Pro Thr Phe Gly Gln Gly Thr Lys Val Glu
225                 230                 235                 240

Ile Lys
```

<210> SEQ ID NO 225
<211> LENGTH: 243
<212> TYPE: PRT
<213> ORGANISM: Artificial Sequence
<220> FEATURE:
<223> OTHER INFORMATION: Synthetic: 1447-D11 / scFv

<400> SEQUENCE: 225

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asn Thr
            20                  25                  30

Asp Met Ser Trp Val Arg Gln Ala Pro Gly Lys Gly Leu Glu Trp Val
        35                  40                  45

Gly Val Ile Asn Gly Ser Gly Gly Ser Ser Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Glu Thr Glu Trp Glu Val Ser Leu Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Ile Val Leu Thr Gln Ser Pro Gly
    130                 135                 140

Thr Leu Ser Leu Ser Pro Gly Glu Arg Ala Thr Leu Ser Cys Arg Ala
145                 150                 155                 160

Ser Gln Ser Val Ser Ser Ser Tyr Leu Ala Trp Tyr Gln Gln Lys Pro
                165                 170                 175

Gly Gln Ala Pro Arg Leu Leu Ile Tyr Gly Ala Ser Ser Arg Ala Thr
            180                 185                 190

Gly Ile Pro Asp Arg Phe Ser Gly Ser Gly Ser Gly Thr Asp Phe Thr
        195                 200                 205

Leu Thr Ile Ser Arg Leu Glu Pro Glu Asp Phe Ala Val Tyr Tyr Cys
    210                 215                 220

Gln His Asn Gln Pro Thr Pro Pro Thr Phe Gly Gln Gly Thr Lys Val
225                 230                 235                 240

Glu Ile Lys
```

<210> SEQ ID NO 226
<211> LENGTH: 243
<212> TYPE: PRT
<213> ORGANISM: Artificial Sequence
<220> FEATURE:
<223> OTHER INFORMATION: Synthetic: 1447-E08 / scFv

<400> SEQUENCE: 226

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asp Thr
            20                  25                  30

Asp Met Ser Trp Val Arg Gln Ala Pro Gly Lys Gly Leu Glu Trp Val
        35                  40                  45

Gly Met Ile Asn Gly Ala Gly Gly Ala Ser Phe Tyr Ala Asp Ser Val
    50                  55                  60
```

Arg Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Phe Glu Asn Gln Trp Glu Val Thr Phe Asp Tyr Trp Gly Gln
100 105 110

Gly Thr Leu Val Thr Val Ser Ser Gly Gly Gly Gly Ser Gly Gly Gly
115 120 125

Gly Ser Gly Gly Gly Gly Ser Glu Ile Val Leu Thr Gln Ser Pro Gly
130 135 140

Thr Leu Ser Leu Ser Pro Gly Glu Arg Ala Thr Leu Ser Cys Arg Ala
145 150 155 160

Ser Gln Arg Val Ala Gly Ile Asp Leu Ser Trp Tyr Gln Gln Lys Pro
165 170 175

Gly Gln Ala Pro Arg Leu Leu Ile Tyr Gly Ala Ser Ser Arg Ala Thr
180 185 190

Gly Ile Pro Asp Arg Phe Ser Gly Ser Gly Ser Gly Thr Asp Phe Thr
195 200 205

Leu Thr Ile Ser Arg Leu Glu Pro Glu Asp Phe Ala Val Tyr Tyr Cys
210 215 220

Gln Gln His Asn Thr Thr Pro Pro Thr Phe Gly Gln Gly Thr Lys Val
225 230 235 240

Glu Ile Lys

<210> SEQ ID NO 227
<211> LENGTH: 243
<212> TYPE: PRT
<213> ORGANISM: Artificial Sequence
<220> FEATURE:
<223> OTHER INFORMATION: Synthetic: 1447-F11 / scFv

<400> SEQUENCE: 227

Glu Val Gln Leu Leu Glu Ser Gly Gly Gly Leu Val Gln Thr Gly Gly
1 5 10 15

Ser Leu Arg Leu Ser Cys Ala Ala Ser Gly Phe Thr Phe Asp Asn Thr
20 25 30

Asp Met Ser Trp Val Arg Gln Ala Pro Gly Lys Gly Leu Glu Trp Val
35 40 45

Gly Ile Ile Asn Gly Ser Gly Gly Val Thr Asn Tyr Ala Asp Ser Val
50 55 60

Arg Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Tyr Glu Ser Glu Trp Glu Val Ser Leu Asp Tyr Trp Gly Gln
100 105 110

Gly Thr Leu Val Thr Val Ser Ser Gly Gly Gly Gly Ser Gly Gly Gly
115 120 125

Gly Ser Gly Gly Gly Gly Ser Glu Ile Val Leu Thr Gln Ser Pro Gly
130 135 140

Thr Leu Ser Leu Ser Pro Gly Glu Arg Ala Thr Leu Ser Cys Arg Ala
145 150 155 160

Ser Gln Ser Val Tyr Arg Ser Tyr Leu Ala Trp Tyr Gln Gln Lys Pro
165 170 175

```
Gly Gln Ala Pro Arg Leu Leu Ile Tyr Gly Ala Ser Ser Arg Ala Thr
            180                 185                 190

Gly Ile Pro Asp Arg Phe Ser Gly Ser Gly Ser Gly Thr Asp Phe Thr
        195                 200                 205

Leu Thr Ile Ser Arg Leu Glu Pro Glu Asp Phe Ala Val Tyr Tyr Cys
    210                 215                 220

Gln Gln His Gln Thr Ala Pro Pro Thr Phe Gly Gln Gly Thr Lys Val
225                 230                 235                 240

Glu Ile Lys


<210> SEQ ID NO 228
<211> LENGTH: 243
<212> TYPE: PRT
<213> ORGANISM: Artificial Sequence
<220> FEATURE:
<223> OTHER INFORMATION: Synthetic:  1447-G01 / scFv

<400> SEQUENCE: 228

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr Ser
            20                  25                  30

Asp Met Ser Trp Val Arg Gln Ala Pro Gly Lys Gly Leu Glu Trp Val
        35                  40                  45

Gly Ile Ile Asn Gly Ser Gly Gly Ala Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Glu Asn Glu Met Glu Val Ser Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Ile Val Leu Thr Gln Ser Pro Gly
    130                 135                 140

Thr Leu Ser Leu Ser Pro Gly Glu Arg Ala Thr Leu Ser Cys Arg Ala
145                 150                 155                 160

Ser Gln Ser Val Ser Ser Arg Glu Leu Gly Trp Tyr Gln Gln Lys Pro
                165                 170                 175

Gly Gln Ala Pro Arg Leu Leu Ile Tyr Gly Ala Ser Ser Arg Ala Thr
            180                 185                 190

Gly Ile Pro Asp Arg Phe Ser Gly Ser Gly Ser Gly Thr Asp Phe Thr
        195                 200                 205

Leu Thr Ile Ser Arg Leu Glu Pro Glu Asp Phe Ala Val Tyr Tyr Cys
    210                 215                 220

Gln Gln Gln Cys Ser Trp Pro Pro Thr Phe Gly Gln Gly Thr Lys Val
225                 230                 235                 240

Glu Ile Lys


<210> SEQ ID NO 229
<211> LENGTH: 503
<212> TYPE: PRT
<213> ORGANISM: Artificial Sequence
<220> FEATURE:
<223> OTHER INFORMATION: Synthetic:  1251-B08-g_1337-A09-g scFv-Fc
```

<400> SEQUENCE: 229

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Asn Phe Ser Asp Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Ile Ser Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Thr Val Glu His Gly Ala Val Tyr Gly Thr Asp Val
            100                 105                 110

Trp Gly Gln Gly Thr Thr Val Thr Val Ser Ser Gly Gly Gly Gly Ser
        115                 120                 125

Gly Gly Gly Gly Ser Gly Gly Gly Gly Ser Asp Ile Gln Met Thr Gln
    130                 135                 140

Ser Pro Ser Ser Val Ser Ala Ser Val Gly Asp Arg Val Thr Ile Thr
145                 150                 155                 160

Cys Arg Ala Ser Gln Gly Ile Gly Ser Trp Leu Ala Trp Tyr Gln Gln
                165                 170                 175

Lys Pro Gly Lys Ala Pro Lys Leu Leu Ile Tyr Ala Ala Asp Arg Leu
            180                 185                 190

Gln Ser Gly Val Pro Ser Arg Phe Ser Gly Ser Gly Ser Gly Thr Asp
        195                 200                 205

Phe Thr Leu Thr Ile Ser Ser Leu Gln Pro Glu Asp Phe Ala Thr Tyr
    210                 215                 220

Tyr Cys Gln Gln Tyr His Thr Tyr Pro Leu Thr Phe Gly Gly Gly Thr
225                 230                 235                 240

Lys Val Glu Ile Lys Ala Ala Gly Ser Asp Gln Glu Pro Lys Ser Ser
                245                 250                 255

Asp Lys Thr His Thr Cys Pro Pro Cys Ser Ala Pro Glu Leu Leu Gly
            260                 265                 270

Gly Ser Ser Val Phe Leu Phe Pro Pro Lys Pro Lys Asp Thr Leu Met
        275                 280                 285

Ile Ser Arg Thr Pro Glu Val Thr Cys Val Val Val Asp Val Ser His
    290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
        355                 360                 365

Glu Lys Thr Ile Ser Lys Ala Lys Gly Gln Pro Arg Glu Pro Gln Val
    370                 375                 380

Tyr Thr Leu Pro Pro Ser Arg Asp Glu Leu Thr Lys Asn Gln Val Ser
385                 390                 395                 400

Leu Thr Cys Leu Val Lys Gly Phe Tyr Pro Ser Asp Ile Ala Val Glu
                405                 410                 415
```

```
Trp Glu Ser Asn Gly Gln Pro Glu Asn Asn Tyr Lys Thr Thr Pro Pro
            420                 425                 430

Val Leu Asp Ser Asp Gly Ser Phe Phe Leu Tyr Ser Lys Leu Thr Val
        435                 440                 445

Asp Lys Ser Arg Trp Gln Gln Gly Asn Val Phe Ser Cys Ser Val Met
    450                 455                 460

His Glu Ala Leu His Asn His Tyr Thr Gln Lys Ser Leu Ser Leu Ser
465                 470                 475                 480

Pro Gly Lys Gly Ser Gly Asp Tyr Lys Asp Asp Asp Asp Lys Gly Ser
            485                 490                 495

Gly His His His His His His
            500
```

```
<210> SEQ ID NO 230
<211> LENGTH: 120
<212> TYPE: PRT
<213> ORGANISM: Artificial Sequence
<220> FEATURE:
<223> OTHER INFORMATION: Synthetic:  1198-A01 / VH

<400> SEQUENCE: 230

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ser Trp Val Arg Gln Ala Pro Gly Lys Gly Leu Glu Trp Val
        35                  40                  45

Gly Phe Ile Ala Gln Asp Gly Ser Tyr Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Lys Leu Phe Arg Ala Gly Gln Phe Asp Tyr Trp Gly Gln
            100                 105                 110

Gly Thr Leu Val Thr Val Ser Ser
        115                 120
```

```
<210> SEQ ID NO 231
<211> LENGTH: 120
<212> TYPE: PRT
<213> ORGANISM: Artificial Sequence
<220> FEATURE:
<223> OTHER INFORMATION: Synthetic:  1198-B10 / VH

<400> SEQUENCE: 231

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Gly Ser
            20                  25                  30

Trp Ile His Trp Val Arg Gln Ala Pro Gly Lys Gly Leu Glu Trp Val
        35                  40                  45

Gly Tyr Ile Tyr Pro Asp Asp Gly Asp Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
```

```
                85                  90                  95

Ala Arg Glu Gly Ser His Asn Leu Asp Lys Met Asp Tyr Trp Gly Gln
            100                 105                 110

Gly Thr Leu Val Thr Val Ser Ser
        115                 120


<210> SEQ ID NO 232
<211> LENGTH: 120
<212> TYPE: PRT
<213> ORGANISM: Artificial Sequence
<220> FEATURE:
<223> OTHER INFORMATION: Synthetic:  1198-D03 / VH

<400> SEQUENCE: 232

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Asn Asn Tyr
            20                  25                  30

Asp Ile His Trp Val Arg Gln Ala Pro Gly Lys Gly Leu Glu Trp Val
        35                  40                  45

Ala Asn Ile Asp Pro Tyr Asn Gly Ala Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Val Leu Trp Gly Phe Trp Ala Pro Phe Asp Tyr Trp Gly Gln
            100                 105                 110

Gly Thr Leu Val Thr Val Ser Ser
        115                 120


<210> SEQ ID NO 233
<211> LENGTH: 120
<212> TYPE: PRT
<213> ORGANISM: Artificial Sequence
<220> FEATURE:
<223> OTHER INFORMATION: Synthetic:  1198-D04 / VH

<400> SEQUENCE: 233

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Asn Asn Tyr
            20                  25                  30

Asp Ile His Trp Val Arg Gln Ala Pro Gly Lys Gly Leu Glu Trp Val
        35                  40                  45

Ala Asn Ile Asp Pro Tyr Asn Gly Thr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Val Pro Trp Gly Phe Trp Ala Pro Phe Asp Tyr Trp Gly Gln
            100                 105                 110

Gly Thr Leu Val Thr Val Ser Ser
        115                 120


<210> SEQ ID NO 234
<211> LENGTH: 123
```

<212> TYPE: PRT
<213> ORGANISM: Artificial Sequence
<220> FEATURE:
<223> OTHER INFORMATION: Synthetic: 1251-A02 / VH

<400> SEQUENCE: 234

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Ser Asp His
            20                  25                  30

Gly Met His Trp Val Arg Gln Ala Pro Asp Lys Gly Leu Glu Trp Val
        35                  40                  45

Ala Val Ile Trp Tyr Asp Gly Ser His Lys Ile Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Leu Ala Gly Gly Ala Val Tyr Gly Thr Asp Val
            100                 105                 110

Trp Gly Gln Gly Thr Thr Val Thr Val Ser Ser
        115                 120
```

<210> SEQ ID NO 235
<211> LENGTH: 123
<212> TYPE: PRT
<213> ORGANISM: Artificial Sequence
<220> FEATURE:
<223> OTHER INFORMATION: Synthetic: 1251-A03 / VH

<400> SEQUENCE: 235

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Ser Asp His
            20                  25                  30

Gly Met His Trp Val Arg Gln Ala Pro Asp Lys Gly Leu Glu Trp Val
        35                  40                  45

Ala Val Ile Trp Tyr Asp Gly Ser His Lys Ile Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Leu Ala Gly Gly Ala Val Tyr Gly Thr Asp Val
            100                 105                 110

Trp Gly Gln Gly Thr Thr Val Thr Val Ser Ser
        115                 120
```

<210> SEQ ID NO 236
<211> LENGTH: 123
<212> TYPE: PRT
<213> ORGANISM: Artificial Sequence
<220> FEATURE:
<223> OTHER INFORMATION: Synthetic: 1251-A06 / VH

<400> SEQUENCE: 236

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Asp Phe Ser Ser Tyr
```

```
            20                  25                  30

Gly Met His Trp Val Arg Gln Ala Pro Asp Lys Gly Leu Glu Trp Val
        35                  40                  45

Ala Val Ile Trp Asp Asp Gly Ser Asp Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Thr Arg Val Leu Gly Ala Ile His Gly Thr Asp Val
            100                 105                 110

Trp Gly Gln Gly Thr Thr Val Thr Val Ser Ser
        115                 120


<210> SEQ ID NO 237
<211> LENGTH: 123
<212> TYPE: PRT
<213> ORGANISM: Artificial Sequence
<220> FEATURE:
<223> OTHER INFORMATION: Synthetic:  1251-A06-g / VH

<400> SEQUENCE: 237

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Asp Phe Ser Ser Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Asp Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Thr Arg Val Leu Gly Ala Ile His Gly Thr Asp Val
            100                 105                 110

Trp Gly Gln Gly Thr Thr Val Thr Val Ser Ser
        115                 120


<210> SEQ ID NO 238
<211> LENGTH: 123
<212> TYPE: PRT
<213> ORGANISM: Artificial Sequence
<220> FEATURE:
<223> OTHER INFORMATION: Synthetic:  1251-B08 / VH

<400> SEQUENCE: 238

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Asn Phe Ser Asp Tyr
            20                  25                  30

Gly Met His Trp Val Arg Gln Ala Pro Asp Lys Gly Leu Glu Trp Val
        35                  40                  45

Ala Val Ile Trp Tyr Asp Gly Ser Ile Ser Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Gly Gly Thr Val Glu His Gly Ala Val Tyr Gly Thr Asp Val
            100                 105                 110

Trp Gly Gln Gly Ala Thr Val Thr Val Ser Ser
        115                 120


<210> SEQ ID NO 239
<211> LENGTH: 123
<212> TYPE: PRT
<213> ORGANISM: Artificial Sequence
<220> FEATURE:
<223> OTHER INFORMATION: Synthetic:  1251-B08-g / VH

<400> SEQUENCE: 239

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Asn Phe Ser Asp Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Ile Ser Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Thr Val Glu His Gly Ala Val Tyr Gly Thr Asp Val
            100                 105                 110

Trp Gly Gln Gly Thr Thr Val Thr Val Ser Ser
        115                 120


<210> SEQ ID NO 240
<211> LENGTH: 123
<212> TYPE: PRT
<213> ORGANISM: Artificial Sequence
<220> FEATURE:
<223> OTHER INFORMATION: Synthetic:  1251-B09 / VH

<400> SEQUENCE: 240

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Asn Phe Ser Asp Tyr
            20                  25                  30

Gly Met His Trp Val Arg Gln Ala Pro Asp Lys Gly Leu Glu Trp Val
        35                  40                  45

Ala Val Thr Trp Tyr Asp Gly Ser Arg Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Thr Leu Val His Gly Ala Leu Tyr Gly Asn Asp Val
            100                 105                 110

Trp Gly Gln Gly Thr Thr Val Thr Val Ser Ser
        115                 120


<210> SEQ ID NO 241
```

```
<211> LENGTH: 123
<212> TYPE: PRT
<213> ORGANISM: Artificial Sequence
<220> FEATURE:
<223> OTHER INFORMATION: Synthetic:  1251-B10 / VH

<400> SEQUENCE: 241

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Asn Phe Ser Ser His
            20                  25                  30

Gly Met His Trp Val Arg Gln Ala Pro Asp Lys Gly Leu Glu Trp Val
        35                  40                  45

Ala Val Ile Trp His Asp Gly Ser Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Thr Arg Val Leu Gly Ala Val Tyr Gly Leu Asp Val
            100                 105                 110

Trp Gly Gln Gly Thr Thr Val Thr Val Ser Ser
        115                 120


<210> SEQ ID NO 242
<211> LENGTH: 123
<212> TYPE: PRT
<213> ORGANISM: Artificial Sequence
<220> FEATURE:
<223> OTHER INFORMATION: Synthetic:  1251-C03 / VH

<400> SEQUENCE: 242

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Asn Phe Ser Ser Tyr
            20                  25                  30

Gly Met His Trp Val Arg Gln Ala Pro Asp Lys Gly Leu Glu Trp Val
        35                  40                  45

Ala Val Ile Trp Tyr Asp Gly Ser Ile Lys Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ala Leu Met Arg Gly Glu Phe Ser Gly His Asp Val
            100                 105                 110

Trp Gly Gln Gly Thr Thr Val Thr Val Ser Ser
        115                 120


<210> SEQ ID NO 243
<211> LENGTH: 123
<212> TYPE: PRT
<213> ORGANISM: Artificial Sequence
<220> FEATURE:
<223> OTHER INFORMATION: Synthetic:  1251-D02 / VH

<400> SEQUENCE: 243

Gln Val Gln Leu Val Glu Ser Gly Gly Gly Val Val Gln Pro Gly Arg
1               5                   10                  15
```

```
Ser Leu Arg Leu Ser Cys Ala Ala Ser Gly Phe Ser Phe Ala Ser His
            20                  25                  30

Gly Met His Trp Val Arg Gln Ala Pro Asp Lys Gly Leu Glu Trp Val
        35                  40                  45

Ala Val Ile Trp Asp Asp Gly Ser Asp Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Thr Arg Val Leu Gly Ala Ile His Gly Thr Asp Val
            100                 105                 110

Trp Gly Gln Gly Thr Thr Val Thr Val Ser Ser
        115                 120


<210> SEQ ID NO 244
<211> LENGTH: 123
<212> TYPE: PRT
<213> ORGANISM: Artificial Sequence
<220> FEATURE:
<223> OTHER INFORMATION: Synthetic:  1251-D06 / VH

<400> SEQUENCE: 244

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Gly Ser Tyr
            20                  25                  30

Gly Met His Trp Val Arg Gln Ala Pro Asp Lys Gly Leu Glu Trp Val
        35                  40                  45

Ala Val Val Trp Tyr Asp Gly Ser Lys Thr Ile Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Thr Leu Val Arg Gly Ala Val Tyr Gly Leu Asp Val
            100                 105                 110

Trp Gly Gln Gly Thr Thr Val Thr Val Ser Ser
        115                 120


<210> SEQ ID NO 245
<211> LENGTH: 123
<212> TYPE: PRT
<213> ORGANISM: Artificial Sequence
<220> FEATURE:
<223> OTHER INFORMATION: Synthetic:  1251-D09 / VH

<400> SEQUENCE: 245

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Tyr
            20                  25                  30

Gly Met His Trp Val Arg Gln Ala Pro Asp Lys Gly Leu Glu Trp Val
        35                  40                  45

Ala Val Ile Trp Tyr Asp Ala Ser Ile Arg Lys Tyr Ala Gly Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Gly Gly Thr Val Glu Arg Gly Ala Ile Tyr Gly Thr Asp Val
            100                 105                 110

Trp Gly Gln Gly Thr Thr Val Thr Val Ser Ser
        115                 120


<210> SEQ ID NO 246
<211> LENGTH: 123
<212> TYPE: PRT
<213> ORGANISM: Artificial Sequence
<220> FEATURE:
<223> OTHER INFORMATION: Synthetic:  1251-E06 / VH

<400> SEQUENCE: 246

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asp Ser Tyr
            20                  25                  30

Gly Met His Trp Val Arg Gln Ala Pro Asp Lys Gly Leu Glu Trp Val
        35                  40                  45

Ala Val Ile Trp Tyr Asp Gly Ser Asn Lys Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Met Val Gly Gln Gly Ala Met Phe Gly Leu Asp Val
            100                 105                 110

Trp Gly Gln Gly Thr Thr Val Thr Val Ser Ser
        115                 120


<210> SEQ ID NO 247
<211> LENGTH: 123
<212> TYPE: PRT
<213> ORGANISM: Artificial Sequence
<220> FEATURE:
<223> OTHER INFORMATION: Synthetic:  1251-F06 / VH

<400> SEQUENCE: 247

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Asp Lys Gly Leu Glu Trp Val
        35                  40                  45

Ala Val Ile Trp Tyr Asp Gly Ser Asn Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Leu Val Thr Arg Gly Val Tyr Gly Leu Asp Val
            100                 105                 110

Trp Gly Gln Gly Thr Thr Val Thr Val Ser Ser
        115                 120
```

<210> SEQ ID NO 248
<211> LENGTH: 123
<212> TYPE: PRT
<213> ORGANISM: Artificial Sequence
<220> FEATURE:
<223> OTHER INFORMATION: Synthetic: 1251-F07 / VH

<400> SEQUENCE: 248

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser His
            20                  25                  30

Gly Met His Trp Val Arg Gln Ala Pro Asp Lys Gly Leu Glu Trp Val
        35                  40                  45

Ala Val Ile Trp Asp Asp Gly Ser Asn Glu Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Thr Arg Ile Arg Gly Leu Arg Tyr Gly Thr Asp Val
            100                 105                 110

Trp Gly Gln Gly Thr Thr Val Thr Val Ser Ser
        115                 120
```

<210> SEQ ID NO 249
<211> LENGTH: 123
<212> TYPE: PRT
<213> ORGANISM: Artificial Sequence
<220> FEATURE:
<223> OTHER INFORMATION: Synthetic: 1251-G02 / VH

<400> SEQUENCE: 249

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Asp Lys Gly Leu Glu Trp Val
        35                  40                  45

Ala Val Ile Trp His Asp Gly Ser Lys Asp Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gln Leu Asp His Gly Ala Ile Tyr Gly Leu Asp Val
            100                 105                 110

Trp Gly Gln Gly Thr Thr Val Thr Val Ser Ser
        115                 120
```

<210> SEQ ID NO 250
<211> LENGTH: 121
<212> TYPE: PRT
<213> ORGANISM: Artificial Sequence
<220> FEATURE:
<223> OTHER INFORMATION: Synthetic: 1445-A03 / VH

<400> SEQUENCE: 250

```
Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Asn Ile Ser Gly Tyr
            20                  25                  30

Tyr Ile His Trp Val Arg Gln Ala Pro Gly Lys Gly Leu Glu Trp Val
        35                  40                  45

Ala Glu Ile Ser Pro Thr Gly Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu His Gly Leu Val Tyr Gly Gln Pro Met Asp Tyr Trp Gly
            100                 105                 110

Gln Gly Thr Leu Val Thr Val Ser Ser
        115                 120


<210> SEQ ID NO 251
<211> LENGTH: 121
<212> TYPE: PRT
<213> ORGANISM: Artificial Sequence
<220> FEATURE:
<223> OTHER INFORMATION: Synthetic:  1445-B09 / VH

<400> SEQUENCE: 251

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Thr Gly Thr
            20                  25                  30

Gly Ile His Trp Val Arg Gln Ala Pro Gly Lys Gly Leu Glu Trp Val
        35                  40                  45

Gly Ile Ile Thr Pro Tyr Asn Gly Thr Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Gly Tyr Tyr Tyr Pro Pro Phe Asp Tyr Trp Gly
            100                 105                 110

Gln Gly Thr Leu Val Thr Val Ser Ser
        115                 120


<210> SEQ ID NO 252
<211> LENGTH: 123
<212> TYPE: PRT
<213> ORGANISM: Artificial Sequence
<220> FEATURE:
<223> OTHER INFORMATION: Synthetic:  VH11-[19] / VH

<400> SEQUENCE: 252

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Asp Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
```

```
65                  70                  75                  80

Leu Gln Met Asn Ser Leu Arg Ala Glu Asp Thr Ala Val Tyr Tyr Cys
                85                  90                  95

Ala Arg Gly Gly Thr Leu Val Arg Gly Ala Met Tyr Gly Thr Asp Val
            100                 105                 110

Trp Gly Gln Gly Thr Thr Val Thr Val Ser Ser
        115                 120


<210> SEQ ID NO 253
<211> LENGTH: 124
<212> TYPE: PRT
<213> ORGANISM: Artificial Sequence
<220> FEATURE:
<223> OTHER INFORMATION: Synthetic:  VH5-[7] / VH

<400> SEQUENCE: 253

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Gly Arg Tyr Tyr Gly Ser Gly Ser Tyr Ser Ser Tyr Phe Asp
            100                 105                 110

Tyr Trp Gly Gln Gly Thr Leu Val Thr Val Ser Ser
        115                 120


<210> SEQ ID NO 254
<211> LENGTH: 124
<212> TYPE: PRT
<213> ORGANISM: Artificial Sequence
<220> FEATURE:
<223> OTHER INFORMATION: Synthetic:  VH6-[11] / VH

<400> SEQUENCE: 254

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Phe Tyr Cys
                85                  90                  95

Ala Arg Gly Arg Glu Ile Thr Ser Gln Asn Ile Val Ile Leu Leu Asp
            100                 105                 110

Tyr Trp Gly Gln Gly Thr Leu Val Thr Val Thr Ser
        115                 120
```

<210> SEQ ID NO 255
<211> LENGTH: 124
<212> TYPE: PRT
<213> ORGANISM: Artificial Sequence
<220> FEATURE:
<223> OTHER INFORMATION: Synthetic: VH8-[15] / VH

<400> SEQUENCE: 255

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Glu Ile Thr Ser Gln Asn Ile Val Ile Leu Leu Asp
            100                 105                 110

Tyr Trp Gly Gln Gly Thr Leu Val Thr Val Ser Ser
        115                 120
```

<210> SEQ ID NO 256
<211> LENGTH: 107
<212> TYPE: PRT
<213> ORGANISM: Artificial Sequence
<220> FEATURE:
<223> OTHER INFORMATION: Synthetic: 1275-C10 / VL

<400> SEQUENCE: 256

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Val Ser Ser Trp
            20                  25                  30

Leu Ala Trp Tyr Gln Gln Lys Pro Glu Lys Ala Pro Lys Ser Leu Ile
        35                  40                  45

Tyr Ser Ala Arg Tyr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Leu Tyr Pro Leu
                85                  90                  95

Thr Phe Gly Gly Gly Thr Lys Val Glu Ile Lys
            100                 105
```

<210> SEQ ID NO 257
<211> LENGTH: 107
<212> TYPE: PRT
<213> ORGANISM: Artificial Sequence
<220> FEATURE:
<223> OTHER INFORMATION: Synthetic: 1275-C10-g / VL

<400> SEQUENCE: 257

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Val Ser Ser Trp
```

```
            20                  25                  30

Leu Ala Trp Tyr Gln Gln Lys Pro Gly Lys Ala Pro Lys Leu Leu Ile
        35                  40                  45

Tyr Ser Ala Arg Tyr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Leu Tyr Pro Leu
                85                  90                  95

Thr Phe Gly Gly Gly Thr Lys Val Glu Ile Lys
            100                 105


<210> SEQ ID NO 258
<211> LENGTH: 107
<212> TYPE: PRT
<213> ORGANISM: Artificial Sequence
<220> FEATURE:
<223> OTHER INFORMATION: Synthetic:  1275-D01 / VL

<400> SEQUENCE: 258

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Gly Arg Trp
            20                  25                  30

Leu Ala Trp Tyr Gln Gln Lys Pro Glu Lys Ala Pro Lys Ser Leu Ile
        35                  40                  45

Tyr Gly Arg Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Leu
                85                  90                  95

Thr Phe Gly Gly Gly Thr Lys Val Glu Ile Lys
            100                 105


<210> SEQ ID NO 259
<211> LENGTH: 107
<212> TYPE: PRT
<213> ORGANISM: Artificial Sequence
<220> FEATURE:
<223> OTHER INFORMATION: Synthetic:  1275-D10 / VL

<400> SEQUENCE: 259

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Val Phe Ser Trp
            20                  25                  30

Leu Ala Trp Tyr Gln Gln Lys Pro Glu Lys Ala Pro Lys Ser Leu Ile
        35                  40                  45

Tyr Asn Ala Thr Gln Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Tyr Tyr Pro Leu
                85                  90                  95

Thr Phe Gly Gly Gly Thr Lys Val Glu Ile Lys
            100                 105
```

<210> SEQ ID NO 260
<211> LENGTH: 107
<212> TYPE: PRT
<213> ORGANISM: Artificial Sequence
<220> FEATURE:
<223> OTHER INFORMATION: Synthetic: 1275-G02 / VL

<400> SEQUENCE: 260

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Leu Gly Ser Phe
20 25 30

Leu Ala Trp Tyr Gln Gln Lys Pro Glu Lys Ala Pro Lys Ser Leu Ile
35 40 45

Tyr Leu Gly Asn Leu Leu Gln Ile Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asn Ala Tyr Pro Leu
85 90 95

Thr Phe Gly Gly Gly Thr Lys Val Glu Ile Lys
100 105

<210> SEQ ID NO 261
<211> LENGTH: 107
<212> TYPE: PRT
<213> ORGANISM: Artificial Sequence
<220> FEATURE:
<223> OTHER INFORMATION: Synthetic: 1337-A04 / VL

<400> SEQUENCE: 261

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Gly Arg Trp
20 25 30

Val Ala Trp Tyr Gln Gln Lys Pro Glu Lys Ala Pro Lys Ser Leu Ile
35 40 45

Tyr Gly Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asn Thr Tyr Pro Leu
85 90 95

Thr Phe Gly Gly Gly Thr Lys Val Glu Ile Lys
100 105

<210> SEQ ID NO 262
<211> LENGTH: 107
<212> TYPE: PRT
<213> ORGANISM: Artificial Sequence
<220> FEATURE:
<223> OTHER INFORMATION: Synthetic: 1337-A05 / VL

<400> SEQUENCE: 262

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Gly Arg Trp
20 25 30

Val Ala Trp Tyr Gln Gln Lys Pro Glu Lys Ala Pro Lys Ser Leu Ile

```
        35                  40                  45

Tyr Gly Ala Asp Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105


<210> SEQ ID NO 263
<211> LENGTH: 107
<212> TYPE: PRT
<213> ORGANISM: Artificial Sequence
<220> FEATURE:
<223> OTHER INFORMATION: Synthetic:  1337-A06 / VL

<400> SEQUENCE: 263

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Ser Trp
            20                  25                  30

Val Ala Trp Tyr Gln Gln Lys Pro Glu Lys Ala Pro Lys Ser Leu Ile
        35                  40                  45

Tyr Gly Ala Asp Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105


<210> SEQ ID NO 264
<211> LENGTH: 107
<212> TYPE: PRT
<213> ORGANISM: Artificial Sequence
<220> FEATURE:
<223> OTHER INFORMATION: Synthetic:  1337-A07-g / VL

<400> SEQUENCE: 264

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Val Ala Trp Tyr Gln Gln Lys Pro Gly Lys Ala Pro Lys Leu Leu Ile
        35                  40                  45

Tyr Gly Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr His Thr Tyr Pro Leu
                85                  90                  95

Thr Phe Gly Gly Gly Thr Lys Val Glu Ile Lys
            100                 105


<210> SEQ ID NO 265
<211> LENGTH: 107
```

```
<212> TYPE: PRT
<213> ORGANISM: Artificial Sequence
<220> FEATURE:
<223> OTHER INFORMATION: Synthetic:  1337-A07 / VL

<400> SEQUENCE: 265

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Val Ala Trp Tyr Gln Gln Lys Pro Glu Lys Ala Pro Lys Ser Leu Ile
        35                  40                  45

Tyr Gly Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr His Thr Tyr Pro Leu
                85                  90                  95

Thr Phe Gly Gly Gly Thr Lys Val Glu Ile Lys
            100                 105


<210> SEQ ID NO 266
<211> LENGTH: 107
<212> TYPE: PRT
<213> ORGANISM: Artificial Sequence
<220> FEATURE:
<223> OTHER INFORMATION: Synthetic:  1337-A08 / VL

<400> SEQUENCE: 266

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Ser Trp
            20                  25                  30

Val Ala Trp Tyr Gln Gln Lys Pro Glu Lys Ala Pro Lys Ser Leu Ile
        35                  40                  45

Tyr Ala Ser Asp Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105


<210> SEQ ID NO 267
<211> LENGTH: 107
<212> TYPE: PRT
<213> ORGANISM: Artificial Sequence
<220> FEATURE:
<223> OTHER INFORMATION: Synthetic:  1337-A09 / VL

<400> SEQUENCE: 267

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Gly Ser Trp
            20                  25                  30

Leu Ala Trp Tyr Gln Gln Lys Pro Glu Lys Ala Pro Lys Ser Leu Ile
        35                  40                  45

Tyr Ala Ala Asp Arg Leu Gln Ser Gly Val Pro Ser Arg Phe Ser Gly
```

```
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr His Thr Tyr Pro Leu
                85                  90                  95

Thr Phe Gly Gly Gly Thr Lys Val Glu Ile Lys
            100                 105


<210> SEQ ID NO 268
<211> LENGTH: 107
<212> TYPE: PRT
<213> ORGANISM: Artificial Sequence
<220> FEATURE:
<223> OTHER INFORMATION: Synthetic:  1337-A09-g / VL

<400> SEQUENCE: 268

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Gly Ser Trp
            20                  25                  30

Leu Ala Trp Tyr Gln Gln Lys Pro Gly Lys Ala Pro Lys Leu Leu Ile
        35                  40                  45

Tyr Ala Ala Asp Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr His Thr Tyr Pro Leu
                85                  90                  95

Thr Phe Gly Gly Gly Thr Lys Val Glu Ile Lys
            100                 105


<210> SEQ ID NO 269
<211> LENGTH: 107
<212> TYPE: PRT
<213> ORGANISM: Artificial Sequence
<220> FEATURE:
<223> OTHER INFORMATION: Synthetic:  1337-A10 / VL

<400> SEQUENCE: 269

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Val Ala Trp Tyr Gln Gln Lys Pro Glu Lys Ala Pro Lys Ser Leu Ile
        35                  40                  45

Tyr Gly Ser Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Thr Tyr Pro Leu
                85                  90                  95

Thr Phe Gly Gly Gly Thr Lys Val Glu Ile Lys
            100                 105


<210> SEQ ID NO 270
<211> LENGTH: 107
<212> TYPE: PRT
<213> ORGANISM: Artificial Sequence
<220> FEATURE:
```

<223> OTHER INFORMATION: Synthetic: 1337-A10-g / VL

<400> SEQUENCE: 270

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Val Ala Trp Tyr Gln Gln Lys Pro Gly Lys Ala Pro Lys Leu Leu Ile
        35                  40                  45

Tyr Gly Ser Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Thr Tyr Pro Leu
                85                  90                  95

Thr Phe Gly Gly Gly Thr Lys Val Glu Ile Lys
            100                 105
```

<210> SEQ ID NO 271
<211> LENGTH: 107
<212> TYPE: PRT
<213> ORGANISM: Artificial Sequence
<220> FEATURE:
<223> OTHER INFORMATION: Synthetic: VL5-[23] / VL

<400> SEQUENCE: 271

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Phe Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105
```

<210> SEQ ID NO 272
<211> LENGTH: 107
<212> TYPE: PRT
<213> ORGANISM: Artificial Sequence
<220> FEATURE:
<223> OTHER INFORMATION: Synthetic: VL6-[26] / VL

<400> SEQUENCE: 272

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
```

```
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105


<210> SEQ ID NO 273
<211> LENGTH: 120
<212> TYPE: PRT
<213> ORGANISM: Artificial Sequence
<220> FEATURE:
<223> OTHER INFORMATION: Synthetic:  1193-B06 / VH

<400> SEQUENCE: 273

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Gly Asn
            20                  25                  30

Trp Met Ser Trp Val Arg Gln Ala Pro Gly Lys Gly Leu Glu Trp Val
        35                  40                  45

Gly Ile Ile Tyr Gly Thr Ser Gly Ala Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Ser Met Ser Gly Ser Arg Gly Phe Asp Tyr Trp Gly Gln
            100                 105                 110

Gly Thr Leu Val Thr Val Ser Ser
        115                 120


<210> SEQ ID NO 274
<211> LENGTH: 120
<212> TYPE: PRT
<213> ORGANISM: Artificial Sequence
<220> FEATURE:
<223> OTHER INFORMATION: Synthetic:  1193-C08 / VH

<400> SEQUENCE: 274

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asn Asn
            20                  25                  30

Trp Met Ser Trp Val Arg Gln Ala Pro Gly Lys Gly Leu Glu Trp Val
        35                  40                  45

Gly Ile Ile Asn Gly Asp Asp Gly Tyr Thr Tyr Tyr Ala Asp Arg Val
    50                  55                  60

Lys Gly Arg Phe Thr Ile Ile Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Ala Leu Gly Arg Pro Arg Arg Phe Asp Tyr Trp Gly Gln
            100                 105                 110

Gly Thr Leu Val Thr Val Ser Ser
        115                 120


<210> SEQ ID NO 275
<211> LENGTH: 120
```

<212> TYPE: PRT
<213> ORGANISM: Artificial Sequence
<220> FEATURE:
<223> OTHER INFORMATION: Synthetic: 1193-E06b / VH

<400> SEQUENCE: 275

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asn Thr
            20                  25                  30

Asp Met Ser Trp Val Arg Gln Ala Pro Gly Lys Gly Leu Glu Trp Val
        35                  40                  45

Gly Ile Ile Asn Gly Ser Gly Gly Ala Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Glu Asn Glu Trp Glu Val Ser Met Asp Tyr Trp Gly Gln
            100                 105                 110

Gly Thr Leu Val Thr Val Ser Ser
        115                 120
```

<210> SEQ ID NO 276
<211> LENGTH: 120
<212> TYPE: PRT
<213> ORGANISM: Artificial Sequence
<220> FEATURE:
<223> OTHER INFORMATION: Synthetic: 1193-H04b / VH

<400> SEQUENCE: 276

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Ser Ser
            20                  25                  30

Trp Met Ser Trp Val Arg Gln Ala Pro Gly Lys Gly Leu Glu Trp Val
        35                  40                  45

Gly Ile Ile Asn Gly Tyr Asn Gly Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Ser Ala Pro Gly Ala Arg Arg Phe Asp Tyr Trp Gly Gln
            100                 105                 110

Gly Thr Leu Val Thr Val Ser Ser
        115                 120
```

<210> SEQ ID NO 277
<211> LENGTH: 120
<212> TYPE: PRT
<213> ORGANISM: Artificial Sequence
<220> FEATURE:
<223> OTHER INFORMATION: Synthetic: 1447-D11 / VH

<400> SEQUENCE: 277

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asn Thr
```

```
            20                  25                  30

Asp Met Ser Trp Val Arg Gln Ala Pro Gly Lys Gly Leu Glu Trp Val
        35                  40                  45

Gly Val Ile Asn Gly Ser Gly Gly Ser Ser Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Glu Thr Glu Trp Glu Val Ser Leu Asp Tyr Trp Gly Gln
            100                 105                 110

Gly Thr Leu Val Thr Val Ser Ser
        115                 120


<210> SEQ ID NO 278
<211> LENGTH: 120
<212> TYPE: PRT
<213> ORGANISM: Artificial Sequence
<220> FEATURE:
<223> OTHER INFORMATION: Synthetic:  1447-E08 / VH

<400> SEQUENCE: 278

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asp Thr
            20                  25                  30

Asp Met Ser Trp Val Arg Gln Ala Pro Gly Lys Gly Leu Glu Trp Val
        35                  40                  45

Gly Met Ile Asn Gly Ala Gly Gly Ala Ser Phe Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Glu Asn Gln Trp Glu Val Thr Phe Asp Tyr Trp Gly Gln
            100                 105                 110

Gly Thr Leu Val Thr Val Ser Ser
        115                 120


<210> SEQ ID NO 279
<211> LENGTH: 120
<212> TYPE: PRT
<213> ORGANISM: Artificial Sequence
<220> FEATURE:
<223> OTHER INFORMATION: Synthetic:  1447-F11 / VH

<400> SEQUENCE: 279

Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Asp Asn Thr
            20                  25                  30

Asp Met Ser Trp Val Arg Gln Ala Pro Gly Lys Gly Leu Glu Trp Val
        35                  40                  45

Gly Ile Ile Asn Gly Ser Gly Gly Val Thr Asn Tyr Ala Asp Ser Val
    50                  55                  60

Arg Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Tyr Glu Ser Glu Trp Glu Val Ser Leu Asp Tyr Trp Gly Gln
            100                 105                 110

Gly Thr Leu Val Thr Val Ser Ser
        115                 120


<210> SEQ ID NO 280
<211> LENGTH: 120
<212> TYPE: PRT
<213> ORGANISM: Artificial Sequence
<220> FEATURE:
<223> OTHER INFORMATION: Synthetic:  1447-G01 / VH

<400> SEQUENCE: 280

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr Ser
            20                  25                  30

Asp Met Ser Trp Val Arg Gln Ala Pro Gly Lys Gly Leu Glu Trp Val
        35                  40                  45

Gly Ile Ile Asn Gly Ser Gly Gly Ala Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Glu Asn Glu Met Glu Val Ser Met Asp Tyr Trp Gly Gln
            100                 105                 110

Gly Thr Leu Val Thr Val Ser Ser
        115                 120


<210> SEQ ID NO 281
<211> LENGTH: 108
<212> TYPE: PRT
<213> ORGANISM: Artificial Sequence
<220> FEATURE:
<223> OTHER INFORMATION: Synthetic:  1193-B06 / VL

<400> SEQUENCE: 281

Glu Ile Val Leu Thr Gln Ser Pro Gly Thr Leu Ser Leu Ser Pro Gly
1               5                   10                  15

Glu Arg Ala Thr Leu Ser Cys Arg Ala Gly Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Tyr Thr Thr Pro
                85                  90                  95

Pro Thr Phe Gly Gln Gly Thr Lys Val Glu Ile Lys
            100                 105


<210> SEQ ID NO 282
<211> LENGTH: 108
<212> TYPE: PRT
<213> ORGANISM: Artificial Sequence
```

<220> FEATURE:
<223> OTHER INFORMATION: Synthetic: 1193-C08 / VL

<400> SEQUENCE: 282

```
Glu Ile Val Leu Thr Gln Ser Pro Gly Thr Leu Ser Leu Thr Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Met Tyr Tyr Cys Gln Gln His Tyr Thr Thr Pro
                85                  90                  95

Pro Thr Phe Gly Gln Gly Thr Lys Val Glu Ile Lys
            100                 105
```

<210> SEQ ID NO 283
<211> LENGTH: 108
<212> TYPE: PRT
<213> ORGANISM: Artificial Sequence
<220> FEATURE:
<223> OTHER INFORMATION: Synthetic: 1193-E06b / VL

<400> SEQUENCE: 283

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Tyr Thr Thr Pro
                85                  90                  95

Pro Thr Phe Gly Gln Gly Thr Lys Val Glu Ile Lys
            100                 105
```

<210> SEQ ID NO 284
<211> LENGTH: 107
<212> TYPE: PRT
<213> ORGANISM: Artificial Sequence
<220> FEATURE:
<223> OTHER INFORMATION: Synthetic: 1193-H04b / VL

<400> SEQUENCE: 284

```
Glu Ile Val Leu Thr Gln Ser Pro Gly Thr Leu Ser Leu Ser Pro Gly
1               5                   10                  15

Glu Ala Thr Leu Ser Cys Arg Ala Ser Gln Ser Val Ser Ser Ser Tyr
            20                  25                  30

Leu Ala Trp Tyr Gln Gln Arg Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60
```

```
Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln His Tyr Thr Thr Pro Pro
                85                  90                  95

Thr Phe Gly Gln Gly Thr Lys Val Glu Ile Lys
            100                 105


<210> SEQ ID NO 285
<211> LENGTH: 108
<212> TYPE: PRT
<213> ORGANISM: Artificial Sequence
<220> FEATURE:
<223> OTHER INFORMATION: Synthetic:  1447-D11 / VL

<400> SEQUENCE: 285

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Asn Gln Pro Thr Pro
                85                  90                  95

Pro Thr Phe Gly Gln Gly Thr Lys Val Glu Ile Lys
            100                 105


<210> SEQ ID NO 286
<211> LENGTH: 108
<212> TYPE: PRT
<213> ORGANISM: Artificial Sequence
<220> FEATURE:
<223> OTHER INFORMATION: Synthetic:  1447-E08 / VL

<400> SEQUENCE: 286

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ala Gly Ile
            20                  25                  30

Asp Leu Ser Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Asn Thr Thr Pro
                85                  90                  95

Pro Thr Phe Gly Gln Gly Thr Lys Val Glu Ile Lys
            100                 105


<210> SEQ ID NO 287
<211> LENGTH: 108
<212> TYPE: PRT
<213> ORGANISM: Artificial Sequence
<220> FEATURE:
<223> OTHER INFORMATION: Synthetic:  1447-F11 / VL
```

<400> SEQUENCE: 287

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Tyr Arg Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Gln Thr Ala Pro
                85                  90                  95

Pro Thr Phe Gly Gln Gly Thr Lys Val Glu Ile Lys
            100                 105
```

<210> SEQ ID NO 288
<211> LENGTH: 108
<212> TYPE: PRT
<213> ORGANISM: Artificial Sequence
<220> FEATURE:
<223> OTHER INFORMATION: Synthetic: 1447-G01 / VL

<400> SEQUENCE: 288

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Arg
            20                  25                  30

Glu Leu Gly Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gln Cys Ser Trp Pro
                85                  90                  95

Pro Thr Phe Gly Gln Gly Thr Lys Val Glu Ile Lys
            100                 105
```

<210> SEQ ID NO 289
<211> LENGTH: 252
<212> TYPE: PRT
<213> ORGANISM: Artificial Sequence
<220> FEATURE:
<223> OTHER INFORMATION: Synthetic: IgG1 Fc from scFv-Fc

<400> SEQUENCE: 289

```
Ala Ala Gly Ser Asp Gln Glu Pro Lys Ser Ser Asp Lys Thr His Thr
1               5                   10                  15

Cys Pro Pro Cys Ser Ala Pro Glu Leu Leu Gly Gly Ser Ser Val Phe
            20                  25                  30

Leu Phe Pro Pro Lys Pro Lys Asp Thr Leu Met Ile Ser Arg Thr Pro
        35                  40                  45

Glu Val Thr Cys Val Val Val Asp Val Ser His Glu Asp Pro Glu Val
    50                  55                  60

Lys Phe Asn Trp Tyr Val Asp Gly Val Glu Val His Asn Ala Lys Thr
65                  70                  75                  80
```

```
Lys Pro Arg Glu Glu Gln Tyr Asn Ser Thr Tyr Arg Val Val Ser Val
                85                  90                  95

Leu Thr Val Leu His Gln Asp Trp Leu Asn Gly Lys Glu Tyr Lys Cys
            100                 105                 110

Lys Val Ser Asn Lys Ala Leu Pro Ala Pro Ile Glu Lys Thr Ile Ser
        115                 120                 125

Lys Ala Lys Gly Gln Pro Arg Glu Pro Gln Val Tyr Thr Leu Pro Pro
    130                 135                 140

Ser Arg Asp Glu Leu Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Phe Leu Tyr Ser Lys Leu Thr Val Asp Lys Ser Arg Trp
        195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Gly Lys Gly Ser
225                 230                 235                 240

Gly Asp Tyr Lys Asp Asp Asp Asp Lys Gly Ser Gly
                245                 250


<210> SEQ ID NO 290
<211> LENGTH: 107
<212> TYPE: PRT
<213> ORGANISM: Artificial Sequence
<220> FEATURE:
<223> OTHER INFORMATION: Synthetic:  Trastuzumab LC

<400> SEQUENCE: 290

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105


<210> SEQ ID NO 291
<211> LENGTH: 463
<212> TYPE: PRT
<213> ORGANISM: Artificial Sequence
<220> FEATURE:
<223> OTHER INFORMATION: Synthetic:  1251-A06-(wt) / HC

<400> SEQUENCE: 291

Met Gln Val Gln Leu Val Glu Ser Gly Gly Gly Val Val Gln Pro Gly
1               5                   10                  15

Arg Ser Leu Arg Leu Ser Cys Ala Ala Ser Gly Phe Asp Phe Ser Ser
            20                  25                  30
```

```
Tyr Gly Met His Trp Val Arg Gln Ala Pro Asp Lys Gly Leu Glu Trp
        35                  40                  45

Val Ala Val Ile Trp Asp Asp Gly Ser Asp Arg Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Gly Gly Thr Arg Val Leu Gly Ala Ile His Gly Thr Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Glu Asp Tyr Phe Pro Glu Pro
145                 150                 155                 160

Ala Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445
```

```
Ser Leu Ser Pro Gly Lys Gly Gly Ser His His His His His His
    450                 455                 460


<210> SEQ ID NO 292
<211> LENGTH: 454
<212> TYPE: PRT
<213> ORGANISM: Artificial Sequence
<220> FEATURE:
<223> OTHER INFORMATION: Synthetic:  1251-A06-(g) / HC

<400> SEQUENCE: 292

Met Gln Val Gln Leu Val Glu Ser Gly Gly Gly Val Val Gln Pro Gly
1               5                   10                  15

Arg Ser Leu Arg Leu Ser Cys Ala Ala Ser Gly Phe Asp Phe Ser Ser
            20                  25                  30

Tyr Gly Met His Trp Val Arg Gln Ala Pro Gly Lys Gly Leu Glu Trp
        35                  40                  45

Val Ala Val Ile Trp Asp Asp Gly Ser Asp Arg Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Gly Gly Thr Arg Val Leu Gly Ala Ile His Gly Thr Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350
```

```
Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450


<210> SEQ ID NO 293
<211> LENGTH: 463
<212> TYPE: PRT
<213> ORGANISM: Artificial Sequence
<220> FEATURE:
<223> OTHER INFORMATION: Synthetic:  1251-B08-(wt) / HC

<400> SEQUENCE: 293

Met Gln Val Gln Leu Val Glu Ser Gly Gly Gly Val Val Gln Pro Gly
1               5                   10                  15

Arg Ser Leu Arg Leu Ser Cys Ala Ala Ser Gly Phe Asn Phe Ser Asp
            20                  25                  30

Tyr Gly Met His Trp Val Arg Gln Ala Pro Asp Lys Gly Leu Glu Trp
        35                  40                  45

Val Ala Val Ile Trp Tyr Asp Gly Ser Ile Ser Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Gly Gly Thr Val Glu His Gly Ala Val Tyr Gly Thr Asp
            100                 105                 110

Val Trp Gly Gln Gly Ala Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255
```

```
Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys Gly Gly Ser His His His His His His
    450                 455                 460


<210> SEQ ID NO 294
<211> LENGTH: 454
<212> TYPE: PRT
<213> ORGANISM: Artificial Sequence
<220> FEATURE:
<223> OTHER INFORMATION: Synthetic:  1251-B08-(g) / HC

<400> SEQUENCE: 294

Met Gln Val Gln Leu Val Glu Ser Gly Gly Gly Val Val Gln Pro Gly
1               5                   10                  15

Arg Ser Leu Arg Leu Ser Cys Ala Ala Ser Gly Phe Asn Phe Ser Asp
            20                  25                  30

Tyr Gly Met His Trp Val Arg Gln Ala Pro Gly Lys Gly Leu Glu Trp
        35                  40                  45

Val Ala Val Ile Trp Tyr Asp Gly Ser Ile Ser Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Gly Gly Thr Val Glu His Gly Ala Val Tyr Gly Thr Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160
```

```
Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450


<210> SEQ ID NO 295
<211> LENGTH: 215
<212> TYPE: PRT
<213> ORGANISM: Artificial Sequence
<220> FEATURE:
<223> OTHER INFORMATION: Synthetic:  1275-C10-(wt) / LC

<400> SEQUENCE: 295

Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Gly Val Ser Ser
            20                  25                  30

Trp Leu Ala Trp Tyr Gln Gln Lys Pro Glu Lys Ala Pro Lys Ser Leu
        35                  40                  45

Ile Tyr Ser Ala Arg Tyr Leu Gln Ser Gly Val Pro Ser Arg Phe Ser
    50                  55                  60
```

```
Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Tyr Asn Leu Tyr Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 296
<211> LENGTH: 215
<212> TYPE: PRT
<213> ORGANISM: Artificial Sequence
<220> FEATURE:
<223> OTHER INFORMATION: Synthetic:  1275-C10-(g) / LC

<400> SEQUENCE: 296

Met Asp Ile Gln Met Thr Gln Ser Pro Ser Ser Val Ser Ala Ser Val
1               5                   10                  15

Gly Asp Arg Val Thr Ile Thr Cys Arg Ala Ser Gln Gly Val Ser Ser
            20                  25                  30

Trp Leu Ala Trp Tyr Gln Gln Lys Pro Gly Lys Ala Pro Lys Leu Leu
        35                  40                  45

Ile Tyr Ser Ala Arg Tyr Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Tyr Asn Leu Tyr Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205
```

```
Ser Phe Asn Arg Gly Glu Cys
    210                 215


<210> SEQ ID NO 297
<211> LENGTH: 215
<212> TYPE: PRT
<213> ORGANISM: Artificial Sequence
<220> FEATURE:
<223> OTHER INFORMATION: Synthetic:  1337-A07-(wt) / LC

<400> SEQUENCE: 297

Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Gly Ile Ser Ser
            20                  25                  30

Trp Val Ala Trp Tyr Gln Gln Lys Pro Glu Lys Ala Pro Lys Ser Leu
        35                  40                  45

Ile Tyr Gly Ala Ser Arg Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Tyr His Thr Tyr Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 298
<211> LENGTH: 215
<212> TYPE: PRT
<213> ORGANISM: Artificial Sequence
<220> FEATURE:
<223> OTHER INFORMATION: Synthetic:  1337-A07-(g) / LC

<400> SEQUENCE: 298

Met Asp Ile Gln Met Thr Gln Ser Pro Ser Ser Val Ser Ala Ser Val
1               5                   10                  15

Gly Asp Arg Val Thr Ile Thr Cys Arg Ala Ser Gln Gly Ile Ser Ser
            20                  25                  30

Trp Val Ala Trp Tyr Gln Gln Lys Pro Gly Lys Ala Pro Lys Leu Leu
        35                  40                  45

Ile Tyr Gly Ala Ser Arg Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80
```

```
Pro Glu Asp Phe Ala Thr Tyr Tyr Cys Gln Gln Tyr His Thr Tyr Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 299
<211> LENGTH: 215
<212> TYPE: PRT
<213> ORGANISM: Artificial Sequence
<220> FEATURE:
<223> OTHER INFORMATION: Synthetic:  1337-A09-(wt) / LC

<400> SEQUENCE: 299

Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Gly Ile Gly Ser
            20                  25                  30

Trp Leu Ala Trp Tyr Gln Gln Lys Pro Glu Lys Ala Pro Lys Ser Leu
        35                  40                  45

Ile Tyr Ala Ala Asp Arg Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Tyr His Thr Tyr Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 300
<211> LENGTH: 215
<212> TYPE: PRT
<213> ORGANISM: Artificial Sequence
<220> FEATURE:
<223> OTHER INFORMATION: Synthetic: 1337-A09-(g) / LC

<400> SEQUENCE: 300

```
Met Asp Ile Gln Met Thr Gln Ser Pro Ser Ser Val Ser Ala Ser Val
1               5                   10                  15

Gly Asp Arg Val Thr Ile Thr Cys Arg Ala Ser Gln Gly Ile Gly Ser
            20                  25                  30

Trp Leu Ala Trp Tyr Gln Gln Lys Pro Gly Lys Ala Pro Lys Leu Leu
        35                  40                  45

Ile Tyr Ala Ala Asp Arg Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Tyr His Thr Tyr Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 301
<211> LENGTH: 215
<212> TYPE: PRT
<213> ORGANISM: Artificial Sequence
<220> FEATURE:
<223> OTHER INFORMATION: Synthetic: 1337-A10-(wt) / LC

<400> SEQUENCE: 301

```
Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Gly Ile Ser Ser
            20                  25                  30

Trp Val Ala Trp Tyr Gln Gln Lys Pro Glu Lys Ala Pro Lys Ser Leu
        35                  40                  45

Ile Tyr Gly Ser Ser Arg Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Tyr Asn Thr Tyr Pro
```

```
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 302
<211> LENGTH: 215
<212> TYPE: PRT
<213> ORGANISM: Artificial Sequence
<220> FEATURE:
<223> OTHER INFORMATION: Synthetic:  1337-A10-(g) / LC

<400> SEQUENCE: 302

Met Asp Ile Gln Met Thr Gln Ser Pro Ser Ser Val Ser Ala Ser Val
1               5                   10                  15

Gly Asp Arg Val Thr Ile Thr Cys Arg Ala Ser Gln Gly Ile Ser Ser
            20                  25                  30

Trp Val Ala Trp Tyr Gln Gln Lys Pro Gly Lys Ala Pro Lys Leu Leu
        35                  40                  45

Ile Tyr Gly Ser Ser Arg Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Tyr Asn Thr Tyr Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 303
<211> LENGTH: 9
<212> TYPE: PRT
<213> ORGANISM: Artificial Sequence
<220> FEATURE:
<223> OTHER INFORMATION: Synthetic: C-term His Tag

<400> SEQUENCE: 303

```
Gly Gly Ser His His His His His His
1               5
```

<210> SEQ ID NO 304
<211> LENGTH: 330
<212> TYPE: PRT
<213> ORGANISM: Artificial Sequence
<220> FEATURE:
<223> OTHER INFORMATION: Synthetic: HC Constant

<400> SEQUENCE: 304

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 305
<211> LENGTH: 107
<212> TYPE: PRT
<213> ORGANISM: Artificial Sequence
<220> FEATURE:
<223> OTHER INFORMATION: Synthetic:  LC Constant

<400> SEQUENCE: 305

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 306
<211> LENGTH: 463
<212> TYPE: PRT
<213> ORGANISM: Artificial Sequence
<220> FEATURE:
<223> OTHER INFORMATION: Synthetic:  1251-A03 / HC

<400> SEQUENCE: 306

Met Gln Val Gln Leu Val Glu Ser Gly Gly Gly Val Val Gln Pro Gly
1               5                   10                  15

Arg Ser Leu Arg Leu Ser Cys Ala Ala Ser Gly Phe Ala Phe Ser Asp
            20                  25                  30

His Gly Met His Trp Val Arg Gln Ala Pro Asp Lys Gly Leu Glu Trp
        35                  40                  45

Val Ala Val Ile Trp Tyr Asp Gly Ser His Lys Ile Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Gly Gly Ser Leu Ala Gly Gly Ala Val Tyr Gly Thr Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175
```

```
Phe Pro Ala Val Leu Gln Ser Ser Gly Leu Tyr Ser Leu Ser Ser Val
            180                 185                 190

Val Thr Val Pro Ser Ser Ser Leu Gly Thr Arg Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys Gly Gly Ser His His His His His His
    450                 455                 460
```

```
<210> SEQ ID NO 307
<211> LENGTH: 463
<212> TYPE: PRT
<213> ORGANISM: Artificial Sequence
<220> FEATURE:
<223> OTHER INFORMATION: Synthetic:  1251-B09 / HC

<400> SEQUENCE: 307

Met Gln Val Gln Leu Val Glu Ser Gly Gly Gly Val Val Gln Pro Gly
1               5                   10                  15

Arg Ser Leu Arg Leu Ser Cys Ala Ala Ser Gly Phe Asn Phe Ser Asp
            20                  25                  30

Tyr Gly Met His Trp Val Arg Gln Ala Pro Asp Lys Gly Leu Glu Trp
        35                  40                  45

Val Ala Val Thr Trp Tyr Asp Gly Ser Arg Glu Tyr Tyr Ala Asp Ser
    50                  55                  60

Val Lys Gly Arg Phe Thr Ile Ser Arg Asp Asn Ser Lys Asn Thr Leu
65                  70                  75                  80
```

```
Tyr Leu Gln Met Asn Ser Leu Arg Ala Glu Asp Thr Ala Val Tyr Tyr
                85                  90                  95

Cys Ala Arg Gly Gly Thr Leu Val His Gly Ala Leu Tyr Gly Asn Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys Gly Gly Ser His His His His His His
    450                 455                 460
```

<210> SEQ ID NO 308
<211> LENGTH: 463
<212> TYPE: PRT
<213> ORGANISM: Artificial Sequence
<220> FEATURE:

<223> OTHER INFORMATION: Synthetic: 1251-B10 / HC

<400> SEQUENCE: 308

```
Met Gln Val Gln Leu Val Glu Ser Gly Gly Gly Val Val Gln Pro Gly
1               5                   10                  15

Arg Ser Leu Arg Leu Ser Cys Ala Ala Ser Gly Phe Asn Phe Ser Ser
            20                  25                  30

His Gly Met His Trp Val Arg Gln Ala Pro Asp Lys Gly Leu Glu Trp
        35                  40                  45

Val Ala Val Ile Trp His Asp Gly Ser Asp Lys Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Gly Gly Thr Arg Val Leu Gly Ala Val Tyr Gly Leu Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Ser Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400
```

```
Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys Gly Gly Ser His His His His His His
    450                 455                 460


<210> SEQ ID NO 309
<211> LENGTH: 238
<212> TYPE: PRT
<213> ORGANISM: Artificial Sequence
<220> FEATURE:
<223> OTHER INFORMATION: Synthetic:  Fc Constant

<400> SEQUENCE: 309

Ala Ala Gly Ser Asp Gln Glu Pro Lys Ser Ser Asp Lys Thr His Thr
1               5                   10                  15

Cys Pro Pro Cys Ser Ala Pro Glu Leu Leu Gly Gly Ser Ser Val Phe
            20                  25                  30

Leu Phe Pro Pro Lys Pro Lys Asp Thr Leu Met Ile Ser Arg Thr Pro
        35                  40                  45

Glu Val Thr Cys Val Val Val Asp Val Ser His Glu Asp Pro Glu Val
    50                  55                  60

Lys Phe Asn Trp Tyr Val Asp Gly Val Glu Val His Asn Ala Lys Thr
65                  70                  75                  80

Lys Pro Arg Glu Glu Gln Tyr Asn Ser Thr Tyr Arg Val Val Ser Val
                85                  90                  95

Leu Thr Val Leu His Gln Asp Trp Leu Asn Gly Lys Glu Tyr Lys Cys
            100                 105                 110

Lys Val Ser Asn Lys Ala Leu Pro Ala Pro Ile Glu Lys Thr Ile Ser
        115                 120                 125

Lys Ala Lys Gly Gln Pro Arg Glu Pro Gln Val Tyr Thr Leu Pro Pro
    130                 135                 140

Ser Arg Asp Glu Leu Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Phe Leu Tyr Ser Lys Leu Thr Val Asp Lys Ser Arg Trp
        195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Gly Lys
225                 230                 235


<210> SEQ ID NO 310
<211> LENGTH: 463
<212> TYPE: PRT
<213> ORGANISM: Artificial Sequence
<220> FEATURE:
<223> OTHER INFORMATION: Synthetic:  1251-A06 HC / HC

<400> SEQUENCE: 310

Met Gln Val Gln Leu Val Glu Ser Gly Gly Gly Val Val Gln Pro Gly
1               5                   10                  15
```

```
Arg Ser Leu Arg Leu Ser Cys Ala Ala Ser Gly Phe Asp Phe Ser Ser
            20                  25                  30

Tyr Gly Met His Trp Val Arg Gln Ala Pro Asp Lys Gly Leu Glu Trp
        35                  40                  45

Val Ala Val Ile Trp Asp Asp Gly Ser Asp Arg Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Gly Gly Thr Arg Val Leu Gly Ala Ile His Gly Thr Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430
```

```
Ser Val Met His Glu Ala Leu His Asn His Tyr Thr Gln Lys Ser Leu
        435                 440                 445

Ser Leu Ser Pro Gly Lys Gly Gly Ser His His His His His His
    450                 455                 460


<210> SEQ ID NO 311
<211> LENGTH: 463
<212> TYPE: PRT
<213> ORGANISM: Artificial Sequence
<220> FEATURE:
<223> OTHER INFORMATION: Synthetic:  1251-F07 HC / HC

<400> SEQUENCE: 311

Met Gln Val Gln Leu Val Glu Ser Gly Gly Gly Val Val Gln Pro Gly
1               5                   10                  15

Arg Ser Leu Arg Leu Ser Cys Ala Ala Ser Gly Phe Thr Phe Ser Ser
            20                  25                  30

His Gly Met His Trp Val Arg Gln Ala Pro Asp Lys Gly Leu Glu Trp
        35                  40                  45

Val Ala Val Ile Trp Asp Asp Gly Ser Asn Glu Val Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Gly Gly Thr Arg Ile Arg Gly Leu Arg Tyr Gly Thr Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335
```

-continued

```
Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys Gly Gly Ser His His His His His His
    450                 455                 460
```